(12) United States Patent
Hu et al.

(10) Patent No.: US 7,288,396 B2
(45) Date of Patent: Oct. 30, 2007

(54) BIOSYNTHETIC GENE CLUSTER FOR LEPTOMYCINS

(75) Inventors: Zhihao Hu, Castro Valley, CA (US); Ralph Reid, San Rafael, CA (US)

(73) Assignee: Kosan Biosciences Incorporated, Hayward, CA (US)

( * ) Notice: Subject to any disclaimer, the term of this patent is extended or adjusted under 35 U.S.C. 154(b) by 288 days.

(21) Appl. No.: 10/937,730

(22) Filed: Sep. 8, 2004

(65) Prior Publication Data

US 2005/0112726 A1  May 26, 2005

Related U.S. Application Data

(60) Provisional application No. 60/502,423, filed on Sep. 11, 2003, provisional application No. 60/553,384, filed on Mar. 15, 2004.

(51) Int. Cl.
*C12N 9/00* (2006.01)

(52) U.S. Cl. .................................................. 435/183

(58) Field of Classification Search ..................... None
See application file for complete search history.

*Primary Examiner*—Nashaat T. Nashed
(74) *Attorney, Agent, or Firm*—Robin C. Chiang; Gary W. Ashley

(57) ABSTRACT

Polypeptides and domains of leptomycin polyketide synthase and the nucleic acids encoding them are provided. Methods to prepare leptomycin, leptomycin analogs, and leptomycin derivatives are described, as are methods to prepare other polyketides using the nucleic acids encoding leptomycin polyketide synthase domains or modifying enzymes.

1 Claim, 39 Drawing Sheets

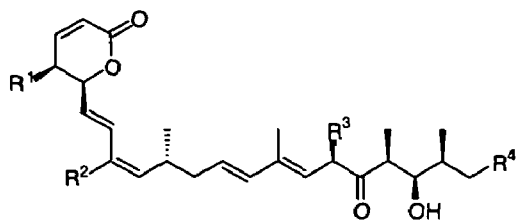

Figure 3:
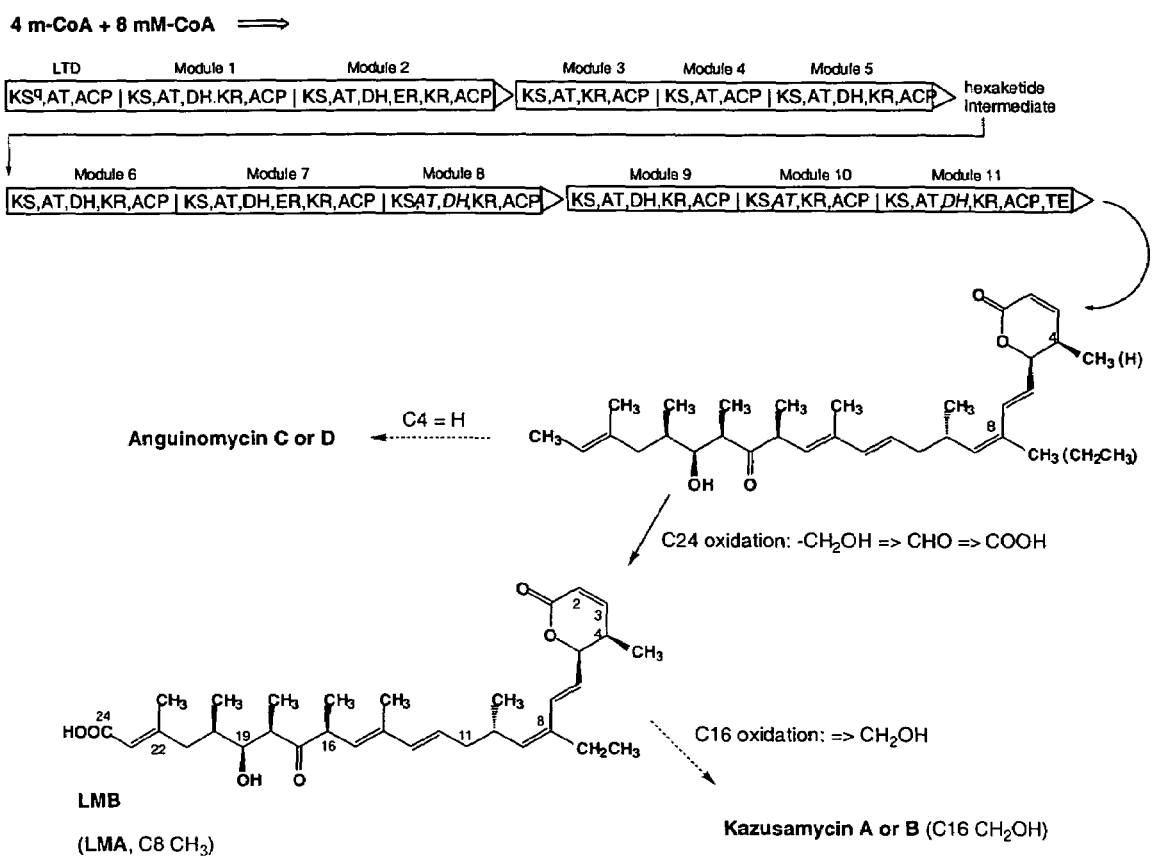

| Compound | Source | Reference | R¹ | R² | R³ | R⁴ |
|---|---|---|---|---|---|---|
| Leptomycin A | Streptomyces ATCC 39366 | US 4,792,522 20 Dec 1988 | Me | Me | Me | A |
| Leptomycin B | Streptomyces ATCC 39366 | US 4,792,522 20 Dec 1988 | Me | Et | Me | A |
| Anguinomycin A | Streptomyces R2827 | | H | Me | Me | A |
| Anguinomycin B | Streptomyces R2827 | | H | Et | Me | A |
| Anguinomycin C | Streptomyces KR2827-2 | | H | Me | Me | Me |
| Anguinomycin D | Streptomyces KR2827-2 | | H | Et | Me | Me |
| Callystatin A | Callyspongia truncata | | H | Et | Me | Et |
| Kazusamycin A | Streptomyces 81-484 | | Me | Et | CH₂OH | A |
| Kazusamycin B | Streptomyces 81-484 | US 4,725,621 16 Feb 1988 | Me | Me | CH₂OH | A |
| Leptolstatin | Streptomyces SAM1595 | | Me | Me | Me | A |
| Leptofuranin A | Streptomyces tanashiensis 3007-H1 | | Me | Me | Me | B |
| Leptofuranin B | Streptomyces tanashiensis 3007-H1 | | Me | Et | Me | B |
| Leptofuranin C | Streptomyces tanashiensis 3007-H1 | | Me | Me | Me | B |
| Leptofuranin D | Streptomyces tanashiensis 3007-H1 | | Me | Et | Me | B |

FIGURE 1

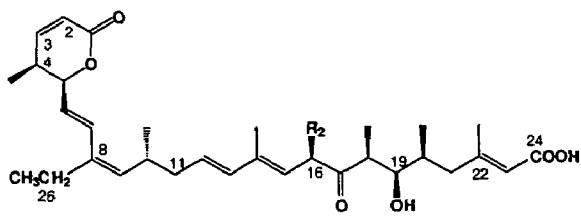
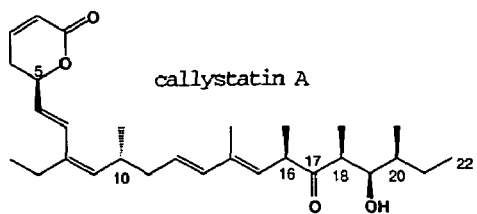
|  | rel IC$_{50}$ | |
|---|---|---|
|  | REV | Tox |
| LMB | 1 | 0.12 |
| 26-hydroxy-LMB | 12 | 16 |
| 4,11-dihydroxy-LMB | 120 | 232 |
| 2,3-dihydro-LMB | 1200 | 775 |
| LMB-24-glutaminamide | 120 | 211 |
|  | rel IC$_{50}$ |
|---|---|
| CLYA | 1 |
| 5-epi CLYA | 350 |
| 10-desMe CLA | 60 |
| 17-dihydro CLA | 590 |
| 16,18,20-tridesMe CLA | 3400 |
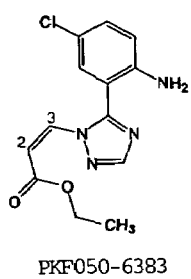
PKF050-6383
|  | rel IC$_{50}$ | |
|---|---|---|
|  | REV | Tox |
| LMB | 1 | 250 |
| PKF050-6383 | 80 | 6200 |
| (E) 2,3-PKF050-63833 | 3960 | 6600 |
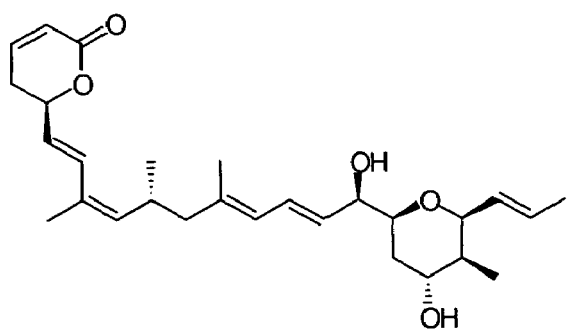
ratjadone
FIGURE 2

FIGURE 5. DNA Sequence of the Leptomycin Biosynthetic Gene Cluster (SEQ ID NO:3).

```
   1 CGGTGGGCTC GGGTGAGAAA AAATTAGTCC GAATCGATGC GCTCCCGTGC TGTTGCGCAT
  61 GTGACCGATA TGTAAGCGAC ATGTGAACGT TCGTCGCAAG CAGGTGCGTT CGCCCCCGCC
 121 GGCGGGTCGT CGGGACCGCG CGCGCGGGCG TGCGAGCCGG GTGCGCGGCC GGTCTGATCA
 181 AGGGTTCTCG CGCGTCGACG ACGCAGGTCG AAGGCGGGCG TGCGCGGGGC GTTCGCGCAC
 241 TACACCAGGT GACCCGAATG GTTCAACCGC GCCGTCGAAA GCGCCCGAAC GGGGCCTGAA
 301 TTCACCCCTT GCGGCCGATC GACCCGGTAC TCCAATGTGT TGATCTGTGT TCGTCCGTGT
 361 ACTCAACGTA TGCAGGTCAT GGAGCGCGGA ATGACGGAAT TCAACGCCGA TGCCCATCGC
 421 GCACACCCCG CGCCGGAAGA CGCGGTGGCC ATCGTCGGGT TGGCCTGCCG ACTCCCCGGC
 481 GCCGACGGCC CCGACGAGTT CTGGGACCTG CTGAGCAACG GACGCGACAC GATCACCGAA
 541 GTGCCCCGCC ATCGCCGGGA CGCGAGAGCG GCGGACGACA CGAATCGAAC GGCCGGCGGA
 601 TCCCCCCACC CAGCCGCGAA CCGACCGCGA AGAGGCGGAT TCCTGGACGC GGTGGACCGG
 661 TTCGACGCCG CCTTCTTCGG CATCACCCCG GGCGAGGCCG CCCTGATCGA CCCGCAACAG
 721 CGCCTGATGC TCGAACTGTG CTGGGAGGCC CTGGAACACG CGGGCATCCC GCCGACCCGG
 781 ATTCGGGGCA GCGCCACCGG GGTGTTCGCC GGCGCGATCT GGGACGACTA CGCCACCCTG
 841 CTGCGCCGCG CCGGCGTCGA GCCCGGCCCC CGACACGCCA CCGGCCTGCA CCGCAGCATG
 901 ATCGCCAACC GGGTCTCGTA CACCCTCGGC CTGCGCGGCC CCAGCATGAC GGTGGACGCG
 961 GCCCAGTCCT CGTCCCTGGT CGCGGTACAC CTGGCCGGCG AGAGCCTGCG CCGGGGCGAG
1021 TCGACACTGG CCCTGGTCGG CGGGGTCAAC CTGGACCTGG TTCCCGACCA CGACGGCGAC
1081 GCGGCCAAGT TCGGCGGGCT CTCCCCGCAG GGCCGCTGCT TCACCTTCGA CGCCCGGGCC
1141 GACGGCTACG TGCGCGGCGA GGGCGGCGCG GTGGTGGTGC TCAAGCCGCT GTCCCGGGCG
1201 CTGGCCGACG GCGACGTCGT GCACGGCGTG ATCCGCGGCA GCGCGATGAA CAACGACGGG
1261 GGCGGCGACG CGCTGACCGC GCCGGACCCC CGGGCCCAGG CGGAGGTGAT CCGGCTGGCC
1321 CGGCGGCGGG CCGGGGTCGC CGCGTCCGCC GTCCAATACG TCGAACTGCA CGGCACGGGC
1381 ACCCCCGTCG GCGACCCGAT CGAAGCCGCC GCACTCGGTG CGGCGCTCGG CACCGAGCGG
1441 GCGAACCGGC CGCCGCTGGC CGTCGGTTCG GTCAAGACCA ACGTCGGGCA CCTGGAGGGT
1501 GCGGCCGGCA TCGTCGGCCT GGTCAAGACG GTGTTGGCGA TCCGACACCG GCGGCTCCCG
1561 GCAAGCCTGA ACTTCGCCGA ACCCCATCCG CGAATCCCGT TGGGCGAACT GGGCCTGCGG
1621 GTGCAGACGG CGGAGGGTGA CTGGCCCTGC CCGGACGAAA CCCTGATCGC CGGGGTGAGT
1681 TCGTTCGGGA TGGGTGGGAC CAACTGCCAT GTGGTGCTCG CGGAGGCGGA GCCCGCGGAT
1741 GGGGTGGGGC CGTCGGTCGC GTCGGCGCCC TCGGGTGGGT CGGATCCGGG CATGGAGTCC
1801 GCCACCGGCC CGGTGCCTTC GGACGCGGTT GCCGTGCCGA TCTCCGGTGT CGACGCCGAC
1861 GGGCTTCGGG CCCAGGCCGG GCGGTGGCAC GGCCATGTAC GCGAACATCC CGACGTGGCG
1921 CCGGCCGACC TCGGCTACTC GGCCGCCACC ACCCGGACCG CGTTTGCCGC CCGCGCCGTC
1981 GTCCTCGCTC GCGACCACGC CGAACTCCTC GCCGGGCTCG ACGCGTTACG CGGAGCCGGC
2041 GCGGATCCAC ACCTGGTCCG AGCCGACGCG CAACCCGGCC GCACCGCCTT CCTGTTCACC
2101 GGACAGGGCA GCCAACGCCC GGCCATGGCG CAAGAGTCGT ACGCCCGCCA CGCCGTCTTC
2161 GCGGCGGCCT TCGACGCCGC CTGCGCCCAC CTGGACCCAC ACCTGCCGCG CCCGCTGCGC
2221 GAGGTGTTGT TCGCGTCGCC CGACAGCCCG GACGCGGCGC TCGTGCACCG CACCGAGTAC
2281 ACCCAACCCG CGCTGTTCGC CGTCGAGGTC GCGCTGTACC GGCTGTTCGA GCACTGGGGA
2341 GTGACCCCGG ACCTGCTGCT CGGCCACTCG ATCGGCGAGC TGTGCGCCGC GCATGTGGCC
2401 GGCGTCTGGT CCCTGCCCGA CGCGTGTGCG CTGGTCGCGG CCCGGGGTCG GCTGATGCAG
2461 GAACTGCCGG ACGGCGGGGC GATGGTGTCG CTGCGGGTCG CCGAGGACGA CGTGCTCGCC
2521 TCGCTCGAAC CGGTCCGCGA CCGGGTCTCG ATCGCGGGCG TCAACGGGCC GCTGGCCACG
2581 GTGATATCGG GCGACCGGGA CGCGGTCCTG GACGTCGCGG CCGGCTGGCG GGCACAGGGC
2641 CACAAGACCA CCCGACTGCG GGTCGCACAC GCCTTCCACT CACCGCGCAT GGACGCGATG
2701 ACGGACGCCT TCGCCGAGGT GGCCGCCGGG TTGACCGCTC GGGCACCCAC CCTGCCCGTC
2761 GTGTCGAACC TGACCGGCCT GCCGCTGACC GCCGAACAGG CCTGCTCCCC GGACTACTGG
2821 GTCCGCCATG TACGGCACAC CGTGCGCTTC CACGACGGAG TGCGCCGGCT GCGCGCGGAA
2881 GGCGCGACGA TACTGCTCGA ACTGGGCCCG GACGGCAGCC TGTCGGCGGC GGCCCGGACC
2941 TGCCTGCTCG ACGGCGAGCG GGACACCGTG CCACGATCC CGACGCTGCG CCGCAACCGC
3001 CCCGAGACGG ACGCGTTGAC CACGGCGGTG GCCCGCCTGT ACGCCAACGG CGTGGACCCG
3061 GACTGGGAGC GGGTGTTCGC GGGGCGCGGG GCGCGCCGGG TCGCGTTGCC CACGTACGCC
3121 TTCCGACGCG CACGCCACTG GCCGGGTGCC TCGGCGGAAG CCGCCGACAC CGCCGTGCCG
3181 GACGAATCGC TCGCCGTGGT ACCGACGTTG GCCGAGCGGT TGGCCGCCCT GTCCGCTGTC
3241 GAGCAGCATC GGATCCTGCT CGACCTGATC CGGGCACACG CGACCGCGGT CCTGGGCCCC
3301 GGCGCGACCA CGACCGTCGA ACCCGACCGC ACCTACCGCG AATCGGGCCT GGACTCGCTC
3361 GGCACCGTCG AACTGATCAC CAGGCTGGCC CGGGACACCG GCCTCGACCT GCCCCCGACC
3421 ACGGTCTTCG ACCACCCCAC ACCCACCGCG CTCGCCCACC ACCTGCGCAC CCGGGCGCTC
3481 GACCTGCCCG TGCCGACCCG CCCCGGACCG ACACCCGGGC CGGCCCGGCG CGACGAACCG
3541 ATCGCCATCG TGGCAATGGG CTGCCGGTTG CCCGGCGCGG TGCGCACCCC CGAGGACCTG
3601 TGGCGGCTGG TCGCGGACGG CGTGGACGCG ATCACGGCCT TCCCCACCGA CCGCGGCTGG
```

FIGURE 5 (Continued)

```
3661 GACCTGGACC GGCTCCACCA CGACGACCCG GACCGACCCG GCACCAGCTA TGTACGATCC
3721 GGCGGATTCC TGGACCGCGC GGGCGACTTC GACGCGGAGT TCTTCGGGAT CGGCCCGCGC
3781 GAGGCGCTGG CCATGGACCC GCAGCAACGG CTGCTCCTGG AGACCTCCTG GGAGGCGATC
3841 GAACGCGCCG GACTCGACCC GAGCACGCTG CGCGGCGAGC GGGTGGGGGT GTTCGTCGGC
3901 GCCACCGCGC AGGAATACGG CCCGCGCATG CACGAATCCA CCGACGCCCT CGCCGGGTTC
3961 CTGCTGACCG GCACCACGCC CAGCGTCGCG TCCGGGCGGA TCGCATACAC CCTCGGCCTG
4021 TCGGGCCCGG CGCTCACCGT CGACACCGCC TGCTCGTCCT CGCTGGTCGC GGTGCACCTG
4081 GCCGCCCGTT CGCTGGCGAG CGGGGAATGT GCGCTGGCCC TGGCGGGCGG CGCCACCGTG
4141 ATGGCCGGTC CCGGCATGTT CGTCGAGTTC GCCCGGCAGC GCGGCTTGGC CCCCGACGGT
4201 CGTTGCAAGC CGTTCTCGGC GGACGCCGAC GGCACGGCCT GGGCCGAGGG CGTCGGCGTG
4261 CTCCTGCTGG AACGCCTGTC CGACGCGCGC CGCAACGGCC ATCCCGTACT CGCCGTGCTG
4321 CGCGGCTCGG CGATCAACCA GGACGGGGCC AGCAACGGGC TCAGCGCGCC CAACGGGACC
4381 GCCCAGCAGC GGGTGATCCG GGACGCGCTG GCCGCCGCCG GGCTCGATCC GCAAGACGTC
4441 GACCTGGTCG AGGCACACGG CACCGGGACA CCGCTGGGCG ACCCGATCGA GGCGCAGGCG
4501 CTGCTGGCGA CGTACGGGCG CGATCGGGCC GCCGATCGGC CGCTGCTGCT CGGCTCGGTG
4561 AAGTCCAACA TCGGCCACAC CCAGGCCGCG GCGGGTGTGG CCGGGCTGAT CAAGACCGTG
4621 CTGGCCCTGC GACACGGCGC GATACCGGGG ACGCTGCACC TGCGCGAACC GTCGCCCCAC
4681 GTGCGGTGGT CGGACGGGGC GATCACGCTG CCGACGACGA CCACGGACTG GCCCGCGTAC
4741 GACCGTCCGC GCCGCGCGGC GGTGTCGTCG TTCGGGATCA GCGGGACGAA CGCGCACGTG
4801 ATCGTGGAGG AGGCGGGCGG GGGCGCGGAG ATACCGGGGC CTGCCCCTGC CCGCGGGCTT
4861 GCGTCCGCCG GTGTCGCCGA CCCCGTGCCG CTGGTGGTTT CCGCGCGGAG CGAGGCCGCG
4921 TTGCGGGGGC AGGCGGAGCA GCTTGCGGGA CTGCTGCGAG CGGCGGACGC TCCGGCCCTG
4981 GCCGATGTCG GATATTCGCT GCTGCGCGGC CGGGCCGGGT TCGAGTACAC CGCCGTGATA
5041 CCGGCGCGCA CCCACGCCGA GGCGCTGCAC GGGTTGACCG CGCTCGCCGC CGATCGACCC
5101 GCCGACCGGC TGATCCGGGG CGGCGCCGCG GCGGCCCGGG GCGGGACCGT GTTCGTCTTC
5161 CCCGGGCAGG GCACCCAGTG GTCCGGGATG GCGCTGGAAC TCCTTGACAC CAGCGAGCCG
5221 TTCGCCGGCT CCATGCGGGC CTGCACCGAC GCGCTCGACC CGTACGCCGT CGACTGGTCG
5281 CTGCTCGACG TGCTCCGCGA ACCCGGGACG CCGGGGTTGA CGCGCGTCGA TGTCGTGCAG
5341 CCGGCGCTGT TCGCGGTGAT GGTCTCGCTG GCCGCGCTGT GGCGCTCGAT CGGGATCGAA
5401 CCGCAGGCCG TGGTCGGCCA CTCGCAGGGC GAGATCGCCG CCGCGTACGT CGCGGGCGCA
5461 CTGTCCCTGG CCGACGCCGC CAAGGTGGTC GCCCTGCGCA GCGGGCACT GGTCGCGGCG
5521 GCGGGCAGCG GCGGGATGGC CTCCGTGTCG CTGCCCGCCG AACAGGTCGC CGCGCTGCTC
5581 GAACCCTGGG CCGGCCGACT CGGCGTGGCC GCCGTCAACG GGCCGAGCGC CACCGTGGTC
5641 AGCGGCGACA CCGCGGCACT GGACACGTTC CTGGACCGAT GCGCGGCGGA CGACCTGCGG
5701 GCCCGGCGGA TCCCCGTCGA CTACGCGTCG CACTCCGTGC ACATGGAGGA GATCCGCGAT
5761 CGACTCCTGA CCGACCTGGC CGACGTGACC CCGCGAGCCG CGTCGACAGC CTTCTACTCC
5821 ACCCTGACCG GCGGTCGCAT GGCCGACACG AGCGGCCTCG ACGCCGACTA CTGGTACCGC
5881 AACCTGCGTC GAACGGTGCG ATACGAGACG GCCGTTCGGG CATTGAGCGA GGACGGTCAC
5941 CGGCTGTTCG TCGAGGTCGG CCCGCACCCC GTGCTCACGC TCGGTACCCA GGAAACGTTG
6001 GACGCGTGCG GCAGCGGCGG CACCACGATC GGCACGCTGA GCCGCGACGA CGGCGGCCGG
6061 GCCCGCTTTC TGGTTGCGGT GGCGGAGGCC GTCGCGCACG GCGCCCGGCC CGACGCCGAA
6121 GCGCTGTTCG ACCCGCCCGG AACCGGAGTG CGGGCGGTTG CCCTGCCCAC CTACGCGTTC
6181 CAACACCGCC GCTACTGGCT GACCCCGCGT GAGGCGGCTC CCGAGGGTAC GGCTGCCCTC
6241 GGTCTGACGC CGATCTCCCA TCCGCTGCTC GGCGCGCTTG GCGCGCTCGG CGTCGAGCCG
6301 GATGGCACGG TGATCGCGAC CGGTCGGATC TCGCTGCGGG AGTTGCCGTG GCTGGCGGAC
6361 CACGCGGTCG CGGACACCGT GGTGTTGCCG GGACCGCGT TTCTCGAACT GGCCCTGTGC
6421 GTCGGGGAGT CCGTGGGTGC TCCGCAGGTC GAGGAACTGA CCCTGGAGAG CCCGCTGCTC
6481 TTGCCCGAGA CCGGTGACGT GTACCTGCGG GTTGCCGTGG CCCCGGCGGA CGAGGCGCGG
6541 CGACGGGCGG TCACCATCCA CTCCCGGCGT GCGGGTGGGG GCGGTGCCGA TGCGGAGCGG
6601 GAGTCGTGGG TTCGGCATGC GGGCGGGCTG CTCGTTGATT CGGTGCGGGA GGTGGACGAC
6661 GGCGGCAGTG GTGGGCTCAC CCAGTGGCCC CGCCCGGTG CCGATGTGCT CGATCTCGCC
6721 GATGCCTACC CGGTGTTGGC GGGGCTCGGT TACGGCTACG GCCGGCCTT TCGGGGACTG
6781 CGTGCGGCTT GGCGCGGGGC CGGCGGCGAA CTCTTCGCCG AGGTGCGGCT GCCGGATGAA
6841 CTGCGGGAAT CGGAGTCGGG GGTGGTGGGG CCCGAGTTCG GGATTCACCC GGCGCTCTTG
6901 GACGCGGCAC TGCATCCGTT GCTTTCGTCG CTTTCGTTGA CTTCGTTGTC GTCGACGCGG
6961 GACGACCGG CGGGTGCGCC GCCGGTATT CCGTTCTCGC TGGCCGACGT GCGGCTGTAC
7021 GCCACCGGGG CCGACATGTT GCGGGTACGG CTGCGCCGGG CGGATGGCGG GGCCGCGGCG
7081 CTCACGGTTG CCGACGGCGT CGGTGCGCCG GTCCTGTCCA TCGGTGCGCT CACCCTGCGC
7141 GAACTGCCTG CGGACGGGCT GATCGCGGCG GAACCCGGGC CGGGCGAGGC GATGTTCGAC
7201 CTGCGCTGGA TCGCCGGATC GATCCCGGCG GAGCCGACGG GTCTCGGGTA TGCGTTCATC
7261 GGGGACGACC TCGGCCTGGG CGACGGCGAG GTGTATCCGA GCCTCGCGGA TCTCGATGCG
7321 CGACTGCTCG CGACGGGGGA ACCCACGCCC GACGTGGTGT TCGCCGCCGC ACCGGTGGGG
```

FIGURE 5 (Continued)

```
 7381 GTGGACGACG ACGTCCCGGG CGCCGCGCAC GACAGCGCGC GCTGGGCGTT GGACCTGGTC
 7441 GGGGGTTGGC TTGCCGGCGA GCGGTCGAGT GCGGCGCGGC TGGTCGTGGT CACCCGTGGT
 7501 GCGGTTGCTG CTCGGACCGG TGACGCGCTG TCCGGGCTGC CCGCAGCCCC CGTATGGGGG
 7561 CTGTTGCGGA CCGCGCAGTC CGAACACCCC GATCGTTTCG TGCTGATCGA CCTGGACGAT
 7621 GCGGTGCGAT CCCCTTCCGC GCTGCTTGGC GCGGCCGTTG CGGGTGAACC TCAACTCGCC
 7681 CTGCGTGACG GGGTGGTTCA TCTACCCCGC ATGGTGGCGG TGGATTCGGC GGACGCGCAG
 7741 GTGACTCGAC GCCGACCCGA TCCGAACGGG ACCGCGCTGA TCACCGGTGG CACCGGCACC
 7801 CTGGGTGCGC TGATCGCCCG CCGGCTGGCC GCCGAACACG GCATCCGGCA CCTGCTCCTG
 7861 CTCGGACGTG CGGGTCGGGA GGCCCCCGGC GCCGAGGAGT TGATCGCCGA ACTCGGCGCG
 7921 CTCGGCGCCC GGGTGACCGT GGCCGCGTGC GACGTCGCCG ACCGGGCCGC GCTCCGCCGC
 7981 GTGATCGAGG ACATCCCCGC CGAGCACCCG CCCACGATCG TCGTACACGC CGCCGGTGTG
 8041 CTCGACGACG CGACGCTGTT GTCGTTGACC CCGGATCGGC TCGACGCGGT GCTGCGCCCC
 8101 AAGGTGGACG CGGCCTGGCA TCTGCACGAG CTGACCCGAG CGGCGAACCC GGCGGCGTTC
 8161 GTGCTGTTTT CGTCCATCAC CGCGATCACG GGCAACGCCG GCCAGGGCGC GTACACGGCG
 8221 GCCAACACCT TCCTGGACGC CCTCGCCGAA CACCGCCGCG CAGCCGGGCT GCCCGCCAAC
 8281 GCCCTGGCCT GGGGACTGTG GGCCGAGGGC AGCGGGATGA CCCGACACCT CGACCACACC
 8341 GACCGGGCCG GGATGTCCCG GGGCGGGATC GCGGCGCTGC CCACCGAGAC CGGACTCGCG
 8401 CTGTTCGACG CCGCGTTGCA CCGGGACCGC CCGTACACGA TCCCCGCCCG CCTGGACCGC
 8461 GGCGCGCTGC GGGCCCTGGC CGCGAGCGGT GTGCTGCCCG CCGTACTGCG CAGCCTCGTG
 8521 CGTGTCCCGC CGCCGCGTGC CGCCGCCTCC GGCGACGGCA CGGACGCGTC GTCGTGGCCC
 8581 CGGCGGATCC GGGAACTCCC GGGCGAGCAG CGGGAACGGG CGATCACCGA CCTGGTGCGC
 8641 GGGCAACTCG CCGCCGTCCT CGGACACGAC GCACCCGAAC GACTCGACCT CGACCGCGCC
 8701 TTCCGCGAAC TGGGAGTCGA CTCGCTGACC GCACTCGAAC TGCGCAACCG GATCAATGCG
 8761 TTCACCGGCC TGCGACTGCC CGCGACGGTG GTCTTCGACC ACCCCAGCGG TACGGCCCTG
 8821 GTCGCTCGGA TGATGCGCGA GCTGGTCGGT GCGGTGCCGA GCGAGCCGAC CACGCCCGTC
 8881 GTCGCACCGA CCGTGACGGT CGACGAGCCG ATCGCCGTCG TCGGCATCGG CTGTCGCTAT
 8941 CCGGGCGGTG TGGCCGGTCC CGAGGACCTG TGGCGACTGG TCGCGGCCGG CACGGACGCG
 9001 GTCGGCGACT TCCCCGAGGA TCGTGGCTGG GACCTGGCGA AGCTGTACGA CCCCGACCCG
 9061 GACAAGGTCG GCAAGGTCTA CACCCGTCGG GGCGGATTCC TCTACGAGTC GGGGGAGTTC
 9121 GACGCCGAGT TCTTCGGCAT CTCGCCGCGC GAGGCGGCGG CGATGGACCC GCAGCAGCGG
 9181 CTGCTCCTGG AGACCGCGTG GGAGGCGTTC GAGCACGCGG GCCTGGACCC CAGGACGCTG
 9241 CGCGGGAGCA ACACGGGTGT GTTCGCCGGG GTGATGTACA CGACTACGC CTCGCGGCTG
 9301 CACCGCGCCC CCGACGGGTT CGAGGGCATG CTGTTGGCCG GCAACGTGGG CAGCGTCGTG
 9361 ACCGGCAGAG TGTCCTACGC GCTGGGCCTG GAGGGGCCGG CGGTCAGCGT GGACACCGCC
 9421 TGCTCGTCGT CGCTGGTGGC GCTGCACCTG GCGGCCAACG CGCTGCGGTC GGGGGAGTGC
 9481 GATCTGGCGC TCGCCGGTGG GGTGACGGTG ATGTCCACCC CGAACGTCTT CGTCGAGTTC
 9541 TCCCGACAGC GCGGCCTGTC GGCGGACGGC CGGTGCCGGT CGTTCGCGGC GGGCGCGGAC
 9601 GGGACGGGTT GGGGCGAGGG TGTCGGGCTG CTGGTGGTGG AACGACTGTC CGACGCGCGG
 9661 CGCAACGGGC ATCCCGTGCT GGCGCTGCTG CGTGGCTCGG CGGTCAACCA GGACGGCGCC
 9721 TCGAACGGGC TGACCGCGCC GAACGGACCG TCCCAGGAGC GGGTGATCCG GGCGGCGTTG
 9781 GCCGGTGCGG GGTTGTCGGC GACGGACGTG GACGCGGTGG AGGCGCACGG CACCGGGACG
 9841 ACGCTGGGCG ACCCGATCGA GGCGCAGGCG TTGTTGGCCA CGTACGGGCG GGACCGGCCG
 9901 GCGGATCGGC CGCTGTGGCT GGGCTCGATC AAATCGAACA TCGGGCACAC GCAGGCCGCG
 9961 GCGGGGGCGG CCGGCCTGAT CAAGATGATC ATGGCGATGC GGCACGGCGT ACTGCCCGAG
10021 ACACTGCACG TCGACGCGCC GTCGCCGCAC GTGGACTGGT CGACGGGACA CGTCGAGCTG
10081 CTGGCCGAAC GTCGACCGTG GCCCGAGGTC GACCGGGCGC GCCGGGCCGC CGTGTCGTCG
10141 TTCGGGATCA GCGGGACGAA CGCGCACGTG ATCGTCGAAC AGGCGCCGGC GGCCGAGGCG
10201 GTGGTGTCCC GGGACGAGCC GGTGGGTGTG GCGGGCCTGG TGCCGTGGGT GTTGTCGGCC
10261 AGGACCGCCG ACGTCTGCG GCGCAGGCG GCGCGGTTGC GGGAGTGGTC GGCGCGGCAT
10321 CCGGAGGCGG ATCCGGTCGA CGTGGGGTGG TCGTTGGTTC GGGAGCGGTC GGTTTTCGAT
10381 CGGCGGGCGG TGGTCGGTGG CCGCGATCCG GGTGAACTCG GGCTGGGTT GGACAGGTTG
10441 GCCGCGGGTG GCGGTATTGC CGACGGTCGG CCGATGTTTT CGGGTCCCGG TCCGGTGTTC
10501 GTGTTTCCCG GGCAGGGGTC GCAGTGGGTG GGGATGGCCG CCGGGCTGTT GGAGTGCTCG
10561 CCGGTATTTG CGGAGGCGGT GACGGAGTGC GCCGCCGTGA TGGATCCGTT GGTGGCGGAT
10621 TGGTCGTTGT TGGATGTGTT GCGGGGTGGG TCTGCCGGTG AGTTGGAGCG GGTGGATGTT
10681 GTTCAGCCGG TGCTGTTTGC GGTGATGGTG GGGCTTGCGC GGTGGTGGGA GTCGTGTGGG
10741 GTCAAGCCGG GTGCGGTCAT CGGGCACTCG CAGGGGGAGA TCGCTGCCGC GCATGTGGCG
10801 GGTTATCTGT CGCTGGCGGA TGCGGTATGG GTGGTCGTGT GCGGAGTCG GCCCTGCTG
10861 GGGGTCGCGT CCGCCGGGGG CGGGATGGTG TCCGTCGGGG TGTCGGCGGA GCGTGCTCGC
10921 GAGCTGGTCG CCGGGGATGA CCGGCTGTCG TTGGCGGCGG TGAACGGGCC GACGAGTGTG
10981 GTGCTTTCGG GTGATGTCGA AGCGCTGTCG GTGGTTGTCG AGGCGTGCGA GCGGGATGGT
11041 GTGCGGGCTC GGTGGATTCC GGTGGATTAC GCGTCGCATT CGGCGCGGAT GGAGGCCGTG
```

FIGURE 5 (Continued)

```
11101 CGGGACGAGG TGGAGCGGCT GTTGGCGGAT GTGACGCCGC AGGTGGGCCG CGTGCCGATG
11161 TACTCGACCG TGAGCGGGGA GGTGGTCGTC GATCCCGCCG AGTTGGGCGG GGCGTACTGG
11221 TTCGAGAATC TGCGGCGCAC GGTCGAGCTT GAGCGGGCCG TGGGTGCGGC GGTCGCGGAT
11281 GGGCATGGTG CGTTTGTGGA GTGCAGCCCG CATCCGGGGC TGGTGGTGCC GATGGGGGAC
11341 ACCCTGGAGG CGGCCGGGGT GGACGGCGTC GTTCTGGAGA CGTTGCGGCG GGGTGAGGGT
11401 GGGCCCGATC GGCTGGTCGC CGCGCTCTCG GCGGCGTTCG TGGCGGGTGT CGCGGTGGAC
11461 TGGGCCGGAA TGTTGCCGGG GCGCCATGTC GAGCTGCCGA CGTATGCGTT CCAGCGGCGG
11521 CGCTACTGGT TGACGGGTGG GGAACGTGCG GGCGATCCGG CCGGGTTGGG GCTGGTCGCG
11581 GCCGATCATC CGCTGCTGGG GGCTGTGGTC GGTTCGGTGC GGGACGGGGA ACTCCTCTAC
11641 ACCGGCGGT TGTCCGCCGC GACGCACGGC TGGCTTGCGG ACCACGCGGT GTTCGGCTCG
11701 GTGGTGGTAC CGGGGACGGC CTTCGTCGAG CTGGCGTCGT GGGTCGGTGT CGAGGCCGGT
11761 TGCCCGGTCG TCGACGAACT CACGCTGCAT GCGCCCTGG TGCTGCCGGA CGGGGTCGGC
11821 ATCCGGCTTC GGGTGGCGGT GGGCGCGGCG GATTCGGCGG GGCGTCGGGT GGTGGAGTTC
11881 CATTCGCGGC CCGAGGATGC CCCCGACGAG CAGTCGTGGA CTCGGCATGC GACCGGCACG
11941 CTGGGTGCCG CGAGTGTGCC CGGATCCGCG TCGGCCGGGG CCGCGGCGTG GGCGGTCTGG
12001 CCGCCGGCGG ACGCCGAGGT GGTCGACCCG GAGGCCGTTT ACGAGCGACT TGCGGAGCAC
12061 GGGTACGAAT ACGGGCCGAT TTTCCGGGGG TTGCGGGCCG CATGGCGGCG GGGTGACGAC
12121 TTCTTCGCCG AGGTCGCGCT GCCGGAGGCG GCCGGTCGGG ACGCGCACGG CTACGACCTG
12181 CATCCGGCGG TGCTGGACGC CGCGCTGCAT GTGGCCGCGG CCGAGGCGGT GGCGGAGTCG
12241 GGGGCGACGT TGTTGCCGTT CGCCTGGACC GGGGTCGCAC TGCATGGGCC GGGGGCGTCG
12301 GTGCTTCGGG TGATGTTGCG GCGTACCGGG CGGGAGACGC TGGCGGTCGA CGTGGCCGAC
12361 GAGCGTGGTG TTCCGGTGGC GTCGGTCGCG TCGCTGACGC TGCGGCCGGT GGCTGCCGAG
12421 CAGTTGGTGG CGGCCGAGGA AGCGGGCCGC GAGTGGCTTT ACCGGATGGT CTGGGAGATC
12481 GCGGACGCGC CGGTGGCGGA GCACGTCGAG GGTGAACTTC TTGGTTCGGA TGAGGAGTCC
12541 GACGCGTCGG CGGAGCTTGT GGCGGGCGGG ATTCGGTGG TGACCCCTGC GGGCGCCGAA
12601 CAGGTCTCCG AGGTGGGGCT GTTCGATTGC CCGCCCGTGG TCGGCGAAGC CCCCGAGGAG
12661 GTGGCCGGCG CCGTGCATGC GGTGCTGGCC GCGGTTCGGG CGTGGGTGGC GGACGAGCGG
12721 TTTGCCGGGG CGCGGCTGGT GGTTCGTACC CGTGGCGCGG TTGCCACGGA TGCGCAGGAC
12781 CGGGTCGGTT CTCCCGCGCA TGCGGCGATC TGGGGTCTCG TGCGGGTCGC GCAGAGCGAG
12841 CATCCGGGGC GCTTCGTCCT GGTCGATGGG GACGACGTCG ATTCGGGTGC GGCGCTGCGT
12901 GCGGCGGTGG CGTGCGGGCT GCCGCAGGTG GCGATTCGCG AAGGTGTGGT GCTGGCGCCG
12961 CGCCTGGTGG GGGCGGTGCA CGACACGGCG CTGGTGCCGC CGGCGCCGGG TGCGGATCAG
13021 GCGTGGCGGA TCGAGTCCGG GACGGCCGGG ACGCCGGACG ATCGGTGGT GACGGCGCAT
13081 CCGGCCGCCT CGGCGCCGTT GGCGGCCGGG CAGGTGCGGG TGGCGGTGCG GGCGGCCGGG
13141 GTGAACTTCC GCGATGTGCT GATCACGCTC GGCATGTACC CGGGGCGGGC GGTGGTCGGC
13201 GCCGAGGCGG CCGGGGTGGT CGTGGAGGTC GGCCCGGGCG TGTCGGAACC GGCCGTCGGC
13261 GACCGGGTGA TGGGCTTGTT CGAGGGGGCG TTCGGGCCGC TTGCGGTGGC CGATCGGCGG
13321 CTGTTGGCCC GGGTGCCGGC GGGTTGGTCG TTTGCTCAGG CGGCGTCGGT GCCGGTGGTC
13381 TTCCTCACCG CGCTCTACGG GCTGCACGAT CTGGCCGGGC TGCGGTCGGG TGAATCGGTG
13441 CTGGTGCATG CGGCCACGGG TGGGGTCGGC ATGGCCGCCA CCCAGCTGGC CCGGCATCGG
13501 GGCGCCGAGG TGTACGCGAC CGCGAGTGCG ACGAAGTGGG CCACCGTGCG CGGGCTGGGT
13561 GTTCCGGACG AACGGATCGC CTCGTCTCGG GACCTGTCCT TCAACAGCG CTTCGCACGG
13621 GCCACGGACG GGCGCGGGAT CGACGTGGTG TTGAACTCGC TGGCCGGGCGA GTTCACCGAC
13681 GCGTCGTTGC GACTCCTGGC CGAGGGTGGC CGGTTCGTGG AGATGGGCAA GACGGACGTC
13741 CGGACCGAGG GGCTGCCGGC CGGGGTGCGC TATCGGGCCT TCGACCTGAT CGAGGCCGGT
13801 CCGGATCGGA TCGCCAGAGAT GTTCGCCGAA CTGGTCGACC TCTTCGAGCG CGGTGTGCTG
13861 CAACCCCTGC CGATTCGGAC CTGGGACATC CGTCGGGCCC GCGAGGCGCT GCGTTTCCTG
13921 GGCCAGGCCC GGCATGTGGG CAAGGTGGTG CTGACCGTGC CGCAGCCGCT CGCGGCCGAC
13981 GGCACGGTCC TGATCACCGG CGGCACGGGC ACGCTGGGTC GCAGTCTGGC CCGACACCTG
14041 GTCACGCGGT GGGGTGTGCG CCGGCTGGTG CTGACCGGCC GGGCCGGGCC CGCCGCTCCC
14101 GGCGCCGCCG AACTGGTCGC GGAATTGGCC GAGTCGGGTG CCGACACCAC GATCGTGGCC
14161 TGCGATGCGG CGGACCGGGC GGCGATGGCC GAGGTGTTGG CCGCGATCCC GGCCGAACAC
14221 CCGTTGACCG CCGTGGTGCA TGCCGCCGGA ACACTCGACG ACGCGCCGAT CGAGGCGCTG
14281 ACCCCGGAGC GGGTCGACCA CGTGTTGCGG CCCAAGGTGG ACGCCGCCCT CGTACTGGAC
14341 GAACTCACCC GGGACGCGGA CCTGGCCGCG TTCGTGCTGT TCTCGTCGGT GGCCGGCGTA
14401 CTCGGTGTGG CCGGCCAGGG CGGCTATGCA GCGGGGAACG CGTTCCTGGA CGGTCTCGCC
14461 GGTCGGCGCC GCGAGCGGGG GCTGCCCGCG ACCGCTCTGG CCTGGGGCCT GTGGGCGGAA
14521 CGCAGCGCAA TGACCGCGCA GTTGGGCGTC GGCGACCTGA AGCGCCTGGC GCGCGGCGGC
14581 CTGGTGCCGA TCTCGACCGC CCAGGGGCTC GCCCTGTTCG ACGCCGCCTG GCAGGCCGAC
14641 GAGGCGGCGC TGATCCCGGC CCGCCTGGAC CTTGCCGCAC TGCGCGCACA GGCGGCGACC
14701 CAGCCGGTAC ATCCGCTGCT GCGCGGTCTG GTCGGCACCA CCCCGACCCG CCGGAACGGC
14761 ACACCTTCGG AGGCGCCGTG GGCCCGACGG CTCGCCTCGG CCGCGCCCGC CGAGCGGGTG
```

FIGURE 5 (Continued)

```
14821 GACGTGGCAT TGCGGCTGGT CCGGGCCGAG GCGGCGGTGG TCCTGGGGCA CGAGTCGATC
14881 GACGGGGTGC GGCCCGAAGT CACCTTCCGC GACCTCGGGT TCGACTCACT GACGGGTGTG
14941 GAACTGCGCA ACCGGCTGAG CGGCGCCACC GGATTGCGGC TGCCGTCCAC GCTGGTCTTC
15001 GACTTCCCGA CCCCGCTCGG CCTGGCCGGT TTCCTGGTCG CCGAGTCGGT CGGCGAGATG
15061 GACACGGCGC CGACCGGGCC GGTTGCCGGG GGTGCGGTGG TCGCGGCCGA TCCGGTGGTG
15121 ATCGTCGGGA TGGGCTGCCG ATTCCCGGGC GGGGTGGACT CGGCGGCGGG TCTGTGGGAC
15181 CTGGTGGCCG CGGGCGGCGA TGCGATCGGG CCGTTCCCGA CCGACCGTGG CTGGGACGTC
15241 GACGCGCTGT TCGATCCCGA TCCGGAGCGG GTCGGCAAGA GCTACGTCCG TACCGGCGGA
15301 TTCCTCTCCG GGGCGGCCGA GTTCGACGCC GAGTTCTTCG GTGTGTCGCC GCGCGAGGCG
15361 TTGGCGATGG ACCCGCAGCA GCGGCTGCTG CTGGAAACCG CGTGGGAGAC CTTCGAGCAG
15421 GCGGGCATCG ATCCCACCTC GCTCCGGGGC AGCCGGACCG GCGTCTTCGC CGGGATGGCC
15481 GGCCACGACT ACGCGACCGG GGGCGCCCGT TCGCAGGCCG GCTGGAGGG CCACCTGCTG
15541 ACCGGGAACG CGGCCAGCGT GGCCTCGGGA CGGGTGGCCT ACACGTTCGG CCTGGAGGGG
15601 CCGGCGGTGA CCGTGGACAC GGCGTGCTCG TCGTCGCTGG TGGCGCTGCA CCTGGCGGCC
15661 AACGCGCTGC GGGCGGGGGA ATGCGACCTG GCGCTCGCCG GCGGGGTGAC CGCGATGTCC
15721 ACGCCGGACT TCTTCCTGGA GTTCTCCCGG CAGCGCGGAC TGTCCGTGGA CGGCCGTTGC
15781 AAGGCGTTCG CGGCCACGGC GGACGGGATG GGCGCGGCCG AGGGCGTGGG CCTGCTCCTG
15841 GTCGAGCGGC TGTCGGATGC GCGGCGCAAC GGGCATTCGG TACTGGCGGT GGTGCGTGGG
15901 TCGGCGGTGA ACCAGGACGG CGCGTCGAAT GGGTTGACCG CGCCGAACGG GCCGTCGCAG
15961 CAGCGGGTGA TCCGGGCGGC CCTGGCCGAC GCCGGGCTGT CCGCGGCCGA TGTGGATGCG
16021 GTGGAGGCGC ACGGGACCGG CACGACGCTC GGCGATCCGA TCGAGGCGCA GGCGTTGCTC
16081 GCGACCTACG GCGGGATCG GCGCCGGAT CGGCCGCTGT GGTTGGGGTC GGTGAAGTCC
16141 AACATCGGGC ACACCCAGGC GGCGGCGGGT GTGGCCGGGG TGATCAAGAT GGTCTCGGCG
16201 CTGCGGCATG GGATGTTGCC GCGCACGCTG CACGTGGACG AGCCGACGCC GCATGTGGAC
16261 TGGTCGGCGG GTGGGGTCGA ACTGCTCACG AGCGCGCGGG CGTGGCCGGA GGCCGGGCGG
16321 GTGCGTCGGG CGGGGGTGTC GTCGTTCGGG ATCAGCGGGA CGAACGCGCA TGTGATCCTG
16381 GAGCAGGCGG AGGAGAGCCC GGCGGGTTCG GTGCCTTCGG CGACTCCTCC GGTGGCCGGG
16441 ACTCCGGTGT GGGGCGGTCG GGTGCCCTGG GTGTTGTCGG CCCGGTCCGA ACCCGCTTTG
16501 CGGGCACAGG CCGCGCGGTT GCGGGACTGG CTGGCCGTAC ATCCCGACGC CGATCCGCTC
16561 GATGTGGGGC GGTCGTTGGC GACCGGGCGG GCGGCGCTCG ATCACCGGGC GGTGGTGCAT
16621 GGGCGGGACC TCGCGGAATT GCGCCTGGCG GTCGCGAAGT TGGCCGACAG CGGGCCGGGT
16681 GACGAGGCGT CGATCGTCGG CTCGGTCTCC GCCGCCGGTC CGGTTTTCGT GTTTCCGGGG
16741 CAGGGGTCGC AGTGGGTGGG GATGGCGGCC GGGTTGTTGG AGTGTTCGCC GGTGTTTGCG
16801 GGTGTGGTTG CCGAGTGTGC TGCGGTGATG GATCCGTTGG TGGCGGATTG GTCGTTGTTG
16861 GATGTGTTGC GGGGTGGGTC TGCCGGTGGT GAGGCGTTGG CGGAGCGGGT GGATGTGGTT
16921 CAGCCGGCGT TGTTCGTGGT GATGGTGGGG CTTGCGCGGT GGTGGAGTC GTGTGGGGTC
16981 AAGCCGGGTG CGGTGATCGG ACACTCACAG GGGGAGATCG CGGCTGCGCA TGTGGCGGGA
17041 TATCTGTCGC TGGCGGATGC GGTGCGGGTG GTTGTGCTGC GGAGTCGGGC GTTGCTCGGG
17101 GTTGCGTCTT CCGGTGGCGG GATGGTGTCG GTGGGTGTGT CCGCCGATCG GGCCCGGGAG
17161 CTGGTCGCCG AGGACGACCG GTTGTCGCTG GCGGCCGTGA ACGGGCCGAC GAGTGTGGTG
17221 CTTTCGGGTG ATGTCGAAGC GCTGGCCGTG GTTGTCGACG GCTGTGAGCG GGACGGGGTC
17281 CGGGCTCGGT GGATTCCGGT GGATTACGCG TCGCATTCGG CGCGGATGGA GGCCGTGCGG
17341 GACGAGGTGG AGCGGCTGTT GGCGGATGTG ACGCCGCAGG CGGGCCGCGT GCCGATGTAC
17401 TCCACGGTGA GTGGGGGGCA CGTTACCGAC CCGAGTGTGC TCGGTGGTTC GTACTGGTTC
17461 GACAATCTGC GGCGTACGGT CGAGTTGGAG CGGGCCGTCG GAGCGGCGGT TGTCGACGGG
17521 CATTCGGTCT TCGTCGAGTG CAGTCCGCAT CCGGGGCTGG TGGTGCCACT GGGGGACACC
17581 CTGGAGGCGG CCGGGGTGGA TGGCGTCGTT CTGGAGACGC TGCGGCGGGG CGAGGGCGGT
17641 CCCGATCGGC TGGTCGGCGC GCTTTCGGCG GCGTTCCGGA GCGGTCTGGC CGTGGACTGG
17701 GCCGGGTCCG GGATGGTGCC GGGGCGGCGG GTCGAGCTGC CGACCTATGC CTTCCAGCGG
17761 CGGCGGTACT GGGTCGAGCC CGGCGAGAGG GCCGGCGGGG TCGGGTGGGG GCAGTTCACG
17821 GTCGAACATC CGGTGCTGGG CGCCGGGGTC GATCTGGCCG ACGGAGCCGG GACGGTCTTC
17881 ACCGGGCGGC TGTCCGCGGC CTCGCACGGG TGGCTCGCGG AGCATGTGGT GCTCGGCACG
17941 GTGATCGCGC CCGGCACGGC GTTCGTCGAC CTGGCGCTGC GTGCGGGGGC GACGGTCGGC
18001 CGGGCGACGG TCGAGGAACT GACCCTGCAC GCGCCGCTGA TCCTGCCCGA CGCGGGCGGT
18061 GTACGGATTC AGGTCCGGGT CGGCGCACCC GACGCCGCCG GGTCGGATC GGTGGAGATC
18121 CATTCCCGAC CGGAGGACGC GGCCGGCGAC GAGCCATGGA CCCGGCACGC CTCCGGGACC
18181 CTGACCGCGA CCGACCTCGA CCCGGCGGAC GTGGCCACGG AGGCGGCGAT CTGGCCGCCC
18241 GCGGGCAGTA CGCCGGTCGA CTGGACGGA GCCTACGAGC GACTGGCCAC GGCCGGATTC
18301 GAGTACGGTC CCGCCTTCCA GGGGCTGCGA GCCCTGTGGC GGCGCGGCGC CGAGTCGTTC
18361 GCCGAGATCG AACTCGCGGA CGACGCACGG CAGGAGGCCG AACGCTACGA GGTGCATCCC
18421 GCGCTGTTGG ATGCGGCCGT GCATGCGCTG GGGATGGAGC CGACGGCGGA GGTTGCGCCG
18481 GATGAGGCGC GGATTGCCTT CTCCTGGCGA GGGGTTCGGC TGGTTGCCGC CGGAGCGGGG
```

FIGURE 5 (Continued)

```
18541 CGGTTGCGGG TGCGGCTGGC ACCGGTGGGC TCGGACGCGG TGTCGTTGTG GCTGAGCGAC
18601 ATGGACGGTG AGCCGGTCGG GTCGGTCCGG GCCCTGACCG TGCGGCCGGT CGCGGCCGAG
18661 CGGCTGCGTC CGGCTGGGGC GCCGCCGCGC GACTCGATGT TCCGGGTGGA GTGGCGGCCG
18721 GTGTCGGGCG ACGAGTCGGG CGTGGCGGTT CGCTGGGCGG TGGTGGGCGC GGCGGACTCC
18781 GGGCCGCTTG CCCGGCTGGT GGCGGCGTAT CCGGATGTGC CGGTGTACCG CAGTGTGGTC
18841 GAGGCGGCCG GGGATGTGCC GGCGGGACCG CCCGATGTCG TGGTGGTGGG CGTGGGCGAG
18901 GCCGACTGTT CGGAGGGGTC GGTCGAGCGC ACTCGGCGGG TGCTTGCGGA CGTGCTGGCG
18961 TGGATGCAGG ACTGGCTGGC CGACTCCCGC TTCGCGGCGA CGCGCCTGGT CGTGGTGACC
19021 TCCGGGGCCG TCGCCGCCGA CGTGGACGCC GACCCCGACG AGCGGGTGGC GGACCTGGCC
19081 GGCGCGGCGG TGTGGGGGTT GTTGCGCTCG GCCCAGTCCG AACACCCCGA CCGATGCACG
19141 CTGGTCGACC TCGACGAGGA CGCGGCGTCG ATTGACGCCT GGCCGGCGAT TCTTGCCTCC
19201 GCCGAGCCGC AACTCGCCGT CCGGATGGGC CGATTCCGGG TGCCTCGGCT GGCCAGGGTG
19261 ACTGCCGGGG GCGGCGAGCC GGTCGCCTTC GCGCCCGACG GCACGGTGTT GGTCACCGGT
19321 GCCACCGGCG GCCTGGGCGC CCTGGTGGCC CGGCACCTGG TGACCGCGCA CGGCGTGCGC
19381 CGACTTCTGC TGCTGTCCCG CCGGGGCGCG GCCGCACCCG GCGCGGCCGA ACTGGTCGAG
19441 GACCTGACCG CGCAGGGGGC GGAGGTCACC CTCGCCGCCT GCGATCTGGC CGATCGTGCC
19501 GCGCTGGCCG CCGAGTTGGC GCGTATCCCG GCCGAGCACG CGCTGACCGG CGTGATCCAC
19561 ACCGCCGGAG TGGTGGACGA CGCCACCATC GCGAACCTGA CCGATGCGCA CATGGAACAC
19621 GCGCTGCGCC CCAAGGCGGA CGCCGCGTTC CATCTGGACG AGTTGACCCG GACGTGAAC
19681 CCGGCCGCAT TCGTCCTGTT CTCCTCCGGG GCCACCACCT TCGGTGGCCC GGGACAGGGC
19741 AACTACGCGG CGGCCAACGC CTTCCTGGAC GGCCTGGCCC GGCAGCGCCG CGACCGCGGC
19801 CTGCCCGGGA TCTCGCTGGC CTGGGGCCTG TGGGCGGGCG CGCAGGGGAT GGGCGGGCGG
19861 CTGAGCGAGG CCGACCTGGC CCGCTGGGCC CGGACCGGCG CGGTGGCGAT GCCGGCGGCC
19921 GAGGCACTGC GGTTGTTCGA TATCGCGCTG GGCCGGCCCG AGGCGGCCCT GGTGCCGGCA
19981 CACCTGGACC TCCCGGCGAT GCGGGCGGAT GCCGGTGCTC GACCCGCGCT GTTCCGCGAG
20041 TTGCTCGGGA TCGGTACGCG ACGGGCGGCA GTGGGCGCGG GCGGGTCGGC GCTGACCCGG
20101 CGGCTGGCGG GGATGTCTCC GGCCGAGCGG GAGCAGGCGG TCCTGGACGT GGTGCGGACC
20161 GAGGCCGCGA ACACGCTGGG ACACGAGTCG GCCGGGCCGG TGTCGCCGG GCGAGCGTTC
20221 AAGGAGCTGG GGTTCGACTC GCTGACCGGG GTGGAACTGC GCAACCGGTT GAACACCGG
20281 ACCGGGCTGC GGTTGCCGTC CACGCTGGTC TTCGACTACC CGACGCCGGC GGGGCTGGCG
20341 GCGTTCCTGG TCGCCGAGTT GGTCGGTCGT TCGGTACAGG CGGTGCCGGT GCCGCCGGTC
20401 GGTGGGCGGC ACGGGGACGC CGACGATGCG ATCGTGATCG TCGGCATGGG CTGCCGGTTC
20461 CCGGGCGGGG TGGCCTCGCC GGAGGACCTG TGGAATCTGC TGGCCTCGGG TGGGGACGCG
20521 ATCGGACCGT TCCCGACGGA CCGGGGATGG GACCTGGCCG GCTGTTCGA CCCCGATCCC
20581 GAGCGGGCCG GGAAGAGCTA CGTGGAATCG GCGGATTCC TGTATGGGAT CGGCGAGTTC
20641 GACGCGGAGT TCTTCGGGAT CTCGCCGCGT GAGGCGTTGG CGATGGATCC GCAGCAGCGG
20701 TTGCTCCTGG AGACGGCGTG GGAGACGTTC GAGCGGGCGG GCATCGATCC GACCTCGCTG
20761 CGCGGCAGCC GGACCGGGGT TTTCGCCGGG GTGATCGACA ACGACTACGG CGCCCGGGTG
20821 AACCAGGTGC CGGACGAGGT CGAGGGCTAT CTGGGCTACG GCAGTTCGGC CAGCATCGCG
20881 TCCGGGCGGG TCTCGTACGT CCTGGGCCTG GAGGGCCCGG CGGTCAGTAT CGACACCGCG
20941 TGCTCGTCGT CCCTGGTCGC GCTGCACCTG GCGGTGAACG CGGTGCGGTC GGGCGAATGC
21001 GAACTGGCCC TGGCCGGTGG TGTGACGGCG ATGGCCACCA CCGAGTTCTT CGTGGAGTTC
21061 TCCCGACAGC GGGGCCTGTC GCCGGACGGC CGCTGCAAGG CGTTCGCGGC GGCGGCGGAC
21121 GGGATGGGCG CGGCCGAGGG CATCGGGCTG GTGCTGGTGG AGCGGTTGTC GGATGCGCGG
21181 CGCCATGGGC ATTCGGTACT GGCGGTGGTG CGTGGGTCGG CGGTGAACCA GGACGGCGCG
21241 TCGAATGGGT TGACCGCGCC GAACGGGCCG TCGCAGCAGC GGGTGATCCG GCAGGCGTTG
21301 GGTGCTGCGG GCTTGTCTGC GGCGGATGTG GATGCGGTGG AGGCGCACGG GACCGGGACG
21361 ACGTTGGGTG ATCCGATCGA GGCGCAGGCG TTGTTGGCGA CCTATGGGCA GGATCGGCCG
21421 GGGGATCGGC CGCTGTGGTT GGGGTCGGTG AAGTCGAATA TCGGCACAC GCAGGCGGCT
21481 GCGGGTGTGG CCGGGGTGAT CAAGATGGTG TTGGCGCTGC GGCATGGGGT GTTGCCTCGG
21541 ACGTTGCATG TGGACGAGCC GACGCCGCAT GTGGATTGGT CGGCCGGGCG GGTCGAGGTG
21601 TTGGCGGACG AGGTGGCGTG GCCGGCAGGG GAGCGGGTGC GCCGGGCGGG TGTGTCGTCC
21661 TTCGGAATCA GCGGGACGAA CGTGCACGTG GTCCTGGAGG AGGCGCCGGC GGACGCCGCC
21721 GAGCCTGCGC CCGCCGCGCC GGAGGTCCCG GGCGTCGGCG GCGTGCTGCC CTGGGTGGTG
21781 TCGGCGCGCA CCGAGGCCGG GCTGCGGGCG CAGGCGGCGC GGTTGCGGGA TTGGGTGAGC
21841 GAACATCCGG ACGCGGAACC GACGGATGTC GCACGGTCGT TGGTGGTCGG GCGAGCGGTG
21901 TTGGACGTGC GCGCGGTGGT GCGCGGGCGG GAATCGGCGG AACTTGTCGC CGGCCTGGAC
21961 GAGTTGGCGC GGGCCGGGGT GGGAGACCCC GGCTCGCTGG TGAGCGGCTC GGATCCGGTG
22021 TTCGTGTTTC CGGGGCAGGG GTCGCAGTGG GTGGGGATGG CGGCCGGGTT GTTGGAGTGT
22081 TCGCCGGTGT TTGCGGGTGT GGTTGCCGAG TGTGCTGCGG TGATGGATCC GTTGGTGGCG
22141 GATTGGTCGT TGTTGGATGT GTTGCGGGGT GGGTCTGCCG GTGAGTTGGA GCGGGTGGAT
22201 GTTGTTCAGC CGGTGCTGTT TGCGGTGATG GTGGGGCTTG CGCGGTGGTG GGAGTCGTGT
```

FIGURE 5 (Continued)

```
22261 GGGGTCAAGC CGGGTGCGGT GATCGGGCAC TCGCAGGGGG AGATTGCGGC TGCGCACATC
22321 GCGGGTTATC TGTCGCTGGC GGATGCGGTG CGGGTGGTTG TGCTGCGGAG TCGGGCTCTG
22381 CTGGGGGTTG CGTCTTCCGG TGGCGGGATG GTTTCGGTCG GGTGTCTGC GGAGCGGGCG
22441 CGGGAGTTGG TTGCCGGAGC TGACGGGTTG TCGTTGGCGG CGGTGAACGG GCCGACGAGT
22501 GTGGTGCTTT CGGGTGATGT CGAAGCGCTG TCGGTGGTTG TCGAGGCGTG CGAGCGGGAT
22561 GGTGTGCGGG CTCGGTGGAT TCCGGTGGAT TACGCGTCGC ATTCGGCGCG GATGGAGGCC
22621 GTGCGGGACG AGGTGGAGCG GCTGTTGGCG GATGTGACGC CGCAGGTGGG CTGCGTGCCG
22681 ATGTACTCGA CCCTGACCGG TGCGCCGATC GCCGATCCCG CCGAGTTGGG CGGGGCGTAC
22741 TGGTTCGAAA ACCTGCGGCG CACGGTCGAG TTGGAGCGGG CGGTCGGTGC GGCAGTGGCG
22801 GATGGGCGCA CCGTGTTCGT CGAGTCAGT CCGCATCCGG GGCTGGTGGT GCCGCTGGGG
22861 GACACCCTGG AGGCGGCCGG GGTGGATGGC GCGGTTCTGG AGACGTTGCG GCGGGGTGAA
22921 GGTGGGCCCG ATCGGCTGGT CGCCGCGCTC TCGGCGGCGT TCGTGCGTGG TCTGGCGGTG
22981 GATTGGGCCG GGTTGATCGT CGGTGCTCGG GTGGAGTTGC CGACCTACGC CTTCCAACGA
23041 CGGCGCTATT GGTTGGACGA CGGGGCGCGG TCGGGGATC CGGGCGGGTT GGGACTGGCC
23101 GCGGTCGCAC ATCCCCTGCT GGGTGCGGCG GTACGGCCGG CGCAGGGCGC GGGGTTGTTG
23161 TTCACCGGAC GGTTGTCGAC GGCGACCCAC CCGTGGCTCG CGGATCATGT GGTGCTCGGC
23221 TCGACGATCG TGCCCGGCAC GGTGTTCGTG GACCTGGCGC TGTGGGCCGG GGCCGAGGCG
23281 GAGTGCCCGG TGGTGGACGA ACTGACCCTG CACACCCCGC TGGTGCTGCC GGAACACGGC
23341 GGCGTGCATG TACAGGTGAC CGTCGACGGG CCGGACGCCG CCGGGGCCCG GGCGGTCGCG
23401 GTGTACTCCC GGCCGGAGGA CGCTCCCGGC GAGGAGCCGT GGACCCGGCA CGCCGTCGGT
23461 GCCCTCGTTG CCGACGCCGA TACGGGTGCC GCTCCCGACG CGGCTGCGGA GGCGTGGCCG
23521 CCGGTCGGCG CGAAGCCGAT CGAGGTGGCG GACTTCTATG CGCGGCTGGT GGAGTCCGGG
23581 GTCGACTACG GCCGGCGTT TCGCGGGATG CGGGCCGCCT GGCGGCGCGG GGACGAGCTG
23641 TTCGCCGATG TGGCGCTGCC GGCCGAGGAG GAGCGCGACG CACACCGCTT CGGGGTACAT
23701 CCGGCGCTGC TCGACGCGGG CGTGCAGACC CTGCGGGTGG ATCCGGGGCA GGTCGACGAG
23761 GACGACATCC GGGTGGCCTT CTCCTGGCAC GGGGTGCGGC TCTTCGCGGC CGGCGTGACC
23821 CGGCTGCGGG TGTCGTGCGT GCCGTCGGGC GAGGGTGCGG TGTCGTTGCG GATCACGGAC
23881 GAGACCGGAC GGGCGGTCGC CGCGATCGAG GCGTTGACGG TGCGGGCGAT CTCGGCCGAC
23941 CAGCTACGGC GGGCCGGCGG CGGGCGGGAC GTGCTGTACC GGCTCGCGTG GCGGGCATCG
24001 GCGGTTCCCG TACCGGTGGC GACGCCTCGT GTGGCGGTGG TCGGCGGGTG GGATCTGCCC
24061 GGTCTGGGCG GGTTGGTGGA CCGGTATCCG GGCTTTGCCG AACTTGCTTC GTGTGACCCG
24121 CCGTTGCCCG ATCTGGTACT GCTCCCGGTT GGTGATCCGG ATGCGGATGT GCCGTTCTCC
24181 GAGCGGCGTA TGCGGGAGGT GACGGCGGAA CTGATCGGGC GGCTGGAGGC GTTTCTCGGC
24241 GACGAACGGT TCGCGGCGGC CCGGGTGGTC GTGGTGACTC GTTCGGCGGT GCTCGTGGAC
24301 GGGGACGCGG GGCTCGGGGA CCCGGCGTCG GCGTCGGTCT GGGGAGTGGT CCGGGCGGCG
24361 CAGGCCGGGC ATCCGGGGCG GATCGTGCTG GTCGACCTGG ACGACGAGCC GGCTTCGGCG
24421 GCGGCTTTGG CGGCGGTGGC CTCGGCCGGT GGTGAGCCGC AGTTCGCGGT GCGCGGTGGT
24481 CGGGTGTCGG TACCGAGACT GGAGCGGATT CCGGCCTCCG GCGGAGCACG GTCGGCGGTG
24541 GGGACCGGCA CGGTGTTGAT CGCCGGTGCG GACCGGGCGG TCGGCGCGGG GGTGGCCGAG
24601 CATCTGGCCG GGGCGTACGG GGTGGGCCGG TTCGTGTTGT TGTCCGTGGA TCCTTCGGGT
24661 GCGGGGCCGA CCGAACTGGC CGCCCGGCTG GGTGAGGCCG GTGCCGAGGT CGTCTCGGCG
24721 GCCTGGGACG GCACGATCC GGGCGTGCTT GCCGCGCTTG TGACCGAACA CCGGCCGGCG
24781 GGCGTGGTGG ACGCGTCGGG CGAGTCGGAT GCAGCCTGGG CCCTGCACGA GCTGACCGCC
24841 GACGTGGACC CGGCCGTTCTT CGTGCTGTTC TCGTCGCGG CCGAGCCTGCT CGGTTCGTCG
24901 GCGCATGCGG CCACGGCCGG GGTGGATGCC TTCCACGATG CGCTGGCCGC ACATCGGCGG
24961 GCGAGTGGGC TGCCCGGGGT GTCGCTTGCG TGCGGGACGG ATCCGCTGCC GGGGCTGCCC
25021 GACCTGTTCG ACGAGGCGAT ACGCCGGGAG GACGCCGTGT TGGTTTCGGC GTCGACGGAT
25081 CTCACCGGGC CCGCGTCGAC GTCACCATTG TTGCCCTCCC GGAACGGTCG TGGCGCGACC
25141 AACTCCGCCG AGACCTCGAT CGAGGCGGAC GGCGAGGCCC TGGCCCGGCG CCTGGCGGCG
25201 TTGTCCGAGG AGGAGCGCGA GCGCGAACTG GTCGGCCTGG TACGGGCCCA GGCCGCGGCG
25261 GTGCTCGGGC ATGCCGGCAT CGGCGAGATC GGACCCGAAC GGGCGTTCAA GGAGGTCGGG
25321 TTCGACTCGC TCACCGCGGT GGAACTGCGC AACCGGCTGA TCCGGGCAC CGGGGTCGGC
25381 CTGCGCTCCA CCCTCGTCTT CGACTTCCCC ACGCCGCGAA TACTGGCCCG CCACCTGAGC
25441 GGCCGGCTGG TCGAGGCGGC ATCCCCGATC GGTGCGCTGC TGGCCGATCT GGACCGATTC
25501 GAGGGCGAGT TGCACGCGGT GCTCGGCGAG GCGGAGGCCC GCGACCGGCT GGCCGAGCGG
25561 CTGCGTCGGC TGTTGGCCGA CTGTACCGCG CCGGACGAGA GCGCCCCGC CGCCGACGAT
25621 GTCTCGGACG TGCAGTCGGC CACCGACGAC GAGTTGTTCT CGCTCGTCGA CCAGGGCTTC
25681 GAATGACCCG GCCCATCCAC GCATACGACC GTGTCGGCAA GGAGTAGAGG CAACGTGGCT
25741 GAGTCGGAAG AGAAACTGCG CTCGTACCTG CGGAAGGCCA TCACCGATGC GCGCGACGCG
25801 CATCGCCGGG TACGCGAGTT GGAGGACCGG CAGCGCGAGC CGATCGCGAT CGTGGGCATG
25861 GCCTGCCGCT TCCCCGGCGG TTTGGGTACG CCGGAGGACC TGTGGCGGTT CGTCGTCGAA
25921 GGCGGCGATG CGATCGGCGA GTTCCCGACC GACCGGGGCT GGGACCTCGA CGGCCTGTAC
```

FIGURE 5 (Continued)

```
25981 GACCCGGATC CCGACCGGCC GGGCACGTCG TACGTCCGCG AGGGCGGATT CCTGTACGAC
26041 GTCGCCGACT TCGACGCCGA GTTCTTCGGC ATCTCGCCCC GCGAGGCGGC GGCGATGGAC
26101 CCGCAGCAGC GACTGCTTCT GGAGACCTCT TGGGAGGCCG TGGAACGCGC GGGCATCGAC
26161 CCGACGTCGC TGCGGCACAG CCGGACCGGG ATCTACACCG GATCAACGG CCTCGACTAC
26221 ACGACCGTGT TGGCCCGCAC CGCCAAGGGC CGGGACGGCA CGCTCGGCAT GGCCAACGGG
26281 GCCAGCCTGC TGGCGGGTCG GGTGGCGTAC ATCCTCGGCC TGGAGGGGCC GGCGGTGACC
26341 GTGGACACGG CGTGTTCGTC GTCCCTGGTG GCACTGCACC TGGCGAGCAA CGCACTGCGG
26401 TCGGGGGAAT GCGACCTGGC CCTGGCCGGC GGTGCGACGG TGATGTGCAC GCCGGAGATC
26461 TTCGTCAACT TCAGCCGGCA GCGCGGACTG GCCCGCGACG GCCGATGCAA GCCGTTCTCG
26521 GCGGCGGCCG ACGGGTTCAT CCTCTCCGAC GGCGCGGGCC TGTTCCTGAT CGAACGGCTC
26581 TCCGACGCGC GGCGCAACGG ACATCCGGTA CTGGCCGTGC TGCGCGGTTC GGCGATCAAC
26641 CAGGACGGCG CGTCGAACGG GCTGACCGCG CCGAACGCC CGGCCCAGGA GCGGGTGATC
26701 CGGCAGGCCC TGCAGAGCGC CGGGTTGGTG ACCGGTGACG TGGACGCCGT GGAGGCACAC
26761 GGCACCGGGA CCACGCTCGG CGACCCCATC GAGGCGCACG CGCTGTTGGC GACCTACGGG
26821 CAGGATCGGC CGCGGATCG GCCGCTGAGG CTCGGGTCGA TCAAGTCCAA CATCGGACAC
26881 ACCCAGGCCG CCGCGGGGGT GGCCGGGATG ATCAAGATGG TGTTGGCCCT GCGGCACGGC
26941 GTGCTGCCCA GGACGCTGCA CGTCGACGCG CCCTCGCCGC ACATCGACTG GTCGGCCGGG
27001 CGGGTGGAAC TGCTCACGGA GCCCGTGCCG TGGCCGAGGT CGGACCGGCC GCGCCGGGCC
27061 GGTGTCTCGT CGTTCGGGGC GAGCGGGACG AACGCGCACG TGGTGGTGGA GGAGGCGCCG
27121 TCGGACGGCG ACGACGGTGT CGTGGAGGTG CCCGCGCCCA CGGGCATCGG CAGTGTCCTG
27181 CCGTGGGTGT TGTCGGCCCG ATCCGAGGCG GCGTTGCGCG CGCAGGCGGG GCGATTGCGG
27241 GACTGGCTGG CCGAGCACCC CGAGGCGGAT CCGGTCGACG TGGGCCGGTC GTTGGCGGTG
27301 GGGCGTGCGG TGCTGGAACG TCGCGCCGTG GTGCGCGGGC GGGATGTCGC CGAACTCGCC
27361 GTCGGGATCG GCGAGGTGGC CGACCGCGGA GAACTCGCCG GTGGGCGGCC GATGTTCGCC
27421 GGACCCGGTC CGGTGTTCGT GTTTCCGGGG CAGGGGTCGC AGTGGGTGGG GATGGCGGCC
27481 GGGTTGTTGG AGTGTTCGCC GGTGTTTGCG GGTGTGGTTG CCGAGTGTGC TGCGGTGATG
27541 GATCCGTTGG TGGCGGATTG GTCGTTGTTG GATGTGTTGC GGGGTGGGTC TGCCGGTGGT
27601 GAGGCGTTGG CGGAGCGGGT GGATGTGGTT CAGCCGGCGT TGTTCGCGGT GATGGTGGGG
27661 CTTGCGCGGT GGTGGGAGTC GTGTGGGGTC AAGCCGGGTG CGGTGATCGG ACACTCACAG
27721 GGGGAGATCG CGGCTGCGCA TGTGGCGGGA TATCTGTCGC TGGCGGATGC GGTACGGATC
27781 GTGGTGTTCC GCAGTCGGGC GCTGCGCGGG ATCGCGGCGG CCGGTGGCGG CATGGTCTCC
27841 GTGGGCGTGT CCGTCGAGCG TGCCGAGGAA CTGGTGGCCG GCTCTGCCGG GTTGTCGCTC
27901 GCGGCCGTCA ACGGGCCGCA GAGCGTGGTG CTTTCCGGCG ACCGTGAGGC ACTGGCCGCC
27961 GTCGTCGACG CGTGCGAGCG CGAGGGTGCG CGAGCCCGGT GGATCCCCGT GGACTACGCG
28021 TCGCATTCCG CGCACATGGA GGTGGTCCGG GACGAGGTCG AGCGTTTGTC GGCCGAGGTG
28081 ACGCCGCGGG CGGGTCGGGT GCCGATGTAC TCGACGCTGA CCGGGGAAGT CGTCACGGAC
28141 CCGGCCGAGT TGGGCGCCGG CTACTGGTTC GAGAACCTGC GCGGGACGGT ACGGCTGACC
28201 ACCGCAGTGG GGGCAGCCGT TGCCGACGGA CACGTCGCCT TCGTCGAGTG CAGCCCGCAT
28261 CCGGGCCTGG TCGTGCCGCT CGCGGACACC CTCGATGAGC TGGGCGTCGA CGACGGCACG
28321 GTCCTGGAGA CGTTACGGCG GGACGACGGC GGCCCCGATC GGCTGGTCGC CGCGCTCTCG
28381 GCGGCGTTCG TGGCGGGTGT GCCGGTGGAC TGGGCCGCAC TGTTTCCGGG CGAGGGGCGG
28441 GCCGACCTGC CCACGTACGC CTTCCAACAT CGGCGCTATT GGGCCGAGGC CGAATCGCCC
28501 GCAGGCGGCG GCGTGGCCTG GGGGCAGCGC GCGGTGACGC ATCCGGTACT CGGCGCCGCC
28561 GTCGACCTGG CCGGCGACGC GGGCACCGTG TTCACCGGGC GGCTGTCGAC GACCGCCCAA
28621 CCGTGGCTGG CCGACCACGC CGTGCTCGGC ACGGTGATCG TGCCCGGGAC GGCGTTCCTG
28681 GACCTGGTCC TGCGGGCCGG AGCCGAGGTC GGCTACCCGG CGATCGAGGA ACTGACCCTG
28741 CACACGCCGC TCGTGCTGCC GGACGCCTCG GCGTCCTGG TACAGGTCGT GGTCGGTGCC
28801 GCGGACGGCG ACGGCGGCGA CGGCGGCGAC GGGGCCCGGA CGGTCGATGT GCACTCGCGG
28861 GCCGAGGACG CGCCGCCGGA CCACCCGTGG ACCCGGCACG CCTCGGGGGT GCTGGTCGCG
28921 GCGGGCGAGG AGCGGGCCGA GGACGCGCCG GCCGGGCGGT GGCCGCCGAC CGGTGCCGAG
28981 GTGGTGGGGG TCGACGACGC CTACGAGCGG CTGGCGGTGG CGGGCTTCGA CTACGGCCCC
29041 GTGTTCCAGG GGCTGCGGTC GGTCCGGGCG CGAGGCGACG AGTTGTTCGC CGAGGTGGAG
29101 TTGCCGGAGG AGGGGCACGC GGACGCGGAC CGGTTCGCGG TGCACCCGGC GCTGCTCGAT
29161 GCCGCGTTGC ACCCGCTGGT GGTCGCGGCC GGTGCCGACG CGCCGGTCGT GGCCGGGCTG
29221 CCGTTCGTGT GGCACGGCAT TCGGGCGGGT GTTCCCGGGG CGCGACGGTT GCGGGTTCGG
29281 CTGGTGCGCT CGGCGTCGGG GTCGGCGTCG GGGTCGGCTG CGGGCTCGGA CTCGGCTTCC
29341 GGCGAGGTGT CGGTCCGGGC GTGGGACGGA GGCGGCCGGG AGGTGGTGGC GATCGAGTCG
29401 CTGACCATTC GCCCGGTCTC GGCGGACGGG TTGCGGACGC CCGATGCTTT GGTCCGCGAC
29461 TCCCTGTTCA CGCTCGCGTG GACCGCGTTG GAGCTACCGG ACGTCGATGA CGACGTGCCG
29521 AACGCGACCC TGCTGGGCGG CGACGGTGCG GCCGATCTCG CCGCGCTGGT GGCTGCCATG
29581 GACACCGGAA CGGACGTACC GGCTCTGGTG GCTCTGCCCG TATCGGTCGA CGACGCGGAC
29641 CCCGTGGCGG CGGCGCACAC GGCCGGCCGG CAGGTGCTGG CGGTACTCCG GGACTGGCTG
```

FIGURE 5 (Continued)

```
29701 GCGGACGAGC GGTTCGCCGA CTCTCGGCTG GTGTTCGTCA CCTCCGGCGC GGTCGCGGTC
29761 GCCGACGAGC AGGTACGTCC GGCCTCGGCG GCTGTCTGGG GCCTGGTCCG CTCCGCCCAG
29821 TCCGAACACC CGGGGCGCTT CGTCCTGGTG GACGCGGACT CCGTCGCCGA CCCCGGCCCG
29881 GAGTTCGACC GGGCCCTGCG GACCGGTGCG GACCAGCTGA TCCTGCGAGA TGGAACGGCC
29941 CTGATACCGA GGCTGGTTCG AGCCCGGCG GACGGCGGAT CGGGCGGATT CGTGCCCGCT
30001 GCCGACGGCA CGGTCCTGAT CACCGGCGGC ACCGGCACCC TGGGCACGCT GCTTGCCCGG
30061 CACCTGGTCA CCGAACACGG CGTGCGCCGG CTCCTGTTGC TCAGTCGGCG CGGCGGTACG
30121 GCCGCCGGCG CGACGGACCT GGTCGCGGAA CTCGCCGCGT TCGGTGCCGA GGTGACCTGC
30181 GTGGCCGGGG ACGCCGCAGA CCGCGCCACG CTGGAGCGGG TGTTGGCGGA CATCCCCGCC
30241 GAACACCCGC TGACGGCGGT GATCCACGCG GCGGGTGTGG TGGACGACGG CGTCGTACAG
30301 TCCCTCACCG CCGACCGGCT GGACGCGGTG TTGCGCCCTA AGGTGGACGC CGCGTGGAAC
30361 CTGCACGAGG CGACCCGGCA CCTGGACCTG ACCGCGTTTG TGCTGTTCTC CTCTGCGGCG
30421 GGTGTGCTCG GAAACCCCGG CCAGGGCAAC TACGCGGCGG CCAACGCCTT TCTCGACGCG
30481 CTCGCACGCC GCCGGCGCCG TGAGGGCCTG CCCGGCAGCT CGTTGGCGTG GGGCTGGTGG
30541 GCGCCGACCA GCGAGATGAC CGCGGGGCTC GGCGACGCCG ACCGGCAGCG GATGGCGCGT
30601 TTGGGTGTAC TGCCCCTGGC GCCGGAACAG GGGTTGGCCC TGTTCGACGC GGCGACGAAC
30661 CATGCCGAAC CGACACCGAC CGTGGTCCGG ATGGACCTCG CGGTGCTACG CACCGCCGGA
30721 TCGGTGGTGC CCACGCTGCT GCGCGGTCTG GCCCGGGTGC CCAACCGGCG GGCTGCGACG
30781 GCGGGTTCGG TGGCCGAGCT GCGCCGTCGT CCGGCCGGCG TATCGGCCTT CGACTGGGAG
30841 CAGACGCTGA TCCGGGCGGT GTGCGTGCAT GCCGCCGCCG TCATCGGCCA CGCCGACGCG
30901 ACCGAGATCG ATGAGACACG GGCGTTCCGC GACCTGGGCT TCGATTCGCT CACAGGTCTG
30961 GAGCTGCGCA ATCGACTGAA CACGGCAACC GGACTGCGGC TGCCCGCCAC GCTGGTCTTC
31021 GACTACCCCA GCCCGGTGGT CCTGGGCCGG TGGTTGCGTG ATCGGCTCGC CGAGGAGGAC
31081 GCCGGGGGCC CGGTCGGCTC GACCCTCGGA GCGCAGGTGG TGTCGCCGGT CGGTTCCGAC
31141 GCCGGCGAGG ACTCGATCGT GATCGTCGGC ATGGGCTGCC GGTTCCCCGG CGGGATCACC
31201 GCGCCCGAAC ACCTGTGGA CGTGGTGGCC GGTGGGGTGG ACACCCTCAC CGACTTCCCC
31261 ACCGATCGTG GCTGGGATGT CGAGCGCATC TTCGACCCGG ACCCGGACCG ACCCGGCAGC
31321 ACCTACGTGC GCACCGGCGG ATTCGTGGAC TCGGCCGCCG ACTTCGACCC GGACCTCTTC
31381 GGGATCTCGC CGCGTGAGGC GTTGGCGATG GATCCGCAGC AGCGATTGCT CCTGGAGACG
31441 GCGTGGGAGA CGTTCGAGCG GGCGGGCATC GATCCGACCT CGCTGCGCGG CAGCCGGACC
31501 GGGGTTTTCG CCGGCGCCAT CTACTACGAC TACGCGGGTG GCCGGCTGCG GAAGGTGCCG
31561 GACGAACTGG AAGGCTACAT CGGCAACGGC AATGTGGGCA GCGTCGCCTC GGGCCGGGTG
31621 GCCTACACGT TCGGTCTGGA GGGGCCGGCG GTCACCGTGG ACACGGCGTG CTCGTCGTCC
31681 CTGGTGGCGC TGCACCTGGC GGTGAACGCG GTGCGGTCGG GCGAGTGTGA ACTGGCCCTG
31741 GCGGGTGGCG TCACCGTGAT GTCGACGCCC AGCGTCTTCC TCGACTTCTC CCGGCAGCGC
31801 GGCCTGTCGT CCGACGGCCG GTGCCGGTCG TTCGCGGCGG CGGCGGACGG CACCGGGTGG
31861 GGTGAGGGTG TCGGGTTGGT GCTGGTGGAG CGGTTGTCGG ATGCGCGGCG CAATGGGCAT
31921 CCGGTTCTGG CGGTGGTGCG TGGGTCGGCG GTGAACCAGG ACGGCGCGTC GAATGGTTTG
31981 ACCGCGCCGA ACGGGCCGTC GCAGCAGCGG GTGATCCGGC AGGCGTTGGG CAGCGCCGGG
32041 TTGTCGCCGG CCGATGTGGA CGCCGTGGAG GCGCACGGAA CCGGGACGAC GTTGGGTGAT
32101 CCGATCGAGG CGCAGGCGTT GTTGCGCGACC TATGGGCAGG ATCGGCCGGG GGATCGGCCG
32161 CTGTGGCTCG GGTCGGTCAA GTCCAACCTC GGGCACACGC AGGCGGCTGC GGGTGTGGCC
32221 GGGGTGATCA AGATGGTGTT GGCGCTGCGG CATGGGGTGT TGCCTCGGAC GTTGCATGTG
32281 GACGAGCCGA CGCCGCATGT GGATTGGTCG GCCGGGCGGG TCGAGGTGTT GGCGGACGAG
32341 GTGGCGTGGC CGGCGGGGGA GCGGGTGCGC CGGGCGGGTG TGTCGTCCTT CGGAATCAGC
32401 GGGACGAATG CACACGTGGT GCTGGAAGAG CCGCCGCCGG TGACCGAAGT GCCGGATGTG
32461 GCCGTCGAGT CCGGGCTGGG CGGGCGGCAC ACCTGGGTGG TGTCGGCGCG GTCCGAGGCA
32521 GCGGTACGGG AACAGGCGGC CCGGCTGCGC GACTGGGTCA CGGCCCGTCC GGATCTCGAT
32581 CCGGCGCACG TGGCCCGGTC GTTGGTGTGC GAACGGGCGC TGTTCGGCCA TCGGGCGGTG
32641 GTCTCCGGCG CCGATCTCGC CGAGCTGGCC GATGGGTTGT CCGCCGTGGC GGCGGGCGCC
32701 GAGGGCGCGG TGGTCGGTGC GGTGGGTCGC GGGCCGGGGA AGACGGCCGT GCTGTGCACG
32761 GGTCAGGGGG TGCGGGCGCT CGGTATAGGC CGCGAACTTC ACGCGGCGTT CCCGGTGTTC
32821 GCCGGCGCCC TGGACGAGGT GTGTGCGGCC TTCGACGATG TGGTGCCGTT CTCGGTGCGG
32881 GACGTCGTGC TCGGTGCCGA AGGGGTGGCG GATGCCGACG CGCAGGACAC CGGGGTGGCC
32941 CAGCCGGCGG TGTTCGCCGTT CGAGGTGGCG CTGTACCGGC TGTGGGCCTC GTGGGGGCAG
33001 GCGCCCGACT TCGTGGTGGG GCATTCGCTC GGCGAGATCG TTGCGGCGCA TGTGGCGGGA
33061 GTGTTCTCGC TCGCGGATGC GGTGGTCTTC GTCGCGGCGC GGGCTCGGTT GATGAGTGCG
33121 CTGCCGAGTG GAGGGGCGAT GCTGCCGTC GGTGCGAGCG AGGCCGAGGT GGCGGCGTCG
33181 TGCCCGGCCG AGGTGACGAT CGCAGCGGTG AACGGCCCGG CGAGTGTGGT GGTTTCCGGA
33241 CCCGCCGAGG CGGTGGCCGC GCTCGAACCG GACTGCGTGA TGCGCGGGTG GCGGATCTCG
33301 CGCCTGTCGG TGTCGCACGC CTTCCACTCG GCGCTGATGC AACCGATGTT GGCCGAACTC
33361 CGCGAGGTGC TGACCGGGTT GACCTACGGC ACGCCCGAGA TCGCGGTGGT GTCGGACACC
```

FIGURE 5 (Continued)

```
33421 ACCGGGCGGG TTGCGGGCGC CGAAGAGTTG GCTGATCCCG AGTACTGGGT GCGGCACGTA
33481 CGCCGCGCGG TGCGCTTCGG GGATGCGATC GCCACGCTGC GCGCCGAAGG GGTACGGACC
33541 TTCGTGGAGA TCGGCCGGA GGCGGCGTTG ACCGCGATGG TGGTCGAGGG CACGGCCGGC
33601 GCGGAGGACG TGGCCGCCGT AGCGACCCGG CGTCGGGGTC GAGCGGCCGT GTCGAGTGTG
33661 GTGGAGGCGC TCGCCCGGGT GTTCGTGCAC GGCGCGACGG TGGATTGGGC CGCGTTGTCC
33721 ACCGGTTCCG GGCCCGGGGG ACGGGTGGAT CTGCCGACCT ACGCCTTCGA GCGGCGGCGC
33781 TTCTGGTTGC ACGCCGGTGT GGACGCGGGC GACGCGGTCG GGCTGGGGCA GGGTGTGGTG
33841 GACCATCCGC TGCTCGGTGC GGTCGTGGGC CTGGCGGACG ACCAGGGCGT CCTGTTCACC
33901 GGCCGGTTGG CCCTGGACAC CCATCCGTGG TTGGCCGAAC ACACCGTCTT GGGCACGGTA
33961 TTGCTGCCGG GCACGGCATT CCTGGAGCTG GCCCTGCACG TCGGCCGCCT CCTGGACTGC
34021 GCGCGGGTCG ACGAGCTGAC CCTGTCGGCC CCGCTGGCGC TGCCGTCGAC GGGCGGTGTG
34081 CAGGTCCAGG TCCGAGTCGG TGTACCGGAG GAGAGCGGGA CACGGACGAT CACGGTGCAT
34141 GCCCGCCCGG ATTCGGCGGA GGAGGCGCCT TGGACGCTGC ACGCCGCCGG GGCCCTGGGT
34201 CCATCAGCCG AGGTGGATGC ACCCTCGGAT GCCGCGAGTT GGCCGCCTGC CGATGCGACC
34261 GCGATGGACT CGGCGGGGCT GTATCCCTGG TTCGCCGAGA CCGGCGTCGA CTACGGACCC
34321 TCGTTCCGGG GCGTACAAGC GACCTGGCGC CGTGATGACG AGGTGTTCGC GGAGATCGTG
34381 CTCGCGGCCG ACGACCCGGC CGCCGACGGC CGGTTCGAGC TGCACCCCGC GCTGTTCGAC
34441 GCCGCGTTGC ACCCGCTGGG CCTGACCCTG CTCGACGCGG CGGAGCCGCG CCTGCGGCTG
34501 CCGTTCTCCT GGCGCGGAGT GGCGCTGCAC ACGTCCGGGG CTCGCACGTT GCGGGTTCGG
34561 CTGCGTCCCA CCGGGCCCGA CACCATCGCG GTGACGGCCA CCGACGAGAC GGGTCGACCG
34621 GTGGTCGCGG TCGAGGCCCT GGCGGTGCGC GAACCCTCGC GGGACCGACT GCCACGACCC
34681 GACGCGAACG CGGGCGAGTT GTTCGAGCCG CAGTGGACGC CGCTGTCACC GGCGGACACG
34741 GCGGACATGG CGGACACGCT CGGGGCGGTG GTGGGCGGCC CCGAACTCGC CTCGACAGCC
34801 ACCCGATTCG GTGCCACACA TCACCGTGAC CTGGCCGCCC TGGCCGAATC GGCAATCCCC
34861 GAGACGGTCC TGTACGACCT GGTCACCGGC GTTCCCGGCG TATCCGCCGA AGCCGTACAC
34921 CAAGCCGCCG CCCAAGCGCT GGACCTGGCC CGATCCTGGC TCGCCGACGA GCGCTTCGAG
34981 TCGGCCCGCC TGATCGTGCG CACCCGACAC GCGGTCGCCG CCGCCGAAGG CGACGCGCCG
35041 GACCCGGCCG CCGCCGCGAC CCATGGCCTG TTTCGTACCG CCTGCTCCGA ACACCCCGAG
35101 CGGTTCGCGC TCGTCGACGC CGACGACCTC GACGAGGTCT CGCCCGAGGC CATCGCCGCC
35161 GTCGTGGTCG AGCCCGAGGC GGCCGTGCGG GCCGGTCGCG TCCTGGTTCC GCGCCTGCGC
35221 CGAGCGGCCG TGGCGCCCAA GGCCGACTTC GGCTTCGCCG CCGAAGGCAC CGTTCTGATC
35281 ACCGGTGGCA CCGGAGCACT GGGCCGGCAG GTCGCCCGGC ACCTGGTGCG CGTACACGGG
35341 GTGCGCCGCC TCCTCCTGCT CTCCCGTCGC GGCGACGAAG CCCCCGAGGC CGCCGAGTTG
35401 CGGGCCGAAC TGATCGAGGC CGGCGCGCAC GTCACCTTCG CCGCCGGAGA CGCTGCCGAA
35461 CGTGGCGTGC TGGCCGACGT GTTGGCCGCG ATCCCGGCCG CCCACCCGCT GACCGGCGTG
35521 GTGCACCTGG CCGGGGTGAC CGACGACGGG CTGGTCGGGA CGCTGACCCC CGAGCGGCTG
35581 GCGGCGGTGT TGCGCCCCAA GATCGACGCG GCGCTGCACC TGGACGAACT CACCGCCGAC
35641 GCCGACCTGT CGGCGTTCGT CCTGTTCTCC TCGGCCGCCG GTCCGGTCGG CAACCCCGGC
35701 CAGGCCAACT ACGCGGCGG CAATGTCGCC CTCGACGCGC TGGCCCGCCG GCGCCGAGCG
35761 CGCGGCCGAC CGGCCGTGTC GTTGCAGTGG GGGTTGTGGG CCGAACGCAG TGCGCTGACC
35821 GCGACGATGA GCGCGACCGA TCGGCGACGG GCGGCCGGCG CGGGTGTGCG GGCGTTGTCC
35881 GTGGAGCAGG GCCTCGCACT GCTGGACGCG GCGGCCGGGC GGCCGAGGC GGTGCTGACG
35941 CCGCTGCGCC TCGATCCGGC GATCCTGCGC GGTCCGGAGG AGCGGGTGGC GCCCGTGTTG
36001 CGCGGGCTGG TGCCGACCCG GGCCCGGCGT GCGCCGGCCC GTACCTCGGA CACCGCCCGC
36061 TCACTGGTGC GCCGATTGGC CGCGTTGCCC GAGGCCGAGC AGGACCGGCT GTTGGTCGAC
36121 CTGGTCCGTA CCCACGCGG CGGTGTGCTC GGCCACGCCG ACGCGCGCAC GATCGACCCG
36181 GACCGCGCGT TCGGCGAACT GGGCCTGGAC TCGCTGGCGG CGTTGGAACT GCGCACCCGG
36241 TTGAGCACGG CGGTCGGGCT GCGCCTGCCC GCCACGATGT TGTTCGACCA TCCGTGCGCG
36301 CGTGCCGTGG GCGTACACCT GCGCGCGCAA CTGCTCGACG CGCCGACACC CGGGCGGGCG
36361 GCGGGTGTCG CCCGGCCGGT GTCGGACGAG CCGGTCGCGG TGGTGGCGAT CAGCTGCCGC
36421 TTCCCCGGCG GCGTCGCGAG CCCCGAGGAC CTGTGGCGGC TGGTGTCGGA ACACACCGAC
36481 GCCATCTCGG AGTTCCCGCA GGATCGGGGC TGGGACCTGG CCGAGCTGTT CCACCCGGAC
36541 CCCGAACATG CCGGTACCTC GTATGTAAGC GAGGGCGGAT TCCTTTACGA GGCAACCGAG
36601 TTCGACCCGG AGTTCTTCGG CATCTCGCCG CGCGAGGCGC TGGCCATGGA CCCGCAGCAG
36661 CGGTTGCTCC TGGAGGCGTC CTGGGAGGCG ATCGAGCGCG CCGGCGTGGA TCCCAGGTCG
36721 CTGCGCGGCA GTCGTACCGG GGTGTACGCG GGCCTGATGT ACGCCGACTA CGCGTCGCGG
36781 CTGGGCAGCG CGCCGGAGGG CGTGGACGGC TATCTCGGCA ACGGCAGCGC GGGCAGTATC
36841 GCGTCCGGGC GGGTGGCCTA CACGCTGGGT CTGGAGGGCC CCGCGGTGAC CGTGGACACC
36901 GCCTTCCGT CGTCCTTGGT CGCACTGCAC CTGGCCGCA ACGCACTGCG CCAGGGTGAG
36961 TGTGATCTGG CGCTGGCGGG CGGGGTGACG GTGATGTCCA GCCCGGCCAC GTTCGTCGAG
37021 TTCTCCCGGC AGCGCGGCCT GGCCCCGGAT GCGCGGTGCA AGTCGTTCGC GGCCGGCGCC
37081 GACGGTACCT CGTGGTCCGA GGGCATCGGT CTGCTCCTGG TGGAACGCCT GTCGGACGCG
```

FIGURE 5 (Continued)

```
37141 CGCCGGTTGG GCCATCCGGT GCTGGCCGTG GTGCGCGGCA GTGCGATCAA CCAGGACGGC
37201 GCCAGCAACG GCCTGGCCGC GCCCAACGGG CTCGCCCAGG AGCGGGTGAT CCGGGATGCG
37261 CTCGCGCACG CCGAGTTGCG TCCGTCCGAC GTGGACGCGG TGGAGGCGCA CGGCACCGGC
37321 ACGCCGCTGG GCGACCCGAT CGAGGCGCGC GCCCTGCTCG CCACCTACGG GCAGGACCGG
37381 CCGGCGGATC GGCCGTTGTG GCTGGGGTCG GTCAAGTCCA ACCTCGGGCA CACCCAGGCG
37441 GCGGCGGGCG TGGCCGGCGT GATCAAGATG ATCATGGCGA TGCGGCATGC CGAACTGCCC
37501 GGGACGCTGC ACGTGGACGC CCCCTCACCG CACGTGGACT GGTCGGCGGG GGCGGTGTCG
37561 CTGCTCACCG CCGCGACCCC GTGGCCGCAG ACCGGGCGTC CGCCGTGC GGGGGTGTCG
37621 TCGTTCGGGA TCAGCGGGAC CAACGCGCAC GTGATCCTGG AACAGGGCGA CCCCGCCCCG
37681 ACCGCGCCCG CCGAACCGGC ACCGGCGTCG GCGCCTTTGG CCGCGCTGGC GTGGCCACTG
37741 TCCGGGGCGA GCGCGGTGGC ACTGCGCGGG CAGGCCGAGC GGCTGCGCGC ACATCTGGAC
37801 GCGCACCCCG AGTACGGGCC GGTCGACATC GCGCACGCGC TCGTCGGCGG CCGATCCCGG
37861 TTCGAACACC GCGCCGTGGT GGTCGCCGAG GACGCGGCGG GCCTGCGGGC CGGGCTGGAC
37921 GCGCTGAGCG CCGACCGGCC CGACGCGGCG GTGCCGGTGG GCGTGGCCGG CGAACCCGGC
37981 CGGATCGCCT TCGTGTTCGG CGGACAGGGT TCGCAGTGGC CCGGCATGGG CGCCCGACTG
38041 CTCACCGAGT CGCCGGTCTT CGCCGCCCGG ATCCGCGACT GCGACGCGGC ACTCGCGCCG
38101 CACACCGACT GGTCGCTGCT CGCCGTGCTG CGCGGCGAGC CCGACGCGCC GCCGCTCGAC
38161 CGGGTCGACG TGGTGCAACC GGTGTTGTTC GCGGTGATGG TCGCGCTCGC CGAACTGTGG
38221 CGCTCGCTGG GCGTACGGCC GGCTTCGGTG GTCGGCCACT CGCAGGGCGA GATCGCCGCC
38281 GCCCACATCG CGGGCGCGCT CACCCTCGAC GACGCGGCCC GGATCGTCGC ACTGCGCAGC
38341 CGCGCCCTGC GCGGGTTGTC CGGCGACGGC GGGATGATGT CCGTCGCGGC CGGCCCGGAG
38401 CAGATCGCCC GATTGCTCGA CGGATTCGCG GACCGGCTCG GCATCGCCGC CGTCAACGGC
38461 CCCGCCGCCG TGGTGATTTC CGGCGCGGCC GACGCGCTCG CCGAACTGCA CGCCCACTGC
38521 GAGGCGGACG GGATCCGCGC CCGGGTGCTC CCGGTCGACT ACGCCTCGCA CTCCGCCCAG
38581 GTCGAGCAGG TCCGCGAGGA ACTGCTCGCC GCCCTGGGCG AGATCGTGCC CACGCCGACC
38641 ACCGACGCGG TCTTCTACTC CTCGGTCACC GGCGAACCCG TCGAGGGCAC CGCGCTCGAC
38701 GCCGAGTACT GGTACCGCAA CCTGCGCGCC ACCGTCGCCT TCGACCGGGC CACCGATGCC
38761 CTGCTGCGGG ACGGCCACAC GGTGTTCGTC GAGACCAGCC CGCATCCGGT CCTTGCGCCC
38821 GCCGTCGAGG ATAGTGCCCA GCGCGCCGGT ACGGACGTGA CGGTCGTGGG CAGCCTCCAG
38881 CGCGACACCG ACACCCTCGC CCGTTTCCTC ACCGCCGCGG CCGGCCTGCA CGTGCACGGC
38941 GTCCCGGTGG ACTGGTCCGC GACCCACGCC GGACACCGGC CCCGGCCGGT CGACCTGCCC
39001 ACCTACGCAT TCCAACGCGA GCGCTACTGG CTGGAGGCGG GCAAGACGCC CACCGACGCG
39061 GCCGGCCTCG GCCTGCACCC GGCGGCACAC CCCCTGTTGG GCGCGGCCGT GGTACCCGCC
39121 GAGGGCGACC GGCACATCCT CACCGGCCGC ATCTCGCTGC GCACCCACCC CTGGCTCGCC
39181 GACCACACGA TCCTGGACAC GGTGCTGCTC CCGGGCACCG CGTTCGTCGA ACTCGCCCTC
39241 CAGGCGGGCG ATCGGGCCGA CTGTGACCTG ATCGAGGAGC TGACCGTCGA GGCCCCGCTG
39301 CGGCTCACCG ACACCGGCGC CGTACACCTG CAGGTGTTGC TGGACGAGCC GGACGAGCAG
39361 GGCCGCCGAG CGCTGACCAT CCACTCCCGA GCCGACGACG CGCCCGCGGA GCAGACGTGG
39421 ACGCGGCACG CGAGCGGGGT ACTGGCGCCG GTCGCGGACG GCCTCGACGC CGTGCCGGCG
39481 ACCGACGCCG CGTGGCCGCC CGCCGGGGCC GTCGCGCTGG ACGTGGACGG GCTGTACGAG
39541 CGGTTGGCCG GGCAGGGCTA CCGGTACGGA CCGGCCTTCC GGGCGGTGCG GGCCGCGTGG
39601 CGCCTGGGCG ATACGGTCCT GGCCGAGGTC GCGCCGGGCG ACGAGGCGCA CGGCCGCACGG
39661 GACTTCGCGC TGCACCCGGC CCTGCTGGAC GCCGCGCTGC ACGCCGCCGG CGCCGCCGAC
39721 AGCGGAACAT CCGGCGGGGA CGGTGCCATC GGCCTACCCT TCGCCTGGAC CGACGTACGC
39781 CTGCACGCCG TCGGCGCCGC CGCGCTCCGG GTCCGCCTGG AACGCCGCGG CCCGGACACC
39841 GTCGGCCTCG AACTCACCGA TCACACCGGC GCCTTGGTCG CCACCGTCGG TGCCCTGGTC
39901 GGCCGCCCCG CGACCGCCGA CCGGCTCGCG CCCGCCGCCG ACCCGGCCCA CCGCGACCTC
39961 CACCACGTCG ACTGGTCCCC GCTGCCCACT CCCACCGAAC CCAGCACCGC CCGCTGGTCG
40021 TTGCTCGGCC CGGACGAACT GGAGGCGGTG GCCGGGCTGC GCGCCGCCGG CGCCGAGGTG
40081 CACGCGGACG GCGACCCCGA CCCCGCCGAC GTACTGCTGA TCACCTGCGC CGGCCGGACC
40141 GGGGACGACG TCCCCGAAGC CGCCCGGGCC GCCACACACC GCGTACTCGA CCTGCTCCAG
40201 CGCGCACTGA CCGACCCACG CCTCACCGCA TGCACCCTGG TCGTGCTGAC CCGGGGCGCA
40261 GTACCCGGGC ACCACGGCGA GGACGTGTGC GACCTGGTCG CCGCGCCGAT CGTGGGCCTG
40321 GTCCGCTCCG CGCAGACCGA ACACCGGGGC CGGATCGTGC TGGTCGACCT GGACGACCAC
40381 GCCGACTCCT TCGCCGCGCT GCGCGCCGCC GTCGTCACCG ACGTCGGCGA ACCGCAACTG
40441 GCCATCCGCA CGGGCACCGT GTCCGCACCC CGACTCGATCC GCACCGGCAC CGAACCGCGC
40501 CTGAGCCCGC CCGCCGGCGC CCCGGCCTGG CGGCTCGACC TGCTCGGCGG TGGCCACCCTG
40561 GACCGGCTCG CGCTGCTCCC GAACGCCGAC GCGGCGGTCC CGCTCGCGCC CGGACAGGTC
40621 CGGATCGCCG TCCGCGCCGC CGGGCTGAAC TTCCGCGACG TCGTGGTCGC CCTCGGCATG
40681 GTCACCGACA CCCGCCCGCC CGGCGGCGAG GGGGCCGGAA TCGTAGTGGA GGTCGGCCCC
40741 GATGTGCCCG AACTCGTCCC GGGCGACCGG GTGATGGGCC TGTTCGGCGG CGGCACCGGA
40801 CCGATTACCG TGGCCGACCA CCGGCTGCTC GCGCCGATCC CCACCGGCTG GACCTACGCC
```

FIGURE 5 (Continued)

```
40861 CAGGCCGCGG CCGTCCCGGT GGTGTTCCTG ACCGCCTACT ACGGCCTGGC CGACCTCGGC
40921 GGGCTGCGCG CCGGCGAATC GCTGCTCGTC CACGCCGCCA CCGGCGGAGT GGGCATGGCG
40981 GCCGTGCAAC TGGCCCGGCA CTGAACGTG GAGGTGTTCG GCACCGCCTC GCCCGGCAAA
41041 TGGGCCACCC TGCGCGGCCA GGGCGTGGAC GACGCGCATC TGGCGTCCTC GCGCGATCTC
41101 GACTTCGCGC ACCGGTTCGG CGAGGTCGAC GTGGTGCTCA ACTCGCTCGC GCACGAATTC
41161 GTCGACGCCT CACTGCGGTT GCTCGCGCCC GGCGGCCGAT TCCTGGAGAT GGGCAAGACC
41221 GACATCCGCG ACCGGGACGA GGTGCTTGCC GCCCATCCGG GCCGCGACTA CCGGGCGTTC
41281 GACCTGATGG ACGCGGGGCC GGAGCGGATC CGGGAGATGC TGGCCGACCT GTACCGGCTC
41341 TTCGAGACCG GCGTGCTGCA CCCGCTGCCC GTGACCCCGT GGGATGTGCG CGGTGCGGTC
41401 GGCGCGTTCC GGCACCTGAG CCAGGCCCGG CACACCGGCA AGATCGTGCT GACCCTGCCG
41461 CCCACCCTCG GCGCCGCTCC CGACCCGGAG GGCACGGTCC TGATCACCGG CGGCACCGGC
41521 ACCCTCGGCG GCCTGCTCGC CCGCCACCTC GTACGCACCG CCGGGGTACG ACACCTGCTC
41581 CTGATCGGCC GGCGCGGCCC GGCCGCCGAC GGCGCGGCCG AGTTGTCCGC CGAACTGACC
41641 GCGCTCGGCG CCCGGGTGAC CATCGCGGCC TGCGACGCCG CCGACCGTGC GGCGCTGGCC
41701 GCGCTGCTCG CCGACATCCC GGCCGAACAC GCGCTCACCT CGGTGATCCA CGCCGCCGGC
41761 GTGATCGACG ACGCGGCGCT GACCGCGCTC ACCCCCGAGC GGCTGGACCG GGTGCTGCGC
41821 CCGAAACTGC ACGCCGCCTG GAACCTGCAC GAGCTGACCC GCGACCTCGA CCTGGCCGAG
41881 TTCGTGCTGT CTCCTCGAT GGCCGGCACC TTCGGCGGCG CCGGACAGGC CAACTACGCC
41941 GCCGCGAACG CCTTCCTGGA CGCGCTCGCC CAGCACCGCC GAGCGCGG CCTGGCCGCG
42001 ACCGCGGCCG CCTGGGGTCT GTGGGCGCAG GCCAGCGGGA TGACCGGACA CCTGGGCGCC
42061 GAGGACCTGG ACCGCATTGC CCGCACCGGC GTCGCCGCGC TGGAGACCGC CCACGCACTC
42121 ACCCTGTACG ACGCGCTCCG CGCGGCCGAC CGCCCCACGA TCGTGCCCGC CCGCCTGGAC
42181 CCGGACGCGC TGCGCGCCGC CGCCCCGACC GTACCCGCAC TGCTGCGCGA CCTGGTGCGC
42241 GACCTGGTGC GCCCGCGCGG ACGCCGCGCC GCCGCCGACA CCGCGCCGGA CGCCGCGTCC
42301 CTGGCCGAGC GGCTGGCCCG ACTGCCCGAG GAGCGGCGCC GGCAGACGCT GCTGACCCTC
42361 GTCCGCACCG AGACCGCCGC CGTCCTGGGC CACGCCACCC GGACGCGGT CGCCCCGCTG
42421 CGCCCGTTCA AGGCCCTCGG CTTCGACTCG CTCACGTCGG TCGAACTGCG CAACCGCATC
42481 GGTGCGGCGA CCGGCCTGCG CCTGCCCGTC ACCCTGGTCT TCGACCACCC GACCCCGCAG
42541 GCCCTCGCCG ACCACGTCGG CGCCGAACTC CTGGGCGTAG CGCCCGTGGT CGTCGAACCC
42601 GAGCGACCCG CCGCACACAC CGACGACGAC CCGATCGTGA TCGTGAGCGT CGGCTGCCGC
42661 TACCCGGGCG GGGTGGCCGG ACAGGACGAG ATGTGGCGGA TGCTCGCCGA GGGCACCGAC
42721 ACCATCGGGC CCTTCCCCCA AGACCGGGGT TGGGAGTTGG ACACACTCTT CGACCCGGAC
42781 CCCGACCGGG TGGGCAAGTC GTACGTCCGT GAAGGCGGAT TCGTCGCCGA CGCGGTGCAC
42841 TTCGACGCCG AGTTCTTCGG GATCTCGCCC CGCGAGGCGA CCTCGATGGA CCCGCAGCAG
42901 CGGCTCCTGT TGGAGACCGC GTGGGAAACG TTCGAGCAGG CCGGCATCGA CCCCACCACG
42961 CTGCGCGGCA GCGGCACGGG CGTGTTCGTC GGGGCCATGG CGCAGGACTA CCACGGCACT
43021 TCGCAGGCGA TGGCCGAGGG CCAGGAGGGC TACCTGCTGA CCGGGACCGC CACCAGCGTG
43081 ATCTCCGGCC GGGTCTCCTA CGTCCTGGGC CTGGAGGGCC CGGCGGTGAC CGTGGACACC
43141 GCGTGCTCGT CATCCCTGGT CGCCCTGCAC CTTGCGGCGA ACGCACTGCG TGCGGGTGAG
43201 TGCGATCTCG CGCTTGCGGG CGGGGTGGCG GTGTTGACGT CGCCGCAGGC GTTCATCGAG
43261 TTCAGCCGGC AGCGCGGACT GGCCGCGGAC GGGCGCTGCA AGCCCTTCGC GGCGGCGGCC
43321 AACGGCACCG GCTGGGGCGA GGGTGTCGGC CTGGTACTCG TCGAGCGGCT GTCCGACGCG
43381 CGCCGGCGCG GCATCCGGT GCTGGCCGTG GTGCGCGGCT CGGCGGTCAA CCAGGACGGC
43441 GCCTCGAACG GCTGACCGC ACCCAACGGC CCCTCGCAAC AGCGGGTGAT CCGACAGGCG
43501 TTGCGCAACG CGGGCCTGCT CGCGACGGAC GTCGACGCGG TCGAGGCGCA CGGCACCGGG
43561 ACCACGCTCG GCGACCCGAT CGAGGCGCAG GCGCTGCTGG CGACCTACGG GCAGGACCGG
43621 CCGGCGCAAC GGCCGCTGTG GCTGGGGTCG GTCAAGTCCA ACATCGGGCA CACTCAGGCC
43681 GCGGCGGGGG TCGCCGGGGT GATCAAGATG GTGCTCGCGC TGCGGCACGG GACGTTGCCG
43741 CCGACGTTGC ACGTGGACGC GCCCACGCCC CATGTGGACT GGGCGTCGGG ACAGGTGCGG
43801 CTGCTCACCG AGCCGGTGGC GTGGCCGGCG GGGAACGGG TGCGTCGGGC CGGGATCTCC
43861 TCGTTCGGGG TGAGCGGGAC CAACGCGCAC GTGATCATCG AGCAGGCGCC GGCGGAGGGC
43921 GCGGTCGATG CCGCGCCGGT CGATGCCGCG CCGGCCGCCG CGCTCGGGGG GATCGTGCCG
43981 TGGGTGGTGT CCGCGCGATC CCAGGCCGGG TTGCGGGCGC AGGCGGCGCG GCTGCGGGAC
44041 TGGGCCGCCG TGCATCCGGA GTTTGCCCCG GCCGACGTGG CCGCCTCGCT GGTGCGCGGG
44101 CGGCGGTGT TCGAGCGGCG CGCAGTGGTC CGGGGTCGGG ATACCGACGA ACTGGTCGCC
44161 GCACTCGCTG AGTTGGTCGA CTCGTCGGCA ACGGGCGAGG CGCCGACGGC GATCGGGCCC
44221 GGGCCGGTGT TCGTCTTCCC CGGCCAGGGA TCGCAATGGG TGGGCATGGC GGCGGAGTTG
44281 CTGACGTGCT GCCCGGTCTT CGCGGAGACC GTCACGCAGT GCGCCGAGGT GATGGACCCG
44341 CTGCTGCCGG GCTGGGCGCT GCTCGACGTG CTGCGCGGCA CCGACGACGA GACGGCCGAA
44401 CTGCTGCGCC GGGTCGAGGT GGTGCAACCC GTGCTGTTCG CGGTGATGGT GGGTCTGGCC
44461 CGCTGGTGGG AGTCGTGCGG GGTGCGACCG GCCGCGGTGA TCGGGCACTC CCAGGGCGAG
44521 ATCGCCGCCG CGTACATAGC CGGCCACCTG ACCCTGCCGG ACGCCGCCCG GATCGCCGCG
```

FIGURE 5 (Continued)

```
44581 CTGCGGATCC GCGCGGTGCA GGCCGCCGAC ATGATCCGCG GCGCGATGGT GGCTGTCGCG
44641 GTATCCGCCC TGCGGGCCGA GGAGTTGATC ACCCGCACCG GCACCGGGGA CCTGGTCAAC
44701 GTGGGCGGGA TCAACAGCCC GACCAACACC GTGTTGTCCG GCGACACCGA CGCCTTGGCC
44761 CTGATCGTGG CCGACTGCGA GCGCGAGGGT GTACGGGCGC GCTGGATCCC GGCCGCGTAC
44821 TCCTCGCACT CGCCGCAGAT GGACGCTGTA CGCGGCGACC TGGAACGCCT GCTCGCGGGC
44881 ATCCAACCCA CCCCCGGGCG GGTGCCGATG TACTCCACGG TCACCGGCGG CCGACTCGCC
44941 GACGACGCGC TGCTCGACAT CGACTACTGG TTCGAGAACA TGCGGCGCAC CGTGCGGTTC
45001 GAGGAGGCGA TCGGCGCGGC GGCGGCCGAC GGACACACCG TGTTCCTCGA ATGCAGCTCG
45061 CACCCCGGCC TGGTGGTGCC GCTCGGCGAC ACCCTGGACT CGCTCGGCGT GCACGGCGCC
45121 ACCCTGGAGA CGCTGCGCCG CGCGGACGGC GGCGCCGATC GGCTGCTCGC CGCGCTCTCC
45181 GCGATGTTCG TGCACGGCGG CGCGGTGGAC TGGGCCGGGC TGCTACCGGG TCGCCGGGTC
45241 GCGCTGCCCA CGTACGCCTT CCAGCGTCGG CGGCACTGGG TGGAGCCCGT CGGACCGGCC
45301 CGAGGGGGCG TCGGCTGGGG GCAGTTCGCG GTGGAGCACC CGATCCTGGG CGCCGGGGTC
45361 GACCTGGCCG ACGGCTCGGC GACCGTGTTC ACCGGGCGCC TGGACACCAC CACACACGGT
45421 TGGCTCGCCG ACCACCTCGT GCTCGGCGAA GTCCTGGTCC CGGGCACGGT GTTCGTGGAC
45481 CTGGCGCTGC GCGCGGGCGG CGCCCTCGGC TGTGCGGTGG TCGAGGAGTT GGCCCTGCAC
45541 GAGCCGCTGG TGTTGCCGGA CGCGGACGGG GTGCGGATCC AGGTCACCGT CGAGGCACCG
45601 GACGACGCGG GTACGCGGGC GCTGACCATA CACTCCCGGC CCGAGGACGC GCCCGCCGCC
45661 GAGCCGTGGA CCCGACACGC CTCGGGCACG GTGGCCCCCG GCGCGCACCG GCCGCAGCAG
45721 GAGTCCGGGC CATGGCCGCC GATCGGGGCG ACGCCGCTGG ACGTGGCGGA CGTATATCTG
45781 CGGTTGACCG AACTGGGCCT GGGCTACGGC CCGACGCTCG CCGGACTGCG GGCCGCGTGG
45841 CGGCGCGGCG ACGACCTGTT CGCCGAGGTC GCGCGCACCG CCGACGGCGA ACGTGGCACC
45901 GCCCGCTTCG GCCTGCACCC GGCCCTGCTC GATGCGGCCC TGCACGGGCT TGCCCCCGGC
45961 TCGGCACCCG GCGGCGCACC TACCGAGGTG CGGCTGGCCG GCGCCTGGCG CGGGGTGACG
46021 CTGGGCGGCG ATGCCGGTAC CGCCGGCCGG ATTCGGCTGC GGGGCGTCGA CGGGGACGGC
46081 GTCGAGGTCG AACTGGCCGA CGAGGCAGGT CGATCCATGG CCCGGATCGA GTCGGTGGCG
46141 CTGCGGCCAT GGAGCGCGGG GCAGGTGCGG GCGGCCGGGC GGGCCCGACC GTGGTTGACC
46201 CGCTGGGAGT GGGCCCGGGT CGAGCCGACC GACCCGGCGG CGGCAGGAGG TCGCTGGGCC
46261 GTGCTCGGTG CGCGGGCTTG GACGGGGTG CCGGCCTATG CGACCGCCGC CGAACTGATC
46321 GCGGCCGTCG AGGTCGGCGT CCCGGTTCCG GATCTGGTCG CGCTGCCCGT GCGGATCGAC
46381 CCGGCCGGCG GGCTCGATCC GGAGGCGATC CGGGCCACGA TCCGGGCGGT GCGCGAGACC
46441 CTGCGGCAGT GGCGGGCCGA GCCGCGGCTG GCGGCCTCCC GCCTGGTCGT GGTGACCCAC
46501 GACGCGGTCT CGGCGCGGCC CGAGGACCGG GTCACCGATC CGGGCGCGGC GGCGGTGTGG
46561 GGCGTGGTCC GGGCGGCCCG GGCGGCGGAC CCCGAGCGGT TCGTGCTCGC CGACGTGGAC
46621 GGGGAGGACG GGTCCTGGCC GGTGCTGCTG GCCGAAGCGT CCGCCGGTCG CGCCGAGTTC
46681 GCGATCCGCG CGGGCACGGT ACTGCTGCCG GGCCTGGCCC GGGTACCGGC GGGCGAGACC
46741 GGCACGGCGG GCTTCCCGAC CGACGGCACG GTATTGGTCA CTGTCGCGAC CGACCCGACC
46801 GACCCGACCG ACGGCACCGA CCCGGTCGGC ACACTGCTGG CTCGGCACCT GGTGACCGCC
46861 CACGGAGTGC GCCGGCTGAT CCTGGCCGGC GGGCCCGCCG CCGGGATGCC GCTTGCCCGG
46921 GAACTGGCCG CGCAGGGCGC GGAGATCCAC GTGGTCGTCT GCGACGTGAC CGACCGCACC
46981 GAACTGGCGA AGCTGCTGGC CACGATCCCC GAGCACAGCC CGCTGACCGC CGTGGTGCAC
47041 ACCGCCGGGC TCGGCCGGTC GCACACCGAG GCCATGCTGC GGGCCCGGGT GGACGCGGCC
47101 GTACACCTGC ACGAACCTCAC CCGACGCGCC GACCTGTCCG CCTTCGTGCT CTGCACCGCC
47161 CTGGACGGCG TACTCGCCGA CCCCGGCCGG GGCGAACACG CGGCGGGCGA CGCCTTCCTG
47221 GACGCCCTGG CCCGGCACCG GCACGCCGCC GGGCTGCCCG CGCTCGCGCT GGCCTGGGCA
47281 CCGGGGGCCG AACCGGTCGC CGGGCTGCTG CCGTTGCCCG GCGAGCAGGC CACGGTCCTG
47341 TTCGACCGGG CCCTCGGGCT GCCCGAACCG GCCCTGATCC CGCTCGCGCC GGACACCTCG
47401 GCGCTGCGCC GGGCCGAACC GGGCGCACTG CCGGCGCTGT TGACCACGCT GGTGGCCGAC
47461 CCGAACCACC GCGTCGGCGC CGCCGCCGAG GCGGCGCCCG CACTGATCGG CCGACTGCTC
47521 GACCTGCCGG ACGACGAGCG GGAAAGCGTC CTGGTCGACC TGGTTCGCGG CTGCGCCGCC
47581 GCGATCCTCG GTCATGCCGA TCCGACCGCG ATCGAGACGG GAGCGGCGTT CAAGGATCTC
47641 GGCTTCGACT CGCTGACCGC CCTGGAGATG CGCAACCGAC TGCGCGCCGC GCTGGGCCTG
47701 ACCCTGCCGG CCACGCTGAT CTTCAGCCAC CCCAACGCGG CGGCCCTGGG CCGGCACCTG
47761 CACGGCCTGC TGCGCCGCGA GCACGGGGTC TCGTGGGACT CGGTGCTCGG CGAGATCGAC
47821 CGGGTCGAGG CGATGCTCGC ACAACTCGAC GACGCGGACC GCGCCAGGGC GACGGAGCGG
47881 CTGCGGGACC TGATCGGCGG CCCGGAAGCC CCGCTCGCCG GCGCGAGTC GGGCGCGAAC
47941 GGCGCACGCG GCCCGGCGGA CCGGAACACG GCCCGGCGGT CCGGCGCACG ACGAGGAGCT GTTCGACTTC
48001 ATCACGCGCG GGATCGAGCA CTGATTCGAC AACGGCGGGA TCGAGGACCG ACGACAGATC
48061 GCGGGGCTGG GACTCTCCCG TCCTCCTGAA CAGGCAAGGA GAAGCACCGA TGGCGAACGA
48121 AGACAAGCTC CGCGACTATC TGCGCCGGGC CACCACCGAA CTGCAGGAGA CCCGACTGCG
48181 GTTGCGCGAG ACAGAGGACA AGTGGCACGA ACCGCTCGCC ATCGTCGGCA TGCACTGCCG
48241 CTACCCGGGC GGGGTGGCCT CGCCGGACGA CCTGTGGGAC CTGGTCGACG CGGGCACCGA
```

FIGURE 5 (Continued)

```
48301 CGCGATCACC GGACTGCCCC CGGGCCGGGG CTGGGAGGTG GACGAGGCCG CGAACGGCAC
48361 GTCGTACCGG GGCGGTTTCC TGACCGACGC GGCCGACTTC GACGCCGACT TCTTCGGCAT
48421 CTCGCCGCGC GAGGCGCTGG CCATGGATCC GCAGCAGCGG GTGCTCCTGG AGGCGTCCTG
48481 GACGGTCTTC GAGCACGCCG GGATCGATCC GACCACGCTG CGCGGCAGCC GTACCGGGGT
48541 GTTCGTCGGG GTGATCGCCA GTGACTACCT GTCGCGCCTG GCCCGGGTGC CAAGGAGGT
48601 CGAGGGCCAT CTGCTGACCG GCAGCCTGGT CAGCGTGGCG TCCGGTCGTC TCGCCTACCA
48661 CTTCGGGCTG GAGGGCGCGG CGGTCACCGT GGACACCGCC TGCTCGTCCT CGCTGGTGGC
48721 GGTACACCTG GCCGGCCAGG CGCTGCGCGC GGGCGAGTGC GACCTGGCCC TGGTCGGCGG
48781 GGCCACCGTC CTGGCCACCC CAGGCGCGTT CGACGAGTTC TCCCGGCAGC AGGGCCTGGC
48841 CGGCGACGGT CGTTGCAAGT CCTTCGCGGC CGGTGCAGAC GGCACCGGCT GGAGCGAGGG
48901 TGTGGGCCTG CTGTTGATGG AGCGGTTGTC CGACGCGCGC CGCAACGGAC ACCGGGTGCT
48961 CGCGGTGGTG CGCGGCTCGG CGGTCAACCA GGACGGCGCC TCAACGGAC TGACCGCGCC
49021 GAACGACCTG GCCCAGGAGC GGGTGATCCG GCAGGCGCTG GCCAATGCCC GACTGGCCGC
49081 GAGCGACGTG GACGCGGTGG AGGCACACGG CACCGGCACC CGACTCGGCG ACCCGATCGA
49141 GGCCCAGGCG CTGCTGGCGA CCTACGGGCA GAACCGGCCG GCCGCACGGC CGTTGCGGCT
49201 GGGCTCGATC AAGTCGAACA TCGGCCACGC CCAGGCGGCG GCCGGGGTGG CGGGCGTGAT
49261 CAAGATGGTG CAGGCGCTGC GGCACGGTGT GCTGCCGCGC ACGTTGCACG TGGACGAGCC
49321 GACGCCGCAC GTGGACTGGT CCGCCGGGCG GGTGGCGCTG CTCACCGAGC CGATGGCGTG
49381 GCCGGCGGGT GAACGGGTGC GCCGCGCGGG GGTGTCCTCG TTCGGGGTGA GCGGGACCAA
49441 CGCGCACGTG ATCGTGGAGG AGGCGCCGCC GGTCGAGGAA CCGGTCGGGG CGGCCGATCC
49501 GGCGCGCGCC CTCGGCGTAG TGACGCCGTG GGTGGTGTCG GCGCGCACCG AGGACGGCCT
49561 GCGGGCCCAG GTGGAGAGGT TGCGGGAGTG GGCGATCGAG CATCCGGAGG CCGATCCGGC
49621 CGACGTGGGC CGGTCGTTGG CCTCGGGGCG GGCACTGCCC GGCCACCGGG CCGTGGTACT
49681 CGGCCGGGAC GCGGCGGAGT TGGTCGAGGG GTTGTCCGTC GTGGTGGACG GCGAGCCCGA
49741 GGCGATCGTG GGCGAGGCCC GGCGCGGATC GGGCCGTACC GCCGTGTTGT TCACCGGGCA
49801 GGGGGTGCGC TCGCGCGGGA TGGCGCGCGA ACTGCACGCG GCGTTCCCGG TGTTCGCGGC
49861 GGCGCTGGAC GAGGTGTGTG CCGCGTTCGA CGCGGTGTTG CCGTTCTCGG TACGGGACGT
49921 GCTGCTGGCA GAGGGCGAGG GCGGCGGCGC GGACGGTGAC GGCGGCGAGG ACACCGGTGT
49981 GGCGCAACCG GCGTTGTTCG CCTACGAGGT GGCGCTGTAC CGGTTGTGGA CCTCGTGGGC
50041 GGCGGCGCCC GACGCGGTGG CCGGGCACTC GCTCGGCGAG GTGGTCGCGG CCTATGTGGC
50101 AGGGGTGTTC TCGCTCGCCG ACGCAACCAC GTTCGTCGCG GCCCGCGCCA CGCTGATGAG
50161 CGCGCTGCCG CCCGGTGGCG CGATGGTCGC GGTGGGCACG TCGGAGAGCG CGGCGGCCCG
50221 GTTGCTCGCC GACCATCCGG GAGTGGGCAT CGCGGCGGTG AACGGGCCGA CCGGCGTGGT
50281 GCTTTCCGGC GAGGCGGCGG CCGTGGCGGA GGTTGCCCGG GTGTGTGCCG AGCGCGGGCT
50341 CCGCATCTCC CGGCTGCGGG TGTCGCATGC GTTCCACTCG GCGCTGATGG AACCGATGCT
50401 GGACGAACTG GCCGAGGTCG TCTCGGGATT GACGCTGCGT CCGGCGCGCA TGGCGATCGG
50461 GTCGAACGTG ACCGGCCGGA TCGGGTCGGC GGAGCAGCTG TGCGATCCGC GCTATTGGGT
50521 GGACCACGTG CGGCGCGCGG TGCGCTTCGG CGATGTGCTG GACGCGCTGC GCGCCGACGG
50581 GGTGCGTACG TTCGTCGAGA TCGGGCCGGA CGCCGCGTTG ACCCCGATGG TTGCCGATGT
50641 CACGGCCGAC GCCGACGATG TGGTGGCGGT CGCCACCCGG CGGCGTGACC GCGACCCGGT
50701 GACGGGTGTG GTCGAGGCGC TGGCCCGGGT GTTCGTGCGC GGCGCGGTGG TGGACTGGGC
50761 GGCGTTGGTG CCCGGACGGT GGGTCGAGCT GCCCACGTAC GCCTTCACCC GGCGGCGCTT
50821 TTGGCTGGAC GCCGGTACCG GCGCGGGCGA CCCGACCGGC CTGGGGCAGG GGACGGTGGA
50881 TCACCCGCTG CTCGGTGCGG TGGTCGGCCT GGCCGATGGA CACGGTTCGT TGTTCACCGG
50941 GCGGTTGTCC CTGGACACCC ATCCGTGGCT GGCCGATCAC GTCGTCCTGG ACACCGTCCT
51001 GCTGCCCGGG ACCGCGTTCC TGGAACTGGC CCTGCACACC GGGCGCCGGG TGGGCTGCGA
51061 TCGGGTCGAG GAACTGTCCC TGGAGACCCC GTTGGCGTTC GGCGAGCGCG GTGGTTGCCA
51121 GGTGCAGGTA TGGATCGAGG CGGCCGGCCC CGACGAGCGG CGGCGGGCGA TCACCATCCA
51181 CTCCCGGCCG GACGACGGAG ACGGCGACGA GGGGTGGATC CGCAACGCGG TGGGCACGGT
51241 CGCGCCGGTC GAGGACAAGG CGCCCGCCGA CGCCGTGGCC GACCCGACCC CCTGGCCGCC
51301 GACGGGCGCG ACACCCGTGC CGATCGACGA CTTCTACCCC TGGCTGGCCG ACAACGGCGT
51361 GGCCTACGGA CCGTGCTTCC GGGCGGTGCG CGCGGTCTGG CGTCGCGGGG AGGAGATCTT
51421 CGGCGAGATT GCGCTACCCG AGCAGGTCGG GTACGAGGCC GACCGGTTCG GCGTGCACCC
51481 CGCGCTGATG GACGCCACCC AACACCTTCT CGGGGTGGCC GCGTTCGCGG ACCCGGCGGA
51541 GAGCGAGGGC GGCGGTTTGG CGCTGCCGTT CTCGTGGCGT GAGGTACGGC TGCACACTCC
51601 CGGCGCGGCC TCGGTACGGG CGCGGGTGGT GCGGACCGGG CCGGAGTCGG TGACGCTGAG
51661 CCTGGCCGAC GAGGACGGCC GACCCGTCGC CGAGGTCGAG TCGTTGGCCG TGCGGCCGAT
51721 CTCGGCCGAA CAACTGCGCA CCTCCACGGC GGGTCGCCGC GACCCGCTGT ACACGCTGCG
51781 CTGGACGCAA CTGCCCCGGC CGTCGGCCGC GCCGGGCATC GGATCCCCGG CGATCATCGC
51841 CGATTCGGGC TCGGGGGACC CGTTCGCGGG CCGGCTCGGC GCACCGTAC ATCCCGATCT
51901 CGACCGCGCTC GCCGACGCGG TGGACGCCGG GCTGCCGACG CCCGAGGTCG TCGTCCTCGC
51961 GTGGCCCACG ATCCCGGCCG GACCGCTCGG CGACGTGCCG GACCCGGACA CGTACACGC
```

FIGURE 5 (Continued)

```
52021 CGCCGTACAC CGGGCGTTGG CCACCGTGCA GACCTGGCTC GGGGACGAAC GCTTCACCGG
52081 CGCCCGCCTC GTCGTGGTCA CCCGGGGCGC GGTCGCCGTC GCGGACGAGG AGGTGCGGGA
52141 TCCGGCCGCC GCCGCCGTCG GCGGCCTGGT GCGGTCGGCC CAGTCCGAGC ACCCGGACCG
52201 GCTCGTCCTC GTCGACCTGG ACGAGGACGC GGCCTCGCCC GGGGCGCTGC CGGCCGCGAT
52261 CGGCGCGGGC GAGCCGCAAC TCGCGGTACG GGCCGGGGTG GCGTACCTGC CCAGGCTCAC
52321 CCGGACACCC GCGATCGAGC CGAGCACGCC ACTGTTCGCG CCCGACGGTA CGACCCTGGT
52381 CACCGGCGGC ACCGGTGCGC TCGGCGCCCT GGTCGCCCGG CACCTGGTGG TCGCGCACGG
52441 GGTGCGCCGG CTGCTCCTGG TCAGCCGGCG CGGGATCGCC GCACCGGGCG CCGGGTCGCT
52501 CGCCGCCGAA CTCACCGGCC TGGGCGCGAC GGTCGACGTG GTGGCCTGCG ACGTGTCGGA
52561 CCGGGCCGAC CTGGCCAAGA AGCTGGCCGC GATCCCGTCC GCACACCCAC TGTCCGCCGT
52621 CGTGCACGTC GCGGGAGTGG TCGACGACGG GGTGATCGGC GCACTGACGC CCGAGCGGGT
52681 CGACCGGGTG TTGCGGCCCA AGGTCGACGC GGCGCTGCAC CTGCACGAGT TGACCCGGGA
52741 CGCGGACCTG ACCGCGTTCG TGCTGTTCTC CTCGGTGGCC GGGGTGATCG GCAGCCTCGG
52801 ACAGGCGAAC TACGCAGCCG GCAACGCCTT CCTGGACGCC TTCGCACAGC GGCGACGTGC
52861 CCTCGGCTG CCCGCGGTGT CCATGGCCTG GGGATTGTGG GCCGAGGAAA GCGGGCTGAT
52921 GCGTGAGGAG TTCGCCGAGA CCGACCGGCA ACGCATCAAC CGCAGCGGTG TATTGCCGCT
52981 GTCCGACGAA CAGGGCCTGG CACTGTTCGA CGCGGCGCTC GCGCACGGCG AGCCGATCCT
53041 GGCCCCGGTC CGCCTGGACC TGAGCGCGCT GCGCCGCCTG GAGGACGAAC TTCCCGCCAT
53101 CCTGGGCGGA TTGGTGCCCA CCTCGCGCCG CGACGGCGCC CGCCCCGGCG CGGCGGACAC
53161 CCGCCGACTG GCCCAGCGGC TCGCCGGCCG CTCCGAGCCG GAGCAGCTGC GCCTGCTCAC
53221 CGAACTGACC CGCGCCCAGG CCGCCGTGGT GCTCGGGCAC GCGGGCGCCG ACGCGGTCGC
53281 CGCCGACCGC GCGTTCACCG AACTGGGCTT CGACTCGCTC ACCGCGCTGG AGATGCGCAA
53341 CCGGCTCAAC ACGGTCACCG GCCTGCGGCT GCCCGCCACG GTGCTGTTCG ACTATCCCAA
53401 CGCCGCCGCG CTGCCCGCT TCCTGCGCGC CGAGACGCTG CGCGTACCGC AGTACACCCA
53461 GGCCGGCGCG AACACTGCCG CCAAGGCCCG GACTTCGGAC GAACCGATCG CGATCGTGGC
53521 GATGAGCTGT CGCTACCCGG GCGGCATCGA CACCCCCGAG GAGTTGTGGC GCTGCGTCGC
53581 CGGCGGAGTG GACCTGACCT CGCCGTTCCC GACCGACCGC GGCTGGGACC TGGGCGCGCT
53641 GTACGACCCG GACCCGGACC GCTCCGGGCG CTGCTACACC CGCGAGGGCT CGTTCATGCG
53701 CGACATCGAC CGCTTCGACG CCGAACTGTT CGGGATCTCC CCGCGCGAGG CGCTGGCCAT
53761 GGACCCGCAA CAGCGGCTGC TCCTGGAGAC CTCCTGGGAG GCGTTCGAAC GCGCGGGCAT
53821 CGACCCGTCC TCGCTGCGCG GGAGCAATAC GGCGGTCTTT GCGGGCCTGA TGTACGCGGA
53881 CTACGCCGCG GGTCGAGTGG GTGACGTCGG CGACGAGTTG GAGGCGTACA TCGGCAACGG
53941 CAACTCGTTC GGCGTCGCCT CCGGTCGGGT CGCCTACACG CTGGGACTGG AGGGCCCGGC
54001 GGTGACCGTG GACTCGGCCT GCTCGTCCTC GCTGGTCGCG CTGCACTGGG CGGCGCACGC
54061 GCTGCGCAGC GGGGAATGTG ATCTCGCGCT GGCGGGCGGG GCGACGGTGA TGTCCACGCC
54121 CAGTGTCTTC GTGGAGTTCG CCCGGCAGCG CGGCCTGGCA CCCGACGGCC GGTGCAAGTC
54181 GTTCGCCGCG GCGGCCGACG GCACGGCGTG GGGCGAGGGC ATCGGCATGT TGCTGGTGGA
54241 GCGGCTGGCC GATGCGCGCC GCAACGGGCA TCCGGTCCTC GCGGTGCTGC GGGGTTCGGC
54301 GATCAACCAG GACGGCGCCT CCAACGGCCT CACCGCGCCC AACGGCCCGT CGCAACAGCG
54361 GGTGATCCGG CAGGCGCTGG CGAACGCCGG GCTGGCCACG GCCGATGTGG ACGCGGTCGA
54421 GGCGCACGCG ACCGGGACGG TACTCGGCGA CCCGATCGAG GCCCAGGCGC TGCTGGCCAC
54481 CTACGGTCGG GACCGGCCGG CGGAACGGCG GCTGTGGTTG GGATCGATCA AGTCGAACTT
54541 CGGCCACACC CAGGCGGCGG CCGGGGTGGC CGGGGTGATC AAGATGGTGA TGGCGATGCG
54601 GCACGGGATG TTGCCGCCGA CGCTGCACGT GGACGAACCC TCGCCGCATG TGGACTGGTC
54661 GACCGGGCGG GTCGAACTGC TCGCCGAGGG GCGGCCGTGG CCCGAGGTGG GGCGGGCCCG
54721 TCGGGTGGCG GTGTCCTCGT TCGGGATCAG CGGGACCAAC GCGCACGTCA TCCTCGAACA
54781 GGCCGACGAG GAGCCGGAAC CCGCCGCCCG AACCACGTCC GGCACCGGCA TCGGCGGGGT
54841 GCTGCCGTGG GTGCTCTCGG CCCGGACCGA GGCGGGCGTG CGGGCCCAGG CGGCCCGGCT
54901 GAGGGACTGG GCCGGGCCC GGCCCGAGGT CGATCCGGCC GACGTGGGCT GGTCGTTGGC
54961 GTCGGGACGG TCCGTATTCG AGCGGCGCGC GGTGGTGTGG GGCCGGGACG GCGCGGAGTT
55021 GACGGCGGGC CTGGACGCGC TGGCGGCCGG GCGGGATGCG GGAGCACGTG CCGTGCTTGC
55081 CGGCGGCACC GGCGTGTCGG CGAGGCGG CGTCGGGCCG GTGTTCGTGT TCCCGGTCA
55141 GGGCTCGCAG TGGGTCGGGA TGGCGGCGGA ACTGCTGACC TGCTGCCCGG TGTTCGCCGA
55201 GTCGGTGGCG GAGTGCGCGG CGGCGATGGA TCCGCTGCTG GCCGACTGGG CACTGCTCGA
55261 CGTGCTCCGG GACGCGTCCG CCGCGCTGTT GGAGCGGGTG GATGTGATCC AGCCCGTGCT
55321 GTTCGCCGTG ATGGTCGGCC TGGCCCGGTG GTGGGAGTCG TGCGGGGTGC GACCGAGCGC
55381 GGTGATCGGG CATTCCCAGG GGGAGATCGC CGCCGCGCAT GTGGCGGGCT TCCTGTCCCT
55441 GGAGGACGCG GTCCGGATCG TGGTGCTGCG CAGCGGGCA CTGCGGGGC TCGCGGCCGA
55501 CCGGTGACGG ATGTTGTCGG TGGGCGTGTC CGCCGAGCGT GCCGGCGATCA TCGTGGCACG
55561 CGTGCAGGGA TTGTCCCTGG CGGCGGTCAA CGGGCCCGAC AGCGTGGTGC TTTCCGGGCC
55621 GGTCGAGGGT CTGACGCCAA TCGCCGCCGC GTGCGAGCGC GACGGGTTC GGGCGCGATG
55681 GATCCCGGTG GACTACGCCT CGCACTCGGC GCGGATGGAC GACGTACGCG AGGTGCTGGC
```

FIGURE 5 (Continued)

```
55741 CGAGTCGCTG GCCGGGGTCG AGCCGGGGAT CGGGCGGGTG CCGATGTACT CGACCGTGAG
55801 CGGGCTGAAG GTCACCGATG CGGCGGATCT GGGCGGGGAG TACTGGTTCG AGAACTTGCG
55861 TCGCACCGTG CAGTTGGCCA CGGCGGTCGG GGCGGCGGCG GCCGACGGGC ACAGCGTGTT
55921 CGTCGAATGC AGCCCGCACC CCGGTCTGGT GGTGCCGCTC GGCGACACCC TCGACGCCCT
55981 CGGGAGCACG TCCGGCACGG TCCTGGAGAC GCTGCGCCGG GGCGAGGGCG GCCCCGAACG
56041 CCTGGTCGCG GCACTGGCAG CGGCCTTCGT GAGCGGCCTG CCGGTCGACT GGGCCGGGCT
56101 GCTGCACCAC GACGGGGTCC GGCGAGTACA GCTGCCGACA TACGCCTTCC AGGGCCGCCG
56161 CTTCTGGCTC GAACCGGACA TGGGCACGGC GCTGCCCGGC CGGACGACAC CGACGCCGGT
56221 GGTGGGCGAC ACCGAGGACA GCAGGTTGTG GGAGGCGCTG GAGGCGGCGG GCGCCGAGGA
56281 CTTGGCCGCC GAACTGGAGG TGGCGGCGGA CGCGCCGCTG AGCGACGTGT TGCCGGCGCT
56341 GACGTCCTGG CGGGCGCGGC GGCGGGCGGA CGCGACGGTG CGGTCCTGGC GGTACGGAGT
56401 GCGGTGGGAG CCGTGGGCGG CGCCGGCCGC CTCCGCCGAC AGGATGGGGC GTCTGCTGCT
56461 CGTCGCTCCG GACGGGGAGA TCGGGGACGT GCTCGCGGGC GCGCTGGCCG AGTGTGGTGC
56521 CGAGGTGGTG GTGCTGTCCG CGGAGGGGGA ACGGACCGCG TTGGCGCGGC GGCTCGCGGC
56581 AATCGGCGAG GAGGGTGTGC CGGCCGGGGT GGTGTCGTTG TCGGCGGTGG GTTGCGCCGC
56641 CGACGCGGAT CCCGTGCCCG CGCTCGCGCC GGTGCTCACG CTGGTGCAGG CGCTGGGCGA
56701 CGCCGGGATG GAGGCACCGT TGTGGGTGCT GACGCGCGGC GCGGTGTCGG TGCTGGGCGA
56761 GGAGCCGACC GGCCCGGCGG GTGCGGCCGT GCAGGGGCTC GGGCGGGTGG TCGGGCTGGA
56821 ACATCCCGGG CGGTGGGGTG GGCTGATCGA TCTGCCGCAG GTGGTGGACG GCCGGGTGGC
56881 GGAGACGCTG GCGGGGATCC TGGCGGCCGG CGCGGGCGGC ACCGGCTCGG GTGAGGACGA
56941 GATCGCGATC CGGCCGCTGG GAGTGTTCGT CCGGCGGTTG GCGCGGATGG CCGGGCCGGA
57001 GGGCAGCGGG ACGAGCCGGT GGCGCCCCGG TGGTACGGCG TTGGTCACCG GCGGTACCGG
57061 TGCGCTGGGC GGGCGGGTCG CGCGGTGGCT GGTCCGGGAG GGCGTCGAGC GGGTGGTGTT
57121 GGCCGGGCGG CGTGGGCCCG ACGCGCCGGG CGCGGACCGA CTGCGCGAGG AACTGGCGGC
57181 GGCCGGGGCC GAGGTGGCGG TGCTCGCCTG TGACCTGGGC GATCGCGACG CGGTGGCCGC
57241 GCTGTTGGCG GAGGTGCGGG CCGGCGGCCG GCGGATCGAC ACCGTCGTAC ACGCGGCCGG
57301 CGCGGTGGTG GTCGGCCCGC TGGCGGACAG CACCGTCGCG GATCTCGCCG ACGCCTCGGC
57361 GGCCAAGGTC GGCGGCGCGC TGCTCCTGGA CGAGTTGTTG CGGGCCGACG AGCCCGACAC
57421 CGTGGTGCTG TTCTCCTCCG CCGCCGGGGT GTGGGCGGCC GCGGGGCAGG GGGCGTACGC
57481 GGCGGCCAAT GCCTGCCTCG ACACGATCGC CGAGCGGCGC CGGGCGCGCG GGCTGCGTAC
57541 CGTCTCGATC GCTTGGGGGC AGTGGGCCGG TGGCGGGATG GCCGACGGCG CGGCCGGCGC
57601 GCACCTCGAC CGGATCGGGG TCCCGGCGAT GGACCCGGAT CGGGCCCTGG AGGCACTGCG
57661 GCAGGCCCTG GACGAGGACC TGACCTGCGT CACCGTGGCC GACGTGGACT GGCCGAGGTT
57721 CGCCGCCGGG TACACGGCGG CCCGGCCGCG ACCGCTGATC GCGGACCTGG TGGCGGCGGA
57781 GGTCGCGGCG GCGCCGGTCA CCGAAGCGCG CGGGGCGGGC GAGCCGGACG GTCCGAGTGT
57841 GTGGCGGGCC CGACTGGCCG AACTGGGCGC GGCGGATCGG GAGGCGGAAC TGCTCGCGCT
57901 GGTCCGCACC GAGGTCGCCG CGCAGTTGGG CCACGCCGAC CCGGCCGCGA TCGAACCCGA
57961 ACGGCCGTTC CGCGATCTCG GGTTCGACTC GCTCGCGGCG GTGGGCCTGC GCAACCGACT
58021 GACCGAGACC ATCGGTCTGC GGCTGCCCAG CACGCTGGTC TTCGACCACC CGACGGCCGT
58081 CGCACTGGCC GCGCACATCG ACGGCGAACT CTTCGCCGAG ACCGTCGGGA CGGTCTCCGT
58141 CTTCGCCGAA CTGGACCGCC TGGAAGCGGC GCTCGGCGAA CTGGGCGGCG ACTTCGCCGA
58201 ACGGGGCAGG GTCGGTGCCC GGTTGGCCGA ACTCGCCGGG AAATGGCGGG AGATCGAGGC
58261 CGCGAGCCAA AAGGCCGAGC CCGAGGGAGC CGACTTCGCG GCAGCGGAGG ACGAGGAGAT
58321 GTTCGACATG CTCGGAAAGG AGTTCGCAT CTCCTGAGCG GGGCCGGCGA CGACCGCCGG
58381 TCACGGGTCC CGACGGCACA CGGCTCGATC AGGTTCGACC AGGCAGAGGA CGGACGTACG
58441 GACATGTCGA ACGAAGAACG GCTGCGGCAC TTCCTCCGGG AGACCGCCAC GGATCTGCGC
58501 CGCACCAAGC AGCGGCTGCA CGAGGTGGAG TCGGCCGCCC GCGAGCCGGT GGCGATCGTG
58561 GCGATCGGGT GCCGACTGCC GGGCGGCGTG CGCTCCGCCG AGGACCTGTG GGAGCTGGTG
58621 CGGACCGGGA CGGACGCGAT CGCCGGCTTC CCGTCCGACC GGGGTTGGGA TCCGGCGAAC
58681 GTCTACGCGG ACCTGCCGGG CGGCGAGGGC GTCTCGGGCG GTTCGGCCGG ATCCGGCGGG
58741 TCGACCACCC GGCAGGGCGG ATTCGTCTAC GACGCGGCTG CGTTCGACGC CGAGTTCTTC
58801 GGCGTCTCGC CGCACGAGGC GTTGGCGATG GACCCGCAGC AGCGGCTGCT CCTGGAGACC
58861 GCGTGGGAGA CCTTCGAGCG GGCCGGCATC GATCCGCTGT CGATGCGGCG CAGCCGGACC
58921 GGCGTGTTCG TCGGCGCCGG TGCGCTCGGC TACGGCGGCG GGATGCGGGC GGACAACGCC
58981 GAGATCCAGG CCCATCGGGT CACCGGCGGC TCGATGTCCG TGGTGTCGGG GCGGATCGCC
59041 TACACGCTCG GTCTGGAGGG CCCGGCGGTC ACCCTCGACA CGGCGTGTTC GTCGTCGCTG
59101 GTGGCGCTGC ACCTGGCGGC CAACGCGCTG CGCTCGGGGG AGTGCGACCT GGCCCTGGCC
59161 GGGGGCGTCA CGGTGATGGC CCGGCCGACC GCCTTCGTGG AGTTCTCCCG GCAGGGCGGA
59221 TTGGCCTCGG ACGGCCGGTC CCGGTCGTTC GCGGCGGCGG CGGACGGCAC CGGGTGGGGT
59281 GAGGGTGTCG GGCTGCTGCT GGTGGAGCGG TTGTCGGATG CGCGCGCAA CGGCCATCCC
59341 GTACTGGCGG TGCTGCGCGG CTCGGCGGTG AACCAGGACG GCGCGTCGAA CGGGTTGACC
59401 GCGCCGAACG GGCCGTCGCA ACAGCGGGTG ATTCGACAGG CGTTGGCGGC GGCGGGCTTG
```

FIGURE 5 (Continued)

```
59461 TCGGCCGCCG ATGTGGACGC GGTGGAGGCG CATGGGACCG GGACGGTGCT CGGCGACCCG
59521 ATCGAGGCGC ACGCGCTGTT GGCCACCTAC GGGCGGGATC GGCCCGCGGA TCGGCCGTTG
59581 TGGCTGGGGT CGGTCAAGTC CAACATGGGC ACACCCAGT CCGCGGCCGG GGTCGCCGGG
59641 GTGATCAAGA TGGTGATGGC CCTGCGGCAC GGGCTGCTGC CGCGCACCCT GCATGTGGAC
59701 CGGCCGTCGC CGCACGTGGA CTGGGCCTCG GACGGGTCG AGCTGCTGAC CGACGAGGTG
59761 CCGTGGCCCG CGGGCGGTCG GGTGCGTCGG GCGGGTGTGT CGTCGTTCGG GATCAGCGGG
59821 ACGAACGCGC ACGTGGTCCT GGAGGAGGCG CCGGCCGTCG AGGGGGCCTC GGGGGAGGGG
59881 GCCGAACCCG CGCCGGGTGT CGGTGGGTTG ATTCCGTGGG TGGTATCGGC GCGCTCCCCG
59941 GAGGCGTTGC GCGCGCAGGC GGCGCGGTTG CGGGAGCCGG CGGTCGCGGA TCCGGCGGAT
60001 GTCGGTCGGT CCTTGGTGAC GGGACGGGCG TTGCTCGACC ATCGGCGGT GGTGCTGGGT
60061 CGGGACGCCG CCGAGTTGGG CCGTGGACTG GCCGCGTTGG CGGCCGGGTC TCCGGGTGCG
60121 GTCGAGCCGT CGGAGGGGGG AACTCCGGTC GTGGTGACCG GGAATGTGCC CCGAGCGGGT
60181 GGTGCGGGTG GTCGGGTCGC CGGGCGGGGC GCGGTGGTGT TCACCGGGCA GGGGGGTCGG
60241 TTGCCCGGGA TCGGGCGGGA ACTGTACGCG GGTTTCCCGG TGTTCGCTCG CGCGCTGGAC
60301 GAGGTGGGTG CGGCGTTCGA CGCGGTGGTG CCGTTCTCGG TCCGGGACGT GTTGCTCGGC
60361 GTGGAGGGCA CGGTCGGCGT CGATGCCGAC GACACCGGCG TGGCTCAGCC GGTGTTGTTC
60421 GCGTTCGAGG TGGCGCTGTA CCGGCTGTGG AGTTCGCTGG GGTCGGTCCC GGATTTCGTG
60481 GTCGGACACT CGTTGGGTGG GATCGTCGCG GCGCATGTGG CGGGGGTGTT CTCGCTCGCG
60541 GACGCGGTGG CGTTCGTCGC GGCGCGCGCC CGGTTGATGA GCGCGTTGCC GGGCGGGGGC
60601 GCGATGCTCG CGGTGGGGGC GAGCGAGGCG CAGGTCACCG CGCTGTCGGA TGGGCTGCCG
60661 GTGTCGATCG CGGCGGTCAA CGGACCGGCG AGTGTGGTGG TTTCGGGCGC GGTGGCGGCG
60721 GTGGACGAGG TGGCGGCGCG GTGTGCGGCG CGCAGTTGGC GCAGTTCGCG GTTGCGGGTC
60781 TCGCACGCCT TCCATTCGGT GCTGATGGAG CCGATGTTGG CCGAACTACG GGACGTGCTG
60841 CGCCGGTTGT CGTTCGGGGC GCCGGAGATC GGGTTGGTGT CGGATACCAC CGGGCGGGTC
60901 GTTACGGCCG AGGAGGTGGG TGATCCCGAG TACTGGGTGG GGCATGTGCG CGACGCGGTG
60961 CGGTTCGCGG ATGCGGTCGG CACGTTCGT GAGCGGGGTG TGGCCACCTT CGTGGAACTG
61021 GGTCCGGACG CGGCGTTGAC CGCGATGGTG GCCGAGTGCA CGGCGGGTGT GGGCGAGGTG
61081 CTGGGGGTGC CGGCCCAGCG GCGTGGCCGA CCGGCCGTGG CGACGCTGGC CGGCGCGCTG
61141 GCCACGGCGT TCGTGCGGGG GCTGCCGGTG GACTGGGTCG GGGCTCTCGG CGGCCCGGGC
61201 GGGCGGCGGG TGGAGCTGCC GACCTACGCG TTCCAGGGGC GGCGCTATTG GCTGGAGCCG
61261 GGGAAGGCTT CGGTGACGCC GGCCGGGCCG GATTCGGTGG ACGGTCCGCT GTGGGACGCG
61321 GTCGAGCGGG CCGGGGCGGG CGAACTGGCG GCGATCCTGG CGGTGTCCGA GGACGCGACG
61381 CTGCGCGAGG TGGTGCCGGC GCTGTCGTCC TGGCGAGCCC GACGACGGGT GGACGCGACG
61441 GCCGCGTCGT GGCGCTACGC GGTGCGGTGG GAGCCGTGGG CGGGTGGTTC GTCCGACGCG
61501 GCCGCGTTGT CCGGGCGTTG GCTGCTCGTG CACCCGGCGG CGAGCGAGCT GGCGGATGCG
61561 GTGGCCCGGG AGCTGACCGA GCGTGGCGCG GAGGTGGTGC GGGTCGGGGG CGAGGGCATC
61621 GGGTCGCACG TCGGTGCCGA ACCCGTCGCC GGGGTGGTGT CGTTGATCGG CTCCGGTTCG
61681 GGCTCCGGCT CCACTTCGGG TTCGGGCTCG GCTCCGGTT CCGCTTCGGG CTCGGGCTCC
61741 GGGTCCGGTT CGGGCTCCGG CTCCGGCTCT GGTTCGAGTT GCGGCTCCGG TTCGGTGCCG
61801 GGCTTGGGTT CGTGCGCGGG CGACGACTGC GCCGACCTCG TGGCCGCCGT GGTGGCGATG
61861 GGCGAACTGC TCGCGGAGCT GCGCCGGTTC GAGGTCGCCG CCCCGCTCTG TGTGTGACC
61921 CGGGCGGCGG TGTCGGTTCT GGGCGAGGAC CTGGCCAATC CGTGGGCGC CGGCCTGTGG
61981 GGCAGGGGCC TGGTGGCGAG CCTGGAGCAA CCCGGGTGCT GGGGCGGCCT GGTCGACCTG
62041 CCGGCCGTCG CGGATACCCG CGCGCTGGGG GTGCTGGCCA CGATCCTGGC CGGGACTTCG
62101 GACGAGGACC AGTTCGCCAT CCGCCCGCTG GGCGTGTTCA CCCGGCGGCT GACCCCGCTG
62161 CCGGCCGAGG GATCGGGCCG GGTGGTGCGT ACCCGCGAAG CGGCGCTGAT CACCGGCGGC
62221 ACCGGCGTGT TGGGCGCGCA CGCCGCCCGC TGGCTGGTCG CGCACGGCAC CGAGCGGGTG
62281 ATCCTGCTGG GCCGACGCGG CGCTCGGGCG CCCGGATTCG ATGCGCTGCG GGCCGACCTC
62341 GAGGCGGCCG CGCCGAGGT GGTGGCGATC GCCTGCGACC TGACCGCGCC CGACGCGGCG
62401 GAGCGGCTGC GGGCCGCGTT GCCCGCGACG GGTGCGCCGA TCCGTACCGT CGTGCACGCG
62461 GCGGGCGTGC CCGGATCGCC CACCGCGACC GGCGCCGACG CCGTCGCGGA CACCGTCACC
62521 GCCAAGGTCG CCGGCGCGCT GGCCCTGGAC ACGCTTTTTG GGCGGACCG GGCCCTGGAC
62581 GCGTTCGTGC TCTACTCCTC CGGCGCGGGG GTGTGGGGCG CGCCGGACA GGGCGCCTAC
62641 GCGGCGGCCA ACGCCTTCCT GGACGCGCTC GCCGTACGCC GTCGGCAACG CGGCCTGCCC
62701 GCCACGGCGA TCGCGTGGGG GCCGTGGGCG CCGGCGGGA TGCGGACGG CGAGGGGGAA
62761 CGGCTGCTGG CCCGGGTCGG TGTACGGGCG ATGGACCCGG CCGCGGCGCT GGCCGCACTG
62821 GGCCGGGCCC TGGTCGAGGA CCTCACCTGC GTGACGGTGG CCGACCTGGA CCGGCCCCGA
62881 TTCGCGGCGG GCTACACCTC CGCCCGTCCC CGGCCGCTGA TCGCCGACCT GATCGACGCG
62941 GAGCCGCCGA CCGCGACCGC CCGCCGACCC GGCCCGGCG GGTGTGGGA CCCGGCGGTG
63001 ACCCGCTCGC CGGCCCGGCT CGCGGCCGAA CTGCTCGACC TGGTCCGCGC CGAGGTCGCC
63061 GCGCAACTCG GCCACGCGGG CGTCGAGGCG ATCGAACCCG ACCGGCCGTT CCGCGACCTC
63121 GGCTTCGACT CGCTGGCCGC CGTCGGACTG CGCAACCGGA TCGCCGAGGC CACCGGGGTA
```

FIGURE 5 (Continued)

```
63181 CACCTGGCCG GCACCCTGAT CTACGACCAC GAGACACCCG CGGCCCTGGC CGCACACCTG
63241 GCCGACGCCC TGCGCGAGGG TGTGCCCGAG ACCCGCCCGG CGCCGACGGC ACCCGGCGGC
63301 GCCGAGGACT CGAACGACAT GCTCGGCACG GTCTACCGCA AACTGGCCCT GCTCGGCCGG
63361 ATGGACGACG CGGAATCGCT CCTGGTCGGC GCTGCCGGCC TGCGGCAGAC CTTCGAGGAC
63421 CCGAACCGGC TCCCGAAGAC ACCCGGCTTC ACCCGGCTCG CGCGCGGACC GGCCCGGCCC
63481 CGGGTGATCT GCTTCCCGCC GTTCGCGCCG GTCGAGGGCG CCATCCAGTT CGGCCGGCTG
63541 GCGGGCACGT TCGAGGGCCG GCACGACACG GCGGTGGTGA CCGTACCGGG CTTTCGGCCC
63601 GGCGAGCCGC TGGCCGCCTC GCTGGACGTG CTGCTCGACC TGCTGGCCGA CGCGACGCTG
63661 CGGTGCGCCG GAGACGACCC GTTCGCCGTG CTCGGCTACT CCTCCAGCGG CTGGCTCGCC
63721 CAGGGGGTGG CCGGCCGCCT GGAGGCGACC GGCCGTACGC CCGCCGGGGT CGTACTGCTC
63781 GACACCTACC TGCCCGCCAC GATGTCGCGG CGCATGCGCA AGGCGATGAA CTACGAGGTG
63841 ATCGTGCGCC GGCAGGCGTT CACCGCGCTC GACTACATCG GCTGACCGC GATCGGCACC
63901 TACCGCCGGA TGTTCCGGGG CTGGGAGCCC AAGCCCGGCT CCGCGCCGAC GCTCGTGGTG
63961 CGGCCCTCGC GCTGCGTCCC GGGCTCGCCG GAGGAGCCGA TGACCGGCGA GGACTGGCGT
64021 TCCACCTGGC CGTACGAGCA CACCGCCGCC GAGGTGGAGG GCGACCACTG CACGATGATC
64081 GGCGAACACG CGGAGCAGAC CGGTGCGGTG GTGCGCGCGT GGCTGGCCGG TGACAGGACG
64141 GTTTCGATCG ACACGAGGGA AGGCACGGCA TGACCGACCC GCGCTATCCG CGATACCCGC
64201 AACCCGGCTC CGTCGACCAT CTCGACGCGG AGTTCCTGGT CCACCGGGCC GCGATCCAGG
64261 ATCTCGTCGC CGCGTACAGC CTGCTCTACG ACGCGGGCGA CTACGACGGG CTCGGCGACC
64321 TGTTCACCGA GGACGCGACG TACGCGTTCA CTCCCGCCCC CGAGGGATTT CCGCCCTCGG
64381 TGTCCGGCCG GGACAAGATC GTCGCGGCGA TGGCCGCGCT GCGCGAGCAC AACCTGCGCA
64441 CCCGGGCCGC CCACCAGCGG CACTTCGTGA CCAACACGGT GATCACCCGC CTCGACGGCG
64501 ACACCGCCGA GGCGCGGTCG CTGATGGCGG TGGCGTTCGC CCATCCGGGG GACGGCCGCC
64561 AAGAGTTCAC CCGCAGTGGG GTGTACGCCG ACGTGCTGGC CGACAGGGA AGCCGGTGGC
64621 GCATCGCCGA CCGGCACCTG TGGTTGGCCG AGTTGCCGGC GCCGCGTCCC GGCGACACAT
64681 CCGCTCCCGA GGAGAGTCGG CCATGATTCC CGTGCTCGAA CTGGTCCAGA TCTCCACACT
64741 CCCCGACGCC GAACGGGAAC TGGAGCAACT GGCCCGGCGA TACCCGATCA TCCGCACCCG
64801 ACAGGTCGGC GGCATCGAGG CGTGGACCGT GCTCGGCGCC GGGCTGACCC GGCAACTCCT
64861 CGGCGACCCA AGGCTGTCCA ACGACCTGCA CACGCACGCG CCGCACGCGG CCCAGTCCGC
64921 CGACGGTCCG ACCGTGCTGT TCGAGCAGGA CAATCCGGAC CACGCCCGCT ACCGCCGCCT
64981 GGTCAGCGCC GCGTTCGCGT CGCGGGCCGT GCGCAACCTC GAACCGCGGA TCGTCGACAT
65041 CGCGCGCGCA CTGCTCGACC GGCTGCCGGC CGAAGGCGGC ACGGTGGACA TCGTCGAGGC
65101 GTTCGCCAAC CCCTTCCCGC TGGAGGTGAT CTGCGAACTG CTCGGGGTAC CGATGGCGGA
65161 CCGCGAGGTG TTCCGCACCC GGGTGGAGAA CATGGACTCG CCCTCGACGG CGGTACGCCG
65221 GGCGGCGATG GACGCGTTCG TCGCCTACTG CGCCAACCTC GTCGACGCCA AGCGCACCGA
65281 ACCGACCGAG GACCTGCTGA GCGAGCTGGT ACAGGCCGAA CTCGACGACG GATCACGGCT
65341 GTCGGCCAAT GAACTGATCG GCTTCGGCTC CGTGCTGCTG TTCGCGGGGC ACGTCACCAC
65401 GGCCTACCTG ATCGCCGCCG CGCTGTACGA ACTCATCACC CACAACGACC AGTTGGCCGC
65461 ACTCCGGGCC GATCCCACGC TCGTCGAGGG CACCGTCGAG GAGGCGCTGC GCTTTCGCGG
65521 CTCGTTGTTG TCCACCACGA ACCGGGTGGC GCTGACCGAC CTGGAGATCG GCGGCGTGCT
65581 CGTGCGCCGT GGCGACCTGG TGCGCTTCCT GCTCTCCGCC GCCAACCGCG ACCCGGCGAT
65641 CCGCGAGGAC CCGCACACCT TCGACATCAC CCGGTCCACC ACCGCCCACC TGGGCTTCGG
65701 CCACGGCCCC CACTTCTGCC TCGGCCAACG CCTGGCCCGC CAGGAGATCA AGGTCGCCCT
65761 CACCGAGATC GTCACCCGCT TCCCGACCCT CGAACTGGCG GTCCCGGCGG AAAAGCTGCG
65821 CTGGCGCGCC TCGGACTTCC TGCGCGGCCT TGCCGAACTA CCCCTGACGT ACGCCCCGTG
65881 ACCACCGACG AGGACAGGCG GCCCGGACCC GGGCCGCCCG GCTCCGCGG CGGTCCGCGC
65941 CGGTGTCCGG CGAGTGTGAC GCGCCGTCGA ACAGTCGATG TCGGCTGCGC GGCGTCCGTC
66001 GCGGATCCCG GACCCGTCGT GGTTGCGTAG CATCTCCGGG GGTCGGCGGG CGACGCCGGG
66061 CCACGAACGG CAGGGGCGCG CGCCATGGA CGGACCGGCG GGGAGCCGAA GGCACCCACG
66121 GGCCTGCGCG AGCGCAAGAA GGCCCGCACC CGGCAGGTGA TCTCCACGGT CGCGTTCGAC
66181 CTGTTCGAGG AACAGGGCTT CGAACAGACC ACCGTCGACA TGATCTGCCG CCGCCACGCG
66241 ATGACGGTCA GCCACGGCAA CCTCGAAGAC CACGCCGAAC AAACCGCCCG CCGACACGCG
66301 CTGCGCCGCC GCTTCCTGGG CGTGCGCTCG GTCCACGACC ACGGCGTGGC CCTGATCGAC
66361 ACGGTCGCCC ACCGCATCGT CACCACCGCC GCCGCCCGCC TCGGGGTCGA CCCGGCCGTG
66421 GACCTGCGCC CCCACGCCCT CGGCGCCCTG GTCGCGGCGA TGACCCGCCG CGTGGTGATC
66481 GACGACATCG CCCCGGGCCC GATCAACGAG TGGGCGGAGG CCTTCCGCAC CCTGCTCCCG
66541 ACGCCGGCCG CACACACCGA CTGACACACC GCCCGGGCGC CGACCCGGAA ACCGCCGGGT
66601 TCCTTCGCAC CGCAGGGTGA TCACCGGTCT TCGTCCGTGC GGACACATCT TCGGCCCGCC
66661 GCTCGTGTAC GGATCCGAGG CTCCCGGCCC GGCCGCGGGC GATACTCGGG AAACGTCGGG
66721 GCCCGGGGAG GCGGCGGGTT CCCCATACCC GAGAGGTTCC ACATGCAGCC CGACCCGCGG
66781 TTCGACCCGC AACCCGACAC GGCCGTCGAA ACACCCGTGG ACGAGCACGC CGCCGGCGCG
66841 CCCGCCGATC GGCTCGTCGA CCTCGTCGTC CGGGCCGGTT CCCTCGTCGA CGGCAGCGGA
```

FIGURE 5 (Continued)

```
66901 TCCCCCGCGT ACGACGGCGA CCTCGCGATC GACGGCGGGC GGATCGTCGC GCTCGGCGAC
66961 ATCGGCGCCA TCACGGGGCG TGACGAGATC GACGCACAGG GCTGCGTGGT GTGTCCGGGC
67021 TTCGTCAACG TGCTGAGCCA CGCCTACTTC ACCCTCCAGC AGGACCCCCG TGGCCTGTCC
67081 GACCTGTACC AGGGCGTGAC CACCCAGATC TTCGGCGAGG GCGTCTCGCT CGGCCCGGTG
67141 ACCGGGGCGA TGACCGAGTC CATGATC
```

Figure 6. Amino acid sequence of the *lepA* gene.

```
FEATURES             Location/Qualifiers
    source           1..67167
    misc_feature     <1..23206
                     /note="pKOS279-128.PF27 (partial insert)"
    misc_feature     8184..47817
                     /note="pKOS279-128.2L78 (insert)"
    misc_feature     32653..67167
                     /note="pKOS279-130.PFA42 (insert)"
    CDS              370..25686
                     /note="LepA"
                     /note="PKS (modules 0-4)"
```

/note="sequence=MQVMERGMTEFNADAHRAHPAPEDAVAIVGLACRLPGADGPDE

FWDLLSNGRDTITEVPRHRRDARAADDTNRTAGGSPHPAANRPRRGGFLDAVDRFDAAF

FGITPGEAALIDPQQRLMLELCWEALEHAGIPPTRIRGSATGVFAGAIWDDYATLLRRA

GVEPGPRHATGLHRSMIANRVSYTLGLRGPSMTVDAAQSSSLVAVHLAGESLRRGESTL

ALVGGVNLDLVPDHDGDAAKFGGLSPQGRCFTFDARADGYVRGEGGAVVVLKPLSRALA

DGDVVHGVIRGSAMNNDGGGDALTAPDPRAQAEVIRLARRRAGVAASAVQYVELHGTGT

PVGDPIEAAALGAALGTERANRPPLAVGSVKTNVGHLEGAAGIVGLVKTVLAIRHRRLP

ASLNFAEPHPRIPLGELGLRVQTAEGDWPCPDETLIAGVSSFGMGGTNCHVVLAEAEPA

DGVGPSVASAPSGGSDPGMESATGPVPSDAVAVPISGVDADGLRAQAGRWHGHVREHPD

VAPADLGYSAATTRTAFAARAVVLARDHAELLAGLDALRGAGADPHLVRADAQPGRTAF

LFTGQGSQRPAMAQESYARHAVFAAAFDAACAHLDPHLPRPLREVLFASPDSPDAALVH

RTEYTQPALFAVEVALYRLFEHWGVTPDLLLGHSIGELCAAHVAGVWSLPDACALVAAR

GRLMQELPDGGAMVSLRVAEDDVLASLEPVRDRVSIAAVNGPLATVISGDRDAVLDVAA

GWRAQGHKTTRLRVAHAFHSPRMDAMTDAFAEVAAGLTARAPTLPVVSNLTGLPLTAEQ

ACSPDYWVRHVRHTVRFHDGVRRLRAEGATILLELGPDGSLSAAARTCLLDGERDTVAT

IPTLRRNRPETDALTTAVARLYANGVDPDWERVFAGRGARRVALPTYAFRRARHWPGAS

AEAADTAVPDESLAVVPTLAERLAALSAVEQHRILLDLIRAHATAVLGPGATTTVEPDR

TYRESGLDSLGTVELITRLARDTGLDLPPTTVFDHPTPTALAHHLRTRALDLPVPTRPR

PTPGPARADEPIAIVAMGCRLPGAVRTPEDLWRLVADGVDAITAFPTDRGWDLDRLHHD

DPDRPGTSYVRSGGFLDRAGDFDAEFFGIGPREALAMDPQQRLLLETSWEAIERAGLDP

STLRGERVGVFVGATAQEYGPRMHESTDALAGFLLTGTTPSVASGRIAYTLGLSGPALT

VDTACSSSLVAVHLAARSLASGECALALAGGATVMAGPGMFVEFARQRGLAPDGRCKPF

SADADGTAWAEGVGVLLLERLSDARRNGHPVLAVLRGSAINQDGASNGLSAPNGTAQQR

VIRDALAAAGLDPQDVDLVEAHGTGTPLGDPIEAQALLATYGRDRAADRPLLLGSVKSN

IGHTQAAAGVAGLIKTVLALRHGAIPGTLHLREPSPHVRWSDGAITLPTTTTDWPAYDR

FIGURE 6 (Continued)

```
PRRAAVSSFGISGTNAHVIVEEAGGGAEIPGPAPARGLASAGVADPVPLVVSARSEAAL
RGQAEQLAGLLRAADAPALADVGYSLLRGRAGFEYTAVIPARTHAEALHGLTALAADRP
ADRLIRGGAAAARGGTVFVFPGQGTQWSGMALELLDTSEPFAASMRACTDALDPYAVDW
SLLDVLREPGTPGLTRVDVVQPALFAVMVSLAALWRSIGIEPQAVVGHSQGEIAAAYVA
GALSLADAAKVVALRSRALVAAAGSGGMASVSLPAEQVAALLEPWAGRLGVAAVNGPSA
TVVSGDTAALDTFLDRCAADDLRARRIPVDYASHSVHMEEIRDRLLTDLADVTPRAAST
AFYSTLTGGRMADTSGLDADYWYRNLRRTVRYETAVRALSEDGHRLFVEVGPHPVLTLG
TQETLDACGSGGTTIGTLSRDDGGRARFLVAVAEAVAHGARPDAEALFDPPGTGVRAVA
LPTYAFQHRRYWLTPREAAPEGTAALGLTPISHPLLGALGALGVEPDGTVIATGRISLR
ELPWLADHAVADTVVLPGTAFLELALCVGESVGAPQVEELTLESPLLLPETGDVYLRVA
VAPADEARRRAVTIHSRRAGGGGADAERESWVRHAGGLLVDSVREVDDGGSGGLTQWPP
PGADVLDLADAYPVLAGLGYGYGPAFRGLRAAWRGAGGELFAEVRLPDELRESESGVVG
PEFGIHPALLDAALHPLLSSLSLTSLSSTRDGPAGAPPRIPFSLADVRLYATGADMLRV
RLRRADGGAAALTVADGVGAPVLSIGALTLRELPADGLIAAEPGPGEAMFDLRWIAGSI
PAEPTGLGYAFIGDDLGLGDGEVYPSLADLDARLLATGEPTPDVVFAAAPVGVDDDVPG
AAHDSARWALDLVGGWLAGERSSAARLVVVTRGAVAARTGDALSGLPAAPVWGLLRTAQ
SEHPDRFVLIDLDDAVRSPSALLGAAVAGEPQLALRDGVVHLPRMVAVDSADAQVTRRR
PDPNGTALITGGTGTLGALIARRLAAEHGIRHLLLLGRAGREAPGAEELIAELGALGAR
VTVAACDVADRAALRRVIEDIPAEHPPTIVVHAAGVLDDATLLSLTPDRLDAVLRPKVD
AAWHLHELTRAANPAAFVLFSSITAITGNAGQGAYTAANTFLDALAEHRRAAGLPANAL
AWGLWAEGSGMTRHLDHTDRARMSRGGIAALPTETGLALFDAALHRDRPYTIPARLDRG
ALRALAASGVLPAVLRSLVRVPPPRAAASGDGTDASSWPRRIRELPGEQRERAITDLVR
GQLAAVLGHDAPERLDLDRAFRELGVDSLTALELRNRINAFTGLRLPATVVFDHPSGTA
LVARMMRELVGAVPSEPTTPVVAPTVTVDEPIAVVGIGCRYPGGVAGPEDLWRLVAAGT
DAVGDFPEDRGWDLAKLYDPDPDKVGKVYTRRGGFLYESGEFDAEFFGISPREAAAMDP
QQRLLLETAWEAFEHAGLDPRTLRGSNTGVFAGVMYNDYASRLHRAPDGFEGMLLAGNV
GSVVTGRVSYALGLEGPAVSVDTACSSSLVALHLAANALRSGECDLALAGGVTVMSTPN
VFVEFSRQRGLSADGRCRSFAAGADGTGWGEGVGLLVVERLSDARRNGHPVLALLRGSA
VNQDGASNGLTAPNGPSQERVIRAALAGAGLSATDVDAVEAHGTGTTLGDPIEAQALLA
TYGRDRPADRPLWLGSIKSNIGHTQAAAGAAGLIKMIMAMRHGVLPETLHVDAPSPHVD
WSTGHVELLAERRPWPEVDRARRAAVSSFGISGTNAHVIVEQAPAAEAVVSRDEPVGVA
```

FIGURE 6 (Continued)

```
GLVPWVLSARTADGLRAQAARLREWSARHPEADPVDVGWSLVRERSVFDRRAVVGGRDP
GELGAGLDRLAAGGGIADGRPMFSGPGPVFVFPGQGSQWVGMAAGLLECSPVFAEAVTE
CAAVMDPLVADWSLLDVLRGGSAGELERVDVVQPVLFAVMVGLARWWESCGVKPGAVIG
HSQGEIAAAHVAGYLSLADAVWVVVLRSRALLGVASAGGGMVSVGVSAERARELVAGDD
RLSLAAVNGPTSVVLSGDVEALSVVVEACERDGVRARWIPVDYASHSARMEAVRDEVER
LLADVTPQVGRVPMYSTVSGEVVVDPAELGGAYWFENLRRTVELERAVGAAVADGHGAF
VECSPHPGLVVPMGDTLEAAGVDGVVLETLRRGEGGPDRLVAALSAAFVAGVAVDWAGM
LPGRHVELPTYAFQRRRYWLTGGERAGDPAGLGLVAADHPLLGAVVGSVRDGELLYTGR
LSAATHGWLADHAVFGSVVVPGTAFVELASWVGVEAGCPVVDELTLHAPLVLPDGVGIR
LRVAVGAADSAGRRVVEFHSRPEDAPDEQSWTRHATGTLGAASVPGSASAGAAAWAVWP
PADAEVVDPEAVYERLAEHGYEYGPIFRGLRAAWRRGDDFFAEVALPEAAGRDAHGYDL
HPAVLDAALHVAAAEAVAESGATLLPFAWTGVALHGPGASVLRVMLRRTGRETLAVDVA
DERGVPVASVASLTLRPVAAEQLVAAEEAGREWLYRMVWEIADAPVAEHVEGELLGSDE
ESDASAELVAGGIRVVTPAGAEQVSEVGLFDCPPVVGEAPEEVAGAVHAVLAAVRAWVA
DERFAGARLVVRTRGAVATDAQDRVGSPAHAAIWGLVRVAQSEHPGRFVLVDGDDVDSG
AALRAAVACGLPQVAIREGVVLAPRLVGAVHDTALVPPAPGADQAWRIESGTAGTPDDL
VVTAHPAASAPLAAGQVRVAVRAAGVNFRDVLITLGMYPGRAVVGAEAAGVVVEVGPGV
SEPAVGDRVMGLFEGAFGPLAVADRRLLARVPAGWSFAQAASVPVVFLTALYGLHDLAG
LRSGESVLVHAATGGVGMAATQLARHRGAEVYATASATKWATVRGLGVPDERIASSRDL
SFEQRFARATDGRGIDVVLNSLAGEFTDASLRLLAEGGRFVEMGKTDVRTEGLPAGVRY
RAFDLIEAGPDRIAEMFAELVDLFERGVLQPLPIRTWDIRRAREALRFLGQARHVGKVV
LTVPQPLAADGTVLITGGTGTLGRSLARHLVTRWGVRRLVLTGRAGPAAPGAAELVAEL
AESGADTTIVACDAADRAAMAEVLAAIPAEHPLTAVVHAAGTLDDAPIEALTPERVDHV
LRPKVDAALVLDELTRDADLAAFVLFSSVAGVLGVAGQGGYAAGNAFLDGLAGRRRERG
LPATALAWGLWAERSAMTAQLGVGDLKRLARGGLVPISTAQGLALFDAAWQADEAALIP
ARLDLAALRAQAATQPVHPLLRGLVGTTPTRRNGTPSEAPWARRLASAAPAERVDVALR
LVRAEAAVVLGHESIDGVRPEVTFRDLGFDSLTGVELRNRLSGATGLRLPSTLVFDFPT
PLGLAGFLVAESVGEMDTAPTGPVAGGAVVAADPVVIVGMGCRFPGGVDSAAGLWDLVA
AGGDAIGPFPTDRGWDVDALFDPDPERVGKSYVRTGGFLSGAAEFDAEFFGVSPREALA
MDPQQRLLLETAWETFEQAGIDPTSLRGSRTGVFAGMAGHDYATGGARSQAGLEGHLLT
GNAASVASGRVAYTFGLEGPAVTVDTACSSSLVALHLAANALRAGECDLALAGGVTAMS
```

FIGURE 6 (Continued)

TPDFFLEFSRQRGLSVDGRCKAFAATADGMGAAEGVGLLLVERLSDARRNGHSVLAVVR

GSAVNQDGASNGLTAPNGPSQQRVIRAALADAGLSAADVDAVEAHGTGTTLGDPIEAQA

LLATYGRDRAPDRPLWLGSVKSNIGHTQAAAGVAGVIKMVSALRHGMLPRTLHVDEPTP

HVDWSAGGVELLTSARAWPEAGRVRRAGVSSFGISGTNAHVILEQAEESPAGSVPSATP

PVAGTPVWGGRVPWVLSARSEPALRAQAARLRDWLAVHPDADPLDVGRSLATGRAALDH

RAVVHGRDLAELRLAVAKLADSGPGDEASIVGSVSAAGPVFVFPGQGSQWVGMAAGLLE

CSPVFAGVVAECAAVMDPLVADWSLLDVLRGGSAGGEALAERVDVVQPALFVVMVGLAR

WWESCGVKPGAVIGHSQGEIAAAHVAGYLSLADAVRVVVLRSRALLGVASSGGGMVSVG

VSADRARELVAEDDRLSLAAVNGPTSVVLSGDVEALAVVVDGCERDGVRARWIPVDYAS

HSARMEAVRDEVERLLADVTPQAGRVPMYSTVSGGHVTDPSVLGGSYWFDNLRRTVELE

RAVGAAVVDGHSVFVECSPHPGLVVPLGDTLEAAGVDGVVLETLRRGEGGPDRLVGALS

AAFRSGLAVDWAGSGMVPGRRVELPTYAFQRRRYWVEPGERAGGVGWGQFTVEHPVLGA

GVDLADGAGTVFTGRLSAASHGWLAEHVVLGTVIAPGTAFVDLALRAGATVGRATVEEL

TLHAPLILPDAGGVRIQVRVGAPDAAGVGSVEIHSRPEDAAGDEPWTRHASGTLTATDL

DPADVATEAAIWPPAGSTPVDLDGAYERLATAGFEYGPAFQGLRALWRRGAESFAEIEL

ADDARQEAERYEVHPALLDAAVHALGMEPTAEVAPDEARIAFSWRGVRLVAAGAGRLRV

RLAPVGSDAVSLWLSDMDGEPVGSVRALTVRPVAAERLRPAGAPPRDSMFRVEWRPVSG

DESGVAVRWAVVGAADSGPLARLVAAYPDVPVYRSVVEAAGDVAAGPPDVVVVGVGEAD

CSEGSVERTRRVLADVLAWMQDWLADSRFAATRLVVVTSGAVAADVDADPDERVADLAG

AAVWGLLRSAQSEHPDRCTLVDLDEDAASIDAWPAILASAEPQLAVRMGRFRVPRLARV

TAGGGEPVAFAPDGTVLVTGATGGLGALVARHLVTAHGVRRLLLLSRRGAAAPGAAELV

EDLTAQGAEVTLAACDLADRAALAAELARIPAEHALTGVIHTAGVVDDATIANLTDAHM

EHALRPKADAAFHLDELTRDVNPAAFVLFSSGATTFGGPGQGNYAAANAFLDGLARQRR

DRGLPGISLAWGLWAGAQGMGGRLSEADLARWARTGAVAMPAAEALRLFDIALGRPEAA

LVPAHLDLPAMRADAGARPALFRELLGIGTRRAAVGAGGSALTRRLAGMSPAEREQAVL

DVVRTEAANTLGHESAGAVSAGRAFKELGFDSLTGVELRNRLNTATGLRLPSTLVFDYP

TPAGLAAFLVAELVGRSVQAVPVPPVGGRHGDADDAIVIVGMGCRFPGGVASPEDLWNL

LASGGDAIGPFPTDRGWDLAGLFDPDPERAGKSYVESGGFLYGIGEFDAEFFGISPREA

LAMDPQQRLLLETAWETFERAGIDPTSLRGSRTGVFAGVIDNDYGARVNQVPDEVEGYL

GYGSSASIASGRVSYVLGLEGPAVSIDTACSSSLVALHLAVNAVRSGECELALAGGVTA

MATTEFFVEFSRQRGLSPDGRCKAFAAAADGMGAAEGIGLVLVERLSDARRHGHSVLAV

FIGURE 6 (Continued)

```
VRGSAVNQDGASNGLTAPNGPSQQRVIRQALGAAGLSAADVDAVEAHGTGTTLGDPIEA

QALLATYGQDRPGDRPLWLGSVKSNIGHTQAAAGVAGVIKMVLALRHGVLPRTLHVDEP

TPHVDWSAGRVEVLADEVAWPAGERVRRAGVSSFGISGTNVHVVLEEAPADAAEPAPAA

PEVPGVGGVLPWVVSARTEAGLRAQAARLRDWVSEHPDAEPTDVARSLVVGRAVLDVRA

VVRGRESGELVAGLDELARAGVGDPGSLVSGSDPVFVFPGQGSQWVGMAAGLLECSPVF

AGVVAECAAVMDPLVADWSLLDVLRGGSAGELERVDVVQPVLFAVMVGLARWWESCGVK

PGAVIGHSQGEIAAAHIAGYLSLADAVRVVVLRSRALLGVASSGGGMVSVGVSAERARE

LVAGADGLSLAAVNGPTSVVLSGDVEALSVVVEACERDGVRARWIPVDYASHSARMEAV

RDEVERLLADVTPQVGCVPMYSTLTGAPIADPAELGGAYWFENLRRTVELERAVGAAVA

DGRTVFVECSPHPGLVVPLGDTLEAAGVDGAVLETLRRGEGGPDRLVAALSAAFVRGLA

VDWAGLIVGARVELPTYAFQRRRYWLDDGARSGDPGGLGLAAVAHPLLGAAVRPAQGAG

LLFTGRLSTATHPWLADHVVLGSTIVPGTVFVDLALWAGAEAECPVVDELTLHTPLVLP

EHGGVHVQVTVDGPDAAGARAVAVYSRPEDAPGEEPWTRHAVGALVADADTGAAPDAAA

EAWPPVGAKPIEVADFYARLVESGVDYGPAFRGMRAAWRRGDELFADVALPAEEERDAH

RFGVHPALLDAGVQTLRVDPGQVDEDDIRVAFSWHGVRLFAAGVTRLRVSCVPSGEGAV

SLRITDETGRAVAAIEALTVRAISADQLRRAGGGRDVLYRLAWRASAVPVPVATPRVAV

VGGWDLPGLGGLVDRYPGFAELASCDPPLPDLVLLPVGDPDADVPFSERRMREVTAELI

GRLEAFLGDERFAAARVVVVTRSAVLVDGDAGLGDPASASVWGVVRAAQAGHPGRIVLV

DLDDEPASAAALAAVASAGGEPQFAVRGGRVSVPRLERIPASGGARSAVGTGTVLIAGA

DRAVGAGVAEHLAGAYGVGRFVLLSVDPSGAGPTELAARLGEAGAEVVSAAWDGHDPGV

LAALVTEHRPAGVVDASGESDAAWALHELTADVDPAFFVLFSSAASLLGSSAHAATAGV

DAFHDALAAHRRASGLPGVSLACGTDPLPGLPDLFDEAIRREDAVLVSASTDLTGPAST

SPLLPSRNGRGATNSAETSIEADGEALARRLAALSEEERERELVGLVRAQAAAVLGHAG

IGEIGPERAFKEVGFDSLTAVELRNRLIRGTGVGLRSTLVFDFPTPRILARHLSGRLVE

AASPIGALLADLDRFEGELHAVLGEAEARDRLAERLRRLLADCTAPDESAPAADDVSDV

QSATDDELFSLVDQGFE*
```

Figure 7. Amino acid sequence of the lepB gene.

```
CDS            25735..48024
                    /note="LepB"
                    /note="PKS (modules 5-8)"
```

/note="sequence=MAESEEKLRSYLRKAITDARDAHRRVRELEDRQREPIAIVGMA

CRFPGGLGTPEDLWRFVVEGGDAIGEFPTDRGWDLDGLYDPDPDRPGTSYVREGGFLYD

VADFDAEFFGISPREAAAMDPQQRLLLETSWEAVERAGIDPTSLRHSRTGIYTGINGLD

YTTVLARTAKGRDGTLGMANGASLLAGRVAYILGLEGPAVTVDTACSSSLVALHLASNA

LRSGECDLALAGGATVMCTPEIFVNFSRQRGLARDGRCKPFSAAADGFILSDGAGLFLI

ERLSDARRNGHPVLAVLRGSAINQDGASNGLTAPNGPAQERVIRQALQSAGLVTGDVDA

VEAHGTGTTLGDPIEAHALLATYGQDRPADRPLRLGSIKSNIGHTQAAAGVAGMIKMVL

ALRHGVLPRTLHVDAPSPHIDWSAGRVELLTEPVPWPRSDRPRRAGVSSFGASGTNAHV

VVEEAPSDGDDGVVEVPAPTGIGSVLPWVLSARSEAALRAQAGRLRDWLAEHPEADPVD

VGRSLAVGRAVLERRAVVRGRDVAELAVGIGEVADRGELAGGRPMFAGPGPVFVFPGQG

SQWVGMAAGLLECSPVFAGVVAECAAVMDPLVADWSLLDVLRGGSAGGEALAERVDVVQ

PALFAVMVGLARWWESCGVKPGAVIGHSQGEIAAAHVAGYLSLADAVRIVVFRSRALRG

IAAAGGGMVSVGVSVERAEELVAGSAGLSLAAVNGPQSVVLSGDREALAAVVDACEREG

ARARWIPVDYASHSAHMEVVRDEVERLSAEVTPRAGRVPMYSTLTGEVVTDPAELGAGY

WFENLRGTVRLTTAVGAAVADGHVAFVECSPHPGLVVPLADTLDELGVDDGTVLETLRR

DDGGPDRLVAALSAAFVAGVPVDWAALFPGEGRADLPTYAFQHRRYWAEAESPAGGGVA

WGQRAVTHPVLGAAVDLAGDAGTVFTGRLSTTAQPWLADHAVLGTVIVPGTAFLDLVLR

AGAEVGYPAIEELTLHTPLVLPDASGVLVQVVVGAADGDGGDGGDGARTVDVHSRAEDA

PPDHPWTRHASGVLVAAGEERAEDAPAGRWPPTGAEVVGVDDAYERLAVAGFDYGPVFQ

GLRSVRARGDELFAEVELPEEGHADADRFAVHPALLDAALHPLVVAAGADAPVVAGLPF

VWHGIRAGVPGARRLRVRLVRSASGSASGSAAGSDSASGEVSVRAWDEGGREVVAIESL

TIRPVSADGLRTPDALVRDSLFTLAWTALELPDVDDDVPNATLLGGDGAADLAALVAAM

DTGTDVPALVALPVSVDDADPVAAAHTAGRQVLAVLRDWLADERFADSRLVFVTSGAVA

VADEQVRPASAAVWGLVRSAQSEHPGRFVLVDADSVADPGPEFDRALRTGADQLILRDG

TALIPRLVRAPADGGSGGFVPAADGTVLITGGTGTLGTLLARHLVTEHGVRRLLLLSRR

GGTAAGATDLVAELAAFGAEVTCVAGDAADRATLERVLADIPAEHPLTAVIHAAGVVDD

GVVQSLTADRLDAVLRPKVDAAWNLHEATRHLDLTAFVLFSSAAGVLGNPGQGNYAAAN

AFLDALARRRREGLPGSSLAWGWWAPTSEMTAGLGDADRQRMARLGVLPLAPEQGLAL

FIGURE 7 (Continued)

```
FDAATNHAEPTPTVVRMDLAVLRTAGSVVPTLLRGLARVPNRRAATAGSVAELRRRPAG

VSAFDWEQTLIRAVCVHAAAVIGHADATEIDETRAFRDLGFDSLTGLELRNRLNTATGL

RLPATLVFDYPSPVVLGRWLRDRLAEEDAGGPVGSTLGAQVVSPVGSDAGEDSIVIVGM

GCRFPGGITAPEHLWDVVAGGVDTLTDFPTDRGWDVERIFDPDPDRPGSTYVRTGGFVD

SAADFDPDLFGISPREALAMDPQQRLLLETAWETFERAGIDPTSLRGSRTGVFAGAIYY

DYAGGRLRKVPDELEGYIGNGNVGSVASGRVAYTFGLEGPAVTVDTACSSSLVALHLAV

NAVRSGECELALAGGVTVMSTPSVFLDFSRQRGLSSDGRCRSFAAAADGTGWGEGVGLV

LVERLSDARRNGHPVLAVVRGSAVNQDGASNGLTAPNGPSQQRVIRQALGSAGLSPADV

DAVEAHGTGTTLGDPIEAQALLATYGQDRPGDRPLWLGSVKSNLGHTQAAAGVAGVIKM

VLALRHGVLPRTLHVDEPTPHVDWSAGRVEVLADEVAWPAGERVRRAGVSSFGISGTNA

HVVLEEPPPVTEVPDVAVESGLGGRHTWVVSARSEAAVREQAARLRDWVTARPDLDPAH

VARSLVCERALFGHRAVVSGADLAELADGLSAVAAGAEGAVVGAVGRGPGKTAVLCTGQ

GVRALGIGRELHAAFPVFAGALDEVCAAFDDVVPFSVRDVVLGAEGVSDADAQDTGVAQ

PALFAFEVALYRLWASWGQAPDFVVGHSLGEIVAAHVAGVFSLADAVVFVAARARLMSA

LPSGGAMLAVGASEAEVAASCPAEVTIAAVNGPASVVVSGPAEAVAALEPDCVMRGWRI

SRLSVSHAFHSALMQPMLAELREVLTGLTYGTPEIAVVSDTTGRVAGAEELADPEYWVR

HVRRAVRFGDAIATLRAEGVRTFVEIGPEAALTAMVVEGTAGAEDVAAVATRRRGRAAV

SSVVEALARVFVHGATVDWAALSTGSGPGGRVDLPTYAFERRRFWLHAGVDAGDAVGLG

QGVVDHPLLGAVVGLADDQGVLFTGRLALDTHPWLAEHTVLGTVLLPGTAFLELALHVG

RLLDCARVDELTLSAPLALPSTGGVQVQVRVGVPEESGTRTITVHARPDSAEEAPWTLH

AAGALGPSAEVDAPSDAASWPPADATAMDSAGLYPWFAETGVDYGPSFRGVQATWRRDD

EVFAEIVLAADDPAADGRFELHPALFDAALHPLGLTLLDAAEPRLRLPFSWRGVALHTS

GARTLRVRLRPTGPDTIAVTATDETGRPVVAVEALAVREPSRDRLPRPDANAGELFEPQ

WTPLSPADTADMADTLGAVVGGPELASTATRFGATHHPDLAALAESAIPETVLYDLVTA

VPGVSAEAVHQAAAQALDLARSWLADERFESARLIVRTRHAVAAAEGDAPDPAAAATHG

LFRTACSEHPERFALVDADDLDEVSPEAIAAVVVEPEAAVRAGRVLVPRLRRAAVAPKA

DFGFAAEGTVLITGGTGALGRQVARHLVRVHGVRRLLLLSRRGDEAPEAAELRAELIEA

GAHVTFAAGDAAERGVLADVLAAIPAAHPLTGVVHLAGVTDDGLVGTLTPERLAAVLRP

KIDAALHLDELTADADLSAFVLFSSAAGPVGNPGQANYAAANVALDALARRRRARGRPA

VSLQWGLWAERSALTATMSATDRRRAAGAGVRALSVEQGLALLDAAAGRPEAVLTPLRL

DPAILRGPEERVAPVLRGLVPTRARRAPARTSDTARSLVRRLAALPEAEQDRLLVDLVR
```

FIGURE 7 (Continued)

THAAGVLGHADARTIDPDRAFGELGLDSLAALELRTRLSTAVGLRLPATMLFDHPCARA
VGVHLRAQLLDAPTPGRAAGVARPVSDEPVAVVAISCRFPGGVASPEDLWRLVSEHTDA
ISEFPQDRGWDLAELFHPDPEHAGTSYVSEGGFLYEATEFDPEFFGISPREALAMDPQQ
RLLLEASWEAIERAGVDPRSLRGSRTGVYAGLMYADYASRLGSAPEGVDGYLGNGSAGS
IASGRVAYTLGLEGPAVTVDTACSSSLVALHLAANALRQGECDLALAGGVTVMSSPATF
VEFSRQRGLAPDARCKSFAAGADGTSWSEGIGLLLVERLSDARRLGHPVLAVVRGSAIN
QDGASNGLAAPNGLAQERVIRDALAHAELRPSDVDAVEAHGTGTPLGDPIEARALLATY
GQDRPADRPLWLGSVKSNLGHTQAAAGVAGVIKMIMAMRHAELPGTLHVDAPSPHVDWS
AGAVSLLTAATPWPQTGRPRRAGVSSFGISGTNAHVILEQGDPAPTAPAEPAPASAPLA
ALAWPLSGASAVALRGQAERLRAHLDAHPEYGPVDIAHALVGGRSRFEHRAVVVAEDAA
GLRAGLDALSADRPDAAVPVGVAGEPGRIAFVFGGQGSQWPGMGARLLTESPVFAARIR
DCDAALAPHTDWSLLAVLRGEPDAPPLDRVDVVQPVLFAVMVALAELWRSLGVRPASVV
GHSQGEIAAAHIAGALTLDDAARIVALRSRALRGLSGDGGMMSVAAGPEQIARLLDGFA
DRLGIAAVNGPAAVVISGAADALAELHAHCEADGIRARVLPVDYASHSAQVEQVREELL
AALGEIVPTPTTDAVFYSSVTGEPVEGTALDAEYWYRNLRATVAFDRATDALLRDGHTV
FVETSPHPVLAPAVEDSAQRAGTDVTVVGSLQRDTDTLARFLTAAAGLHVHGVPVDWSA
THAGHRPRPVDLPTYAFQRERYWLEAGKTPTDAAGLGLHPAAHPLLGAAVVPAEGDRHI
LTGRISLRTHPWLADHTILDTVLLPGTAFVELALQAGDRADCDLIEELTVEAPLRLTDT
GAVHLQVLLDEPDEQGRRALTIHSRADDAPAEQTWTRHASGVLAPVADGLDAVPATDAA
WPPAGAVALDVDGLYERLAGQGYRYGPAFRAVRAAWRLGDTVLAEVAPGDEAHGARDFA
LHPALLDAALHAAGAADSGTSGGDGAIGLPFAWTDVRLHAVGAAALRVRLERRGPDTVG
LELTDHTGALVATVGALVGRPATADRLAPAADPAHRDLHHVDWSPLPTPTEPSTARWSL
LGPDELEAVAGLRAAGAEVHADGDPDPADVLLITCAGRTGDDVPEAARAATHRVLDLLQ
RALTDPRLTACTLVVLTRGAVPGHHGEDVCDLVAAPIVGLVRSAQTEHPGRIVLVDLDD
HADSFAALRAAVVTDVGEPQLAIRTGTVSAPRLIRTGTEPRLSPPAGAPAWRLDLLGGG
TLDRLALLPNADAAVPLAPGQVRIAVRAAGLNFRDVVVALGMVTDTRPPGGEGAGIVVE
VGPDVPELVPGDRVMGLFGGGTGPITVADHRLLAPIPTGWTYAQAAAVPVVFLTAYYGL
ADLGGLRAGESLLVHAATGGVGMAAVQLARHWNVEVFGTASPGKWATLRGQGVDDAHLA
SSRDLDFAHRFGEVDVVLNSLAHEFVDASLRLLAPGGRFLEMGKTDIRDRDEVLAAHPG
RDYRAFDLMDAGPERIREMLADLYRLFETGVLHPLPVTPWDVRGAVGAFRHLSQARHTG
KIVLTLPPTLGAAPDPEGTVLITGGTGTLGGLLARHLVRTAGVRHLLLIGRRGPAADGA

FIGURE 7 (Continued)

```
AELSAELTALGARVTIAACDAADRAALAALLADIPAEHALTSVIHAAGVIDDAALTALT
PERLDRVLRPKLHAAWNLHELTRDLDLAEFVLFSSMAGTFGGAGQANYAAANAFLDALA
QHRRARGLAATAAAWGLWAQASGMTGHLGAEDLDRIARTGVAALETAHALTLYDALRAA
DRPTIVPARLDPDALRAAAPTVPALLRDLVRDLVRPRGRRAAADTAPDAASLAERLARL
PEERRRQTLLTLVRTETAAVLGHATPDAVAPLRPFKALGFDSLTSVELRNRIGAATGLR
LPVTLVFDHPTPQALADHVGAELLGVAPVVVEPERPAAHTDDDPIVIVSVGCRYPGGVA
GQDEMWRMLAEGTDTIGPFPQDRGWELDTLFDPDPDRVGKSYVREGGFVADAVHFDAEF
FGISPREATSMDPQQRLLLETAWETFEQAGIDPTTLRGSGTGVFVGAMAQDYHGTSQAM
AEGQEGYLLTGTATSVISGRVSYVLGLEGPAVTVDTACSSSLVALHLAANALRAGECDL
ALAGGVAVLTSPQAFIEFSRQRGLAADGRCKPFAAAANGTGWGEGVGLVLVERLSDARR
RGHPVLAVVRGSAVNQDGASNGLTAPNGPSQQRVIRQALRNAGLLATDVDAVEAHGTGT
TLGDPIEAQALLATYGQDRPAQRPLWLGSVKSNIGHTQAAAGVAGVIKMVLALRHGTLP
PTLHVDAPTPHVDWASGQVRLLTEPVAWPAGERVRRAGISSFGVSGTNAHVIIEQAPAE
GAVDAAPVDAAPAAALGGIVPWVVSARSQAGLRAQAARLRDWAAVHPEFAPADVAASLV
RGRAVFERRAVVRGRDTDELVAALAELVDSSATGEAPTAIGPGPVFVFPGQGSQWVGMA
AELLTCCPVFAETVTQCAEVMDPLLPGWALLDVLRGTDDETAELLRRVEVVQPVLFAVM
VGLARWWESCGVRPAAVIGHSQGEIAAAYIAGHLTLPDAARIAALRIRAVQAADMIRGA
MVAVAVSALRAEELITRTGTGDLVNVGGINSPTNTVLSGDTDALALIVADCEREGVRAR
WIPAAYSSHSPQMDAVRGDLERLLAGIQPTPGRVPMYSTVTGGRLADDALLDIDYWFEN
MRRTVRFEEAIGAAAADGHTVFLECSSHPGLVVPLGDTLDSLGVHGATLETLRRADGGA
DRLLAALSAMFVHGGAVDWAGLLPGRRVALPTYAFQRRRHWVEPVGPARGGVGWGQFAV
EHPILGAGVDLADGSATVFTGRLDTTTHGWLADHLVLGEVLVPGTVFVDLALRAGGALG
CAVVEELALHEPLVLPDADGVRIQVTVEAPDDAGTRALTIHSRPEDAPAAEPWTRHASG
TVAPGAHRPQQESGPWPPIGATPLDVADVYLRLTELGLGYGPTLAGLRAAWRRGDDLFA
EVARTADGERGTARFGLHPALLDAALHGLAPGSAPGGAPTEVRLAGAWRGVTLGGDAGT
AGRIRLRGVDGDGVEVELADEAGRSMARIESVALRPWSAGQVRAAGRARPWLTRWEWAR
VEPTDPAAAGGRWAVLGARAWDGVPAYATAAELIAAVEVGVPVPDLVALPVRIDPAGGL
DPEAIRATIRAVRETLRQWRAEPRLAASRLVVVTHDAVSARPEDRVTDPGAAAVWGVVR
AARAADPERFVLADVDGEDGSWPVLLAEASAGRAEFAIRAGTVLLPGLARVPAGETGTA
GFPTDGTVLVTVATDPTDPTDGTDPVGTLLARHLVTAHGVRRLILAGGPAAGMPLAREL
AAQGAEIHVVVCDVTDRTELAKLLATIPEHSPLTAVVHTAGLGRSHTEAMLRARVDAAV
```

FIGURE 7 (Continued)

HLHELTRDADLSAFVLCTALDGVLADPGRGEHAAGDAFLDALARHRHAAGLPALALAWA

PGAEPVAGLLPLPGEQATVLFDRALGLPEPALIPLAPDTSALRRAEPGALPALLTTLVA

DPNHRVGAAAEAAPALIGRLLDLPDDERESVLVDLVRGCAAAILGHADPTAIETGAAFK

DLGFDSLTALEMRNRLRAALGLTLPATLIFSHPNAAALGRHLHGLLRREHGVSWDSVLG

EIDRVEAMLAQLDDADRARATERLRDLIGGPEAPLAGRESGANGDAAGGRGFDAATDEE

LFDFIDGGIEH*

Figure 8. Amino acid sequence of the lepC gene.

CDS             48110..58357
                /note="LepC"
                /note="PKS (modules 9-10)"

MANEDKLRDYLRRATTELQETRLRLRETEDKWHEPLAIVGMHC

RYPGGVASPDDLWDLVDAGTDAITGLPPGRGWEVDEAANGTSYRGGFLTDAADFDADFF

GISPREALAMDPQQRVLLEASWTVFEHAGIDPTTLRGSRTGVFVGVIASDYLSRLARVP

KEVEGHLLTGSLVSVASGRLAYHFGLEGAAVTVDTACSSSLVAVHLAGQALRAGECDLA

LVGGATVLATPGAFDEFSRQQGLAGDGRCKSFAAGADGTGWSEGVGLLLMERLSDARRN

GHRVLAVVRGSAVNQDGASNGLTAPNDLAQERVIRQALANARLAASDVDAVEAHGTGTR

LGDPIEAQALLATYGQNRPAARPLRLGSIKSNIGHAQAAAGVAGVIKMVQALRHGVLPR

TLHVDEPTPHVDWSAGRVALLTEPMAWPAGERVRRAGVSSFGVSGTNAHVIVEEAPPVE

EPVGAADPARPLGVVTPWVVSARTEDGLRAQVERLREWAIEHPEADPADVGRSLASGRA

LSGHRAVVLGRDAAELVEGLSVVVDGEPEAIVGEARRGSGRTAVLFTGQGVRSRGMARE

LHAAFPVFAAALDEVCAAFDAVLPFSVRDVLLAEGEGGADGDGGEDTGVAQPALFAYE

VALYRLWTSWAAAPDAVAGHSLGEVVAAYVAGVFSLADATTFVAARATLMSALPPGGAM

VAVGTSESAAARLLADHPGVGIAAVNGPTGVVLSGEAAAVAEVARVCAERGLRISRLRV

SHAFHSALMEPMLDELAEVVSGLTLRPARMAIGSNVTGRIGSAEQLCDPRYWVDHVRRA

VRFGDVLDALRADGVRTFVEIGPDAALTPMVADVTADADDVVAVATRRRDRDPVTGVVE

ALARVFVRGAVVDWAALVPGRWVELPTYAFTRRRFWLDAGTGAGDPTGLGQGTVDHPLL

GAVVGLADGHGSLFTGRLSLDTHPWLADHVVLDTVLLPGTAFLELALHTGRRVGCDRVE

ELSLETPLAFGERGGCQVQVWIEAAGPDERRRAITIHSRPDDGDGDEGWIRNAVGTVAP

VEDKAPADAVADPTPWPPTGATPVPIDDFYPWLADNGVAYGPCFRAVRAVWRRGEEIFG

EIALPEQVGYEADRFGVHPALMDATQHLLGVAAFADPAESEGGGLALPFSWREVRLHTP

GAASVRARVVRTGPESVTLSLADEDGRPVAEVESLAVRPISAEQLRTSTAGRRDPLYTL

RWTPLPRPSAAPGIGSPAIIADSGSGDPFAGRLGGTVHPDLTALADAVDAGLPTPEVVV

LAWPTIPAGPLGDVPDPDDVHAAVHRALATVQTWLGDERFTGARLVVVTRGAVAVADEE

VRDPAAAAVGGLVRSAQSEHPCRLVLVDLDEDAASPGALPAAIGAGEPQLAVRAGVAYL

PRLTRTPAIEPSTPLFAPDGTTLVTGGTGALGALVARHLVVAHGVRRLLLVSRRGIAAP

GAGSLAAELTGLGATVDVVACDVSDRADLAKKLAAIPSAHPLSAVVHVAGVVDDGVIGA

LTPERVDRVLRPKVDAALHLHELTRDADLTAFVLFSSVAGVIGSLGQANYAAGNAFLDA

FAQRRRALGLPAVSMAWGLWAEESGLMREEFAETDRQRINRSGVLPLSDEQGLALFDAA

FIGURE 8 (Continued)

```
LAHGEPILAPVRLDLSALRRLEDELPAILGGLVPTSRRDGARPGAADTRRLAQRLAGRS
EPEQLRLLTELTRAQAAVVLGHAGADAVAADRAFTELGFDSLTALEMRNRLNTVTGLRL
PATVLFDYPNAAALARFLRAETLRVPQYTQAAANTAAKARTSDEPIAIVAMSCRYPGGI
DTPEELWRCVAGGVDLTSPFPTDRGWDLGALYDPDPDRSGRCYTREGSFMRDIDRFDAE
LFGISPREALAMDPQQRLLLETSWEAFERAGIDPSSLRGSNTAVFAGLMYADYAAGRVG
DVGDELEAYIGNGNSFGVASGRVAYTLGLEGPAVTVDSACSSSLVALHWAAHALRSGEC
DLALAGGATVMSTPSVFVEFARQRGLAPDGRCKSFAAAADGTAWGEGIGMLLVERLADA
RRNGHPVLAVLRGSAINQDGASNGLTAPNGPSQQRVIRQALANAGLATADVDAVEAHGT
GTVLGDPIEAQALLATYGRDRPAERPLWLGSIKSNFGHTQAAAGVAGVIKMVMAMRHGM
LPPTLHVDEPSPHVDWSTGRVELLAEGRPWPEVGRARRVAVSSFGISGTNAHVILEQAD
EEPEPAARTTSGTGIGGVLPWVLSARTEAGVRAQAARLRDWAGARPEVDPADVGWSLAS
GRSVFERRAVVWGRDGAELTAGLDALAAGRDAGARAVLAGGTGVSGEAAVGPVFVFPGQ
GSQWVGMAAELLTCCPVFAESVAECAAAMDPLLADWALLDVLRDASAALLERVDVIQPV
LFAVMVGLARWWESCGVRPSAVIGHSQGEIAAAHVAGFLSLEDAVRIVVLRSRALRGLA
ADGDGMLSVGVSAERGRELVARVQGLSLAAVNGPDSVVLSGPVEGLTPIAAACERDGVR
ARWIPVDYASHSARMDDVREVLAESLAGVEPGIGRVPMYSTVSGLKVTDAADLGGEYWF
ENLRRTVQLATAVGAAAADGHSVFVECSPHPGLVVPLGDTLDALGSTSGTVLETLRRGE
GGPERLVAALAAAFVSGLPVDWAGLLHHDGVRRVQLPTYAFQGRRFWLEPDMGTALPGR
TTPTPVVGDTEDSRLWEALEAAGAEDLAAELEVAADAPLSDVLPALTSWRARRRADATV
RSWRYGVRWEPWAAPAASADRMGRLLLVAPDGEIGDVLAGALAECGAEVVVLSAEGERT
ALARRLAAIGEEGVPAGVVSLSAVGCAADADPVPALAPVLTLVQALGDAGMEAPLWVLT
RGAVSVLGEEPTGPAGAAVQGLGRVVGLEHPGRWGGLIDLPQVVDGRVAETLAGILAAG
AGGTGSGEDEIAIRPLGVFVRRLARMAGPEGSGTSRWRPGGTALVTGGTGALGGRVARW
LVREGVERVVLAGRRGPDAPGADRLREELAAAGAEVAVLACDLGDRDAVAALLAEVRAG
GRRIDTVVHAAGAVVVGPLADSTVADLADASAAKVGGALLLDELLRADEPDTVVLFSSA
AGVWGGAGQGAYAAANACLDTIAERRRARGLRTVSIAWGQWAGGGMADGAAGAHLDRIG
VPAMDPDRALEALRQALDEDLTCVTVADVDWPRFAAGYTAARPRPLIADLVAAEVAAAP
VTEARGAGEPDGPSVWRARLAELGAADREAELLALVRTEVAAQLGHADPAAIEPERPFR
DLGFDSLAAVGLRNRLTETIGLRLPSTLVFDHPTAVALAAHIDGELFAETVGTVSVFAE
LDRLEAALGELGGDFAERGRVGARLAELAGKWREIEAASQKAEPEGADFAAAEDEEMFD
MLGKEFGIS*
```

Figure 9. Amino acid sequence of the lepD gene.

CDS         58243..64173
            /note="LepD"
            /note="PKS (11 & TE)"

MAGDRGREPKGRARGSRLRGSGGRGDVRHARKGVRHLLSGAGD

DRRSRVPTAHGSIRFDQAEDGRTDMSNEERLRHFLRETATDLRRTKQRLHEVESAAREP

VAIVAIGCRLPGGVRSAEDLWELVRTGTDAIAGFPSDRGWDPANVYADLPGGEGVSGGS

AGSGGSTTRQGGFVYDAAAFDAEFFGVSPHEALAMDPQQRLLLETAWETFERAGIDPLS

MRRSRTGVFVGAGALGYGGGMRADNAEIQAHRVTGGSMSVVSGRIAYTLGLEGPAVTLD

TACSSSLVALHLAANALRSGECDLALAGGVTVMARPTAFVEFSRQGGLASDGRCRSFAA

AADGTGWGEGVGLLLVERLSDARRNGHPVLAVLRGSAVNQDGASNGLTAPNGPSQQRVI

RQALAAAGLSAADVDAVEAHGTGTVLGDPIEAHALLATYGRDRPADRPLWLGSVKSNIG

HTQSAAGVAGVIKMVMALRHGLLPRTLHVDRPSPHVDWASGRVELLTDEVPWPAGGRVR

RAGVSSFGISGTNAHVVLEEAPAVEGASGEGAEPAPGVGGLIPWVVSARSPEALRAQAA

RLREPAVADPADVGRSLVTGRALLDHRAVVLGRDAAELGRGLAALAAGSPGAVEPSEGG

TPVVVTGNVPRAGGAGGRVAGRGAVVFTGQGGRLPGIGRELYAGFPVFARALDEVGAAF

DAVVPFSVRDVLLGVEGTVGVDADDTGVAQPVLFAFEVALYRLWSSLGSVPDFVVGHSL

GGIVAAHVAGVFSLADAVAFVAARARLMSALPGGGAMLAVGASEAQVTALSDGLPVSIA

AVNGPASVVVSGAVAAVDEVAARCAARSWRSSRLRVSHAFHSVLMEPMLAELRDVLRRL

SFGAPEIGLVSDTTGRVVTAEEVGDPEYWVRHVRDAVRFADAVGTLRERGVATFVELGP

DAALTAMVAECTAGVGEVLGVPAQRRGRPAVATLAGALATAFVRGLPVDWVGALGGPGG

RRVELPTYAFQGRRYWLEPGKASVTPAGPDSVDGPLWDAVERAGAGELAAILAVSEDAT

LREVVPALSSWRARRRVDATAASWRYAVRWEPWAGGSSDAAALSGRWLLVHPAASELAD

AVARELTERGAEVVRVGGEGIGSHVGAEPVAGVVSLIGSGSGSGSTSGSGSGSGSASGS

GSGSGSGSGSGSGSSCGSGSVPGLGSCAGDDCADLVAAVVAMGELLAELRRFEVAAPLW

CVTRAAVSVLGEDLANPVGAGLWGRGLVASLEQPGCWGGLVDLPAVADTRALGVLATIL

AGTSDEDQFAIRPLGVFTRRLTPLPAEGSGRVVRTREAALITGGTGVLGAHAARWLVAH

GTERVILLGRRGARAPGFDALRADLEAAGAEVVAIACDLTAPDAAERLRAALPATGAPI

RTVVHAAGVPGSPTATGADAVADTVTAKVAGALALDTLFGADRALDAFVLYSSGAGVWG

GAGQGAYAAANAFLDALAVRRRQRGLPATAIAWGPWAAGGMADGEGERLLARVGVRAMD

PAAALAALGRALVEDLTCVTVADLDRPRFAAGYTSARPRPLIADLIDAEPPTATAPPTR

PGGVWDPAVTRSPARLAAELLDLVRAEVAAQLGHAGVEAIEPDRPFRDLGFDSLAAVGL

FIGURE 9 (Continued)

RNRIAEATGVHLAGTLIYDHETPAALAAHLADALREGVPETRPAPTAPGGAEDSNDMLG

TVYRKLALLGRMDDAESLLVGAAGLRQTFEDPNRLPKTPGFTRLARGPARPRVICFPPF

APVEGAIQFGRLAGTFEGRHDTAVVTVPGFRPGEPLAASLDVLLDLLADATLRCAGDDP

FAVLGYSSSGWLAQGVAGRLEATGRTPAGVVLLDTYLPATMSRRMRKAMNYEVIVRRQA

FTALDYIGLTAIGTYRRMFRGWEPKPGSAPTLVVRPSRCVPGSPEEPMTGEDWRSTWPY

EHTAAEVEGDHCTMIGEHAEQTGAVVRAWLAGDRTVSIDTREGTA*

Figure 10. Amino acid sequence of the lepE gene.

CDS         64703..65881
                /note="LepE"
                /note="P450"

MIPVLELVQISTLPDAERELEQLARRYPIIRTRQVGGIEAWTV

LGAGLTRQLLGDPRLSNDLHTHAPHAAQSADGPTVLFEQDNPDHARYRRLVSAAFASRA

VRNLEPRIVDIARALLDRLPAEGGTVDIVEAFANPFPLEVICELLGVPMADREVFRTRV

ENMDSPSTAVRRAAMDAFVAYCANLVDAKRTEPTEDLLSELVQAELDDGSRLSANELIG

FGSVLLFAGHVTTAYLIAAALYELITHNDQLAALRADPTLVEGTVEEALRFGSLLSTT

NRVALTDLEIGGVLVRRGDLVRFLLSAANRDPAIREDPHTFDITRSTTAHLGFGHGPHF

CLGQRLARQEIKVALTEIVTRFPTLELAVPAEKLRWRASDFLRGLAELPLTYAP*

**Figure 11. Amino acid sequence of the *lepF* gene.**

```
CDS             66124..66564
                /note="LepF"
                /note="putative tetR-family transcriptional regulator"
```

MRERKKARTRQVISTVAFDLFEEQGFEQTTVDMICRRHAMTVS

HGNLEDHAEQTARRHALRRRFLGVRSVHDHGVALIDTVAHRIVTTAAARLGVDPAVDLR

PHALGALVAAMTRRVVIDDIAPGPINEWAEAFRTLLPTPAAHTD*

SEQUENCE LISTING

<160> NUMBER OF SEQ ID NOS: 11

<210> SEQ ID NO 1
<211> LENGTH: 29467
<212> TYPE: DNA
<213> ORGANISM: Streptomyces ap. ATCC 39366

<400> SEQUENCE: 1

| | | | | | |
|---|---|---|---|---|---|
| gatcacgggc | aacgccggcc | agggcgcgta | cacggcggcc | aacaccttcc | tggacgccct | 60 |
| cgccgaacac | cgccgcgcag | ccgggctgcc | cgccaacgcc | ctggcctggg | gactgtgggc | 120 |
| cgagggcagc | gggatgaccc | gacacctcga | ccacaccgac | cgggcccgga | tgtcccgggg | 180 |
| cgggatcgcg | gcgctgccca | ccgagaccgg | actcgccctg | ttcgacgccg | cgttgcaccg | 240 |
| ggaccgcccg | tacacgatcc | ccgcccgcct | ggaccgcggc | gcgctgcggg | ccctggccgc | 300 |
| gagcggtgtg | ctgcccgccg | tactgcgcag | cctcgtgcgt | gtcccgccgc | cgcgtgccgc | 360 |
| cgcctccggc | gacggcacgg | acgcgtcgtc | gtggccccgg | cggatccggg | aactcccggg | 420 |
| cgagcagcgg | gaacgggcga | tcaccgacct | ggtgcgcggg | caactcgccg | ccgtcctcgg | 480 |
| acacgacgca | cccgaacgac | tcgacctcga | ccgcgccttc | cgcgaactgg | gagtcgactc | 540 |
| gctgaccgca | ctcgaactgc | gcaaccggat | caatgcgttc | accggcctgc | gactgcccgc | 600 |
| gacggtggtc | ttcgaccacc | ccagcggtac | ggccctggtc | gctcggatga | tgcgcgagct | 660 |
| ggtcggtgcg | gtgccgagcg | agccgaccac | gcccgtcgtc | gcaccgaccg | tgacggtcga | 720 |
| cgagccgatc | gccgtcgtcg | gcatcggctg | tcgctatccg | ggcggtgtgg | ccggtcccga | 780 |
| ggacctgtgg | cgactggtcg | cggccggcac | ggacgcggtc | ggcgacttcc | ccgaggatcg | 840 |
| tggctgggac | ctggcgaagc | tgtacgaccc | cgacccggac | aaggtcggca | aggtctacac | 900 |
| ccgtcgggc | ggattcctct | acgagtcggg | ggagttcgac | gccgagttct | tcggcatctc | 960 |
| gccgcgcgag | gcggcggcga | tggacccgca | gcagcggctg | ctcctggaga | ccgcgtggga | 1020 |
| ggcgttcgag | cacgcgggcc | tggacccag | acgctgcgc | gggagcaaca | cgggtgtgtt | 1080 |
| cgccggggtg | atgtacaacg | actacgcctc | gcggctgcac | cgcgccccg | acgggttcga | 1140 |
| gggcatgctg | ttggccggca | acgtgggcag | cgtcgtgacc | ggcagagtgt | cctacgcgct | 1200 |
| gggcctggag | gggccggcgg | tcagcgtgga | caccgcctgc | tcgtcgtcgc | tggtggcgct | 1260 |
| gcacctggcg | gccaacgcgc | tgcggtcggg | ggagtgcgat | ctggcgctcg | ccggtgggt | 1320 |
| gacggtgatg | tccaccccga | acgtcttcgt | cgagttctcc | cgacagcgcg | gcctgtcggc | 1380 |
| ggacggccgg | tgccggtcgt | tcgcggcggg | cgcggacggg | acgggttggg | gcgagggtgt | 1440 |
| cgggctgctg | gtggtggaac | gactgtccga | cgcgcggcgc | aacgggcatc | ccgtgctggc | 1500 |
| gctgctgcgt | ggctcggcgg | tcaaccagga | cggcgcctcg | aacgggctga | ccgcgccgaa | 1560 |
| cggaccgtcc | caggagcggg | tgatccgggc | ggcgttggcc | ggtgcggggt | tgtcggcgac | 1620 |
| ggacgtggac | gcggtggagg | cgcacggcac | cgggacgacg | ctgggcgacc | cgatcgaggc | 1680 |
| gcaggcgttg | ttggccacgt | acgggcggga | ccggccggcg | gatcggccgc | tgtggctggg | 1740 |
| ctcgatcaaa | tcgaacatcg | gcacacgca | ggccgcggcg | gggcggccg | gcctgatcaa | 1800 |
| gatgatcatg | gcgatgcggc | acggcgtact | gcccgagaca | ctgcacgtcg | acgcgccgtc | 1860 |
| gccgcacgtg | gactggtcga | cgggacacgt | cgagctgctg | gccgaacgtc | gaccgtggcc | 1920 |
| cgaggtcgac | cgggcgcgcc | gggccgccgt | gtcgtcgttc | gggatcagcg | ggacgaacgc | 1980 |
| gcacgtgatc | gtcgaacagg | cgccggcggc | cgaggcggtg | gtgtcccggg | acgagccggt | 2040 |

-continued

```
gggtgtggcg ggcctggtgc cgtgggtgtt gtcggccagg accgccgacg gtctgcgggc      2100
gcaggcggcg cggttgcggg agtggtcggc gcggcatccg gaggcggatc cggtcgacgt      2160
ggggtggtcg ttggttcggg agcggtcggt tttcgatcgg cgggcggtgg tgggtggccg      2220
cgatccgggt gaactcgggg ctgggttgga caggttggcc gcgggtggcg gtattgccga      2280 cggtcggcc atgttttcgg gtcccggtcc ggtgttcgtg tttcccggc aggggtcgca       2340 gtgggtgggg atggcggccg ggctgttgga gtgctcgccg gtatttgcgg aggcggtgac      2400
ggagtgcgcc gccgtgatgg atccgttggt ggcggattgg tcgttgttgg atgtgttgcg      2460
gggtgggtct gccggtgagt tggagcgggt ggatgttgtt cagccggtgc tgtttgcggt      2520
gatggtgggg cttgcgcggt ggtgggagtc gtgtggggtc aagccgggtg cggtcatcgg      2580
gcactcgcag ggggagatcg ctgccgcgca tgtggcgggt tatctgtcgc tggcggatgc      2640
ggtatgggtg gtcgtgttgc ggagtcgggc cctgctgggg gtcgcgtccg ccggggggcgg     2700 gatggtgtcc gtcggggtgt cggcggagcg tgctcgcgag ctggtcgccg gggatgaccg      2760
gctgtcgttg gcggcggtga acgggccgac gagtgtggtg cttttcgggtg atgtcgaagc     2820 gctgtcggtg gttgtcgagg cgtgcgagcg ggatggtgtg cgggctcggt ggattccggt      2880
ggattacgcg tcgcattcgg cgcggatgga ggccgtgcgg gacgaggtgg agcggctgtt      2940
ggcggatgtg acgccgcagg tgggccgcgt gccgatgtac tcgaccgtga gcggggaggt      3000
ggtcgtcgat cccgccgagt tgggcggggc gtactggttc gagaatctgc ggcgcacggt      3060
cgagcttgag cgggccgtgg gtgcggcggt cgcggatggg catggtgcgt ttgtggagtg      3120
cagcccgcat ccggggctgg tggtgccgat ggggacacc ctggaggcgg ccggggtgga      3180
cggcgtcgtt ctggagacgt tgcggcgggg tgagggtggg cccgatcggc tggtcgccgc      3240
gctctcggcg gcgttcgtgg cgggtgtcgc ggtggactgg gccggaatgt tgccggggcg      3300
ccatgtcgag ctgccgacgt atgcgttcca gcggcggcgc tactggttga cgggtgggga      3360
acgtgcgggc gatccggccg ggttgggggct ggtcgcggcc gatcatccgc tgctgggggc     3420
tgtggtcggt tcggtgcggg acggggaact cctctacacc gggcggttgt ccgccgcgac      3480
gcacggctgg cttgcggacc acgcggtgtt cggctcggtg gtggtaccgg ggacggcctt      3540
cgtcgagctg gcgtcgtggg tcggtgtcga ggccggttgc ccggtcgtcg acgaactcac      3600
gctgcatgcg cccctggtgc tgccggacgg ggtcggcatc cggcttcggg tggcggtggg      3660
cgcggcggat tcggcgggggc gtcgggtggt ggagttccat tcgcggcccg aggatgcccc     3720
cgacgagcag tcgtggactc ggcatgcgac cggcacgctg ggtgccgcga gtgtgcccgg      3780
atccgcgtcg gccggggccg cggcgtgggc ggtctggccg ccggcggacg ccgaggtggt      3840
cgacccggag gccgtttacg agcgacttgc ggagcacggg tacgaatacg ggccgatttt      3900 ccggggggttg cgggccgcat ggcggcgggg tgacgacttc ttcgccgagg tcgcgctgcc      3960
ggaggcggcc ggtcgggacg cgcacggcta cgacctgcat ccggcggtgc tggacgccgc      4020
gctgcatgtg gccgcggccg aggcggtggc ggagtcgggg gcgacgttgt tgccgttcgc      4080
ctggaccggg gtcgcactgc atgggccggg ggcgtcggtg cttcgggtga tgttgcggcg      4140
taccgggcgg gagacgctgg cggtcgacgt ggccgacgag cgtggtgttc cggtggcgtc      4200
ggtcgcgtcg ctgacgctgc ggccggtggc tgccgagcag ttggtggcgg ccgaggaagc      4260
gggccgcgag tggctttacc ggatggtctg ggagatcgcg gacgcgccgg tggcggagca      4320
cgtcgagggt gaacttcttg gttcggatga ggagtccgac gcgtcggcgg agcttgtggc      4380
```

-continued

```
gggcgggatt cgggtggtga cccctgcggg cgccgaacag gtctccgagg tggggctgtt    4440
cgattgcccg cccgtggtcg gcgaagcccc cgaggaggtg gccggcgccg tgcatgcggt    4500
gctggccgcg gttcgggcgt gggtggcgga cgagcggttt gccggggcgc ggctggtggt    4560
tcgtacccgt ggcgcggttg ccacggatgc gcaggaccgg gtcggttctc ccgcgcatgc    4620
ggcgatctgg ggtctcgtgc gggtcgcgca gagcgagcat ccggggcgct tcgtcctggt    4680
cgatggggac gacgtcgatt cgggtgcggc gctgcgtgcg gcggtggcgt gcgggctgcc    4740
gcaggtggcg attcgcgaag gtgtggtgct ggcgccgcgc ctggtggggg cggtgcacga    4800 cacgcgctg gtgccgccgg cgccgggtgc ggatcaggcg tggcggatcg agtccgggac     4860
ggccgggacg ccggacgatc tggtggtgac ggcgcatccg ccgcctcgg cgccgttggc     4920 ggccgggcag gtgcgggtgg cggtgcgggc ggccggggtg aacttccgcg atgtgctgat    4980
cacgctcggc atgtacccgg ggcgggcggt ggtcggcgcc gaggcggccg gggtggtcgt    5040
ggaggtcggc ccgggcgtgt cggaaccggc cgtcggcgac cgggtgatgg gcttgttcga    5100
gggggcgttc gggccgcttg cggtggccga tcggcggctg ttggcccggg tgccggcggg    5160
ttggtcgttt gctcaggcgg cgtcggtgcc ggtggtcttc ctcaccgcgc tctacgggct    5220
gcacgatctg gccgggctgc ggtcgggtga atcggtgctg gtgcatgcgg ccacgggtgg    5280
ggtcggcatg gccgccaccc agctggcccg gcatcgggc gccgaggtgt acgcgaccgc     5340
gagtgcgacg aagtgggcca ccgtgcgcgg gctgggtgtt ccggacgaac ggatcgcctc    5400
gtctcgggac ctgtccttcg aacagcgctt cgcacgggcc acggacgggc gcgggatcga    5460
cgtggtgttg aactcgctgg cgggcgagtt caccgacgcg tcgttgcgac tcctggccga    5520
gggtggccgg ttcgtggaga tgggcaagac ggacgtccgg accgaggggc tgccggccgg    5580
ggtgcgctat cgggccttcg acctgatcga ggccggtccg gatcggatcg ccgagatgtt    5640
cgccgaactg gtcgacctct tcgagcgcgg tgtgctgcaa cccctgccga ttcggacctg    5700
ggacatccgt cgggcccgcg aggcgctgcg tttcctgggc caggcccggc atgtgggcaa    5760
ggtggtgctg accgtgccgc agccgctcgc ggccgacggc acggtcctga tcaccggcgg    5820
cacgggcacg ctgggtcgca gtctggcccg acacctggtc acgcggtggg gtgtgcgccg    5880
gctggtgctg accggccggg ccgggcccgc cgctcccggc gccgcgaac tggtcgcgga     5940 attggccgag tcgggtgccg acaccacgat cttggccttg cgatgcggcg gaccgggcgg    6000
cgaatggccg aaggtgttgg ccgcgatccc ggccgaacac ccgttgaccg ccgtggtgca    6060
tgccgccgga acactcgacg acgcgccgat cgaggcgctg accccggagc gggtcgacca    6120
cgtgttgcgg cccaaggtgg acgccgcccl cgtactggac gaactcaccc gggacgcgga    6180
cctggccgcg ttcgtgctgt tctcgtcggt ggccggcgta ctcggtgtgg ccggccaggg    6240
cggctatgca gcggggaacg cgttcctgga cggtctcgcc ggtcggcgcc gcgagcgggg    6300
gctgcccgcg accgctctgg cctggggcct gtgggcggaa cgcagcgcaa tgaccgcgca    6360
gttgggcgtc ggcgacctga agcgcctggc gcgcggcggc ctggtgccga tctcgaccgc    6420
ccaggggctc gccctgttcg acgccgcctg gcaggccgac gaggcggcgc tgatcccggc    6480
ccgcctggac cttgccgcac tgcgcgcaca ggcggcgacc cagccggtac atccgctgct    6540
gcgcggtctg gtcggcacca ccccgacccg ccggaacggc acaccttcgg aggcgccgtg    6600
ggcccgacgg ctcgcctcgg ccgcgcccgc cgagcgggtg gacgtggcat gcggctggt    6660 ccgggccgag gcgcggtgg tcctggggca cgagtcgatc gacggggtgc ggcccgaagt    6720
caccttccgc gacctcgggt tcgactcact gacgggtgtg gaactgcgca accggctgag    6780
```

```
cggcgccacc ggattgcggc tgccgtccac gctggtcttc gacttcccga ccccgctcgg    6840
cctggccggt ttcctggtcg ccgagtcggt cggcgagatg gacacggcgc cgaccgggcc    6900
ggttgccggg ggtgcgtgg tcgcggccga tccgtggtg atcgtcggga tgggctgccg      6960
attcccgggc ggggtggact cggcggcggg tctgtgggac ctggtggccg cgggcggcga    7020
tgcgatcggg ccgttcccga ccgaccgtgg ctgggacgtc gacgcgctgt tcgatcccga    7080
tccggagcgg gtcggcaaga gctacgtccg taccggcgga ttcctctccg gggcggccga    7140
gttcgacgcc gagttcttcg gtgtgtcgcc gcgcgaggcg ttggcgatgg acccgcagca    7200
gcggctgctg ctggaaaccg cgtgggagac cttcgagcag gcgggcatcg atcccacctc    7260
gctccggggc agccggaccg gcgtcttcgc cgggatggcc ggccacgact acgcgaccgg    7320
gggcgcccgt tcgcaggccg ggctggaggg ccacctgctg accgggaacg cggccagcgt    7380
ggcctcggga cgggtggcct acacgttcgg cctggagggg ccggcggtga ccgtggacac    7440
ggcgtgctcg tcgtcgctgg tggcgctgca cctggcggcc aacgcgctgc gggcggggga    7500
atgcgacctg cgctcgccg gcggggtgac cgcgatgtcc acgccggact tcttcctgga    7560
gttctcccgg cagcgcggac tgtccgtgga cggccgttgc aaggcgttcg cggccacggc    7620
ggacgggatg ggcgcggccg agggcgtggg cctgctcctg gtcgagcggc tgtcggatgc    7680
gcggcgcaac gggcattcgg tactggcggt ggtgcgtggg tcgcggtga accaggacgg     7740 cgcgtcgaat gggttgaccg cgccgaacgg gccgtcgcag cagcgggtga tccgggcggc    7800
cctggccgac gccgggctgt ccgcggccga tgtggatgcg gtggaggcgc acgggaccgg    7860
cacgacgctc ggcgatccga tcgaggcgca ggcgttgctc gcgacctacg gcgggatcg     7920 ggcgccggat cggccgctgt ggttgggggtc ggtgaagtcc aacatcgggc acacccaggc    7980
ggcggcgggt gtggccgggg tgatcaagat ggtctcggcg ctgcggcatg ggatgttgcc    8040
gcgcacgctg cacgtggacg agccgacgcc gcatgtggac tggtcggcgg gtggggtcga    8100
actgctcacg agcgcgcggg cgtggccgga ggccgggcgg gtgcgtcggg cggggtgtc     8160 gtcgttcggg atcagcggga cgaacgcgca tgtgatcctg gagcaggcgg aggagagccc    8220
ggcgggttcg gtgccttcgg cgactcctcc ggtggccggg actccggtgt ggggcggtcg    8280
ggtgccctgg gtgttgtcgg cccggtccga accgctttg cgggcacagg ccgcgcggtt     8340
gcgggactgg ctggccgtac atcccgacgc cgatccgctc gatgtggggc ggtcgttggc    8400
gaccgggcgg gcgcgcgctcg atcaccgggc ggtggtgcat gggcgggacc tcgcggaatt    8460
gcgcctggcg gtcgcgaagt tggccgacag cgggccgggt gacgaggcgt cgatcgtcgg    8520
ctcggtctcc gccgccggtc cggttttcgt gtttccgggg cagggggtcgc agtgggtggg    8580 gatggcggcc gggttgttgg agtgttcgcc ggtgtttgcg ggtgtggttg ccgagtgtgc    8640
tgcggtgatg gatccgttgg tggcggattg gtcgttgttg gatgtgttgc ggggtgggtc    8700
tgccggtggt gaggcgttgg cggagcgggt ggatgtggtt cagccggcgt tgttcgtggt    8760
gatggtgggg cttgcgcggt ggtgggagtc gtgtgggggtc aagccgggtg cggtgatcgg    8820
acactcacag ggggagatcg cggctgcgca tgtggcggga tatctgtcgc tggcggatgc    8880
ggtgcgggtg gttgtgctgc ggagtcgggc gttgctcggg gttgcgtctt ccggtggcgg    8940
gatggtgtcg gtgggtgtgt ccgccgatcg ggcccgggag ctggtcgccg aggacgaccg    9000
gttgtcgctg gcggccgtga acgggccgac gagtgtggtg cttttcgggtg atgtcgaagc    9060 gctggccgtg gttgtcgacg gctgtgagcg ggacgggggtc cgggctcggt ggattccggt    9120
```

```
ggattacgcg tcgcattcgg cgcggatgga ggccgtgcgg gacgaggtgg agccggctgtt    9180
ggcggatgtg acgccgcagg cgggccgcgt gccgatgtac tccacggtga gtgggggca     9240
cgttaccgac ccgagtgtgc tcggtggttc gtactggttc gacaatctgc ggcgtacggt    9300
cgagttggag cgggccgtcg gagcggcggt tgtcgacggg cattcggtct tcgtcgagtg    9360
cagtccgcat ccggggctgg tggtgccact gggggacacc ctggaggcgg ccggggtgga    9420
tggcgtcgtt ctggagacgc tgcggcgggg cgagggcggt cccgatcggc tggtcggcgc    9480
gctttcggcg gcgttccgga gcggtctggc cgtggactgg gccgggtccg gatggtgcc    9540
ggggcggcgg gtcgagctgc cgacctatgc cttccagcgg cggcggtact gggtcgagcc    9600
cggcgagagg gccggcgggg tcgggtgggg gcagttcacg gtcgaacatc cggtgctggg    9660
cgccggggtc gatctggccg acggagccgg gacggtcttc accgggcggc tgtccgcggc    9720
ctcgcacggg tggctcgcgg agcatgtggt gctcggcacg gtgatcgcgc ccggcacggc    9780
gttcgtcgac ctggcgctgc gtgcggggc gacggtcggc cgggcgacgg tcgaggaact    9840
gaccctgcac gcgccgctga tcctgcccga cgcgggcggt gtacggattc aggtccgggt    9900
cggcgcaccc gacgccgccg gggtcggatc ggtggagatc cattcccgac cggaggacgc    9960
ggccggcgac gagccatgga cccggcacgc ctccgggacc ctgaccgcga ccgacctcga    10020
cccggcggac gtgccacgg aggcggcgat ctggccgccc gcgggcagta cgccggtcga    10080
tctggacgga gcctacgagc gactggccac ggccggattc gagtacggtc ccgccttcca    10140
ggggctgcga gccctgtggc ggcgcggcgc cgagtcgttc gccagatcg aactcgcgga     10200
cgacgcacgg caggaggccg aacgctacga ggtgcatccc gcgctgttgg atgcggccgt    10260
gcatgcgctg gggatggagc cgacggcgga ggttgcgccg gatgaggcgc ggattgcctt    10320
ctcctggcga ggggttcggc tggttgccgc cggagcgggg cggttgcggg tgcggctggc    10380
accggtgggc tcggacgcgg tgtcgttgtg gctgagcgac atggacgtg agccggtcgg     10440
gtcggtccgg gccctgaccg tgcggccggt cgcggccgag cggctgcgtc cggctggggc    10500
gccgccgcgc gactcgatgt tccggtgga gtggcggccg gtgtcgggcg acagtcggg     10560
cgtggcggtt cgctgggcgg tggtgggcgc ggcggactcc gggccgcttg cccggctggt    10620
ggcggcgtat ccggatgtgc cggtgtaccg cagtgtggtc gaggcggccg gggatgtggc    10680
ggcgggaccg cccgatgtcg tggtggtggg cgtgggcgag gccgactgtt cggaggggtc    10740
ggtcgagcgc actcggcggg tgcttgcgga cgtgctggcg tggatgcagg actggctggc    10800
cgactcccgc ttgcggcgca cgcgcctggt cgtggtgacc tccggggccg tcgccgccga    10860
cgtggacgcc gaccccgacg agcgggtggc ggacctggcc ggcgcggcgg tgtgggggtt    10920
gttgcgctcg gcccagtccg aacaccccga ccgatgcacg ctggtcgacc tcgacgagga    10980
cgcggcgtcg attgacgcct ggccggcgat tcttgcctcc gccgagccgc aactcgccgt    11040
ccggatgggc cgattccggg tgcctcggct ggccagggtg actgccgggg gcggcgagcc    11100
ggtcgccttc gcgcccgacg gcacggtgtt ggtcaccggt ccaccggcg gcctgggcgc    11160
cctggtggcc cggcacctgg tgaccgcgca cggcgtgcgc cgacttctgc tgctgtcccg    11220
ccggggcgcg gccgcacccg gcgcggccga actggtcgag gacctgaccg cgcaggggc     11280
ggaggtcacc ctcgccgcct gcgatcgtgc gcgctggcc gccgagttgg cgcgtatccc     11340
ggccgagcac gcgctgaccg gcgtgatcca caccgccgga gtggtggacg acgccaccat    11400
cgcgaacctg accgatgcgc acatggaaca cgcgctgcgc cccaaggcgg acgccgcgtt    11460
ccatctggac gagttgaccc gggacgtgaa cccggccgca ttcgtcctgt tctcctccgg    11520
```

```
ggccaccacc ttcggtggcc cgggacaggg caactacgcg gcggccaacg ccttcctgga    11580
cggcctggcc cggcagcgcc gcgaccgcgg cctgcccggg atctcgctgg cctggggcct    11640
gtgggcgggc gcgcagggga tgggcgggcg gctgagcgag gccgacctgg cccgctgggc    11700
ccggaccggc gcggtggcga tgccggcggc cgaggcactg cggttgttcg atatcgcgct    11760
gggccggccc gaggcggccc tggtgccggc acacctggac ctcccggcga tgcgggcgga    11820
tgccggtgct cgacccgcgc tgttccgcga gttgctcggg atcggtacgc gacgggcggc    11880
agtgggcgcg ggcgggtcgg cgctgacccg gcggctggcg gggatgtctc cggccgagcg    11940
ggagcaggcg gtcctggacg tggtgcggac cgaggccgcg aacacgctgg acacgagtc    12000 ggccggggcg gtgtcggccg ggcgagcgtt caaggagctg gggttcgact cgctgaccgg    12060
ggtggaactg cgcaaccggt tgaacaccgc gaccgggctg cggttgccgt ccacgctggt    12120
cttcgactac ccgacgccgg cggggctggc ggcgttcctg gtcgccgagt tggtcggtcg    12180
ttcggtacag gcggtgccgg tgccgccggt cggtgggcgg cacggggacg ccgacgatgc    12240
gatcgtgatc gtcggcatgg gctgccggtt cccgggcggg gtggcctcgc cggaggacct    12300
gtggaatctg ctggcctcgg gtggggacgc gatcggaccg ttcccgacgg accggggatg    12360
ggacctggcc gggctgttcg accccgatcc cgagcgggcc gggaagagct acgtggaatc    12420
gggcggattc ctgtatggga tcggcgagtt cgacgcggag ttcttcggga tctcgccgcg    12480
tgaggcgttg gcgatggatc cgcagcagcg gttgctcctg gagacggcgt gggagacgtt    12540
cgagcgggcg ggcatcgatc cgacctcgct gcgcggcagc cggaccgggg ttttcgccgg    12600
ggtgatcgac aacgactacg gcgcccgggt gaaccaggtg ccggacgagg tcgagggcta    12660
tctgggctac ggcagttcgg ccagcatcgc gtccgggcgg gtctcgtacg tcctgggcct    12720
ggagggcccg gcggtcagta tcgacaccgc gtgctcgtcg tccctggtcg cgctgcacct    12780
ggcggtgaac gcggtgcggt cggcgaatg cgaactggcc ctggccggtg gtgtgacggc    12840
gatggccacc accgagttct tcgtggagtt ctcccgacag cggggcctgt cgccggacgg    12900
ccgctgcaag gcgttcgcgg cggcggcgga cgggatgggc gcggccgagg gcatcgggct    12960
ggtgctggtg gagcggttgt cggatgcgcg gcgccatggg cattcggtac tggcggtggt    13020
gcgtgggtcg gcggtgaacc aggacggcgc gtcgaatggg ttgaccgcgc gaacgggcc    13080 gtcgcagcag cgggtgatcc ggcaggcgtt gggtgctgcg ggcttgtctg cggcggatgt    13140
ggatgcggtg gaggcgcacg ggaccgggac gacgttgggt gatccgatcg aggcgcaggc    13200
gttgttggcg acctatgggc aggatcggcc gggggatcgg ccgctgtggt tggggtcggt    13260
gaagtcgaat atcgggcaca cgcaggcggc tgcgggtgtg gccggggtga tcaagatggt    13320
gttggcgctg cggcatgggg tgttgcctcg gacgttgcat gtggacgagc cgacgccgca    13380
tgtggattgg tcgccgggc gggtcgaggt gttggcggac gaggtggcgt ggccggcagg    13440
ggagcgggtg cgccgggcgg gtgtgtcgtc cttcggaatc agcgggacga acgtgcacgt    13500
ggtcctggag gaggcgccgg cggacgccgc cgagcctgcg cccgccgcgc cggaggtccc    13560
gggcgtcggc ggcgtgctgc cctgggtggt gtcggcgcgc accgaggccg ggctgcgggc    13620
gcaggcggcg cggttgcggg attgggtgag cgaacatccg gacgccgaac cgacggatgt    13680
cgcacggtcg ttggtggtcg ggcgagcggt gttggacgtg cgcgcggtgg tgcgcgggcg    13740
ggaatccggc gaacttgtcg ccggcctgga cgagttggcg cgggccgggg tgggagaccc    13800
cggctcgctg gtgagcggct cggatccggt gttcgtgttt ccggggcagg ggtcgcagtg    13860
```

```
ggtgggatg gcggccgggt tgttggagtg ttcgccggtg tttgcgggtg tggttgccga   13920
gtgtgctgcg gtgatggatc cgttggtggc ggattggtcg ttgttggatg tgttgcgggg   13980
tgggtctgcc ggtgagttgg agcggtggat gttgttcag ccggtgctgt ttgcggtgat    14040
ggtgggcctt gcgcggtggt gggagtcgtg tggggtcaag ccggtgcgg tgatcgggca    14100 ctcgcagggg gagattgcgg ctgcgcacat cgcgggttat ctgtcgctgg cggatgcggt   14160
gcgggtggtt gtgctgcgga gtcgggctct gctgggggtt gcgtcttccg gtggcgggat   14220
ggtttcggtc ggggtgtctg cggagcgggc gcgggagttg gttgccggag ctgacgggtt   14280
gtcgttggcg gcggtgaacg ggccgacgag tgtggtgctt tcgggtgatg tcgaagcgct   14340
gtcggtggtt gtcgaggcgt gcgagcggga tggtgtgcgg gctcggtgga ttccggtgga   14400
ttacgcgtcg cattcggcgc ggatggaggc cgtgcgggac gaggtggagc ggctgttggc   14460
ggatgtgacg ccgcaggtgg gctgcgtgcc gatgtactcg accctgaccg gtgcgccgat   14520
cgccgatccc gccgagttgg gcgggcgta ctggttcgaa aacctgcggc gcacggtcga    14580
gttggagcgg gcggtcggtg cggcagtggc ggatgggcgc accgtgttcg tcgagtgcag   14640
tccgcatccg gggctggtgg tgccgctggg ggacaccctg gaggcggccg gggtggatgg   14700
cgcggttctg gagacgttgc ggcggggtga aggtgggccc gatcggctgg tcgccgcgct   14760 ctcggcggc ttcgtgcgtg gtctggcggt ggattgggcc gggttgatcg tcggtgctcg    14820
ggtggagttg ccgacctacg ccttccaacg acggcgctat tggttggacg acggggcgcg   14880
gtcgggggat ccgggcgggt tgggactggc cgcggtcgca catccctgc tgggtgcggc    14940 ggtacggccg gcgcagggcg cggggttgtt gttcaccgga cggttgtcga cggcgaccca   15000
cccgtggctc gcggatcatg tggtgctcgg ctcgacgatc gtgcccggca cggtgttcgt   15060
ggacctggcg ctgtgggccg gggccgaggc ggagtgcccg gtggtggacg aactgaccct   15120
gcacaccccg ctggtgctgc cggaacacgg cggcgtgcat gtacaggtga ccgtcgacgg   15180
gccggacgcc gccggggccc gggcggtcgc ggtgtactcc cggccggagg acgctcccgg   15240
cgaggagccg tggaccccgg cacgccgtcgg tgccctcgtt gccgacgccg atacgggtgc   15300
cgctcccgac gcggctgcgg aggcgtggcc gccggtcggc gcgaagccga tcgaggtggc   15360
ggacttctat gcgcgctgg tggagtccgg ggtcgactac gggccggcgt ttcgcgggat    15420
gcgggccgcc tggcggcgcg gggacgagct gttcgccgat gtggcgctgc cggccgagga   15480
ggagcgcgac gcacaccgct tcggggtaca tccggcgctg ctcgacgcgg gcgtgcagac   15540
cctgcgggtg gatccggggc aggtcgacga ggacgacatc cgggtggcct tctcctggca   15600
cggggtgcgg ctcttcgcgg ccggcgtgac ccggctgcgg gtgtcgtgcg tgccgtcggg   15660
cgaggtgcgg gtgtcgttgc ggatcacgga cgagaccgga cgggcggtcg ccgcgatcga   15720
ggcgttgacg gtgcgggcga tctcggccga ccagctacgg cgggccggcg gcgggcggga   15780
cgtgctgtac cggctcgcgt ggcgggcatc ggcggttccc gtaccggtgg cgacgcctcg   15840
tgtggcggtg gtcggcgggt gggatctgcc cggtctgggc gggttggtgg accggtatcc   15900
gggctttgcc gaacttgctt cgtgtgaccc gccgttgccc gatctggtac tgctcccggt   15960
tggtgatccg gatgcggatg tgccgttctc cgagcggcgt atgcgggagg tgacggcgga   16020
actgatcggg cggctggagg cgtttctcgg cgacgaacgg ttcgcggcgg ccggtggt    16080 cgtggtgact cgttcggcgg tgctcgtgga cggggacgcg gggctcgggg accggcgtc    16140 ggcgtcggtc tggggagtgg tccggcggg gcaggccggg catccggggc ggatcgtgct   16200
ggtcgacctg gacgacgagc cggcttcggc ggcggctttg gcggcggtgg cctcggccgg   16260
```

-continued

```
tggtgagccg cagttcgcgg tgcgcggtgg tcgggtgtcg gtaccgagac tggagcggat   16320
tccggcctcc ggcggagcac ggtcggcggt ggggaccggc acggtgttga tcgccggtgc   16380
ggaccgggcg gtcggcgcgg gggtggccga gcatctggcc ggggcgtacg gggtgggccg   16440
gttcgtgttg ttgtccgtgg atccttcggg tgcggggccg accgaactgg ccgcccggct   16500
gggtgaggcc ggtgccgagg tcgtctcggc ggcctgggac gggcacgatc cgggcgtgct   16560
tgccgcgctt gtgaccgaac accggccggc gggcgtggtg gacgcgtcgg gcgagtcgga   16620
tgcagcctgg gccctgcacg agctgaccgc cgacgtggac ccggcgttct tcgtgctgtt   16680
ctcgtcggcg gcgagcctgc tcggttcgtc ggcgcatgcg gccacggccg gggtggatgc   16740
cttccacgat gcgctggccg cacatcggcg ggcgagtggg ctgcccgggg tgtcgcttgc   16800
gtgcgggacg gatccgctgc cggggctgcc cgacctgttc gacgaggcga tacgccggga   16860
ggacgccgtg ttggtttcgg cgtcgacgga tctcaccggg cccgcgtcga cgtcaccatt   16920
gttgccctcc cggaacggtc gtggcgcgac caactccgcc gagacctcga tcgaggcgga   16980
cggcgaggcc ctggcccggc gcctggcggc gttgtccgag gaggagcgcg agcgcgaact   17040
ggtcggcctg gtacgggccc aggccgcggc ggtgctcggg catgccggca tcggcgagat   17100
cggacccgaa cgggcgttca aggaggtcgg gttcgactcg ctcaccgcgg tggaactgcg   17160
caaccggctg atccggggca ccggggtcgg cctgcgctcc accctcgtct tcgacttccc   17220
cacgccgcga atactggccc gccacctgag cggccggctg gtcgaggcgg catccccgat   17280
cggtgcgctg ctggccgatc tggaccgatt cgagggcgag ttgcacgcgg tgctcggcga   17340
ggcggaggcc cgcgaccggc tggccgagcg gctgcgtcgg ctgttggccg actgtaccgc   17400
gccggacgag agcgccccg ccgccgacga tgtctcggac gtgcagtcgg ccaccgacga   17460
cgagttgttc tcgctcgtcg accagggctt cgaatgaccc ggcccatcca cgcatacgac   17520
cgtgtcggca aggagtagag gcaacgtggc tgagtcggaa gagaaactgc gctcgtacct   17580
gcggaaggcc atcaccgatg cgcgcgacgc gcatcgccgg gtacgcgagt ggaggaccg    17640
gcagcgcgag ccgatcgcga tcgtgggcat ggcctgccgc ttccccggcg gtttgggtac   17700
gccggaggac ctgtggcggt tcgtcgtcga aggcggcgat gcgatcggcg agttcccgac   17760
cgaccggggc tgggacctcg acggcctgta cgacccggat cccgaccggc cgggcacgtc   17820
gtacgtccgc gagggcggat tcctgtacga cgtcgccgac ttcgacgccg agttcttcgg   17880
catctcgccc cgcgaggcgg cggcgatgga cccgcagcag cgactgcttc tggagacctc   17940
ttgggaggcc gtgaacgcg cgggcatcga cccgacgtcg ctgcggcaca gccggaccgg   18000
gatctacacc gggatcaacg gcctcgacta cacgaccgtg ttggcccgca ccgccaaggg   18060
ccgggacggc acgctcggca tggccaacgg ggccagcctg ctggcgggtc gggtggcgta   18120
catcctcggc ctggagggc cggcggtgac cgtggacacg gcgtgttcgt cgtccctggt   18180
ggcactgcac ctggcgagca acgcactgcg gtcgggggaa tgcgacctgg ccctggccgg   18240
cggtgcgacg gtgatgtgca cgccggagat cttcgtcaac ttcagccggc agcgcggact   18300
ggcccgcgac ggccgatgca agccgttctc ggcggcggcc gacgggttca tcctctccga   18360
cggcgcgggc ctgttcctga tcgaacggct ctccgacgcg cggcgcaacg gacatccggt   18420
actggccgtg ctgcgcggtt cggcgatcaa ccaggacggc gcgtcgaacg ggctgaccgc   18480
gccgaacggc ccggcccagg agcgggtgat ccggcaggcc ctgcagagcg ccgggttggt   18540
gaccggtgac gtggacgccg tggaggcaca cggcaccggg accacgctcg gcgacccat    18600
```

```
cgaggcgcac gcgctgttgg cgacctacgg gcaggatcgg cccgcggatc ggccgctgag   18660
gctcgggtcg atcaagtcca acatcggaca cacccaggcc gccgcggggg tggccgggat   18720
gatcaagatg gtgttggccc tgcggcacgg cgtgctgccc aggacgctgc acgtcgacgc   18780
gccctcgccg cacatcgact ggtcggccgg gcgggtggaa ctgctcacgg agcccgtgcc   18840
gtggccgagg tcggaccggc cgcgccggc cggtgtctcg tcgttcgggg cgagcgggac    18900
gaacgcgcac gtggtggtgg aggaggcgcc gtcggacggc gacgacggtg tcgtggaggt   18960
gcccgcgccc acgggcatcg gcagtgtcct gccgtgggtg ttgtcggccc gatccgaggc   19020
ggcgttgcgc gcgcaggcgg ggcgattgcg ggactggctg gccgagcacc ccgaggcgga   19080
tccggtcgac gtgggccggt cgttggcggt ggggcgtgcg gtgctggaac gtcgcgccgt   19140
ggtgcgcggg cgggatgtcg ccgaactcgc cgtcgggatc ggcgaggtgg ccgaccgcgg   19200
agaactcgcc ggtgggcggc cgatgttcgc cggacccggt ccggtgttcg tgtttccggg   19260
gcaggggtcg cagtgggtgg ggatggcggc cgggttgttg gagtgttcgc cggtgtttgc   19320
gggtgtggtt gccgagtgtg ctgcggtgat ggatccgttg gtggcggatt ggtcgttgtt   19380
ggatgtgttg cggggtgggt ctgccggtgg tgaggcgttg gcggagcggg tggatgtggt   19440
tcagccggcg ttgttcgcgg tgatggtggg gcttgcgcgg tggtgggagt cgtgtggggt   19500
caagccgggt gcggtgatcg gacactcaca ggggagatc gcggctgcgc atgtggcggg    19560
atatctgtcg ctggcggatg cggtacggat cgtggtgttc cgcagtcggg cgctgcgcgg   19620
gatcgcggcg gccggtggcg gcatggtctc cgtgggcgtg tccgtcgagc gtgccgagga   19680
actggtggcc ggctctgccg ggttgtcgct cgcggccgtc aacgggccgc agagcgtggt   19740
gctttccggc gaccgtgagg cactggccgc cgtcgtcgac gcgtgcgagc gcgagggtgc   19800
gcgagcccgg tggatccccg tggactacgc gtcgcattcc gcgcacatgg aggtggtccg   19860
ggacgaggtc gagcgtttgt cggccgaggt gacgccgcgg gcgggtcggg tgccgatgta   19920
ctcgacgctg accggggaag tcgtcacgga cccggccgag ttgggcgccg gctactggtt   19980
cgagaacctg cgcgggacgg tacggctgac caccgcagtg ggggcagccg ttgccgacgg   20040
acacgtcgcc ttcgtcgagt gcagcccgca tccgggcctg gtcgtgccgc tcgcggacac   20100
cctcgatgag ctgggcgtcg acgacggcac ggtcctggag acgttacggc gggacgacgg   20160 cggcccgat cggctggtcg ccgcgctctc ggcggcgttc gtggcgggtg tgccggtgga    20220 ctggccgca ctgttccgg gcgagggcg ggccgacctg cccacgtacg ccttccaaca      20280
tcggcgctat tgggccgagg ccgaatcgcc cgcaggcggc ggcgtggcct gggggcagcg   20340
cgcggtgacg catccggtac tcggcgccgc cgtcgacctg gccggcgacg cgggcaccgt   20400
gttcaccggg cggctgtcga cgaccgccca accgtggctg gccgaccacg ccgtgctcgg   20460
cacggtgatc gtgcccggga cggcgttcct ggacctggtc ctgcgggccg agccgaggt    20520 cggctacccg gcgatcgagg aactgaccct gcacacgccg ctcgtgctgc ggacgcctc    20580 gggcgtcctg gtacaggtcg tggtcggtgc cgcggacggc gacggcggcg acggcggcga   20640
cggggcccgg acgtcgatg tgcactcgcg ggccgaggac gcgccgccgg accacccgtg    20700
gacccggcac gcctcggggg tgctggtcgc ggcgggcgag gagcgggccg aggacgcgcc   20760
ggccgggcgg tggccgccga ccgtgccga ggtggtgggg gtcgacgacg cctacgagcg    20820
gctggcggtg gcgggcttcg actacggccc cgtgttccag gggctgcggt cggtccgggc   20880
gcgaggcgac gagttgttcg ccgaggtgga gttgccggag gaggggcacg cggacgcgga   20940
ccggttcgcg gtgcacccgg cgctgctcga tgccgcgttg cacccgctgg tggtcgcggc   21000
```

-continued

```
cggtgccgac gcgccggtcg tggccgggct gccgttcgtg tggcacggca ttcgggcggg    21060
tgttcccggg gcgcgacggt tgcgggttcg gctggtgcgc tcggcgtcgg ggtcggcgtc    21120
ggggtcggct gcgggctcgg actcggcttc cggcgaggtg tcggtccggg cgtgggacga    21180 ggcggccgg gaggtggtgg cgatcgagtc gctgaccatt cgcccggtct cggcggacgg     21240
gttgcggacg cccgatgctt tggtccgcga ctccctgttc acgctcgcgt ggaccgcgtt    21300
ggagctaccg gacgtcgatg acgacgtgcc gaacgcgacc ctgctgggcg gcgacggtgc    21360
ggccgatctc gccgcgctgg tggctgccat ggacaccgga acggacgtac cggctctggt    21420
ggctctgccc gtatcggtcg acgacgcgga ccccgtggcg gcggcgcaca cggccggccg    21480
gcaggtgctg gcggtactcc gggactggct ggcggacgag cggttcgccg actctcggct    21540
ggtgttcgtc acctccggcg cggtcgcggt cgccgacgag caggtacgtc cggcctcggc    21600
ggctgtctgg ggcctggtcc gctccgccca gtccgaacac ccggggcgct tcgtcctggt    21660
ggacgcggac tccgtcgccg accccggccc ggagttcgac cgggccctgc ggaccggtgc    21720
ggaccagctg atcctgcgag atggaacggc cctgataccg aggctggttc gagccccggc    21780
ggacggcgga tcgggcggat tcgtgcccgc tgccgacggc acggtcctga tcaccggcgg    21840
caccggcacc ctgggcacgc tgcttgcccg gcacctggtc accgaacacg gcgtgcgccg    21900
gctcctgttg ctcagtcggc gcggcggtac ggccgccggc gcgacggacc tggtcgcgga    21960
actcgccgcg ttcggtgccg aggtgacctg cgtggccggg gacgccgcag accgcgccac    22020
gctggagcgg gtgttggcgg acatccccgc cgaacacccg ctgacggcgg tgatccacgc    22080
ggcgggtgtg gtggacgacg gcgtcgtaca gtccctcacc gccgaccggc tggacgcggt    22140
gttgcgccct aaggtggacg ccgcgtggaa cctgcacgag gcgacccggc acctggacct    22200
gaccgcgttt gtgctgttct cctctgcggc gggtgtgctc ggaaacccg gccagggcaa     22260 ctacgcggcg gccaacgcct ttctcgacgc gctcgcacgc cgccggcgcc gtgagggcct    22320
gcccggcagc tcgttggcgt ggggctggtg ggcgccgacc agcgagatga ccgcggggct    22380
cggcgacgcc gaccggcagc ggatggcgcg tttgggtgta ctgcccctgg cgccggaaca    22440
ggggttggcc ctgttcgacg cggcgacgaa ccatgccgaa ccgacaccga ccgtggtccg    22500
gatgaccctc gcggtgctac gcaccgccgg atcggtggtg cccacgctgc tgcgcgtct     22560 ggcccgggtg cccaaccggc gggctgcgac ggcgggttcg gtggccgagc tgcgccgtcg    22620 tccgccggc gtatcggcct tcgactggga gcagacgctg atccgggcgg tgtgcgtgca     22680
tgccgccgcc gtcatcggcc acgccgacgc gaccgagatc gatgagacac gggcgttccg    22740
cgacctgggc ttcgattcgc tcacaggtct ggagctgcgc aatcgactga acacggcaac    22800
cggactgcgg ctgcccgcca cgctggtctt cgactacccc agcccggtgg tcctgggccg    22860
gtggttgcgt gatcggctcg ccgaggagga cgccgggggc ccggtcggct cgaccctcgg    22920
agcgcaggtg gtgtcgccgg tcggttccga cgccggcgag gactcgatcg tgatcgtcgg    22980
catgggctgc cggttccccg gcgggatcac cgcgcccgaa cacctgtggg acgtggtggc    23040
cggtggggtg gacaccctca ccgacttccc caccgatcgt ggctgggatg tcgagcgcat    23100
cttcgacccg gacccggacc gacccggcag cacctacgtg cgcaccggcg gattcgtgga    23160
ctcggccgcc gacttcgacc cggacctctt cgggatctcg ccgcgtgagg cgttggcgat    23220
ggatccgcag cagcgattgc tcctggagac ggcgtgggag acgttcgagc gggcgggcat    23280
cgatccgacc tcgctgcgcg gcagccggac cggggttttc gccggcgcca tctactacga    23340
```

-continued

```
ctacgcgggt ggccggctgc ggaaggtgcc ggacgaactg gaaggctaca tcggcaacgg      23400
caatgtgggc agcgtcgcct cgggccgggt ggcctacacg ttcggtctgg aggggccggc      23460
ggtcaccgtg gacacggcgt gctcgtcgtc cctggtggcg ctgcacctgg cggtgaacgc      23520
ggtgcggtcg ggcgagtgtg aactggccct ggcgggtggc gtcaccgtga tgtcgacgcc      23580
cagcgtcttc ctcgacttct cccggcagcg cggcctgtcg tccgacggcc ggtgccggtc      23640
gttcgcggcg gcggcggacg gcaccggggtg gggtgagggt gtcgggttgg tgctggtgga     23700
gcggttgtcg gatgcgcggc gcaatgggca tccggttctg gcggtggtgc gtgggtcggc      23760
ggtgaaccag gacggcgcgt cgaatggttt gaccgcgccg aacgggccgt cgcagcagcg      23820
ggtgatccgg caggcgttgg gcagcgccgg gttgtcgccc gccgatgtgg acgccgtgga      23880
ggcgcacgga accgggacga cgttgggtga tccgatcgag gcgcaggcgt tgttggcgac      23940
ctatgggcag gatcggccgg gggatcggcc gctgtggctc gggtcggtca agtccaacct      24000
cgggcacacg caggcggctg cgggtgtggc cggggtgatc aagatggtgt tggcgctgcg      24060
gcatggggtg ttgcctcgga cgttgcatgt ggacgagccg acgccgcatg tggattggtc      24120
ggccgggcgg gtcgaggtgt tggcggacga ggtggcgtgg ccggcggggg agcgggtgcg      24180
ccgggcgggt gtgtcgtcct tcggaatcag cgggacgaat gcacacgtgg tgctggaaga      24240
gccgccgccg gtgaccgaag tgccggatgt ggccgtcgag tccggctgg gcgggcggca      24300 cacctgggtg gtgtcggcgc ggtccgaggc agcggtacgg gaacaggcgg cccggctgcg      24360
cgactgggtc acgcccgtc cggatctcga tccggcgcac gtggcccggt cgttggtgtg      24420
cgaacgggcg ctgttcggcc atcgggcggt ggtctccggc gccgatctcg ccgagctggc      24480
cgatgggttg tccgccgtgg cggcgggcgc cgagggcgcg tggtcggtg cggtgggtcg       24540 cgggccgggg aagacggccg tgctgtgcac gggtcagggg gtgcgggcgc tcggtatagg      24600
ccgcgaactt cacgcggcgt tcccggtgtt cgccggcgcc ctggacgagg tgtgtgcggc      24660
cttcgacgat gtggtgccgt tctcggtgcg ggacgtcgtg ctcggtgccg aagggggtgtc    24720 ggatgccgac gcgcaggaca ccggggtggc ccagccggcg ctgttccgcgt tcgaggtggc     24780 gctgtaccgg ctgtgggcct cgtgggggca ggcgcccgac ttcgtggtgg ggcattcgct      24840
cggcgagatc gttgcggcgc atgtggcggg agtgttctcg ctcgcggatg cggtggtctt      24900
cgtcgcggcg cgggctcggt tgatgagtgc gctgccgagt ggaggggcga tgctcgccgt      24960
cggtgcgagc gaggccgagg tggcggcgtc gtgcccggcc gaggtgacga tcgcagcggt      25020
gaacggcccg gcgagtgtgg tggtttccgg acccgccgag gcggtggccg cgctcgaacc      25080
ggactgcgtg atgcgcgggt ggcggatctc gcgcctgtcg gtgtcgcacg ccttccactc      25140
ggcgctgatg caaccgatgt tggccgaact ccgcgaggtc ctgaccgggt tgacctacgg      25200
cacgcccgag atcgcggtgg tgtcggacac caccgggcgg gttgcgggcg ccgaagagtt      25260
ggctgatccc gagtactggg tgcggcacgt acgccgcgcg gtgcgcttcg gggatgcgat      25320
cgccacgctg cgcgccgaag gggtacggac cttcgtggag atcgggccgg aggcggcgtt      25380
gaccgcgatg gtggtcgagg gcacggccgg cgcggaggac gtggccgccg tagcgacccg      25440
gcgtcggggt cgagcggccg tgtcgagtgt ggtggaggcg ctcgcccggg tgttcgtgca      25500
cggcgcgacg gtggattggg ccgcgttgtc caccggttcc gggcccgggg acggggtgga     25560
tctgccgacc tacgccttcg agcggcggcg cttctggttg cacgccggtg tggacgcggg     25620
cgacgcggtc gggctggggc agggtgtggt ggaccatccg ctgctcggtg cggtcgtggg     25680
cctggcggac gaccagggcg tcctgttcac cggccggttg gccctggaca cccatccgtg     25740
```

```
gttggccgaa cacaccgtct tgggcacggt attgctgccg ggcacggcat tcctggagct   25800
ggccctgcac gtcggccgcc tcctggactg cgcgcgggtc gacgagctga ccctgtcggc   25860
cccgctggcg ctgccgtcga cgggcggtgt gcaggtccag gtccgagtcg gtgtaccgga   25920
ggagagcggg acacggacga tcacggtgca tgcccgcccg gattcggcgg aggaggcgcc   25980
ttggacgctg cacgccgccg gggccctggg tccatcagcc gaggtggatg caccctcgga   26040
tgccgcgagt tggccgcctg ccgatgcgac cgcgatggac tcggcggggc tgtatccctg   26100
gttcgccgag accggcgtcg actacggacc ctcgttccgg ggcgtacaag cgacctggcg   26160
ccgtgatgac gaggtgttcg cggagatcgt gctcgcggcc gacgacccgg ccgccgacgg   26220
ccggttcgag ctgcaccccg cgctgttcga cgccgcgttg cacccgctgg gcctgaccct   26280
gctcgacgcg gcggagccgc gcctgcggct gccgttctcc tggcgcggag tggcgctgca   26340
cacgtccggg gctcgcacgt tgcgggttcg gctgcgtccc accggccccg acaccatcgc   26400
ggtgacggcc accgacgaga cgggtcgacc ggtggtcgcg gtcgaggccc tggcggtgcg   26460
cgaaccctcg cgggaccgac tgccacgacc cgacgcgaac gcgggcgagt tgttcgagcc   26520
gcagtggacg ccgctgtcac cggcggacac ggcggacatg gcggacacgc tcggggcggt   26580
ggtgggcggc cccgaactcg cctcgacagc caccccgattc ggtgccacac atcaccctga   26640
cctggccgcc ctggccgaat cggcaatccc cgagacggtc ctgtacgacc tggtcaccgc   26700
cgttcccggc gtatccgccg aagccgtaca ccaagccgcc gcccaagcgc tggacctggc   26760
ccgatcctgg ctcgccgacg agcgcttcga gtcggcccgc ctgatcgtgc gcacccgaca   26820
cgcggtcgcc gccgccgaag gcgacgcgcc ggacccggcc gccgccgcga cccatggcct   26880
gtttcgtacc gcctgctccg aacaccccga gcggttcgcg ctcgtcgacg ccgacgacct   26940
cgacgaggtc tcgcccgagg ccatcgccgc cgtcgtggtc gagcccgagg cggccgtgcg   27000
ggccggtcgc gtcctggttc cgcgcctgcg ccgagcggcc gtggcgccca aggccgactt   27060
cggcttcgcc gccgaaggca ccgttctgat caccggtggc accggagcac tgggccggca   27120
ggtcgcccgg cacctggtgc gcgtacacgg ggtgcgccgc ctcctcctgc tctcccgtcg   27180
cggcgacgaa gccccgagg ccgccgagtt gcgggccgaa ctgatcgagg ccggcgcgca   27240
cgtcaccttc gccgccggag acgctgccga acgtggcgtg ctggccgacg tgttggccgc   27300
gatcccggcc gcccacccgc tgaccggcgt ggtgcacctg gccggggtga ccgacgacgg   27360
gctggtcggg acgctgaccc ccgagcggct ggcggcggtg ttgcgcccca agatcgacgc   27420
ggcgctgcac ctggacgaac tcaccgccga cgccgacctg tcggcgttcg tcctgttctc   27480
ctcggccgcc ggtccggtcg gcaacccggg ccaggccaac tacgcggcgg ccaatgtcgc   27540
cctcgacgcg ctggcccgcc ggcgccgagc gcgcggccga ccggccgtgt cgttgcagtg   27600
ggggttgtgg gccgaacgca gtgcgctgac cgcgacgatg agcgcgaccg atcgcgccg   27660 ggcggccggc gcgggtgtgc gggcgttgtc cgtggagcag ggcctcgcac tgctggacgc   27720
ggcggccggg cggcccgagg cggtgctgac gccgctgcgc ctcgatccgg cgatcctgcg   27780
cggtccggag gagcgggtgg cgcccgtgtt gcgcgggctg gtgccgaccc gggccgggcg   27840
tgcgccggcc cgtacctcgg acaccgcccg ctcactggtg cgccgattgg ccgcgttgcc   27900
cgaggccgag caggaccggc tgttggtcga cctggtccgt acccacgcgg ccggtgtgct   27960
cggccacgcc gacgcgcgca cgatcgaccc ggaccgcgcg ttcggcgaac tgggcctgga   28020
ctcgctggcg gcgttggaac tgcgcacccg gttgagcacg gcggtcgggc tgcgcctgcc   28080
```

-continued

```
cgccacgatg ttgttcgacc atccgtgcgc gcgtgccgtg ggcgtacacc tgcgcgcgca      28140
actgctcgac gcgccgacac ccgggcgggc ggcgggtgtc gcccggccgg tgtcggacga      28200
gccggtcgcg gtggtggcga tcagctgccg cttccccggc ggcgtcgcga gccccgagga      28260
cctgtggcgg ctggtgtcgg aacacaccga cgccatctcg gagttccgc aggatcgggg       28320 ctgggacctg gccgagctgt ccacccgga ccccgaacat gccggtacct cgtatgtaag       28380
cgagggcgga ttcctttacg aggcaaccga gttcgacccg gagttcttcg gcatctcgcc      28440
gcgcgaggcg ctggccatgg acccgcagca gcggttgctc ctggaggcgt cctgggaggc      28500
gatcgagcgc gccggcgtgg atcccaggtc gctgcgcggc agtcgtaccg gggtgtacgg      28560
gggcctgatg tacgccgact acgcgtcgcg ggtgggcagc gcgccgaagg gcgtggacgg      28620
gtatctcggg aacggcagcg cgggcagtat cgcgtccggg cgggtggcct acacgctggg      28680
tctggagggg cccgcggtga ccgtggacac cgcctgctcg tcgtccttgg tcgcactgca      28740
cctggcggcc aacgcactgc gccagggtga gtgtgatctg gcgctggcgg gcgggtgac       28800 ggtgatgtcc agcccggcca cgttcgtcga gttctcccgg cagcgcggcc tggccccgga      28860
tgcgcggtgc aagtcgttcg cggccggcgc cgacggtacc tcgtggtccg agggcatcgg      28920
tctgctcctg gtggaacgcc tgtcggacgc gcgccggttg ggccatccgg tgctggccgt      28980
ggtgcgcggc agtgcgatca accaggacgc gccagcaac ggcctggccg cgcccaacgg       29040
gctcgcccag gagcgggtga tccgggatgc gctcgcgcac gccgagttgc gtccgtccga      29100
cgtggacgcg gtggaggcgc acggcaccgg cacgccgctg ggcgacccga tcgaggcgcg      29160
cgccctgctc gccacctacg gcaggaccg gccggcggat cggccgttgt ggctggggtc       29220
ggtcaagtcc aacctcgggc acacccaggc ggcggcgggc gtggccggcg tgatcaagat      29280
gatcatggcg atgcggcatg ccgaactgcc cgggacgctg cacgtggacg ccccctcacc      29340
gcacgtggac tggtcggcgg gggcggtgtc gctgctcacc gccgcgaccc cgtggccgca      29400
gaccgggcgt ccgcgccgtg cggggggtgtc gtcgttcggg atcagcggga ccaacgcgca     29460
cgtgatc                                                                29467
```

<210> SEQ ID NO 2
<211> LENGTH: 9726
<212> TYPE: DNA
<213> ORGANISM: Streptomyces ap. ATCC 39366

<400> SEQUENCE: 2

```
gatccgcgac tgcgacgcgg cactcgcgcc gcacaccgac tggtcgctgc tcgccgtgct       60
gcgcggcgag cccgacgcgc cgccgctcga ccgggtcgac gtggtgcaac cggtgttgtt      120
cgcggtgatg gtcgcgctcg ccgaactgtg cgctcgctg ggcgtacggc cggcttcggt       180
ggtcggccac tcgcagggcg agatcgccgc cgcccacatc gcgggcgcgc tcaccctcga      240
cgacgcggcc cggatcgtcg cactgcgcag ccgcgccctg cgcgggttgt ccggcgacgg      300
cgggatgatg tccgtcgcgg ccggcccgga gcagatcgcc cgattgctcg acggattcgc      360
ggaccggctc ggcatcgccg ccgtcaacgg ccccgccgcc gtggtgattt ccggcgcggc      420
cgacgcgctc gccgaactgc acgcccactg cgaggcggac gggatccgcg cccgggtgct      480
cccggtcgac tacgcctcgc actccgccca ggtcgagcag gtccgcgagg aactgctcgc      540
cgccctgggc gagatcgtgc ccacgccgac caccgacgcg gtcttctact cctcggtcac      600
cggcgaaccc gtcagggca ccgcgctcga cgccgagtac tggtaccgca acctgcgcgc       660
caccgtcgcc ttcgaccggg ccaccgatgc cctgctgcgg gacggccaca cggtgttcgt      720
```

```
cgagaccagc cgcatccgg tccttgcgcc cgccgtcgag gatagtgccc agcgcgccgg    780
tacggacgtg acgtcgtgg gcagcctcca gcgcgacacc gacaccctcg cccgtttcct    840
caccgccgcg gccggcctgc acgtgcacgg cgtcccggtg gactggtccg cgacccacgc    900
cggacaccgg ccccggccgg tcgacctgcc cacctacgca ttccaacgcg agcgctactg    960
gctggaggcg ggcaagacgc ccaccgacgc ggccggcctc ggcctgcacc cggcggcaca   1020
ccccctgttg ggcgcggccg tggtacccgc cgagggcgac cggcacatcc tcaccggccg   1080
catctcgctg cgcacccacc cctggctcgc cgaccacacg atcctggaca cggtgctgct   1140
cccgggcacc gcgttcgtcg aactcgccct ccaggcgggc gatcgggccg actgtgacct   1200
gatcgaggag ctgaccgtcg aggccccgct gcggctcacc gacaccggcg ccgtacacct   1260
gcaggtgttg ctggacgagc cggacgagca gggccgccga gcgctgacca tccactcccg   1320
agccgacgac gcgcccgcgg agcagacgtg gacgcggcac gcgagcgggg tactggcgcc   1380
ggtcgcggac ggcctcgacg ccgtgccggc gaccgacgcc gcgtggccgc cgccggggc    1440 cgtcgcgctg gacgtggacg ggctgtacga gcggttggcc gggcagggct accggtacgg   1500
accggccttc cgggcggtgc gggccgcgtg gcgcctgggc gatacggtcc tggccgaggt   1560
cgcgccgggc gacgaggcgc acggcgcacg ggacttcgcg ctgcaccgg ccctgctgga    1620 cgccgcgctg cacgccgccg gcgccgccga cagcggaaca tccggcgggg acggtgccat   1680
cggcctaccc ttcgcctgga ccgacgtacg cctgcacgcc gtcggcgccg ccgcgctccg   1740
ggtccgcctg gaacgccgcg gcccggacac cgtcggcctc gaactcaccg atcacaccgg   1800
cgccttggtc gccaccgtcg gtgccctggt cggccgcccc gcgaccgccg accggctcgc   1860
gcccgccgcc gacccggccc accgcgacct ccaccacgtc gactggtccc cgctgcccac   1920
tcccaccgaa accagcaccg cccgctggtc gttgctcggc ccggacgaac tggaggcggt   1980
ggccgggctg cgcgccgccg gcgccgaagt gcacgcgaac gggaaccccg accccgccga   2040
cgtactgctg atcacctgcg ccggccggac cggggacgac gtccccgaag ccgcccgggc   2100
cgccacacac cgcgtactcg acctgctcca gcgcgcactg accgaccac gcctcaccgc    2160 atgcaccctg gtcgtgctga cccggggcgc agtacccggg caccacggcg aggacgtgtg   2220
cgacctggtc gccgcgccga tcgtgggcct ggtccgctcc gcgcagaccg aacacccggg   2280
ccggatcgtg ctggtcgacc tggacgacca cgccgactcc ttcgccgcgc tgcgcgccgc   2340
cgtcgtcacc gacgtcggcg aaccgcaact ggccatccgc acgggcaccg tgtccgcacc   2400
ccgactgatc cgcaccggca ccgaaccgcg cctgagcccg cccgccggcg ccccggcctg   2460
gcggctcgac ctgctcggcg gtggcaccct ggaccggctc gcgctgctcc cgaacgccga   2520
cgcggcggtc ccgctcgcgc cggacaggt ccggatcgcc gtccgcgccg ccgggctgaa    2580
cttccgcgac gtcgtggtcg ccctcggcat ggtcaccgac acccgcccgc cggcggcga    2640 gggggccgga atcgtagtgg aggtcggccc cgatgtgccc gaactcgtcc cgggcgaccg   2700
ggtgatgggc ctgttcggcg gcggcaccgg accgattacc gtggccgacc accggctgct   2760
cgcgccgatc cccaccggct ggacctacgc ccaggccgcg gccgtcccgg tggtgttcct   2820
gaccgcctac tacggcctgg ccgacctcgg cgggctgcgc gccggcgaat cgctgctcgt   2880
ccacgccgcc accggcggag tgggcatggc ggccgtgcaa ctggcccggc actggaacgt   2940
ggaggtgttc ggcaccgcct cgcccggcaa atgggccacc ctgcgcggcc agggcgtgga   3000
cgacgcgcat ctggcgtcct cgcgcgatct cgacttcgcg caccggttcg gcgaggtcga   3060
```

```
cgtggtgctc aactcgctcg cgcacgaatt cgtcgacgcc tcactgcggt tgctcgcgcc   3120
cggcggccga ttcctggaga tgggcaagac cgacatccgc gaccgggacg aggtgcttgc   3180
cgcccatccg ggccgcgact accgggcgtt cgacctgatg gacgcggggc cggagcggat   3240
ccgggagatg ctggccgacc tgtaccggct cttcgagacc ggcgtgctgc acccgctgcc   3300
cgtgaccccg tgggatgtgc gcggtgcggt cggcgcgttc cggcacctga gccaggcccg   3360
gcacaccggc aagatcgtgc tgaccctgcc gcccaccctc ggcgccgctc ccgacccgga   3420
gggcacggtc ctgatcaccg gcggcaccgg caccctcggc ggcctgctcg cccgccacct   3480
cgtacgcacc gccggggtac gacacctgct cctgatcggc cggcgcggcc cggccgccga   3540
cggcgcggcc gagttgtccg ccgaactgac cgcgctcggc gcccgggtga ccatcgcggc   3600
ctgcgacgcc gccgaccgtg cggcgctggc cgcgctgctc gccgacatcc cggccgaaca   3660
cgcgctcacc tcggtgatcc acgccgccgg cgtgatcgac gacgcggcgc tgaccgcgct   3720
cacccccgag cggctggacc gggtgctgcg cccgaaactg cacgccgcct ggaacctgca   3780
cgagctgacc cgcgacctcg acctggccga gttcgtgctg ttctcctcga tggccggcac   3840
cttcggcggc gccggacagg ccaactacgc cgccgcgaac gccttcctgg acgcgctcgc   3900
ccagcaccgc cgagcccgcg gcctggccgc gaccgcggcc gcctggggtc tgtgggcgca   3960
ggccagcggg atgaccggac acctgggcgc cgaggacctg gaccgcattg cccgcaccgg   4020
cgtcgccgcg ctggagaccg cccacgcact caccctgtac gacgcgctcc gcgcggccga   4080
ccgcccacg atcgtgcccg cccgcctgga cccgcacgcg ctgcgcgccg ccgcccgac   4140
cgtacccgca ctgctgcgcg acctggtgcg cgacctggtg cgcccgcgcg gacgccgcgc   4200
cgccgccgac accgcgccgg acgccgcgtc cctggccgag cggctggccc gactgccgcga   4260
ggagcggcgc cggcagacgc tgctgaccct cgtccgcacc gagaccgccg ccgtcctggg   4320
ccacgccacc ccgacgcgg tcgccccgct gcgcccgttc aaggccctcg gcttcgactc   4380
gctcacgtcg gtcgaactgc gcaaccgcat cggtgcggcg accggcctgc gcctgcccgt   4440
caccctggtc ttcgaccacc cgaccccgca ggccctcgcc gaccacgtcg gcgccgaact   4500
cctgggcgta gcgcccgtgg tcgtcgaacc cgagcgaccc gccgcacaca ccgacgacga   4560
cccgatcgtg atcgtgagcg tcggctgccg ctacccgggc ggggtggccg acaggacga   4620
gatgtggcgg atgctcgccg agggcaccga caccatcggg cccttcccccc aagaccgggg   4680
ttggagttg gacacactct tcgacccgga ccccgaccgg gtgggcaagt cgtacgtccg   4740
tgaaggcgga ttcgtcgccg acgcggtgca cttcgacgcc gagttcttcg ggatctcgcc   4800
ccgcgaggcg acctcgatgg acccgcagca gcggctcctg ttggagaccg cgtgggaaac   4860
gttcgagcag gccggcatcg accccaccac gctgcgcggc agcggcacgg gcgtgttcgt   4920
cggggccatg gcgcaggact accacggcac ttcgcaggcg atggccgagg gccaggaggg   4980
ctacctgctg accgggaccg ccaccagcgt gatctccggc cgggtctcct acgtcctggg   5040
cctggagggg ccggcggtga ccgtggacac cgcgtgctcg tcatccctgg tcgccctgca   5100
ccttgcggcg aacgcactgc gtgcgggtga gtgcgatctc gcgcttgcgg gcggggtggc   5160
ggtgttgacg tcgccgcagg cgttcatcga gttcagccgg cagcgcggac tggccgcgga   5220
cgggcgctgc aagcccttcg cggcggcggc caacggcacc ggctgggcg aggtgtcgg   5280
cctggtactc gtcgagcggc tgtccgacgc gcgccggcgc gggcatccgg tgctggccgt   5340
ggtgcgcggc tcggcggtca accaggacgc gcctcgaac gggctgaccg cacccaacgg   5400
ccccctcgcaa cagcggtga tccgacaggc gttgcgcaac gcgggcctgc tcgcgacgga   5460
```

```
cgtcgacgcg gtcgaggcgc acggcaccgg gaccacgctc ggcgacccga tcgaggcgca    5520
ggcgctgctg gcgacctacg gcaggaccg gccggcgcaa cggccgctgt ggctggggtc    5580
ggtcaagtcc aacatcgggc acactcaggc cgcggcgggg gtcgccgggg tgatcaagat    5640
ggtgctcgcg ctgcggcacg ggacgttgcc gccgacgttg cacgtggacg cgcccacgcc    5700
gcatgtggac tgggcgtcgg gacaggtgcg gctgctcacc gagccggtgg cgtggccggc    5760
gggggaacgg gtgcgtcggg ccgggatctc ctcgttcggg gtgagcggga ccaacgcgca    5820
cgtgatcatc gagcaggcgc cggcggaggg gcggtcgat gccgcgccgg tcgatgccgc    5880
gccggccgcc gcgctcgggg ggatcgtgcc gtgggtggtg tccgcgcgat cccaggccgg    5940
gttgcgggcg caggcggcgc ggctgcggga ctgggccgcc gtgcatccgg agtttgcccc    6000
ggccgacgtg gccgcctcgc tggtgcgcgg gcgggcggtg ttcgagcggc gcgcagtggt    6060
ccggggtcgg gataccgacg aactggtcgc cgcactcgct gagttggtcg actcgtcggc    6120
aacgggcgag gcgccgacgg cgatcgggcc cgggccggtg ttcgtcttcc ccggccaggg    6180
atcgcaatgg gtgggcatgg cggcggagtt gctgacgtgc tgcccggtct tcgcggagac    6240
cgtcacgcag tgcgccgagg tgatggaccc gctgctgccg gctgggcgc tgctcgacgt    6300 gctgcgcggc accgacgacg agacggccga actgctgcgc cgggtcgagg tggtgcaacc    6360
cgtgctgttc gcggtgatgg tgggtctggc ccgctggtgg gagtcgtgcg gggtgcgacc    6420
ggccgcggtg atcgggcact cccagggcga gatcgccgcc gcgtacatag ccggccacct    6480
gaccctgccg gacgccgccc ggatcgccgc gctgcggatc cgcgcggtgc aggccgccga    6540
catgatccgc ggcgcgatgg tggctgtcgc ggtatccgcc ctgcgggccg aggagttgat    6600
cacccgcacc ggcaccgggg aacctggtcaa cgtgggcggg atcaacaagc ccgaccaaca    6660
ccgtgtgtcc ggcgacaccg acgccttggc cctgatcgtg gccgactgcg agcgcgaggg    6720
tgtacgggcg cgctggatcc cggccgcgta ctcctcgcac tcgccgcaga tggacgctgt    6780
acgcggcgac ctggaacgcc tgctcgcggg catccaaccc accccggc gggtgccgat    6840 gtactccacg gtcaccggcg gccgactcgc cgacgacgcg ctgctcgaca tcgactactg    6900
gttcgagaac atgcggcgca ccgtgcggtt cgaggaggcg atcggcgcgg cggcggccga    6960
cggacacacc gtgttcctcg aatgcagctc gcaccccgc ctggtggtgc cgctcggcga    7020
caccctggac tcgctcggcg tgcacggcgc caccctggag acgctgcgcc gcgcggacgg    7080
cggcgccgat cggctgctcg ccgcgctctc cgcgatgttc gtgcacgcg gcgcggtgga    7140 ctgggccggg ctgctaccgg gtcgccgggt cgcgctgccc acgtacgcct tccagcgtcg    7200
gcggcactgg gtgagcccg tcggaccggc ccgaggggc gtcggctggg gcagttcgc    7260 ggtggagcac ccgatcctgg gcgccgggt cgacctggcc gacggctcgg cgaccgtgtt    7320
caccgggcgc ctggacacca ccacacacg ttggctcgcc gaccacctcg tgctcggcga    7380
agtcctggtc ccgggcacgg tgttcgtgga cctggcgctg cgcgcgggcg gcgccctcgg    7440
ctgtgcggtg gtcgaggagt tggccctgca cgagccgctg tgttgccgg acgcggacgg    7500 ggtgcggatc caggtcaccg tcgaggcacc ggacgacgcg ggtacgcggg cgctgaccat    7560
acactcccgg cccgaggacg cgcccgccgc cgagccgtgg accgacacg cctcgggcac    7620 ggtggccccc ggcgcgcacc ggccgcagca ggagtccggg ccatggccgc cgatcggggc    7680
gacgccgctg gacgtggcgg acgtatattt gcggttgacc gaactgggcc tgggctacgg    7740
cccgacgctc gccggactgc gggccgcgtg gcggcgcggc gacgacctgt tcgccgaggt    7800
```

```
cgcgcgcacc gccgacggcg aacgtggcac cgcccgcttc ggcctgcacc cggccctgct    7860
cgatgcggcc ctgcacgggc ttgccccegg ctcggcaccc ggcggcgcac ctaccgaggt    7920
gcggctggcc ggcgcctggc gcggggtgac gctgggcggc gatgccggta ccgccggccg    7980
gattcggctg cggggcgtcg acgggacgg cgtcgaggtc gaactggccg acgaggcagg    8040
tcgatccatg gcccggatcg agtcggtggc gctgcggcca tggagcgcgg ggcaggtgcg    8100
ggcggccggg cgggcccgac cgtggttgac ccgctgggag tgggcccggg tcgagccgac    8160
cgacccggcg gcggcaggag gtcgctgggc cgtgctcggt gcgcgggctt gggacggggt    8220
gccggcctat gcgaccgccg ccgaactgat gcgggccgtc gaggtcggcg tcccggttcc    8280
ggatctggtc gcgctgcccg tgcggatcga cccggccggc gggctcgatc cggaggcgat    8340
ccgggccacg atccgggcgg tgcgcgagac cctgcgcag tggcgggccg agccgcggct    8400
ggcggcctcc cgcctggtcg tggtgaccca cgacgcggtc tcggcgcggc ccgaggaccg    8460
ggtcaccgat ccgggcgcgg cggcggtgtg ggcgtggtc cgggcggccc gggcggcgga    8520
ccccgagcgg ttcgtgctcg ccgacgtgga cggggaggac gggtcctggc cggtgctgct    8580
ggccgaagcg tccgccggtc gcgccgagtt cgcgatccgc gcgggcacgg tactgctgcc    8640
gggcctggcc cgggtaccgg cgggcgagac cggcacggcg ggcttcccga ccgacggcac    8700
ggtattggtc actgtcgcga ccgacccgac cgacccgacc gacggcaccg acccggtcgg    8760
cacactgctg gctcggcacc tggtgaccgc ccacggagtg cgccggctga tcctggccgg    8820
cgggcccgcc gccgggatgc cgcttgcccg ggaactggcc gcgcagggcg cggagatcca    8880
cgtggtcgtc tgcgacgtga ccgaccgcac cgaactggcg aagctgctgg ccacgatccc    8940
cgagcacagc ccgctgaccg ccgtggtgca caccgccggg ctcggccggt cgcacaccga    9000
ggccatgctg cgggcccggg tggacgcggc cgtacacctg cacgaactca cccgcgacgc    9060
cgacctgtcc gccttcgtgc tctgcaccgc cctggacggc gtactcgccg accccgggcg    9120
cggcgaacac gcggccggcg acgccttcct ggacgccctg gcccggcacc ggcacgccgc    9180
cgggctgccc gcgctcgcgc tggcctgggc accgggggcc gaaccggtcg ccgggctgct    9240
gccgttgccc ggcgagcagg ccacggtcct gttcgaccgg gccctcgggc tgcccgaacc    9300
ggccctgatc ccgctcgcgc cggacaccte ggcgctgcgc cggccgaac cgggcgcact    9360 gccggcgctg ttgaccacgc tggtggccga cccgaaccac cgcgtcggcg ccgccgccga    9420
ggcggcgccc gcactgatcg gccgactgct cgccctgccg gacgacgagc gggaaagcgt    9480
cctggtcgac ctggttcgcg gctgcgccgc cgcgatcctc ggtcatgccg atccgaccgc    9540
gatcgagacg ggagcggcgt tcaaggatct cggcttcgac tcgctgaccg ccctggagat    9600
gcgcaaccga ctgcgcgccg cgctgggcct gaccctgccg gccacgctga tcttcagcca    9660
ccccaacgcg gcggccctgg gccggcacct gcacggcctg ctgcgccgcg agcacggggt    9720
ctcgtg                                                              9726

<210> SEQ ID NO 3
<211> LENGTH: 67167
<212> TYPE: DNA
<213> ORGANISM: Streptomyces sp. ATCC 39366

<400> SEQUENCE: 3
cggtgggctc gggtgagaaa aaattagtcc gaatcgatgc gctcccgtgc tgttgcgcat      60
gtgaccgata tgtaagcgac atgtgaacgt tcgtcgcaag caggtgcgtt cgccccgcc     120 ggcgggtcgt cgggaccgcg cgcgcgggcg tgcgagccgg gtgcgcggcc ggtctgatca    180
```

-continued

```
agggttctcg cgcgtcgacg acgcaggtcg aaggcgggcg tgcgcggggc gttcgcgcac    240
tacaccaggt gacccgaatg gttcaaccgc gccgtcgaaa gcgcccgaac ggggcctgaa    300 ttcaccccctt gcggccgatc gacccggtac tccaatgtgt tgatctgtgt tcgtccgtgt   360
actcaacgta tgcaggtcat ggagcgcgga atgacggaat tcaacgccga tgcccatcgc    420
gcacaccccg cgccggaaga cgcggtggcc atcgtcgggt tggcctgccg actcccggc     480 gccgacggcc ccgacgagtt ctgggacctg ctgagcaacg gacgcgacac gatcaccgaa    540
gtgccccgcc atcgccggga cgcgagagcg cggacgacga cgaatcgaac ggccggcgga    600
tccccccacc cagccgcgaa ccgaccgcga agaggcggat tcctggacgc ggtggaccgg    660
ttcgacgccg ccttcttcgg catcaccccg ggcgaggccg ccctgatcga cccgcaacag    720
cgcctgatgc tcgaactgtg ctgggaggcc ctggaacacg cgggcatccc gccgacccgg    780
attcggggca cgccaccgg ggtgttcgcc ggcgcgatct gggacgacta cgccaccctg     840
ctgcgccgcg ccggcgtcga gcccggcccc cgacacgcca ccggcctgca ccgcagcatg    900
atcgccaacc gggtctcgta caccctcggc ctgcgcggcc ccagcatgac ggtggacgcg    960
gcccagtcct cgtccctggt cgcggtacac ctggccggcg agagcctgcg ccggggcgag    1020
tcgacactgg ccctggtcgg cggggtcaac ctggacctgg ttcccgacca cgacggcgac    1080
gcggccaagt tcggcgggct ctcccgcag ggccgctgct tcaccttcga cgcccggcc      1140 gacggctacg tgcgcggcga gggcggcgcg gtggtggtgc tcaagccgct gtcccgggcg    1200
ctggccgacg gcgacgtcgt gcacggcgtg atccgcggca gcgcgatgaa caacgacggg    1260
ggcggcgacg cgctgaccgc gccggacccc cgggcccagg cggaggtgat ccggctggcc    1320
cggcggcggg ccggggtcgc cgcgtccgcc gtccaatacg tcgaactgca cggcacgggc    1380 accccgtcg gcgacccgat cgaagccgcc gcactcggtg cggcgctcgg caccgagcgg    1440
gcgaaccggc cgccgctggc cgtcggttcg gtcaagacca acgtcgggca cctggagggt    1500
gcggccggca tcgtcggcct ggtcaagacg gtgttggcga tccgacaccg gcggctcccg    1560
gcaagcctga acttcgccga accccatccg cgaatcccgt tgggcgaact gggcctgcgg    1620
gtgcagacgg cggagggtga ctggcccctgc ccggacgaaa ccctgatcgc cggggtgagt    1680
tcgttcggga tgggtgggac caactgccat gtggtgctcg cggaggcgga gcccgcggat    1740
ggggtggggc cgtcggtcgc gtcggcgccc tcgggtgggt cggatccggg catggagtcc    1800
gccaccggcc cggtgccttc ggacgcggtt gccgtgccga tctccggtgt cgacgccgac    1860
gggcttcggg cccaggccgg gcggtggcac ggccatgtac gcgaacatcc cgacgtggcg    1920
ccggccgacc tcggctactc ggccgccacc acccggaccg cgtttgccgc ccgcgccgtc    1980
gtcctcgctc gcgaccacgc cgaactcctc gccgggctcg acgcgttacg cggagccggc    2040
gcggatccac acctggtccg agccgacgcg caacccggcc gcaccgcctt cctgttcacc    2100
ggacagggca gccaacgccc ggccatggcg caagagtcgt acgcccgcca cgccgtcttc    2160
gcggcggcct tcgacgccgc ctgcgcccac ctggacccac acctgccgcg cccgctgcgc    2220
gaggtgttgt tcgcgtcgcc cgacagcccg gacgcggcgc tcgtgcaccg caccgagtac    2280
acccaacccg cgctgttcgc cgtcgaggtc gcgctgtacc ggctgttcga gcactgggga    2340
gtgaccccgg acctgctgct cggccactcg atcggcgagc tgtgcgccgc gcatgtggcc    2400
ggcgtctggt ccctgcccga cgcgtgtgcg ctggtcgcgg cccggggtcg gctgatgcag    2460
gaactgccgg acggcggggc gatggtgtcg ctgcgggtcg ccgaggacga cgtgctcgcc    2520
```

```
tcgctcgaac cggtccgcga ccgggtctcg atcgcggccg tcaacgggcc gctggccacg    2580
gtgatatcgg gcgaccggga cgcggtcctg gacgtcgcgg ccggctggcg ggcacagggc    2640
cacaagacca cccgactgcg ggtcgcacac gccttccact caccgcgcat ggacgcgatg    2700
acggacgcct tcgccgaggt ggccgccggg ttgaccgctc gggcacccac cctgccgtc     2760 gtgtcgaacc tgaccggcct gccgctgacc gccgaacagg cctgctcccc ggactactgg    2820
gtccgccatg tacggcacac cgtgcgcttc cacgacgag tgcgccggct cgcgcggaa      2880 ggcgcgacga tactgctcga actgggcccg gacggcagcc tgtcggcggc ggcccggacc    2940
tgcctgctcg acgcgagcg ggacaccgtg ccacgatcc cgacgctgcg ccgcaaccgc      3000
cccgagacgg acgcgttgac cacggcggtg gcccgcctgt acgccaacgg cgtggacccg    3060
gactgggagc gggtgttcgc ggggcgcggg gcgcgccggg tcgcgttgcc cacgtacgcc    3120
ttccgacgcg cacgccactg gccgggtgcc tcggcggaag ccgccgacac cgccgtgccg    3180
gacgaatcgc tcgccgtggt accgacgttg gccgagcggt tggccgccct gtccgctgtc    3240
gagcagcatc ggatcctgct cgacctgatc cgggcacacg cgaccgcggt cctgggcccc    3300
ggcgcgacca cgaccgtcga acccgaccgc acctaccgcg aatcgggcct ggactcgctc    3360
ggcaccgtcg aactgatcac caggctggcc cgggacaccg gcctcgacct gccccgacc    3420 acggtcttcg accaccccac acccaccgcg ctcgcccacc acctgcgcac ccgggcgctc    3480
gacctgcccg tgccgacccg ccccggccg acacccgggc cggcccgcgc cgacgaaccg    3540
atcgccatcg tggcaatggg ctgccggttg cccggcgcgg tgcgcacccc cgaggacctg    3600
tggcggctgg tcgcggacgg cgtggacgcg atcacggcct tccccaccga ccgcggctgg    3660
gacctggacc ggctccacca cgacgacccg gaccgacccg gcaccagcta tgtacgatcc    3720
ggcggattcc tggaccgcgc gggcgacttc gacgcggagt tcttcgggat cggcccgcgc    3780
gaggcgctgg ccatggaccc gcagcaacgg ctgctcctgg agacctcctg ggaggcgatc    3840
gaacgcgccg gactcgaccc gagcacgctg cgcggcgagc gggtgggggt gttcgtcggc    3900
gccaccgcgc aggaatacgg cccgcgcatg cacgaatcca ccgacgccct cgccgggttc    3960
ctgctgaccg gcaccacgcc cagcgtcgcg tccgggcgga tcgcatacac cctcggcctg    4020
tcgggcccgg cgctcaccgt cgacaccgcc tgctcgtcct cgctggtcgc ggtgcacctg    4080 gccgccgtt cgctggcgag cggggaatgt gcgctggccc tggcgggcgg cgccaccgtg    4140
atggccggtc ccggcatgtt cgtcgagttc gcccggcagc gcggcttggc ccccgacggt    4200
cgttgcaagc cgttctcggc ggacgccgac ggcacggcct gggccgaggg cgtcggcgtg    4260
ctcctgctgg aacgcctgtc cgacgcgcgc gcaacggcc atcccgtact cgccgtgctg    4320
cgcggctcgc cgatcaacca ggacggggcc agcaacgggc tcagcgcgcc caacgggacc    4380
gcccagcagc gggtgatccg ggacgcgctg gccgccgccg ggctcgatcc gcaagacgtc    4440
gacctggtcg aggcacacgg caccgggaca ccgctgggcg acccgatcga ggcgcaggcg    4500
ctgctggcga cgtacgggcg cgatcgggcc ggcgatcggc cgctgctgct cggctcggtg    4560
aagtccaaca tcgccacac ccaggccgcg gcgggtgtgg ccgggctgat caagaccgtg    4620
ctggccctgc gacacggcgc gataccgggg acgctgcacc tgcgcgaacc gtcgccccac    4680
gtgcggtggt cggacgggc gatcacgctg ccgacgacga ccacggactg gcccgcgtac    4740
gaccgtccgc gccgcgcggc ggtgtcgtcg ttcgggatca gcgggacgaa cgcgcacgtg    4800
atcgtggagg aggcgggcgg gggcgcggag ataccgggc ctgcccctgc ccgcgggctt     4860
gcgtccgccg gtgtcgccga ccccgtgccg ctggtggttt ccgcgcggag cgaggccgcg    4920
```

```
ttgcggggc aggcggagca gcttgcggga ctgctgcgag cggcggacgc tccggccctg      4980
gccgatgtcg gatattcgct gctgcgcggc cgggccgggt tcgagtacac cgccgtgata      5040
ccggcgcgca cccacgccga ggcgctgcac gggttgaccg cgctcgccgc cgatcgaccc      5100
gccgaccggc tgatccgggg cggcgccgcg gcggcccggg gcgggaccgt gttcgtcttc      5160
cccgggcagg gcacccagtg gtccgggatg gcgctggaac tccttgacac cagcgagccg      5220
ttcgccgcct ccatgcgggc ctgcaccgac gcgctcgacc cgtacgccgt cgactggtcg      5280
ctgctcgacg tgctccgcga acccgggacg ccggggttga cgcgcgtcga tgtcgtgcag      5340
ccggcgctgt tcgcggtgat ggtctcgctg gccgcgctgt ggcgctcgat cgggatcgaa      5400
ccgcaggccg tggtcggcca ctcgcagggc gagatcgccg ccgcgtacgt cgcgggcgca      5460
ctgtccctgg ccgacgccgc caaggtggtc gccctgcgca gccgggcact ggtcgcggcg      5520
gcgggcagcg gcgggatggc ctccgtgtcg ctgcccgccg aacaggtcgc cgcgctgctc      5580
gaaccctggg ccggccgact cggcgtggcc gccgtcaacg ggccgagcgc caccgtggtc      5640
agcggcgaca ccgcggcact ggacacgttc tggaccgat gcgcggcgga cgacctgcgg      5700
gcccggcgga tccccgtcga ctacgcgtcg cactccgtgc acatggagga gatccgcgat      5760
cgactcctga ccgacctggc cgacgtgacc ccgcgagccg cgtcgacagc cttctactcc      5820
accctgaccg gcggtcgcat ggccgacacg agcggcctcg acgccgacta ctggtaccgc      5880
aacctgcgtc gaacggtgcg atacgagacg gccgttcggg cattgagcga ggacggtcac      5940
cggctgttcg tcgaggtcgg cccgcacccc gtgctcacgc tcggtaccca ggaaacgttg      6000
gacgcgtgcg gcagcggcgg caccacgatc ggcacgctga ccgcgacga cggcggccgg      6060
gcccgctttc tggttgcggt ggcggaggcc gtcgcgcacg gcgcccggcc cgacgccgaa      6120
gcgctgttcg acccgcccgg aaccggagtg cgggcggttg ccctgcccac ctacgcgttc      6180
caacaccgcc gctactggct gaccccgcgt gaggcggctc ccgagggtac ggctgccctc      6240
ggtctgacgc cgatctccca tccgctgctc ggcgcgcttg gcgcgctcgg cgtcgagccg      6300
gatggcacgg tgatcgcgac cggtcggatc tcgctgcggg agttgccgtg gctggcggac      6360
cacgcggtcg cggacaccgt ggtgttgccg gggaccgcgt ttctcgaact ggccctgtgc      6420
gtcgggagt ccgtgggtgc tccgcaggtc gaggaactga ccctgagag cccgctgctc      6480
ttgcccgaga ccggtgacgt gtacctgcgg gttgccgtgg ccccggcgga cgaggcgcgg      6540
cgacgggcgg tcaccatcca ctcccggcgt gcgggtgggg gcggtgccga tgcggagcgg      6600
gagtcgtggg ttcggcatgc gggcgggctg ctcgttgatt cggtgcggga ggtggacgac      6660
ggcggcagtg gtgggctcac ccagtggccg ccgcccggtg ccgatgtgct cgatctcgcc      6720
gatgcctacc cggtgttggc ggggctcggt tacggctacg ggccggcctt tcgggactg      6780
cgtgcggctt ggcgcggggc cggcggcgaa ctcttcgccg aggtgcgct gccggatgaa      6840
ctgcgggaat cggagtcggg ggtggtgggg cccgagttcg ggattcaccc ggcgctcttg      6900
gacgcggcac tgcatccgtt gctttcgtcg ctttcgttga cttcgttgtc gtcgacgcgg      6960
gacggaccgg cgggtgcgcc gccgcgtatt ccgttctcgc tggcggacgt gcggctgtac      7020
gccaccgggg ccgacatgtt gcgggtacgg ctgcgccggg cggatggcgg ggccgcggcg      7080
ctcacggttg ccgacggcgt cggtgcgccg gtcctgtcca tcggtgcgct cacctgcgc      7140
gaactgcctg cggacgggct gatcgcggcg gaacccgggc cggcgaggc gatgttcgac      7200
ctgcgctgga tcgccggatc gatcccggcg gagccgacgg gtctcgggta tgcgttcatc      7260
```

```
gggacgacc tcggcctggg cgacggcgag gtgtatccga gcctcgcgga tctcgatgcg    7320
cgactgctcg cgacggggga acccacgccc gacgtggtgt tcgccgccgc accggtgggg    7380
gtggacgacg acgtcccggg cgccgcgcac gacagcgcgc gctgggcgtt ggacctggtc    7440
gggggttggc ttgccggcga gcggtcgagt gcggcgcggc tggtcgtggt cacccgtggt    7500
gcggttgctg ctcggaccgg tgacgcgctg tccgggctgc ccgcagcccc cgtatggggg    7560
ctgttgcgga ccgcgcagtc cgaacacccc gatcgtttcg tgctgatcga cctggacgat    7620
gcggtgcgat cccttccgc gctgcttggc gcggccgttg cgggtgaacc tcaactcgcc     7680
ctgcgtgacg gggtggttca tctaccccgc atggtggcgg tggattcggc ggacgcgcag    7740
gtgactcgac gccgacccga tccgaacggg accgcgctga tcaccggtgg caccggcacc    7800
ctgggtgcgc tgatcgcccg ccggctggcc gccgaacacg gcatccggca cctgctcctg    7860
ctcggacgtg cgggtcggga ggcccccggc gccgaggagt tgatcgccga actcggcgcg    7920
ctcggcgccc gggtgaccgt ggccgcgtgc gacgtcgccg accgggccgc gctccgccgc    7980
gtgatcgagg acatccccgc cgagcacccg cccacgatcg tcgtacacgc cgccggtgtg    8040
ctcgacgacg cgacgctgtt gtcgttgacc ccggatcggc tcgacgcggt gctgcgcccc    8100
aaggtggacg cggcctggca tctgcacgag ctgacccgag cggcgaaccc ggcggcgttc    8160
gtgctgtttt cgtccatcac cgcgatcacg gcaacgccg gccagggcgc gtacacggcg     8220
gccaacacct tcctggacgc cctcgccgaa caccgccgcg cagccgggct gcccgccaac    8280
gccctggcct ggggactgtg ggccgagggc agcgggatga cccgacacct cgaccacacc    8340
gaccgggccc ggatgtcccg gggcgggatc gcggcgctgc ccaccgagac cggactcgcc    8400
ctgttcgacg ccgcgttgca ccgggaccgc ccgtacacga tccccgcccg cctggaccgc    8460
ggcgcgctgc gggccctggc cgcgagcggt gtgctgcccg ccgtactgcg cagcctcgtg    8520
cgtgtcccgc cgccgcgtgc cgccgcctcc ggcgacggca cggacgcgtc gtcgtggccc    8580
cggcggatcc gggaactccc gggcgagcag cgggaacggg cgatcaccga cctggtgcgc    8640
gggcaactcg ccgccgtcct cggacacgac gcacccgaac gactcgacct cgaccgcgcc    8700
ttccgcgaac tgggagtcga ctcgctgacc gcactcgaac tgcgcaaccg gatcaatgcg    8760
ttcaccggcc tgcgactgcc cgcgacggtg gtcttcgacc accccagcgg tacgccctg    8820
gtcgctcgga tgatgcgcga gctggtcggt gcggtgccga gcgagccgac cacgcccgtc    8880
gtcgcaccga ccgtgacggt cgacgagccg atcgccgtcg tcggcatcgg ctgtcgctat    8940
ccgggcggtg tggccggtcc cgaggacctg tggcgactgg tcgcggccgg cacggacgcg    9000
gtcggcgact tccccgagga tcgtggctgg gacctggcga agctgtacga ccccgacccg    9060
gacaaggtcg gcaaggtcta cacccgtcgg ggcggattcc tctacgagtc gggggagttc    9120
gacgccgagt tcttcggcat tccgccgcgc gaggcggcgg cgatggaccc gcagcagcgg    9180
ctgctcctgg agaccgcgtg ggaggcgttc gagcacgcgg gcctggaccc caggacgctg    9240
cgcgggagca acacgggtgt gttcgccggg gtgatgtaca acgactacgc ctcgcggctg    9300
caccgcgccc ccgacgggtt cgagggcatg ctgttggccg gcaacgtggg cagcgtcgtg    9360
accggcagag tgtcctacgc gctgggcctg aggggccgg cggtcagcgt ggacaccgcc     9420
tgctcgtcgt cgctggtggc gctgcacctg gcggccaacg cgctgcgtc ggggagtgc     9480
gatctggcgc tcgccggtgg ggtgacggtg atgtccaccc cgaacgtctt cgtcgagttc    9540
tcccgacagc gcggcctgtc ggcggacggc cgtgccggt cgttcgcggc gggcgcggac     9600
gggacgggtt ggggcgaggg tgtcgggctg ctggtggtgg aacgactgtc cgacgcgcgg    9660
```

```
cgcaacgggc atcccgtgct ggcgctgctg cgtggctcgg cggtcaacca ggacggcgcc     9720
tcgaacgggc tgaccgcgcc gaacggaccg tcccaggagc gggtgatccg ggcggcgttg     9780
gccggtgcgg ggttgtcggc gacggacgtg gacgcggtgg aggcgcacgg caccgggacg     9840
acgctgggcg acccgatcga ggcgcaggcg ttgttggcca cgtacgggcg ggaccggccg     9900
gcggatcggc cgctgtggct gggctcgatc aaatcgaaca tcgggcacac gcaggccgcg     9960
gcgggggcgg ccggcctgat caagatgatc atggcgatgc ggcacggcgt actgcccgag    10020
acactgcacg tcgacgcgcc gtcgccgcac gtggactggt cgacgggaca cgtcgagctg    10080
ctggccgaac gtcgaccgtg gcccgaggtc gaccgggcgc gccgggccgc cgtgtcgtcg    10140
ttcgggatca gcgggacgaa cgcgcacgtg atcgtcgaac aggcgccggc ggccgaggcg    10200
gtggtgtccc gggacgagcc ggtgggtgtg gcgggcctgg tgccgtgggt gttgtcggcc    10260
aggaccgccg acggtctgcg ggcgcaggcg gcgcggttgc gggagtggtc ggcgcggcat    10320
ccggaggcgg atccggtcga cgtgggggtgg tcgttggttc gggagcggtc ggttttcgat    10380
cggcgggcgg tggtcggtgg ccgcgatccg ggtgaactcg gggctgggtt ggacaggttg    10440
gccgcgggtg gcggtattgc cgacggtcgg ccgatgtttt cgggtcccgg tccggtgttc    10500
gtgtttcccg gcagggggtc gcagtgggtg gggatggcgg ccgggctgtt ggagtgctcg    10560
ccggtatttg cggaggcggt gacggagtgc gccgccgtga tggatccgtt ggtggcggat    10620
tggtcgttgt tggatgtgtt gcgggtgggg tctgccggtg agttggagcg ggtggatgtt    10680
gttcagccgg tgctgtttgc ggtgatggtg gggcttgcgc ggtggtggga gtcgtgtggg    10740
gtcaagccgg gtgcggtcat cgggcactcg cagggggaga tcgctgccgc gcatgtggcg    10800
ggttatctgt cgctggcgga tgcggtatgg gtggtcgtgt gcggagtcg ggccctgctg    10860 ggggtcgcgt ccgccggggg cgggatggtg tccgtcgggg tgtcggcgga gcgtgctcgc    10920
gagctggtcg ccggggatga ccggctgtcg ttggcggcgg tgaacgggcc gacgagtgtg    10980
gtgctttcgg gtgatgtcga agcgctgtcg gtggttgtcg aggcgtgcga gcgggatggt    11040
gtgcgggctc ggtggattcc ggtggattac gcgtcgcatt cggcgcggat ggaggccgtg    11100
cgggacgagg tggagcggct gttggcggat gtgacgccgc aggtgggccg cgtgccgatg    11160
tactcgaccg tgagcgggga ggtggtcgtc gatcccgccg agttgggcgg ggcgtactgg    11220
ttcgagaatc tgcggcgcac ggtcgagctt gagcgggccg tgggtgcggc ggtcgcggat    11280
gggcatggtg cgtttgtgga gtgcagcccg catccggggc tggtggtgcc gatggggggac    11340 accctggagg cggccggggt ggacggcgtc gttctggaga cgttgcggcg gggtgagggt    11400
gggcccgatc ggctggtcgc cgcgctctcg cggcgttcg tggcgggtgt cgcggtggac    11460
tgggccggaa tgttgccggg gcgccatgtc gagctgccga cgtatgcgtt ccagcggcgg    11520
cgctactggt tgacgggtgg ggaacgtgcg ggcgatccgg ccgggttggg gctggtcgcg    11580
gccgatcatc cgctgctggg ggctgtggtc ggttcggtgc gggacgggga actcctctac    11640 accggcggt tgtccgccgc gacgcacggc tggcttgcgg accacgcggt gttcggctcg    11700
gtggtggtac cggggacggc cttcgtcgag ctggcgtcgt gggtcggtgt cgaggccggt    11760
tgcccggtcg tcgacgaact cacgctgcat gcgcccctgg tgctgccgga cggggtcggc    11820
atccggcttc gggtggcggt gggcgcggcg gattcggcg ggcgtcgggt ggtggagttc    11880
cattcgcggc ccgaggatgc ccccgacgag cagtcgtgga ctcggcatgc gaccggcacg    11940
ctgggtgccg cgagtgtgcc cggatccgcg tcggccgggg ccgcggcgtg ggcggtctgg    12000
```

```
ccgccggcgg acgccgaggt ggtcgacccg gaggccgttt acgagcgact tgcggagcac    12060
gggtacgaat acgggccgat tttccggggg ttgcgggccg catggcggcg gggtgacgac    12120
ttcttcgccg aggtcgcgct gccggaggcg gccggtcggg acgcgcacgg ctacgacctg    12180
catccggcgg tgctggacgc cgcgctgcat gtggccgcgg ccgaggcggt ggcggagtcg    12240
ggggcgacgt tgttgccgtt cgcctggacc ggggtcgcac tgcatggggcc ggggcgtcg    12300 gtgcttcggg tgatgttgcg gcgtaccggg cgggagacgc tggcggtcga cgtggccgac    12360
gagcgtggtg ttccggtggc gtcggtcgcg tcgctgacgc tgcggccggt ggctgccgag    12420
cagttggtgg cggccgagga agcgggccgc gagtggcttt accggatggt ctgggagatc    12480
gcggacgcgc cggtggcgga gcacgtcgag ggtgaacttc ttggttcgga tgaggagtcc    12540
gacgcgtcgc cggagcttgt ggcgggcggg attcgggtgg tgaccctgc gggcgccgaa    12600 caggtctccg aggtggggct gttcgattgc cgcccgtgg tcggcgaagc ccccgaggag    12660
gtggccggcg ccgtgcatgc ggtgctggcc gcggttcggg cgtgggtggc ggacgagcgg    12720
tttgccgggg cgcggctggt ggttcgtacc cgtggcgcgg ttgccacgga tgcgcaggac    12780
cgggtcggtt ctcccgcgca tgcggcgatc tggggtctcg tgcgggtcgc gcagagcgag    12840
catccggggc gcttcgtcct ggtcgatggg gacgacgtcg attcgggtgc ggcgctgcgt    12900
gcggcggtgg cgtgcgggct gccgcaggtg gcgattcgcg aaggtgtggt gctggcgccg    12960
cgcctggtgg gggcggtgca cgacacggcg ctggtgccgc cggcgccggg tgcggatcag    13020
gcgtggcgga tcgagtccgg gacggccggg acgccggacg atctggtggt gacggcgcat    13080
ccggccgcct cggcgccgtt ggcggccggg caggtgcggg tggcggtgcg gcggccgggg    13140
gtgaacttcc gcgatgtgct gatcacgctc ggcatgtacc cggggcgggc ggtggtcggc    13200
gccgaggcgg ccggggtggt cgtggaggtc ggcccgggcg tgtcggaacc ggccgtcggc    13260
gaccgggtga tgggcttgtt cgaggggggcg ttcgggccgc ttgcggtggc cgatcggcgg    13320
ctgttggccc gggtgccggc gggttggtcg tttgctcagg cggcgtcggt gccggtggtc    13380
ttcctcaccg cgctctacgg gctgcacgat ctggccgggc tgcggtcggg tgaatcggtg    13440
ctggtgcatg cggccacggg tggggtcggc atggccgcca cccagctggc ccggcatcgg    13500
ggcgccgagg tgtacgcgac cgcgagtgcg acgaagtggg ccaccgtgcg cgggctgggt    13560
gttccggacg aacggatcgc ctcgtctcgg gacctgtcct tcgaacagcg cttcgcacgg    13620
gccacggacg ggcgcgggat cgacgtggtg ttgaactcgc tggcgggcga gttcaccgac    13680
gcgtcgttgc gactcctggc cgagggtggc cggttcgtgg agatgggcaa gacggacgtc    13740
cggaccgagg ggctgccggc cggggtgcgc tatcgggcct tcgacctgat cgaggccggt    13800
ccggatcgga tcgccgagat gttcgccgaa ctggtcgacc tcttcgagcg cggtgtgctg    13860 caaccctgc cgattcggac ctgggacatc cgtcgggccc gcgaggcgct gcgtttcctg    13920
ggccaggccc ggcatgtggg caaggtggtg ctgaccgtgc cgcagccgct cgcggccgac    13980
ggcacggtcc tgatcaccgg cggcacgggc acgctgggtc gcagtctggc ccgacacctg    14040
gtcacgcggt ggggtgtgcg ccggctggtg ctgaccggcc gggccgggcc cgccgctccc    14100
ggcgccgccg aactggtcgc ggaattggcc gagtcgggtg ccgacaccac gatcgtggcc    14160
tgcgatgcgc cggaccgggc ggcgatggcc gaggtgttgg ccgcgatccc ggccgaacac    14220
ccgttgaccg ccgtggtgca tgccgccgga acactcgacg acgcgccgat cgaggcgctg    14280
accccggagc gggtcgacca cgtgttgcgg cccaaggtgg acgccgccct cgtactggac    14340
gaactcaccc gggacgcgga cctggccgcg ttcgtgctgt tctcgtcggt ggccggcgta    14400
```

```
ctcggtgtgg ccggccaggg cggctatgca gcggggaacg cgttcctgga cggtctcgcc    14460
ggtcggcgcc gcgagcgggg gctgcccgcg accgctctgg cctggggcct gtgggcggaa    14520
cgcagcgcaa tgaccgcgca gttgggcgtc ggcgacctga agcgcctggc gcgcggcggc    14580
ctggtgccga tctcgaccgc ccaggggctc gccctgttcg acgccgcctg gcaggccgac    14640
gaggcggcgc tgatcccggc ccgcctggac cttgccgcac tgcgcgcaca ggcggcgacc    14700
cagccggtac atccgctgct gcgcggtctg gtcggcacca ccccgacccg ccggaacggc    14760
acaccttcgg aggcgccgtg ggcccgacgg ctcgcctcgg ccgcgcccgc cgagcgggtg    14820
gacgtggcat tgcggctggt ccgggccgag gcggcggtgg tcctggggca cgagtcgatc    14880
gacggggtgc ggcccgaagt caccttccgc gacctcgggt tcgactcact gacgggtgtg    14940
gaactgcgca accggctgag cggcgccacc ggattgcggc tgccgtccac gctggtcttc    15000
gacttcccga ccccgctcgg cctggccggt ttcctggtcg ccgagtcggt cggcgagatg    15060
gacacggcgc cgaccgggcc ggttgccggg ggtgcggtgg tcgcggccga tccggtggtg    15120
atcgtcggga tgggctgccg attcccgggc ggggtggact cggcggcggg tctgtgggac    15180
ctggtggccg cgggcggcga tgcgatcggg ccgttcccga ccgaccgtgg ctgggacgtc    15240
gacgcgctgt tcgatcccga tccggagcgg gtcggcaaga gctacgtccg taccggcgga    15300
ttcctctccg gggcggccga gttcgacgcc gagttcttcg gtgtgtcgcc gcgcgaggcg    15360
ttggcgatgg acccgcagca gcggctgctg ctggaaaccg cgtgggagac cttcgagcag    15420
gcgggcatcg atcccacctc gctccggggc agccggaccg cgtcttcgc cgggatggcc    15480 ggccacgact acgcgaccgg gggcgcccgt tcgcaggccg ggctggaggg ccacctgctg    15540
accgggaacg cggccagcgt ggcctcggga cgggtggcct acacgttcgg cctggagggg    15600
ccggcggtga ccgtggacac ggcgtgctcg tcgtcgctgg tggcgctgca cctggcggcc    15660
aacgcgctgc gggcggggga atgcgacctg gcgctcgccg gcggggtgac cgcgatgtcc    15720
acgccggact tcttcctgga gttctcccgg cagcgcggac tgtccgtgga cggccgttgc    15780
aaggcgttcg cggccacggc ggacgggatg ggcgcggcc agggcgtggg cctgctcctg    15840
gtcgagcggc tgtcggatgc gcggcgcaac gggcattcgg tactggcggt ggtgcgtggg    15900
tcggcggtga accaggacgg cgcgtcgaat gggttgaccg cgccgaacgg gccgtcgcag    15960
cagcgggtga tccgggcggc cctggccgac gccgggctgt ccgcggccga tgtggatgcg    16020
gtggaggcgc acgggaccgg cacgacgctc ggcgatccga tcgaggcgca ggcgttgctc    16080
gcgacctacg ggcgggatcg ggcgccggat cggccgctgt ggttgggtc ggtgaagtcc    16140 aacatcgggc acacccaggc ggcggcgggt gtggccgggg tgatcaagat ggtctcggcg    16200
ctgcggcatg gcatgttgcc gcgcacgctg cacgtggacg agccgacgcc gcatgtggac    16260
tggtcggcgg gtggggtcga actgctcacg agcgcgcggg cgtggccgga ggccgggcgg    16320
gtgcgtcggg cgggggtgtc gtcgttcggg atcagcggga cgaacgcgca tgtgatcctg    16380
gagcaggcgg aggagagccc ggcgggttcg gtgccttcgg cgactcctcc ggtggccggg    16440
actccggtgt gggcgggtcg ggtgccctgg gtgttgtcgg cccggtccga accgctttg    16500 cgggcacagg ccgcgcggtt gcgggactgg ctggccgtac atcccgacgc cgatccgctc    16560
gatgtggggc ggtcgttggc gaccggggcg gcggcgctcg atcaccggc ggtggtgcat    16620 gggcgggacc tcgcggaatt gcgcctggcg gtcgcgaagt tggccgacag cgggccgggt    16680
gacgaggcgt cgatcgtcgg ctcggtctcc gccgccggtc cggttttcgt gtttccgggg    16740
```

```
cagggGTCGC AGTGGGTGGG GATGGCGGCC GGGTTGTTGG AGTGTTCGCC GGTGTTTGCG    16800
ggtgtggttg ccgagtgtgc tgcggtgatg gatccgttgg tggcggattg gtcgttgttg    16860
gatgtgttgc ggggtgggtc tgccggtggt gaggcgttgg cggagcgggt ggatgtggtt    16920
cagccggcgt tgttcgtggt gatggtgggg cttgcgcggt ggtgggagtc gtgtgggGTC    16980
aagccgggtg cggtgatcgg acactcacag ggggagatcg cggctgcgca tgtggcggga    17040
tatctgtcgc tggcggatgc ggtgcgggtg gttgtgctgc ggagtcgggc gttgctcggg    17100
gttgcgtctt ccggtggcgg gatggtgtcg gtgggtgtgt ccgccgatcg ggcccgggag    17160
ctggtcgccg aggacgaccg gttgtcgctg gcggccgtga acgggccgac gagtgtggtg    17220
ctttcggGTG atgtcgaagc gctggccgtg gttgtcgacg gctgtgagcg ggacggggtc    17280
cgggctcggt ggattccggt ggattacgcg tcgcattcgg cgcggatgga ggccgtgcgg    17340
gacgaggtgg agcggctgtt ggcggatgtg acgccgcagg cgggccgcgt gccgatgtac    17400
tccacggtga gtgggggcca cgttaccgac ccgagtgtgc tcgGTGGTTC gtactggttc    17460
gacaatctgc ggcgtacggt cgagttggag cgggccgtcg agcggcggt tgtcgacggg    17520 cattcggtct tcgtcgagtg cagtccgcat ccggggctgg tggtgccact gggggacacc    17580
ctggaggcgg ccggggtgga tggcgtcgtt ctggagacgc tgcggcgggg cgagggcggt    17640
cccgatcggc tggtcggcgc gcttgcgcg gcgttccgga gcggtctggc cgtggactgg    17700
gccgggtccg ggatggtgcc ggggcggcgg gtcgagctgc cgacctatgc cttccagcgg    17760
cggcggtact gggtcgagcc cggcgagagg ccggcgggg tcgggtgggg gcagttcacg    17820
gtcgaacatc cggtgctggg cgccggggtc gatctggccg acggagccgg gacggtcttc    17880
accgggcggg tgtccgcggc ctcgcacggg tggctcgcgg agcatgtggt gctcggcacg    17940
gtgatcgcgc ccggcacggc gttcgtcgac ctggcgctgc gtgcgggggc gacggtcggc    18000
cgggcgacgg tcgaggaact gaccctgcac gcgccgctga tcctgcccga cgcgggcggt    18060
gtacggattc aggtccgggt cggcgcaccc gacgccgccg gggtcggatc ggtggagatc    18120
cattcccgac cggaggacgc ggccggcgac gagccatgga cccggcacgc ctccgggacc    18180
ctgaccgcga ccgacctcga cccggcggac gtggccacgg aggcggcgat ctggccgccc    18240
gcgggcagta cgccggtcga tctgacggga gcctacgagc gactggccac ggccggattc    18300
gagtacggtc ccgccttcca ggggctgcga gccctgtggc ggcgcggcgc cgagtcgttc    18360
gccgagatcg aactcgcgga cgacgcacgg caggaggccg aacgctacga ggtgcatccc    18420
gcgctgttgg atgcggccgt gcatgcgctg ggatggagc cgacgcggg ggtttgcgccg    18480 gatgaggcgc ggattgcctt ctcctggcga ggggttcggc tggttccgc ggagcgggg    18540 cggttgcggg tgcggctggc accggtgggc tcggacgcg tgtcgttgtg gctgagcgac    18600
atggacggtg agccggtcgg gtcggtccgg gccctgaccg tgcggccggt cgcggccgag    18660
cggctgcgtc cggctgggc gccgccgcgc gactcgatgt tccgggtgga gtggcggccg    18720
gtgtcgggcg acgagtcggg cgtggcggtt cgctgggcgg tggtgggcgc ggcggactcc    18780
gggccgcttg cccggctggt ggcggcgtat ccggatgtgc cggtgtaccg cagtgtggtc    18840
gaggcggccg gggatgtggc ggcgggaccg cccgatgtcg tggtggtggg cgtgggcgag    18900
gccgactgtt cggagggtc ggtcgagcgc actcggcggg tgcttgcgga cgtgctggcg    18960
tggatgcagg actggctggc cgactcccgc ttcgcggcga cgcgcctggt cgtggtgacc    19020
tccggggccg tcgccgccga cgtggacgcc gaccccgacg agcgggtggc ggacctggcc    19080
ggcgcggcgg tgtgggggtt gttgcgctcg gcccagtccg aacaccccga ccgatgcacg    19140
```

```
ctggtcgacc tcgacgagga cgcggcgtcg attgacgcct ggccggcgat tcttgcctcc   19200
gccgagccgc aactcgccgt ccggatgggc cgattccggg tgcctcggct ggccagggtg   19260
actgccgggg gcggcgagcc ggtcgccttc gcgcccgacg gcacggtgtt ggtcaccggt   19320
gccaccggcg gcctgggcgc cctggtggcc cggcacctgg tgaccgcgca cggcgtgcgc   19380
cgacttctgc tgctgtcccg ccggggcgcg gccgcacccg gcgcggccga actggtcgag   19440
gacctgaccg cgcagggggc ggaggtcacc ctcgccgcct gcgatctggc cgatcgtgcc   19500
gcgctggccg ccgagttggc gcgtatcccg gccgagcacg cgctgaccgg cgtgatccac   19560
accgccggag tggtggacga cgccaccatc gcgaacctga ccgatgcgca catggaacac   19620
gcgctgcgcc ccaaggcgga cgccgcgttc catctggacg agttgacccg ggacgtgaac   19680
ccggccgcat tcgtcctgtt ctcctccggg gccaccacct tcggtggccc gggacagggc   19740
aactacgcgg cggccaacgc cttcctggac ggcctggccc ggcagcgccg cgaccgcggc   19800
ctgcccggga tctcgctggc ctggggcctg tgggcgggcg cgcaggggat gggcgggcgg   19860
ctgagcgagg ccgacctggc ccgctgggcc cggaccggcg cggtggcgat gccggcggcc   19920
gaggcactgc ggttgttcga tatcgcgctg ggccggcccg aggcggccct ggtgccggca   19980
cacctggacc tcccggcgat gcgggcggat gccggtgctc gacccgcgct gttccgcgag   20040
ttgctcggga tcggtacgcg acgggcggca gtggcgcgg gcgggtcggc gctgacccgg   20100
cggctggcgg ggatgtctcc ggccgagcgg gagcaggcgg tcctggacgt ggtgcggacc   20160
gaggccgcga acacgctggg acacgagtcg gccggggcg tgtcggccgg gcgagcgttc   20220
aaggagctgg ggttcgactc gctgaccggg gtggaactgc gcaaccggtt gaacaccgcg   20280
accgggctgc ggttgccgtc cacgctggtc ttcgactacc cgacgccggc ggggctggcg   20340
gcgttcctgg tcgccgagtt ggtcggtcgt tcggtacagg cggtgccggt gccgccggtc   20400
ggtgggcggc acgggacgc cgacgatgcg atcgtgatcg tcggcatggg ctgccggttc   20460
ccgggcgggg tggcctcgcc ggaggacctg tggaatctgc tggcctcggg tggggacgcg   20520
atcggaccgt tcccgacgga ccggggatgg gacctggccg ggctgttcga ccccgatccc   20580
gagcgggccg ggaagagcta cgtggaatcg gccggattcc tgtatgggat cggcgagttc   20640
gacgcggagt tcttcgggat ctcgccgcgt gaggcgttgg cgatggatcc gcagcagcgg   20700
ttgctcctgg agacggcgtg ggagacgttc gagcgggcgg gcatcgatcc gacctcgctg   20760
cgcggcagcc ggaccggggt tttcgccggg gtgatcgaca cgactacgg cgcccgggtg   20820
aaccaggtgc cggacgaggt cgagggctat ctgggctacg gcagttcggc cagcatcgcg   20880
tccggcggg tctcgtacgt cctgggcctg gagggcccgg cggtcagtat cgacaccgcg   20940
tgctcgtcgt ccctggtcgc gctgcacctg gcggtgaacg cggtgcggtc gggcgaatgc   21000
gaactggccc tggccggtgg tgtgacgcg atgccacca ccgagttctt cgtgagttc   21060
tcccgacagc ggggcctgtc gccggacggc cgctgcaagg cgttcgcggc ggcggcggac   21120
gggatgggcg cggccgaggg catcgggctg gtgctggtgg agcggttgtc ggatgcgcgg   21180
cgccatgggc attcggtact ggcggtggtg cgtgggtcgg cggtgaacca ggacggcgcg   21240
tcgaatgggt tgaccgcgcc gaacgggccg tcgcagcagc gggtgatccg gcaggcgttg   21300
ggtgctgcgg gcttgtctgc ggcggatgtg gatgcggtgg aggcgcacgg gaccgggacg   21360
acgtttgggtg atccgatcga ggcgcaggcg ttgttggcga cctatgggca ggatcggccg   21420
ggggatcggc cgctgtggtt ggggtcggtg aagtcgaata tcgggcacac gcaggcggct   21480
```

```
gcgggtgtgg ccgggtgat  caagatggtg ttggcgctgc ggcatgggt  gttgcctcgg  21540
acgttgcatg tggacgagcc gacgccgcat gtggattggt cggccgggcg gtcgaggtg   21600
ttggcggacg aggtggcgtg gccggcaggg gagcgggtgc gccgggcggg tgtgtcgtcc  21660
ttcggaatca gcgggacgaa cgtgcacgtg gtcctggagg aggcgccggc ggacgccgcc  21720
gagcctgcgc ccgccgcgcc ggaggtcccg ggcgtcggcg gcgtgctgcc ctgggtggtg  21780
tcggcgcgca ccgaggccgg gctgcgggcg caggcggcgc ggttgcggga ttgggtgagc  21840
gaacatccgg acgccgaacc gacggatgtc gcacggtcgt tggtggtcgg gcgagcggtg  21900
ttggacgtgc gcgcggtggt gcgcgggcgg gaatccggcg aacttgtcgc cggcctggac  21960
gagttggcgc gggccggggt gggagacccc ggctcgctgg tgagcggctc ggatccggtg  22020
ttcgtgtttc cggggcaggg gtcgcagtgg gtggggatgg cggccgggtt gttggagtgt  22080
tcgccggtgt ttgcgggtgt ggttgccgag tgtgctgcgg tgatggatcc gttggtggcg  22140
gattggtcgt tgttggatgt gttgcggggt gggtctgccg gtgagttgga gcgggtggat  22200
gttgttcagc cggtgctgtt tgcggtgatg gtggggcttg cgcggtggtg ggagtcgtgt  22260
ggggtcaagc cgggtgcggt gatcgggcac tcgcagggg  agattgcggc tgcgcacatc  22320
gcgggttatc tgtcgctggc ggatgcggtg cgggtggttg tgctgcggag tcgggctctg  22380
ctggggttg  cgtcttccgg tggcgggatg gtttcggtcg gggtgtctgc ggagcgggcg  22440
cgggagttgg ttgccggagc tgacgggttg tcgttggcgg cggtgaacgg gccgacgagt  22500
gtggtgcttt cgggtgatgt cgaagcgctg tcggtggttg tcgaggcgtg cgagcgggat  22560
ggtgtgcggg ctcggtggat tccggtggat tacgcgtcgc attcggcgcg gatggaggcc  22620
gtgcgggacg aggtggagcg gctgttggcg gatgtgacgc cgcaggtggg ctgcgtgccg  22680
atgtactcga ccctgaccgg tgcgccgatc gccgatcccg ccgagttggg cggggcgtac  22740
tggttcgaaa acctgcggcg cacggtcgag ttggagcggg cggtcggtgc ggcagtggcg  22800
gatgggcgca ccgtgttcgt cgagtgcagt ccgcatccgg ggctggtggt gccgctgggg  22860
gacaccctgg aggcggccgg ggtggatggc gcggttctgg agacgttgcg gcggggtgaa  22920
ggtgggcccg atcggctggt cgccgcgctc tcggcggcgt tcgtgcgtgg tctggcggtg  22980
gattgggccg ggttgatcgt cggtgctcgg gtggagttgc cgacctacgc cttccaacga  23040
cggcgctatt ggttggacga cggggcgcgg tcggggatc  cgggcgggtt gggactggcc  23100
gcggtcgcac atccctgct  gggtgcggcg gtacggccgg cgcagggcgc ggggttgttg  23160
ttcaccggac ggttgtcgac ggcgacccac ccgtggctcg cggatcatgt ggtgctcggc  23220
tcgacgatcg tgcccggcac ggtgttcgtg gacctggcgc tgtgggccgg ggccgaggcg  23280
gagtgcccgg tggtggacga actgaccctg cacaccccgc tggtgctgcc ggaacacggc  23340
ggcgtgcatg tacaggtgac cgtcgacggg ccggacgccg ccggggcccg ggcggtcgcg  23400
gtgtactccc ggccggagga cgctcccggc gaggagccgt ggaccggca  cgccgtcggt  23460
gccctcgttg ccgacgccga tacgggtgcc gctcccgacg cggctgcgga ggcgtggccg  23520
ccggtcggcg cgaagccgat cgaggtgcg  gacttctatg cgcggctggt ggagtccggg  23580
gtcgactacg gccggcgtt  tcgcgggatg cgggccgcct ggcggcgcgg ggacgagctg  23640
ttcgccgatg tggcgctgcc ggccgaggag gagcgcgacg cacaccgctt cggggtacat  23700
ccggcgctgc tcgacgcggg cgtgcagacc ctgcgggtgg atccggggca ggtcgacgag  23760
gacgacatcc gggtggcctt ctcctggcac ggggtgcggc tcttcgcggc cggcgtgacc  23820
cggctgcggg tgtcgtgcgt gccgtcgggc gagggtgcgg tgtcgttgcg gatcacggac  23880
```

```
gagaccggac gggcggtcgc cgcgatcgag gcgttgacgg tgcgggcgat ctcggccgac  23940
cagctacggc gggccggcgg cgggcgggac gtgctgtacc ggctcgcgtg gcgggcatcg  24000
gcggttcccg taccggtggc gacgcctcgt gtggcggtgg tcggcgggtg ggatctgccc  24060
ggtctgggcg ggttggtgga ccggtatccg ggctttgccg aacttgcttc gtgtgacccg  24120
ccgttgcccg atctggtact gctcccggtt ggtgatccgg atgcggatgt gccgttctcc  24180
gagcggcgta tgcgggaggt gacggcggaa ctgatcgggc ggctggaggc gtttctcggc  24240
gacgaacggt tcgcggcggc ccgggtggtc gtggtgactc gttcggcggt gctcgtggac  24300
ggggacgcgg ggctcgggga cccggcgtcg gcgtcggtct ggggagtggt ccgggcggcg  24360
caggccgggc atccggggcg gatcgtgctg gtcgacctgg acgacgagcc ggcttcggcg  24420
gcggctttgg cggcggtggc ctcggccggt ggtgagccgc agttcgcggt gcgcggtggt  24480
cgggtgtcgg taccgagact ggagcggatt ccggcctccg gcggagcacg gtcggcggtg  24540
gggaccggca cggtgttgat cgccggtgcg gaccgggcgg tcggcgcggg ggtggccgag  24600
catctggccg gggcgtacgg ggtgggccgg ttcgtgttgt tgtccgtgga tccttcgggt  24660
gcggggccga ccgaactggc cgcccggctg ggtgaggccg gtgccgaggt cgtctcggcg  24720
gcctgggacg ggcacgatcc gggcgtgctt gccgcgcttg tgaccgaaca ccggccggcg  24780
ggcgtggtgg acgcgtcggg cgagtcggat gcagcctggg ccctgcacga gctgaccgcc  24840
gacgtggacc cggcgttctt cgtgctgttc tcgtcggcgg cgagcctgct cggttcgtcg  24900
gcgcatgcgg ccacggccgg ggtggatgcc ttccacgatg cgctggccgc acatcggcgg  24960
gcgagtgggc tgcccggggt gtcgcttgcg tgcgggacgg atccgctgcc ggggctgccc  25020
gacctgttcg acgaggcgat acgccgggag gacgccgtgt tggtttcggc gtcgacggat  25080
ctcaccgggc ccgcgtcgac gtcaccattg ttgccctccc ggaacggtcg tggcgcgacc  25140
aactccgccg agacctcgat cgaggcggac ggcgaggccc tggcccggcg cctggcggcg  25200
ttgtccgagg aggagcgcga gcgcgaactg gtcggcctgg tacgggccca ggccgcggcg  25260
gtgctcgggc atgccggcat cggcgagatc ggacccgaac gggcgttcaa ggaggtcggg  25320
ttcgactcgc tcaccgcggt ggaactgcgc aaccggctga tccggggcac cggggtcggc  25380
ctgcgctcca ccctcgtctt cgacttcccc acgccgcgaa tactggcccg ccacctgagc  25440
ggccggctgg tcgaggcggc atccccgatc ggtgcgctgc tggccgatct ggaccgattc  25500
gagggcgagt tgcacgcggt gctcggcgag gcggaggccc gcgaccggct ggccgagcgg  25560
ctgcgtcggc tgttggccga ctgtaccgcg ccggacgaga gcgcccccgc cgccgacgat  25620
gtctcggacg tgcagtcggc caccgacgac gagttgttct cgctcgtcga ccagggcttc  25680
gaatgacccg gcccatccac gcatacgacc gtgtcggcaa ggagtagagg caacgtggct  25740
gagtcggaag agaaactgcg ctcgtacctg cggaaggcca tcaccgatgc gcgcgacgcg  25800
catcgccggg tacgcgagtt ggaggaccgg cagcgcgagc cgatcgcgat cgtgggcatg  25860
gcctgccgct tccccggcgg tttgggtacg ccggaggacc tgtggcggtt cgtcgtcgaa  25920
ggcggcgatg cgatcggcga gttcccgacc gaccggggct gggacctcga cggcctgtac  25980
gacccggatc ccgaccggcc gggcacgtcg tacgtccgcg agggcggatt cctgtacgac  26040
gtcgccgact tcgacgccga gttcttcggc atctcgcccc gcgaggcggc ggcgatggac  26100
ccgcagcagc gactgcttct ggagacctct tgggaggccg tggaacgcgc gggcatcgac  26160
ccgacgtcgc tgcggcacag ccggaccggg atctacaccg ggatcaacgg cctcgactac  26220
```

-continued

```
acgaccgtgt tggcccgcac cgccaagggc cgggacggca cgctcggcat ggccaacggg    26280
gccagcctgc tggcgggtcg ggtggcgtac atcctcggcc tggaggggcc ggcggtgacc    26340
gtggacacgg cgtgttcgtc gtccctggtg gcactgcacc tggcgagcaa cgcactgcgg    26400 tcggggaat gcgacctggc cctggccggc ggtgcgacgg tgatgtgcac gccggagatc     26460
ttcgtcaact tcagccggca cgcggactg gcccgcgacg gccgatgcaa gccgttctcg     26520
gcggcggccg acgggttcat cctctccgac ggcgcgggcc tgttcctgat cgaacggctc    26580
tccgacgcgc ggcgcaacgg acatccggta ctggccgtgc tgcgcggttc ggcgatcaac    26640
caggacggcc cgtcgaacgg gctgaccgcg ccgaacggcc cggcccagga gcgggtgatc    26700
cggcaggccc tgcagagcgc cgggttggtg accggtgacg tggacgccgt ggaggcacac    26760
ggcaccggga ccacgctcgg cgaccccatc gaggcgcacg cgctgttggc gacctacggg    26820
caggatcggc ccgcggatcg gccgctgagg ctcgggtcga tcaagtccaa catcggacac    26880
acccaggccg ccgcggggggt ggccgggatg atcaagatgg tgttggccct gcggcacggc   26940
gtgctgccca ggacgctgca cgtcgacgcg ccctcgccgc acatcgactg gtcggccggg    27000
cgggtggaac tgctcacgga gcccgtgccg tggccgaggt cggaccggcc gcgccggggcc   27060 ggtgtctcgt cgttcggggc gagcgggacg aacgcgcacg tggtggtgga ggaggcgccg    27120
tcggacggcg acgacggtgt cgtggaggtg cccgcgccca cgggcatcgg cagtgtcctg    27180
ccgtgggtgt tgtcggcccg atccgaggcg gcgttgcgcg cgcaggcggg gcgattgcgg    27240
gactggctgg ccgagcaccc cgaggcggat ccggtcgacg tgggccggtc gttggcggtg    27300
gggcgtgcgg tgctggaacg tcgcgccgtg gtgcgcgggc gggatgtcgc cgaactcgcc    27360
gtcgggatcg gcgaggtggc cgaccgcgga gaactcgccg gtgggcggcc gatgttcgcc    27420
ggacccggtc cggtgttcgt gtttccgggg caggggtcgc agtgggtggg gatggcggcc    27480
gggttgttgg agtgttcgcc ggtgtttgcg ggtgtggttg ccgagtgtgc tgcggtgatg    27540
gatccgttgg tggcggattg gtcgttgttg gatgtgttgc ggggtgggtc tgccggtggt    27600
gaggcgttgg cggagcgggt ggatgtggtt cagccggcgt tgttcgcggt gatggtgggg    27660
cttgcgcggt ggtgggagtc gtgtggggtc aagccgggtg cggtgatcgg acactcacag    27720
ggggagatcg cggctgcgca tgtggcggga tatctgtcgc tggcggatgc ggtacggatc    27780
gtggtgttcc gcagtcgggc gctgcgcggg atcgcggcgg ccggtggcgg catggtctcc    27840
gtgggcgtgt ccgtcgagcg tgccgaggaa ctggtggccg gctctgccgg gttgtcgctc    27900
gcggccgtca acgggccgca gagcgtggtg ctttccggcg accgtgaggc actggccgcc    27960
gtcgtcgacg cgtgcgagcg cgagggtgcg cgagcccggt ggatcccgt ggactacgcg     28020 tcgcattccg cgcacatgga ggtggtccgg gacgaggtcg agcgtttgtc ggccgaggtg    28080
acgccgcggg cgggtcgggt gccgatgtac tcgacgctga ccggggaagt cgtcacggac    28140
ccggccgagt tgggcgccgg ctactggttc gagaacctgc gcgggacggt acggctgacc    28200
accgcagtgg gggcagccgt tgccgacgga cacgtcgcct tcgtcgagtg cagcccgcat    28260
ccgggcctgg tcgtgccgct cgcggacacc ctcgatgagc tggcgtcga cgacggcacg    28320 gtcctggaga cgttacggcg ggacgacggc ggccccgatc ggctggtcgc gcgcgctctcg   28380 gcggcgttcg tggcgggtgt gccggtgac tgggccgcac tgtttccggg cgaggggcgg    28440
gccgacctgc ccacgtacgc cttccaacat cggcgctatt gggccgaggc cgaatcgccc    28500
gcaggcggcg gcgtggcctg ggggcagcgc gcggtgacgc atccggtact cggcgccgcc    28560
gtcgacctgg ccggcgacgc gggcaccgtg ttcaccgggc ggctgtcgac gaccgcccaa    28620
```

-continued

```
ccgtggctgg ccgaccacgc cgtgctcggc acggtgatcg tgcccgggac ggcgttcctg    28680
gacctggtcc tgcgggccgg agccgaggtc ggctacccgg cgatcgagga actgaccctg    28740
cacacgccgc tcgtgctgcc ggacgcctcg ggcgtcctgg tacaggtcgt ggtcggtgcc    28800
gcggacggcg acggcggcga cggcggcgac ggggcccgga cggtcgatgt gcactcgcgg    28860
gccgaggacg cgccgccgga ccacccgtgg acccggcacg cctcgggggt gctggtcgcg    28920
gcgggcgagg agcgggccga ggacgcgccg gccgggcggt ggccgccgac cggtgccgag    28980
gtggtggggg tcgacgacgc ctacgagcgg ctggcggtgg cgggcttcga ctacggcccc    29040
gtgttccagg ggctgcggtc ggtccgggcg cgaggcgacg agttgttcgc cgaggtggag    29100
ttgccggagg aggggcacgc ggacgcggac cggttcgcgg tgcacccggc gctgctcgat    29160
gccgcgttgc acccgctggt ggtcgcggcc ggtgccgacg cgccggtcgt ggccgggctg    29220
ccgttcgtgt ggcacggcat tcgggcgggt gttcccgggg cgcgacggtt gcgggttcgg    29280
ctggtgcgct cggcgtcggg gtcggcgtcg gggtcggctg cgggctcgga ctcggcttcc    29340
ggcgaggtgt cggtccgggc gtgggacgag ggcggccggg aggtggtggc gatcgagtcg    29400
ctgaccattc gcccggtctc ggcggacggg ttgcggacgc ccgatgcttt ggtccgcgac    29460
tccctgttca cgctcgcgtg gaccgcgttg gagctaccgg acgtcgatga cgacgtgccg    29520
aacgcgaccc tgctgggcgg cgacggtgcg gccgatctcg ccgcgctggt ggctgccatg    29580
gacaccggaa cggacgtacc ggctctggtg gctctgcccg tatcggtcga cgacgcggac    29640
cccgtggcgg cggcgcacac ggccggccgg caggtgctgg cggtactccg ggactggctg    29700
gcggacgagc ggttcgccga ctctcggctg gtgttcgtca cctccggcgc ggtcgcggtc    29760
gccgacgagc aggtacgtcc ggcctcggcg gctgtctggg gcctggtccg ctccgcccag    29820
tccgaacacc cggggcgctt cgtcctggtg gacgcggact ccgtcgccga ccccggcccg    29880
gagttcgacc gggccctgcg gaccggtgcg gaccagctga tcctgcgaga tggaacggcc    29940
ctgataccga ggctggttcg agccccggcg gacggcggat cgggcggatt cgtgcccgct    30000
gccgacggca cggtcctgat caccggcggc accggcaccc tgggcacgct gcttgcccgg    30060
cacctggtca ccgaacacgg cgtgcgccgg ctcctgttgc tcagtcggcg cggcggtacg    30120
gccgccggcg cgacggacct ggtcgcggaa ctcgccgcgt tcggtgccga ggtgacctgc    30180
gtggccgggg acgccgcaga ccgcgccacg ctggagcggg tgttggcgga catccccgcc    30240
gaacacccgc tgacgcgcgt gatccacgcg gcgggtgtgg tggacgacgg cgtcgtacag    30300
tccctcaccg ccgaccggct ggacgcggtg ttgcgcccta aggtggacgc cgcgtggaac    30360
ctgcacgagg cgaccggca cctggacctg accgcgtttg tgctgttctc ctctgcggcg    30420
ggtgtgctcg gaaaccccgg ccagggcaac tacgcggcgg ccaacgcctt tctcgacgcg    30480
ctcgcacgcc gccggcgccg tgagggcctg cccggcagct cgttggcgtg gggctggtgg    30540
gcgccgacca gcgagatgac cgcggggctc ggcgacgccg accggcagcg gatggcgcgt    30600
ttgggtgtac tgcccctggc gccggaacag gggttggccc tgttcgacgc ggcgacgaac    30660
catgccgaac cgacaccgac cgtggtccgg atggacctcg cggtgctacg caccgccgga    30720
tcggtggtgc ccacgctgct gcgcggtctg gcccgggtgc ccaaccggcg ggctgcgacg    30780
gcgggttcgg tggccgagct gcgccgtcgt ccggccggcg tatcggcctt cgactgggag    30840
cagacgctga tccgggcggt gtgcgtgcat gccgccgccg tcatcggcca cgccgacgcg    30900
accgagatcg atgagacacg ggcgttccgc gacctgggct tcgattcgct cacaggtctg    30960
```

```
gagctgcgca atcgactgaa cacggcaacc ggactgcggc tgcccgccac gctggtcttc   31020
gactacccca gcccggtggt cctgggccgg tggttgcgtg atcggctcgc cgaggaggac   31080
gccgggggcc cggtcggctc gaccctcgga gcgcaggtgg tgtcgccggt cggttccgac   31140
gccggcgagg actcgatcgt gatcgtcggc atgggctgcc ggttccccgg cgggatcacc   31200
gcgcccgaac acctgtggga cgtggtggcc ggtggggtgg acaccctcac cgacttcccc   31260
accgatcgtg gctgggatgt cgagcgcatc ttcgacccgg acccggaccg acccggcagc   31320
acctacgtgc gcaccggcgg attcgtggac tcggccgccg acttcgaccc ggacctcttc   31380
gggatctcgc cgcgtgaggc gttggcgatg gatccgcagc agcgattgct cctggagacg   31440
gcgtgggaga cgttcgagcg ggcgggcatc gatccgacct cgctgcgcgg cagccggacc   31500
ggggttttcg ccggcgccat ctactacgac tacgcgggtg gccggctgcg gaaggtgccg   31560
gacgaactgg aaggctacat cggcaacggc aatgtgggca gcgtcgcctc gggccgggtg   31620
gcctacacgt tcggtctgga ggggccggcg gtcaccgtgg acacgcgtg ctcgtcgtcc   31680
ctggtggcgc tgcacctggc ggtgaacgcg gtgcggtcgg gcgagtgtga actggccctg   31740
gcgggtggcg tcaccgtgat gtcgacgccc agcgtcttcc tcgacttctc ccggcagcgc   31800
ggcctgtcgt ccgacggccg gtgccggtcg ttcgcggcg cggcggacgg caccgggtgg   31860
ggtgagggtg tcgggttggt gctggtggag cggttgtcgg atgcgcggcg caatgggcat   31920
ccggttctgg cggtggtgcg tgggtcggcg gtgaaccagg acggcgcgtc gaatggtttg   31980
accgcgccga acgggccgtc gcagcagcgg gtgatccggc aggcgttggg cagcgccggg   32040
ttgtcgcccg ccgatgtgga cgccgtggag gcgcacggaa ccgggacgac gttgggtgat   32100
ccgatcgagg cgcaggcgtt gttggcgacc tatgggcagg atcggccggg ggatcggccg   32160
ctgtggctcg ggtcggtcaa gtccaacctc gggcacacgc aggcggctgc gggtgtggcc   32220
ggggtgatca agatggtgtt ggcgctgcgg catgggggtgt tgcctcggac gttgcatgtg   32280
gacgagccga cgccgcatgt ggattggtcg gccgggcggg tcgaggtgtt ggcggacgag   32340
gtggcgtggc cggcgggga gcgggtgcgc cgggcgggtg tgtcgtcctt cggaatcagc   32400
gggacgaatg cacacgtggt gctggaagag ccgccgccgg tgaccgaagt gccggatgtg   32460
gccgtcgagt ccgggctggg cgggcggcac acctgggtgg tgtcggcgcg gtccgaggca   32520
gcggtacggg aacaggcggc ccggctgcgc gactgggtca cggcccgtcc ggatctcgat   32580
ccggcgcacg tggcccggtc gttggtgtgc gaacgggcgc tgttcggcca tcgggcggtg   32640
gtctccggcg ccgatctcgc cgagctgccc gatgggttgt ccgccgtggc ggcgggcgcc   32700
gagggcgcgg tggtcggtgc ggtgggtcgc gggccgggga agacggccgt gctgtgcacg   32760
ggtcaggggg tgcgggcgct cggtataggc cgcgaacttc acgcggcgtt cccggtgttc   32820
gccggcgccc tggacgaggt gtgtgcggcc ttcgacgatg tggtgccgtt ctcggtgcgg   32880
gacgtcgtgc tcggtgccga aggggtgtcg gatgccgacg cgcaggacac cggggtggcc   32940
cagccggcgc tgttcgcgtt cgaggtggcg ctgtaccggc tgtgggcctc gtgggggcag   33000
gcgcccgact tcgtgtgggg gcattcgctc ggcgagatcg ttgcggcgca tgtggcggga   33060
gtgttctcgc tcgcggatgc ggtggtcttc gtcgcggcgc gggctcggtt gatgagtgcg   33120
ctgccgagtg gagggcgat gctcgccgtc ggtgcgagcg aggccgaggt ggcggcgtcg   33180
tgcccggccg aggtgacgat cgcagcggtg aacggcccgg cgagtgtggt ggtttccgga   33240
cccgccgagg cggtggccgc gctcgaaccg gactgcgtga tgcgcgggtg gcggatctcg   33300
cgcctgtcgg tgtcgcacgc cttccactcg gcgctgatgc aaccgatgtt ggccgaactc   33360
```

```
cgcgaggtgc tgaccggggtt gacctacggc acgcccgaga tcgcggtggt gtcggacacc    33420
accgggcggg ttgcgggcgc cgaagagttg gctgatcccg agtactgggt gcggcacgta    33480
cgccgcgcgt tgcgcttcgg ggatgcgatc gccacgctgc gcgccgaagg ggtacggacc    33540
ttcgtggaga tcgggccgga ggcggcgttg accgcgatgg tggtcgaggg cacggccggc    33600
gcggaggacg tggccgccgt agcgacccgg cgtcggggtc gagcggccgt gtcgagtgtg    33660
gtggaggcgc tcgcccgggt gttcgtgcac ggcgcgacgg tggattgggc cgcgttgtcc    33720
accggttccg ggcccggggg acgggtggat ctgccgacct acgccttcga gcggcggcgc    33780
ttctggtttgc acgccggtgt ggacgcgggc gacgcggtcg ggctggggca gggtgtggtg    33840
gaccatccgc tgctcggtgc ggtcgtgggc ctggcggacg accagggcgt cctgttcacc    33900
ggccggttgg ccctggacac ccatccgtgg ttggccgaac acaccgtctt gggcacggta    33960
ttgctgccgg gcacggcatt cctggagctg gccctgcacg tcggccgcct cctggactgc    34020
gcgcgggtcg acgagctgac cctgtcggcc ccgctggcgc tgccgtcgac gggcggtgtg    34080
caggtccagg tccgagtcgg tgtaccggag gagagcggga cacggacgat cacggtgcat    34140
gccccgcccgg attcggcgga ggaggcgcct tggacgctgc acgccgccgg ggccctgggt    34200
ccatcagccg aggtggatgc accctcggat gccgcgagtt ggccgcctgc cgatgcgacc    34260
gcgatggact cggcggggct gtatccctgg ttcgccgaga ccggcgtcga ctacggaccc    34320
tcgttccggg gcgtacaagc gacctggcgc cgtgatgacg aggtgttcgc ggagatcgtg    34380
ctcgcggccc acgacccggc cgccgacggc cggttcgagc tgcacccccgc gctgttcgac    34440
gccgcgttgc acccgctggg cctgaccctg tcgacgcggg cggagccgcg cctgcggctg    34500
ccgttctcct ggcgcggagt ggcgctgcac acgtccgggg ctcgcacgtt gcgggttcgg    34560
ctgcgtccca ccgggcccga caccatcgcg gtgacggcca ccgacgagac gggtcgaccg    34620
gtggtcgcgg tcgaggccct ggcggtgcgc gaaccctcgc gggaccgact gccacgaccc    34680
gacgcgaacg cgggcgagtt gttcgagccg cagtggacgc cgctgtcacc ggcggacacg    34740
gcggacatgg cggacacgct cggggcggtg gtgggcggcc ccgaactcgc ctcgacagcc    34800
acccgattcg gtgccacaca tcaccctgac ctggccgccc tggccgaatc ggcaatcccc    34860
gagacggtcc tgtacgacct ggtcaccgcc gttcccggcg tatccgccga agccgtacac    34920
caagccgccg cccaagcgct ggacctggcc cgatcctggc tcgccgacga gcgcttcgag    34980
tcggcccgcc tgatcgtgcg cacccgacac gcggtcgccg ccgccgaagg cgacgcgccg    35040
gacccggccg ccgccgcgac ccatggcctg tttcgtaccg cctgctccga cacccccgag    35100
cggttcgcgc tcgtcgacgc cgacgacctc gacgaggtct cgcccgaggc catcgccgcc    35160
gtcgtggtcg agcccgaggc ggccgtgcgg gccggtcgcg tcctggttcc gcgcctgcgc    35220
cgagcggccg tggcgcccaa ggccgacttc ggcttcgccg ccgaaggcac cgttctgatc    35280
accggtggca ccggagcact gggccggcag gtcgcccggc acctggtgcg cgtacacggg    35340
gtgcgccgcc tcctcctgct ctcccgtcgc ggcgacgaag cccccgaggc cgccgagttg    35400
cgggccgaac tgatcgaggc cggcgcgcac gtcaccttcg ccgccggaga cgctgccgaa    35460
cgtggcgtgc tggccgacgt gttggccgcg atcccggccg cccacccgct gaccggcgtg    35520
gtgcacctgg ccggggtgac cgacgacggg ctggtcggga cgctgacccc cgagcggctg    35580
gcggcggtgt tgcgccccaa gatcgacgcg gcgctgcacc tggacgaact caccgccgac    35640
gccgacctgt cggcgttcgt cctgttctcc tcggccgccg gtccggtcgg caacccccggc    35700
```

```
caggccaact acgcggcggc caatgtcgcc ctcgacgcgc tggcccgccg gcgccgagcg    35760
cgcggccgac cggccgtgtc gttgcagtgg gggttgtggg ccgaacgcag tgcgctgacc    35820
gcgacgatga gcgcgaccga tcggcgccgg gcggccggcg cgggtgtgcg ggcgttgtcc    35880
gtggagcagg gcctcgcact gctggacgcg gcggccgggc ggcccgaggc ggtgctgacg    35940
ccgctgcgcc tcgatccggc gatcctgcgc ggtccggagg agcgggtggc gcccgtgttg    36000
cgcgggctgg tgccgacccg ggcccggcgt gcgccggccc gtacctcgga caccgcccgc    36060
tcactggtgc gccgattggc cgcgttgccc gaggccgagc aggaccggct gttggtcgac    36120
ctggtccgta cccacgcggc cggtgtgctc ggccacgccg acgcgcgcac gatcgacccg    36180
gaccgcgcgt tcggcgaact gggcctggac tcgctggcgg cgttggaact gcgcacccgg    36240
ttgagcacgg cggtcgggct gcgcctgccc gccacgatgt tgttcgacca tccgtgcgcg    36300
cgtgccgtgg gcgtacacct gcgcgcgcaa ctgctcgacg cgccgacacc cgggcgggcg    36360
gcgggtgtcg cccggccggt gtcggacgag ccggtcgcgg tggtggcgat cagctgccgc    36420
ttccccggcg gcgtcgcgag ccccgaggac ctgtggcggc tggtgtcgga acacaccgac    36480
gccatctcgg agttcccgca ggatcggggc tgggacctgg ccgagctgtt ccacccggac    36540
cccgaacatg ccggtacctc gtatgtaagc gagggcggat tcctttacga ggcaaccgag    36600
ttcgacccgg agttcttcgg catctcgccg cgcgaggcgc tggccatgga cccgcagcag    36660
cggttgctcc tggaggcgtc ctgggaggcg atcgagcgcg ccggcgtgga tcccaggtcg    36720
ctgcgcggca gtcgtaccgg ggtgtacgcg ggcctgatgt acgccgacta cgcgtcgcgg    36780
ctgggcagcg cgccggaggg cgtggacggc tatctcggca acggcagcgc gggcagtatc    36840
gcgtccgggc gggtggccta cacgctgggt ctggaggggc ccgcggtgac cgtggacacc    36900
gcctgctcgt cgtccttggt cgcactgcac ctggcggcca acgcactgcg ccagggtgag    36960
tgtgatctgg cgctggcggg cgggtgacg gtgatgtcca gcccggccac gttcgtcgag    37020 ttctccccggc agcgcggcct ggccccggat gcgcggtgca agtcgttcgc ggccggcgcc    37080
gacggtacct cgtggtccga gggcatcggt ctgctcctgg tggaacgcct gtcggacgcg    37140
cgccggttgg gccatccggt gctggccgtg gtgcgcggca gtgcgatcaa ccaggacggc    37200
gccagcaacg gcctggccgc gcccaacggg ctcgcccagg agcgggtgat ccggatgcg    37260 ctcgcgcacg ccgagttgcg tccgtccgac gtggacgcgg tggaggcgca cggcaccggc    37320
acgccgctgg gcgacccgat cgaggcgcgc gccctgctcg ccacctacgg gcaggaccgg    37380
ccggcggatc ggccgttgtg gctggggtcg gtcaagtcca acctcgggca cacccaggcg    37440
gcggcgggcg tggccggcgt gatcaagatg atcatggcga tgcggcatgc cgaactgccc    37500
gggacgctga acgtggacgc cccctcaccg cacgtggact ggtcggcggg ggcggtgtcg    37560
ctgctcaccg ccgcgacccc gtggccgcag accgggcgtc cgcgccgtgc ggggtgtcg    37620 tcgttcggga tcagcgggac caacgcgcac gtgatcctgg aacagggcga ccccgccccg    37680
accgcgcccg ccgaaccggc accggcgtcg gcgcctttgg ccgcgctggc gtggccactg    37740
tccggggcga gcgcggtggc actgcgcggg caggccgagc ggctgcgcgc acatctggac    37800
gcgcaccccg agtacgggcc ggtcgacatc gcgcacgcgc tcgtcggcgg ccgatcccgg    37860
ttcgaacacc gcgccgtggt ggtcgccgag gacgcggcgg gcctgcgggc cgggctggac    37920
gcgctgagcg ccgaccggcc cgacgcggcg gtgccggtgg gcgtggccgg cgaacccggc    37980
cggatcgcct tcgtgttcgg cggacagggt tcgcagtggc ccggcatggg cgcccgactg    38040
ctcaccgagt cgccggtctt cgccgcccgg atccgcgact gcgacgcggc actcgcgccg    38100
```

```
cacaccgact ggtcgctgct cgccgtgctg cgcggcgagc ccgacgcgcc gccgctcgac  38160
cgggtcgacg tggtgcaacc ggtgttgttc gcggtgatgg tcgcgctcgc cgaactgtgg  38220
cgctcgctgg gcgtacggcc ggcttcggtg gtcggccact cgcagggcga gatcgccgcc  38280
gcccacatcg cgggcgcgct caccctcgac gacgcggccc ggatcgtcgc actgcgcagc  38340
cgcgccctgc gcggttgtc cggcgacggc gggatgatgt ccgtcgcggc cggcccggag  38400
cagatcgccc gattgctcga cggattcgcg gaccggctcg gcatcgccgc cgtcaacggc  38460
cccgccgccg tggtgatttc cggcgcggcc gacgcgctcg ccgaactgca cgcccactgc  38520
gaggcggacg ggatccgcgc ccgggtgctc ccggtcgact acgcctcgca ctccgcccag  38580
gtcgagcagg tccgcgagga actgctcgcc gccctgggcg agatcgtgcc cacgccgacc  38640
accgacgcgg tcttctactc ctcggtcacc ggcgaacccg tcgagggcac cgcgctcgac  38700
gccgagtact ggtaccgcaa cctgcgcgcc accgtcgcct tcgaccgggc caccgatgcc  38760
ctgctgcggg acgccacac ggtgttcgtc gagaccagcc cgcatccggt ccttgcgccc  38820
gccgtcgagg atagtgccca gcgcgccggt acggacgtga cggtcgtggg cagcctccag  38880
cgcgacaccg acaccctcgc ccgtttcctc accgccgcgg ccggcctgca cgtgcacggc  38940
gtcccggtgg actggtccgc gacccacgcc ggacaccggc ccggccggt cgacctgccc  39000 acctacgcat tccaacgcga gcgctactgg ctggaggcgg gcaagacgcc caccgacgcg  39060
gccggcctcg gcctgcaccc ggcggcacac ccctgttgg gcgcggccgt ggtacccgcc  39120
gagggcgacc ggcacatcct caccggccgc atctcgctgc gcacccaccc ctggctcgcc  39180
gaccacacga tcctggacac ggtgctgctc ccgggcaccg cgttcgtcga actcgccctc  39240
caggcgggcg atcgggccga ctgtgacctg atcgaggagc tgaccgtcga ggccccgctg  39300
cggctcaccg acaccggcgc cgtacacctg caggtgttgc tggacgagcc ggacgagcag  39360
ggccgccgag cgctgaccat ccactcccga gccgacgacg cgcccgcgga gcagacgtgg  39420
acgcggcacg cgagcggggt actggcgccg gtcgcggacg gcctcgacgc cgtgccggcg  39480
accgacgccg cgtggccgcc cgccggggcc gtcgcgctgg acgtggacgg gctgtacgag  39540
cggttggccg ggcagggcta ccggtacgga ccggccttcc gggcggtgcg ggccgcgtgg  39600
cgcctgggcg atacggtcct ggccgaggtc gcgccgggcg acgaggcgca cggcgcacgg  39660
gacttcgcgc tgcacccggc cctgctggac gccgcgctgc acgccgccgg cgccgccgac  39720
agcggaacat ccggcgggga cggtgccatc ggcctaccct tcgcctggac cgacgtacgc  39780
ctgcacgccg tcggcgccgc cgcgctccgg gtccgcctgg aacgccgcgg cccggacacc  39840
gtcggcctcg aactcaccga tcacaccggc gccttggtcg ccaccgtcgg tgccctggtc  39900
ggccgccccg cgaccgccga ccggctcgcg cccgccgccg accggccca ccgcgacctc  39960 caccacgtcg actggtcccc gctgcccact cccaccgaac ccagcaccgc ccgctggtcg  40020
ttgctcggcc cggacgaact ggaggcggtg gccgggctgc gcgccgccgg cgccgaggtg  40080
cacgcggacg cgaccccga ccccgccgac gtactgctga tcacctgcgc cggccggacc  40140
ggggacgacg tccccgaagc cgcccggggcc gccacacacc gcgtactcga cctgctccag  40200
cgcgcactga ccgacccacg cctcaccgca tgcaccctgg tcgtgctgac ccggggcgca  40260
gtacccgggc accacggcg ggacgtgtgc gacctggtcg ccgcgccgat cgtgggcctg  40320
gtccgctccg cgcagaccga acacccgggc cggatcgtgc tggtcgacct ggacgaccac  40380
gccgactcct tcgccgcgct gcgcgccgcc gtcgtcaccg acgtcggcga accgcaactg  40440
```

```
gccatccgca cggcaccgt gtccgcaccc cgactgatcc gcaccggcac cgaaccgcgc   40500
ctgagcccgc ccgccggcgc cccggcctgg cggctcgacc tgctcggcgg tggcaccctg   40560
gaccggctcg cgctgctccc gaacgccgac gcggcggtcc cgctcgcgcc cggacaggtc   40620
cggatcgccg tccgcgccgc cgggctgaac ttccgcgacg tcgtggtcgc cctcggcatg   40680
gtcaccgaca cccgcccgcc cggcggcgag ggggccggaa tcgtagtgga ggtcggcccc   40740
gatgtgcccg aactcgtccc gggcgaccgg gtgatgggcg tgttcggcgg cggcaccgga   40800
ccgattaccg tggccgacca ccggctgctc gcgccgatcc ccaccggctg gacctacgcc   40860
caggccgcgc ccgtcccggt ggtgttcctg accgcctact acggcctggc cgacctcggc   40920
gggctgcgcg ccggcgaatc gctgctcgtc cacgccgcca ccggcggagt gggcatggcg   40980
gccgtgcaac tggcccggca ctggaacgtg gaggtgttcg gcaccgcctc gcccggcaaa   41040
tgggccaccc tgcgcggcca gggcgtggac gacgcgcatc tggcgtcctc gcgcgatctc   41100
gacttcgcgc accggttcgg cgaggtcgac gtggtgctca actcgctcgc gcacgaattc   41160
gtcgacgcct cactgcggtt gctcgcgccc ggcggccgat tcctggagat gggcaagacc   41220
gacatccgcg accgggacga ggtgcttgcc gcccatccgg gccgcgacta ccgggcgttc   41280
gacctgatgg acgcggggcc ggagcggatc cgggagatgc tggccgacct gtaccggctc   41340
ttcgagaccg cgctgctgca cccgctgccc gtgaccccgt gggatgtgcg cggtgcggtc   41400
ggcgcgttcc ggcacctgag ccaggcccgg cacaccggca agatcgtgct gaccctgccg   41460
cccaccctcg cgccgctcc cgacccgag ggcacggtcc tgatcaccgg cggcaccggc   41520
accctcggcg gcctgctcgc ccgccacctc gtacgcaccg ccggggtacg acacctgctc   41580
ctgatcggcc ggcgcggccc ggccgccgac ggcgcggccc agttgtccgc cgaactgacc   41640
gcgctcggcg cccgggtgac catcgcggcc tgcgacgccg ccgaccgtgc ggcgctggcc   41700
gcgctgctcg ccgacatccc ggccgaacac gcgctcacct cggtgatcca cgccgccggc   41760
gtgatcgacg acgcggcgct gaccgcgctc acccccgagc ggctggaccg ggtgctgcgc   41820
ccgaaactgc acgccgcctg gaacctgcac gagctgaccc gcgacctcga cctgccgag   41880
ttcgtgctgt tctcctcgat ggccggcacc ttcggcggcg ccggacaggc caactacgcc   41940
gccgcgaacg ccttcctgga cgcgctcgcc cagcaccgcc gagcccgcgg cctggccgcg   42000
accgcggccg cctgggtct gtgggcgcag gccagcggga tgaccggaca cctgggcgcc   42060
gaggacctgg accgcattgc ccgcaccggc gtcgccgcgc tggagaccgc ccacgcactc   42120
accctgtacg acgcgctccg cgcggccgac cgccccacga tcgtgcccgc ccgcctggac   42180
ccggacgcgc tgcgcgccgc cgccccgacc gtacccgcac tgctgcgcga cctggtgcgc   42240
gacctggtgc gcccgcgcgg acgccgcgcc gccgccgaca ccgcgccgga cgccgcgtcc   42300
ctggccgagc ggctggcccg actgcccgag gagcggcgcc ggcagacgct gctgaccctc   42360
gtccgcaccg agaccgccgc cgtcctgggc cacgccaccc cggacgcggt cgccccgctg   42420
cgcccgttca aggccctcgg cttcgactcg ctcacgtcgg tcgaactgcg caaccgcatc   42480
ggtgcggcga ccgcctgcg cctgcccgtc accctggtct tcgaccaccc gacccgcag   42540
gccctcgccg accacgtcgg cgccgaactc ctggcgtag cgcccgtggt cgtcgaaccc   42600
gagcgacccg ccgcacacac cgacgacgac ccgatcgtga tcgtgagcgt cggctgccgc   42660
tacccgggcg gggtggccgg acaggacgag atgtggcgga tgctcgccga gggcaccgac   42720
accatcgggc ccttcccca agaccggggt tgggagttgg acacactctt cgacccggac   42780
cccgaccggg tgggcaagtc gtacgtccgt gaaggcggat tcgtcgccga cgcggtgcac   42840
```

```
ttcgacgccg agttcttcgg gatctcgccc cgcgaggcga cctcgatgga cccgcagcag   42900
cggctcctgt tggagaccgc gtgggaaacg ttcgagcagg ccggcatcga ccccaccacg   42960
ctgcgcggca gcggcacggg cgtgttcgtc ggggccatgg cgcaggacta ccacggcact   43020
tcgcaggcga tggccgaggg ccaggagggc tacctgctga ccgggaccgc caccagcgtg   43080
atctccggcc gggtctccta cgtcctgggc ctggaggggc cggcggtgac cgtgacacc    43140
gcgtgctcgt catccctggt cgccctgcac cttgcggcga acgcactgcg tgcgggtgag   43200
tgcgatctcg cgcttgcggg cggggtggcg cgtgttgacgt cgccgcaggc gttcatcgag   43260
ttcagccggc agcgcggact ggccgcggac gggcgctgca agcccttcgc ggcggcggcc   43320
aacggcaccg gctggggcga gggtgtcggc ctggtactcg tcgagcggct gtccgacgcg   43380
cgccggcgcg ggcatccggt gctggccgtg gtgcgcggct cggcggtcaa ccaggacggc   43440
gcctcgaacg ggctgaccgc acccaacggc ccctcgcaac agcgggtgat ccgacaggcg   43500
ttgcgcaacg cgggcctgct cgcgacggac gtcgacgcgg tcgaggcgca cggcaccggg   43560
accacgctcg gcgacccgat cgaggcgcag gcgctgctgg cgacctacgg gcaggaccgg   43620
ccggcgcaac ggccgctgtg gctggggtcg gtcaagtcca acatcgggca cactcaggcc   43680
gcggcggggg tcgccggggt gatcaagatg gtgctcgcgc tgcggcacgg gacgttgccg   43740
ccgacgttgc acgtggacgc gcccacgccg catgtggact gggcgtcggg acaggtgcgg   43800
ctgctcaccg agccggtggc gtggccggcg ggggaacggg tgcgtcgggc cgggatctcc   43860
tcgttcgggg tgagcgggac caacgcgcac gtgatcatcg agcaggcgcc ggcggagggc   43920
gcggtcgatg ccgcgccggt cgatgccgcg ccggccgccg cgctcggggg gatcgtgccg   43980
tgggtggtgt ccgcgcgatc ccaggccggg ttgcgggcgc aggcggcgcg gctgcgggac   44040
tgggccgccg tgcatccgga gtttgccccg gccgacgtgg ccgcctcgct ggtgcgcggg   44100
cgggcggtgt tcgagcggcg cgcagtggtc cggggtcggg ataccgacga actggtcgcc   44160
gcactcgctg agttggtcga ctcgtcggca acgggcgagg cgccgacggc gatcgggccc   44220
gggccggtgt tcgtcttccc cggccaggga tcgcaatggg tgggcatggc ggcggagttg   44280
ctgacgtgct gcccggtctt cgcggagacc gtcacgcagt gcgccgaggt gatggacccg   44340
ctgctgccgg gctgggcgct gctcgacgtg ctgcgcggca ccgacgacga cacggccgaa   44400
ctgctgcgcc gggtcgaggt ggtgcaaccc gtgctgttcg cggtgatggt gggtctggcc   44460
cgctggtggg agtcgtgcgg ggtgcgaccg gccgcggtga tcgggcactc ccagggcgag   44520
atcgccgccg cgtacatagc cggccacctg accctgccgg acgccgcccg gatcgccgcg   44580
ctgcggatcc gcgcggtgca ggccgccgac atgatccgcg cgcgatggt ggctgtcgcg    44640
gtatccgccc tgcgggccga ggagttgatc acccgcaccg gcaccgggga cctggtcaac   44700
gtgggcggga tcaacagccc gaccaacacc gtgttgtccg cgacaccga cgccttggcc    44760
ctgatcgtgg ccgactgcga gcgcgagggt gtacgggcgc gctggatccc ggccgcgtac   44820
tcctcgcact cgccgcagat ggacgctgta cgcggcgacc tggaacgcct gctcgcgggc   44880
atccaaccca ccccgggcg ggtgccgatg tactccacgg tcaccggcgg ccgactcgcc    44940
gacgacgcgc tgctcgacat cgactactgg ttcgagaaca tgcggcgcac cgtgcggttc   45000
gaggaggcga tcggcgcggc ggcggccgac ggacacaccg tgttcctcga atgcagctcg   45060
caccccggcc tggtggtgcc gctcggcgac ccctggact cgctcggcgt gcacggcgcc    45120
accctggaga cgctgcgccg cgcggacggc ggcgccgatc ggctgctcgc cgcgctctcc   45180
```

```
gcgatgttcg tgcacggcgg cgcggtggac tgggccgggc tgctaccggg tcgccgggtc    45240
gcgctgccca cgtacgcctt ccagcgtcgg cggcactggg tggagcccgt cggaccggcc    45300 cgaggggggcg tcggctgggg gcagttcgcg gtgagcacc cgatcctggg cgccggggtc    45360
gacctggcca acggctcggc gaccgtgttc accgggcgcc tggacaccac cacacacggt    45420
tggctcgccg accacctcgt gctcggcgaa gtcctggtcc cgggcacggt gttcgtggac    45480
ctggcgctgc gcgcgggcgg cgccctcggc tgtgcggtgg tcgaggagtt ggccctgcac    45540
gagccgctgg tgttgccgga cgcggacggg gtgcggatcc aggtcaccgt cgaggcaccg    45600
gacgacgcgg gtacgcgggc gctgaccata cactcccggc ccgaggacgc gcccgccgcc    45660
gagccgtgga cccgacacgc ctcgggcacg gtggcccccg gcgcgcaccg gccgcagcag    45720
gagtccgggc catggccgcc gatcggggcg acgccgctgg acgtggcgga cgtatatctg    45780
cggttgaccg aactgggcct gggctacggc ccgacgctcg ccggactgcg ggccgcgtgg    45840
cggcgcggcg acgacctgtt cgccgaggtc gcgcgcaccg ccgacggcga acgtggcacc    45900
gcccgcttcg gcctgcaccc ggccctgctc gatgcggccc tgcacgggct tgccccggc    45960 tcggcacccg gcgcgcacc taccgaggtg cggctggccg gcgcctggcg cggggtgacg    46020
ctgggcggcg atgccggtac cgccggccgg attcggctgc ggggcgtcga cggggacggc    46080
gtcgaggtcg aactggccga cgaggcaggt cgatccatgg cccggatcga gtcggtggcg    46140
ctgcggccat ggagcgcggg gcaggtgcgg gcggccgggc gggcccgacc gtggttgacc    46200
cgctgggagt gggcccgggt cgagccgacc gacccggcgg cggcaggagg tcgctgggcc    46260
gtgctcggtg cgcgggcttg ggacggggtg ccggcctatg cgaccgccgc cgaactgatc    46320
gcggccgtcg aggtcggcgt cccggttccg gatctggtcg cgctgcccgt gcggatcgac    46380
ccggccggcg ggctcgatcc ggaggcgatc cgggccacga tccgggcggt gcgcgagacc    46440
ctgcggcagt ggcgggccga gccgcggctg gcggcctccc gcctggtcgt ggtgacccac    46500
gacgcggtct cggcgcggcc cgaggaccgg gtcaccgatc cgggcgcggc ggcggtgtgg    46560
ggcgtggtcc gggcggcccg ggcggcggac cccgagcggt tcgtgctcgc cgacgtggac    46620
ggggaggacg ggtcctggcc ggtgctgctg gccgaagcgt ccgccggtcg cgccgagttc    46680
gcgatccgcg cgggcacggt actgctgccg ggcctggccc gggtaccggc gggcgagacc    46740
ggcacggcgg gcttcccgac cgacggcacg gtattggtca ctgtcgcgac cgacccgacc    46800
gacccgaccg acggcaccga cccggtcggc acactgctgg ctcggcacct ggtgaccgcc    46860
cacggagtgc gccggctgat cctggccggc gggcccgccg ccgggatgcc gcttgcccgg    46920
gaactggccg cgcagggcgc ggagatccac gtggtcgtct gcgacgtgac cgaccgcacc    46980
gaactggcga agctgctggc cacgatcccc gagcacagcc cgctgaccgc cgtggtgcac    47040
accgccgggc tcggccggtc gcacaccgag gccatgctgc gggcccgggt ggacgcggcc    47100
gtacacctgc acgaactcac ccgcgacgcc gacctgtccg ccttcgtgct ctgcaccgcc    47160
ctggacggcg tactcgccga ccccgggcgc ggcgaacacg cggccggcga cgccttcctg    47220
gacgccctgc cccggcaccg gcacgccgcc gggctgcccg cgctcgcgct ggcctgggca    47280 ccggggggccg aaccggtcgc cgggctgctg ccgttgcccg gcgagcaggc cacggtcctg    47340
ttcgaccggg ccctcgggct gcccgaaccg gccctgatcc cgctcgcgcc ggacacctcg    47400
gcgctgcgcc gggccgaacc gggcgcactg ccggcgctgt tgaccacgct ggtggccgac    47460
ccgaaccacc gcgtcggcgc cgccgccgag gcggcgcccg cactgatcgg ccgactgctc    47520
gacctgccgg acgacgagcg ggaaagcgtc ctggtcgacc tggttcgcgg ctgcgccgcc    47580
```

```
gcgatcctcg gtcatgccga tccgaccgcg atcgagacgg gagcggcgtt caaggatctc  47640
ggcttcgact cgctgaccgc cctggagatg cgcaaccgac tgcgcgccgc gctgggcctg  47700
accctgccgg ccacgctgat cttcagccac cccaacgcgg cggccctggg ccggcacctg  47760
cacggcctgc tgcgccgcga gcacggggtc tcgtgggact cggtgctcgg cgagatcgac  47820
cgggtcgagg cgatgctcgc acaactcgac gacgcggacc gcgccagggc gacggagcgg  47880
ctgcgggacc tgatcggcgg cccggaagcc ccgctcgccg gccgcgagtc gggcgcgaac  47940
ggcgacgcgg ccgcggccg agggttcgac gcggccacgg acgaggagct gttcgacttc  48000
atcgacggcg ggatcgagca ctgattcgac aacggcggga tcgaggaccg acgacagatc  48060
gcggggctgg gactctcccg tcctcctgaa caggcaagga aagcaccga tggcaacga  48120
agacaagctc cgcgactatc tgcgccgggc caccaccgaa ctgcaggaga cccgactgcg  48180
gttgcgcgag acagaggaca agtggcacga accgctcgcc atcgtcggca tgcactgccg  48240
ctacccgggc ggggtggcct cgccggacga cctgtgggac ctggtcgacg cgggcaccga  48300
cgcgatcacc ggactgcccc cgggccgggg ctgggaggtg gacgaggccg cgaacggcac  48360
gtcgtaccgg ggcggtttcc tgaccgacgc ggccgacttc gacgccgact tcttcggcat  48420
ctcgccgcgc gaggcgctgg ccatggatcc gcagcagcgg gtgctcctgg aggcgtcctg  48480
gacggtcttc gagcacgccg ggatcgatcc gaccacgctg cgcggcagcc gtaccggggt  48540
gttcgtcggg gtgatcgcca gtgactacct gtcgcgcctg gcccgggtgc caaggaggt  48600
cgagggccat ctgctgaccg gcagcctggt cagcgtggcg tccggtcgtc tcgcctacca  48660
cttcgggctg gagggcgcgg cggtcaccgt ggacaccgcc tgctcgtcct cgctggtggc  48720
ggtacacctg gccggccagg cgctgcgcgc gggcgagtgc gacctggccc tggtcggcgg  48780
ggccaccgtc ctggccaccc aggcgcgtt cgacgagttc tcccggcagc agggcctggc  48840
cggcgacggt cgttgcaagt ccttcgcggc cggtgcagac ggcaccggct ggagcgaggg  48900
tgtgggcctg ctgttgatgg agcggttgtc cgacgcgcgc cgcaacggac accgggtgct  48960
cgcggtggtg cgcggctcgg cggtcaacca ggacggcgcc tcgaacggac tgaccgcgcc  49020
gaacgacctg gcccaggagc gggtgatccg gcaggcgctg gccaatgccc gactggccgc  49080
gagcgacgtg gacgcggtgg aggcacacgg caccggcacc cgactcggcg acccgatcga  49140
ggcccaggcg ctgctggcga cctacgggca gaaccggccg gccgcacggc cgttgcggct  49200
gggctcgatc aagtcgaaca tcggccacgc ccaggcggcg gccggggtgg cgggcgtgat  49260
caagatggtg caggcgctgc ggcacggtgt gctgccgcgc acgttgcacg tggacgagcc  49320
gacgccgcac gtggactggt ccgccggggcg ggtggcgctg ctcaccgagc cgatggcgtg  49380
gccggcgggt gaacgggtgc gccgcgcggg ggtgtcctcg ttcggggtga gcgggaccaa  49440
cgcgcacgtg atcgtggagg aggcgccgcc ggtcgaggaa ccggtcgggg cggccgatcc  49500
ggcgcggccc ctcggcgtag tgacgccgtg ggtggtgtcg gcgcgcaccg aggacggcct  49560
gcgggcccag gtggagaggt tgcgggagtg gcgatcgag catccggagg ccgatccggc  49620
cgacgtgggc cggtcgttgg cctcggggcg ggcactgtcc ggccaccggg ccgtggtact  49680
cggccgggac gcggcggagt tggtcgaggg gttgtccgtc gtggtggacg gcgagcccga  49740
ggcgatcgtg ggcgaggccc ggcgcggatc gggccgtacc gccgtgttgt tcaccgggca  49800
gggggtgcgc tcgcgcggga tggcgcgcga actgcacgcg gcgttcccgg tgttcgcggc  49860
ggcgctggac gaggtgtgtg ccgcgttcga cgcggtgttg ccgttctcgg tacgggacgt  49920
```

```
gctgctggca gagggcgagg gcggcggcgc ggacggtgac ggcggcgagg acaccggtgt    49980
ggcgcaaccg gcgttgttcg cctacgaggt ggcgctgtac cggttgtgga cctcgtgggc    50040
ggcggcgccc gacgcggtgg ccgggcactc gctcggcgag gtggtcgcgg cctatgtggc    50100
aggggtgttc tcgctcgccg acgcaaccac gttcgtcgcg gcccgcgcca cgctgatgag    50160
cgcgctgccg cccggtggcg cgatggtcgc ggtgggcacg tcggagagcg cggcggcccg    50220
gttgctcgcc gaccatccgg gagtgggcat cgcggcggtg aacgggccga ccggcgtggt    50280
gctttccggc gaggcggcgg ccgtggcgga ggttgcccgg gtgtgtgccg agcgcgggct    50340
ccgcatctcc cggctgcggg tgtcgcatgc gttccactcg cgcgctgatgg aaccgatgct   50400
ggacgaactg gccgaggtcg tctcgggatt gacgctgcgt ccggcgcgca tggcgatcgg    50460
gtcgaacgtg accggccgga tcgggtcggc ggagcagctg tgcgatccgc gctattgggt    50520
ggaccacgtg cggcgcgcgg tgcgcttcgg cgatgtgctg gacgcgctgc gcgccgacgg    50580
ggtgcgtacg ttcgtcgaga tcgggccgga cgccgcgttg accccgatgg ttgccgatgt    50640
cacggccgac gccgacgatg tggtggcggt cgccacccgg cggcgtgacc gcgacccggt    50700
gacggtgtg tcgaggcgc tggcccgggt gttcgtgcgc ggcgcggtgg tggactgggc     50760
ggcgttggtg cccggacggt gggtcgagct gcccacgtac gccttcaccc ggcggcgctt    50820
ttggctggac gccggtaccg gcgcgggcga cccgaccggc ctgggcagg ggacggtgga    50880
tcacccgctg ctcggtgcgg tggtcggcct ggccgatgga cacggttcgt tgttcaccgg    50940
gcggttgtcc ctggacaccc atccgtggct ggccgatcac gtcgtcctgg acaccgtcct    51000
gctgcccggg accgcgttcc tggaactggc cctgcacacc gggcgccggg tgggctgcga    51060
tcgggtcgag gaactgtccc tggagacccc gttggcgttc ggcgagcgcg gtggttgcca    51120
ggtgcaggta tggatcgagg cggccggccc cgacgagcgg cggcgggcga tcaccatcca    51180
ctcccggccg gacgacggag acggcgacga ggggtggatc cgcaacgcgg tgggcacggt    51240
cgcgccggtc gaggacaagg cgcccgccga cgccgtggcc gacccgaccc cctggccgcc    51300
gacgggcgcg acaccggtgc cgatcgacga cttctacccc tggctggccg acaacgcgt    51360
ggcctacgga ccgtgcttcc gggcggtgcg cgcggtctgg cgtcgcgggg aggagatctt    51420
cggcgagatt gcgctacccg agcaggtcgg gtacgaggcc gaccggttcg gcgtgcaccc    51480
cgcgctgatg gacgccaccc aacaccttct cggggtggcc gcgttcgcgg accggcgga    51540
gagcgagggc ggcggtttgg cgctgccgtt ctcgtggcgt gaggtacggc tgcacactcc    51600
cggcgcggcc tcggtacggg cgcgggtggt gcggaccggg ccggagtcgg tgacgctgag    51660
cctggccgac gaggacggcc gacccgtcgc cgaggtcgag tcgttggccg tgcggccgat    51720
ctcggccgaa caactgcgca cctccacggc gggtcgccgc gacccgctgt acacgctgcg    51780
ctggacgcca ctgccccggc cgtcggccgc gccgggcatc ggatccccgg cgatcatcgc    51840
cgattcgggc tcgggggacc cgttcgcggg ccggctcggc ggcaccgtac atcccgatct    51900
gaccgcgctc gccgacgcgg tggacgccgg gctgccgacg cccgaggtcg tcgtcctcgc    51960
gtggcccacg atcccggccg gaccgctcgg cgacgtgccg gacccggacg acgtacacgc    52020
cgccgtacac cgggcgttgg ccaccgtgca gacctggctc ggggacgaac gcttcaccgg    52080
cgcccgcctc gtcgtggtca cccggggcgc ggtcgccgtc gcggacgagg aggtgcggga    52140
tccggccgcc gccgccgtcg gcggcctggt gcggtcggcc cagtccgagc acccggaccg    52200
gctcgtcctc gtcgacctgg acgaggacgg ggcctcgccc ggggcgctgc cggccgcgat    52260
cggcgcgggc gagccgcaac tcgcggtacg ggccggggtg gcgtacctgc ccaggctcac    52320
```

```
ccggacaccc gcgatcgagc cgagcacgcc actgttcgcg cccgacggta cgaccctggt  52380
caccggcggc accggtgcgc tcggcgccct ggtcgcccgg cacctggtgg tcgcgcacgg  52440
ggtgcgccgg ctgctcctgg tcagccggcg cgggatcgcc gcaccgggcg ccgggtcgct  52500
cgccgccgaa ctcaccggcc tgggcgcgac ggtcgacgtg gtggcctgcg acgtgtcgga  52560
ccgggccgac ctggccaaga agctggccgc gatcccgtcc gcacacccac tgtccgccgt  52620
cgtgcacgtc gcgggagtgg tcgacgacgg ggtgatcggc gcactgacgc ccgagcgggt  52680
cgaccgggtg ttgcggccca aggtcgacgc ggcgctgcac ctgcacgagt tgacccggga  52740
cgcggacctg accgcgttcg tgctgttctc ctcggtggcc ggggtgatcg gcagcctcgg  52800
acaggcgaac tacgcagccg gcaacgcctt cctggacgcc ttcgcacagc ggcgacgtgc  52860
cctcgggctg cccgcggtgt ccatggcctg gggattgtgg gccgaggaaa gcgggctgat  52920
gcgtgaggag ttcgccgaga ccgaccggca acgcatcaac cgcagcggtg tattgccgct  52980
gtccgacgaa cagggcctgg cactgttcga cgcggcgctc gcgcacggcg agccgatcct  53040
ggccccggtc cgcctggacc tgagcgcgct gcgccgcctg gaggacgaac ttcccgccat  53100
cctgggcgga ttggtgccca cctcgcgccg cgacggcgcc cgccccggcg cggcggacac  53160
ccgccgactg gcccagcggc tcgccggcc ctccgagccg gagcagctgc gcctgctcac  53220
cgaactgacc cgcgcccagg ccgccgtggt gctcgggcac gcgggcgccg acgcggtcgc  53280
cgccgaccgc gcgttcaccg aactgggctt cgactcgctc accgcgctgg agatgcgcaa  53340
ccggctcaac acggtcaccg gcctgcgcgt gcccgccacg gtgctgttcg actatcccaa  53400
cgccgccgcg ctggccccgct tcctgcgcgc cgagacgctg cgcgtaccgc agtacaccca  53460
ggcggcggcg aacactgccg ccaaggcccg gacttcggac gaaccgatcg cgatcgtggc  53520
gatgagctgt cgctacccgg gcggcatcga caccccgag gagttgtggc gctgcgtcgc  53580
cggcggagtg gacctgacct cgccgttccc gaccgaccgc ggctgggacc tgggcgcgct  53640
gtacgacccg gacccggacc gctccgggcg ctgctacacc cgcgagggct cgttcatgcg  53700
cgacatcgac cgcttcgacg ccgaactgtt cgggatctcc ccgcgcgagg cgctggccat  53760
ggacccgcaa cagcggctgc tcctggagac ctcctgggag gcgttcgaac gcgcgggcat  53820
cgacccgtcc tcgctgcgcg ggagcaatac ggcggtcttc gcgggcctga tgtacgcgga  53880
ctacgccgcg ggtcgagtgg gtgacgtcgg cgacgagttg gaggcgtaca tcggcaacgg  53940
caactcgttc ggcgtcgcct ccggtcgggt cgcctacacg ctgggactgg agggcccggc  54000
ggtgaccgtg gactcggcct gctcgtcctc gctggtcgcg ctgcactggg cggcgcacgc  54060
gctgcgcagc ggggaatgtg atctcgcgct ggcgggcggg gcgacggtga tgtccacgcc  54120
cagtgtcttc gtggagttcg cccggcagcg cggcctggca cccgacggcc ggtgcaagtc  54180
gttcgccgcg gcgccgacg gcacggcgtg gggcgagggc atcggcatgt tgctggtgga  54240
gcggctggcc gatgcgcgcc gcaacgggca tccggtcctc gcggtgctgc ggggttcggc  54300
gatcaaccag gacggcgcct ccaacggcct caccgcgccc aacggccgt cgcaacagcg  54360
ggtgatccgg caggcgctgg cgaacgccgg gctggccacg gccgatgtgg acgcggtcga  54420
ggcgcacggc accgggacgg tactcggcga cccgatcgag gccaggcgc tgctggccac  54480
ctacggtcgg gaccggccgg cggaacggcc gctgtggttg ggatcgatca agtcgaactt  54540
cggccacacc caggcggcgg ccggggtggc cggggtgatc aagatggtga tggcgatgcg  54600
gcacgggatg ttgccgccga cgctgcacgt ggacgaaccc tcgccgcatg tggactggtc  54660
```

-continued

| | |
|---|---|
| gaccgggcgg gtcgaactgc tcgccgaggg gcggccgtgg cccgaggtgg ggcgggcccg | 54720 |
| tcgggtggcg gtgtcctcgt tcgggatcag cgggaccaac gcgcacgtca tcctcgaaca | 54780 |
| ggccgacgag gagccggaac ccgccgcccg aaccacgtcc ggcaccggca tcggcggggt | 54840 |
| gctgccgtgg gtgctctcgg cccggaccga ggcgggcgtg cgggcccagg cggcccggct | 54900 |
| gagggactgg gccggggccc ggcccgaggt cgatccggcc gacgtgggct ggtcgttggc | 54960 |
| gtcgggacgg tccgtattcg agcggcgcgc ggtggtgtgg ggccgggacg gcgcggagtt | 55020 |
| gacggcgggc ctggacgcgc tggcggccgg gcgggatgcg ggagcacgtg ccgtgcttgc | 55080 |
| cggcggcacc ggcgtgtcgg gcgaggcggc cgtcgggccg gtgttcgtgt ttcccggtca | 55140 |
| gggctcgcag tgggtcggga tggcggcgga actgctgacc tgctgcccgg tgttcgccga | 55200 |
| gtcggtggcg gagtgcgcgg cggcgatgga tccgctgctg gccgactggg cactgctcga | 55260 |
| cgtgctccgg gacgcgtccg ccgcgctgtt ggagcgggtg gatgtgatcc agcccgtgct | 55320 |
| gttcgccgtg atggtcggcc tggcccggtg gtgggagtcg tgcggggtgc gaccgagcgc | 55380 |
| ggtgatcggg cattcccagg gggagatcgc cgccgcgcat gtggcgggct tcctgtccct | 55440 |
| ggaggacgcg gtccggatcg tggtgctgcg cagccgggca ctgcggggc tcgcggccga | 55500 |
| cggtgacggg atgttgtcgg tgggcgtgtc cgccgagcgt ggccgcgaac tcgtggcacg | 55560 |
| cgtgcaggga ttgtccctgg cggcggtcaa cgggcccgac agcgtggtgc tttccgggcc | 55620 |
| ggtcgagggt ctgacgccaa tcgccgccgc gtgcgagcgc gacggggttc gggcgcgatg | 55680 |
| gatcccggtg gactacgcct cgcactcggc gcggatggac gacgtacgcg aggtgctggc | 55740 |
| cgagtcgctg gccggggtcg agccggggat cgggcgggtg ccgatgtact cgaccgtgag | 55800 |
| cgggctgaag gtcaccgatg cggcggatct gggcggggag tactggttcg agaacttgcg | 55860 |
| tcgcaccgtg cagttggcca cggcggtcgg ggcggcggcg gccgacgggc acagcgtgtt | 55920 |
| cgtcgaatgc agcccgcacc ccggtctggt ggtgccgctc ggcgacaccc tcgacgccct | 55980 |
| cgggagcacg tccggcacgg tcctggagac gctgcgccgg ggcgagggcg ccccgaacg | 56040 |
| cctggtcgcg gcactggcag cggccttcgt gagcggcctg ccggtcgact gggccgggct | 56100 |
| gctgcaccac gacggggtcc ggcgagtaca gctgccgaca tacgccttcc agggccgccg | 56160 |
| cttctggctc gaaccggaca tgggcacggc gctgccccggc cggacgacac cgacgccggt | 56220 |
| ggtgggcgac accgaggaca gcaggttgtg ggaggcgctg gaggcggcgg gcgccgagga | 56280 |
| cttgccgcc gaactggagg tggcggcgga cgcgccgctg agcgacgtgt tgccggcgct | 56340 |
| gacgtcctgg cgggcgcggc ggcgggcgga cgcgacggtg cggtcctggc ggtacggagt | 56400 |
| gcggtgggag ccgtgggcgg cgccggccgc ctccgccgac aggatggggc gtctgctgct | 56460 |
| cgtcgctccg gacggggaga tcgggacgt gctcgcgggc gcgctggccg agtgtggtgc | 56520 |
| cgaggtggtg gtgctgtccg cggagggga acggaccgcg ttggcgcggc ggctcgcggc | 56580 |
| aatcggcgag gagggtgtgc cggccggggt ggtgtcgttg tcggcggtgg gttgcgccgc | 56640 |
| cgacgcggat cccgtgcccg cgctcgcgcc ggtgctcacg ctggtgcagg cgctgggcga | 56700 |
| cgccgggatg gaggcaccgt tgtgggtgct gacgcgcggc gcggtgtcgg tgctgggcga | 56760 |
| ggagccgacc ggcccggcgg gtgcggccgt gcagggctc gggcgggtgg tcgggctgga | 56820 |
| acatcccggg cggtgggtg ggctgatcga tctgccgcag gtggtggacg gccggtggc | 56880 |
| ggagacgctg gcgggatcc tggcggccgg cgcgggcggc accggctcgg gtgaggacga | 56940 |
| gatcgcgatc cggccgctgg gagtgttcgt ccggcggttg gcgcggatgg ccgggccgga | 57000 |
| gggcagcggg acgagccggt ggcgcccgg tggtacggcg ttggtcaccg gcggtaccgg | 57060 |

```
tgcgctgggc gggcgggtcg cgcggtggct ggtccgggag ggcgtcgagc gggtggtgtt   57120
ggccgggcgg cgtgggcccg acgcgccggg cgcggaccga ctgcgcgagg aactggcggc   57180
ggccggggcc gaggtggcgg tgctcgcctg tgacctgggc gatcgcgacg cggtggccgc   57240
gctgttggcg gaggtgcggg ccggcggccg gcggatcgac accgtcgtac acgcggccgg   57300
cgcggtggtg gtcggccgc tggcggacag caccgtcgcg gatctcgccg acgcctcggc   57360
ggccaaggtc ggcggcgcgc tgctcctgga cgagttgttg cgggccgacg agcccgacac   57420
cgtggtgctg ttctcctccg ccgccggggt gtggggcggc gcggggcagg gggcgtacgc   57480
ggcggccaat gcctgcctcg acacgatcgc cgagcggcgc cgggcgcgcg ggctgcgtac   57540
cgtctcgatc gcttgggggc agtgggccgg tggcgggatg ccgacggcg cggccggcgc   57600 gcacctcgac cggatcgggg tcccggcgat ggacccggat cgggccctgg aggcactgcg   57660
gcaggccctg gacgaggacc tgacctgcgt caccgtggcc gacgtggact ggccgaggtt   57720
cgccgccggg tacacggcgg cccggccgcg accgctgatc gcggacctgg tggcggcgga   57780
ggtcgcggcg gcgccggtca ccgaagcgcg cggggcgggc gagccggacg gtccgagtgt   57840
gtggcgggcc cgactggccg aactgggcgc ggcggatcgg gaggcggaac tgctcgcgct   57900
ggtccgcacc gaggtcgccg cgcagttggg ccacgccgac ccggccgcga tcgaacccga   57960
acggccgttc cgcgatctcg ggttcgactc gctcgcggcg gtgggcctgc gcaaccgact   58020
gaccgagacc atcggtctgc ggctgcccag cacgctggtc ttcgaccacc cgacggccgt   58080
cgcactggcc gcgcacatcg acggcgaact cttcgccgag accgtcggga cggtctccgt   58140
cttcgccgaa ctggaccgcc tggaagcggc gctcggcgaa ctgggcggcg acttcgccga   58200
acggggcagg gtcggtgccc ggttggccga actcgccggg aaatggcggg agatcgaggc   58260
cgcgagccaa aaggccgagc ccgagggagc cgacttcgcg gcagcggagg acgaggagat   58320
gttcgacatg ctcggaaagg agttcggcat ctcctgagcg gggccggcga cgaccgccgg   58380
tcacgggtcc cgacggcaca cggctcgatc aggttcgacc aggcagagga cggacgtacg   58440
gacatgtcga acgaagaacg gctgcggcac ttcctccggg agaccgccac ggatctgcgc   58500
cgcaccaagc agcggctgca cgaggtggag tcggccgccc gcgagccggt ggcgatcgtg   58560
gcgatcgggt gccgactgcc gggcggcgtg cgctccgccg aggacctgtg ggagctggtg   58620
cggaccggga cggacgcgat cgccggcttc ccgtccgacc ggggttggga tccggcgaac   58680
gtctacgcgg acctgccggg cggcgagggc gtctcgggcg gttcggccgg atccggcggg   58740
tcgaccaccc ggcagggcgg attcgtctac gacgcggctg cgttcgacgc cgagttcttc   58800
ggcgtctcgc cgcacgaggc gttggcgatg gacccgcagc agcggctgct cctggagacc   58860
gcgtgggaga ccttcgagcg ggccggcatc gatccgctgt cgatgcggcg cagccggacc   58920
ggcgtgttcg tcgcgccgg tgcgctcggc tacggcggcg ggatgcgggc ggacaacgcc   58980
gagatccagg cccatcgggt caccggcggc tcgatgtccg tggtgtcggg gcggatcgcc   59040
tacacgctcg gtctggaggg cccggcggtc accctcgaca cggcgtgttc gtcgtcgctg   59100
gtggcgctgc acctggcggc caacgcgctg cgctcggggg agtgcgacct ggccctggcc   59160
gggggcgtca cggtgatggc ccggccgacc gccttcgtgg agttctcccg gcagggcgga   59220
ttggcctcgg acgccgctg ccggtcgttc gcggcggcgc cggacggcac cggtgggggt   59280
gagggtgtcg ggctgctgct ggtggagcgg ttgtcggatg cgcggcgcaa cggccatccc   59340
gtactggcgg tgctgcgcgg ctcggcggtg aaccaggacg cgcgtcgaa cgggttgacc   59400
```

```
gcgccgaacg ggccgtcgca acagcgggtg attcgacagg cgttggcggc ggcgggcttg   59460
tcggccgccg atgtggacgc ggtggaggcg catgggaccg ggacggtgct cggcgacccg   59520
atcgaggcgc acgcgctgtt ggccacctac gggcgggatc ggcccgcgga tcggccgttg   59580
tggctggggt cggtcaagtc caacatcggg cacacccagt ccgcggccgg ggtcgccggg   59640
gtgatcaaga tggtgatggc cctgcggcac gggctgctgc cgcgcaccct gcatgtggac   59700
cggccgtcgc cgcacgtgga ctgggcctcg ggacgggtcg agctgctgac cgacgaggtg   59760
ccgtggcccg cgggcggtcg ggtgcgtcgg gcgggtgtgt cgtcgttcgg gatcagcggg   59820
acgaacgcgc acgtggtcct ggaggaggcg ccggccgtcg aggggccctc ggggagggg    59880 gccgaacccg cgccgggtgt cggtggggttg attccgtggg tggtatcggc gcgctccccg   59940
gaggcgttgc gcgcgcaggc ggcgcggttg cgggagccgg cggtcgcgga tccgccggat   60000
gtcggtcggt ccttggtgac gggacgggcg ttgctcgacc atcgggcggt ggtgctgggt   60060
cgggacgccg ccgagttggg ccgtggactg gccgcgttgg cggccgggtc tccggggtgcg   60120 gtcgagccgt cggagggggg aactccggtc gtggtgaccg ggaatgtgcc ccgagcgggt   60180
ggtgcgggtg gtcgggtcgc cgggcggggc gcggtggtgt tcaccgggca ggggggtcgg   60240
ttgcccggga tcggcggga actgtacgcg ggtttcccgg tgttcgctcg cgcgctggac   60300 gaggtggggtg cggcgttcga cgcggtggtg ccgttctcgg tccgggacgt gttgctcggc   60360
gtggagggca cggtcggcgt cgatgccgac gacaccggcg tggctcagcc ggtgttgttc   60420
gcgttcgagg tggcgctgta ccggctgtgg agttcgctgg ggtcggtccc ggatttcgtg   60480
gtcggacact cgttgggtgg gatcgtcgcg gcgcatgtgg cggggtgtt ctcgctcgcg   60540 gacgcggtgg cgttcgtcgc ggcgcgcgcc cggttgatga gcgcgttgcc gggcgggggc   60600
gcgatgctcg cggtgggggc gagcgaggcg caggtcaccg cgctgtcgga tgggctgccg   60660
gtgtcgatcg cggcggtcaa cggaccggcg agtgtggtgg tttcgggcgc ggtggcggcg   60720
gtggacgagg tggcggcgcg gtgtgcggcg cgcagttggc gcagttcgcg gttgcgggtc   60780
tcgcacgcct tccattcggt gctgatggag ccgatgttgg ccgaactacg ggacgtgctg   60840
cgccggttgt cgttcggggc gccggagatc gggttggtgt cggataccac cgggcgggtc   60900 gttacgccg aggaggtggg tgatcccgag tactgggtgc ggcatgtgcg cgacgcggtg   60960
cggttcgcgg atgcggtcgg cacgttgcgt gagcggggtg tggccacctt cgtggaactg   61020
ggtccggacg cggcgttgac cgcgatggtg gccgagtgca cggcgggtgt gggcgaggtg   61080 ctggggggtgc cggcccagcg gcgtggccga ccggccgtgg cgacgctggc cggcgcgctg   61140 gccacgcgcgt tcgtgcgggg gctgccggtg gactgggtcg gggctctcgg cggcccgggc   61200
gggcggcggg tggagctgcc gacctacgcg ttccaggggc ggcgctattg gctggagccg   61260
gggaaggctt cggtgacgcc ggccgggccg gattcggtgg acgtccgct gtgggacgcg   61320 gtcgagcggg ccggggcggg cgaactggcg gcgatcctgg cggtgtccga ggacgcgacg   61380
ctgcgcgagg tggtgccggc gctgtcgtcc tggcgagccc gacgacgggt ggacgcgacg   61440
gccgcgtcgt ggcgctacgc ggtgcggtgg gagccgtggg cgggtggttc gtccgacgcg   61500
gccgcgttgt ccgggcgttg gctgctcgtg cacccggcgg cgagcgagct ggcggatgcg   61560
gtggcccgga agctgaccga gcgtggcgcg gaggtggtgc gggtcggggg cgagggcatc   61620
gggtcgcacg tcggtgccga acccgtcgcc ggggtggtgt cgttgatcgg ctccggttcg   61680
ggctccggct ccactcgggg ttcgggctcg ggctccggtt ccgcttcggg ctcgggctcc   61740
gggtccggtt cgggctccgg ctccggctct ggttcgagtt gcggctccgg ttcggtgccg   61800
```

-continued

```
ggcttgggtt cgtgcgcggg cgacgactgc gccgacctcg tggccgccgt ggtggcgatg   61860
ggcgaactgc tcgcggagct cgccggttc gaggtcgccg ccccgctctg tgtgtgacc    61920 cgggcggcg tgtcggttct gggcgaggac ctggccaatc ccgtgggcgc cggcctgtgg    61980
ggcaggggcc tggtggcgag cctggagcaa cccgggtgct ggggcggcct ggtcgacctg    62040
ccggccgtcg cggatacccg cgcgctgggg gtgctggcca cgatcctggc cgggacttcg    62100
gacgaggacc agttcgccat ccgcccgctg ggcgtgttca cccggcggct gaccccgctg    62160
ccggccgagg gatcgggccg ggtggtgcgt acccgcgaag cggcgctgat caccggcggc    62220
accggcgtgt tgggcgcgca cgccgcccgc tggctggtcg cgcacggcac cgagcgggtg    62280
atcctgctgg gccgacgcgg cgctcgggcg cccggattcg atgcgctgcg ggccgacctc    62340
gaggcggccg cgccgaggt ggtggcgatc gcctgcgacc tgaccgcgcc cgacgcggcg    62400
gagcggctgc gggccgcgtt gcccgcgacg ggtgcgccga tccgtaccgt cgtgcacgcg    62460
gcgggcgtgc ccggatcgcc caccgcgacc ggcgccgacg ccgtcgcgga caccgtcacc    62520
gccaaggtcg ccggcgcgct ggccctggac acgcttttg gggcggaccg ggccctggac    62580
gcgttcgtgc tctactcctc cggcgcgggg gtgtggggcg cgccggaca gggcgcctac    62640 gcggcggcca acgccttcct ggacgcgctc gccgtacgcc gtcggcaacg cggcctgccc    62700
gccacggcga tcgcgtgggg gccgtgggcg gccggcggga tggcggacgg cgaggggaa    62760 cggctgctgg cccgggtcgg tgtacgggcg atggacccgg ccgcggcgct ggccgcactg    62820
ggccgggccc tggtcgagga cctcacctgc gtgacggtgg ccgacctgga ccggccccga    62880
ttcgcggcgg gctacacctc cgcccgtccc cggccgctga tcgccgacct gatcgacgcg    62940
gagccgccga ccgcgaccgc cccgccgacc cggcccggcg gggtgtggga cccggcggtg    63000
acccgctcgc cggcccggct cgcggccgaa ctgctcgacc tggtccgcgc cgaggtcgcc    63060
gcgcaactcg gccacgcggg cgtcgaggcg atcgaacccg accggccgtt ccgcgacctc    63120
ggcttcgact cgctggccgc cgtcggactg cgcaaccgga tcgccgaggc caccggggta    63180
cacctggccg gcaccctgat ctacgaccac gagacacccg cggccctggc cgcacacctg    63240
gccgacgccc tgcgcgaggg tgtgcccgag acccgcccgg cgccgacggc accggcggc    63300 gccgaggact cgaacgacat gctcggcacg gtctaccgca aactggccct gctcggccgg    63360
atggacgacg cggaatcgct cctggtcggc gctgccggcc tgcggcagac cttcgaggac    63420
ccgaaccggc tcccgaagac acccggcttc acccggctcg cgcgcggacc ggcccggccc    63480
cgggtgatct gcttcccgcc gttcgcgccg gtcgagggcg ccatccagtt cggccggctg    63540
gcgggcacgt tcgagggccg gcacgacacg gcggtggtga ccgtaccggg cttctcggccc    63600 ggcgagccgc tggccgcctc gctggacgtg ctgctcgacc tgctggccga cgcgacgctg    63660
cggtgcgccg gagacgaccc gttcgccgtg ctcggctact cctccagcgg ctggctcgcc    63720 caggggtgg ccggccgcct ggaggcgacc ggccgtacgc ccgccggggt cgtactgctc    63780
gacacctacc tgcccgccac gatgtcgcgg cgcatgcgca aggcgatgaa ctacgaggtg    63840
atcgtgcgcc ggcaggcgtt caccgcgctc gactacatcg ggctgaccgc gatcggcacc    63900
taccgccgga tgttccgggg ctgggagccc aagcccggct ccgcgccgac gctcgtggtg    63960
cggccctcgc gctgcgtccc gggctcgccg gaggagccga tgaccggcga ggactggcgt    64020
tccacctggc cgtacgagca caccgccgcc gaggtggagg cgaccactg cacgatgatc    64080 ggcgaacacg cggagcagac cggtgcggtg gtgcgcgcgt ggctggccgg tgacaggacg    64140
```

```
gtttcgatcg acacgaggga aggcacggca tgaccgaccc gcgctatccg cgatacccgc   64200
aacccggctc cgtcgaccat ctcgacgcgg agttcctggt ccaccgggcc gcgatccagg   64260
atctcgtcgc cgcgtacagc ctgctctacg acgcgggcga ctacgacggg ctcggcgacc   64320
tgttcaccga ggacgcgacg tacgcgttca ctcccgcccc cgaggatttt ccgccctcgg   64380
tgtccggccg ggacaagatc gtcgcggcga tggccgcgct cgcgagcac aacctgcgca    64440
cccgggccgc ccaccagcgg cacttcgtga ccaacacggt gatcacccgc ctcgacggcg   64500
acaccgccga ggcgcggtcg ctgatggcgg tggcgttcgc ccatccgggg gacggccgcc   64560
aagagttcac ccgcagtggg gtgtacgccg acgtgctggc ccgacaggga agccggtggc   64620
gcatcgccga ccggcacctg tggttggccg agttgccggc gccgcgtccc ggcgacacat   64680
ccgctcccga ggagagtcgg ccatgattcc cgtgctcgaa ctggtccaga tctccacact   64740
ccccgacgcc gaacgggaac tggagcaact ggcccggcga tacccgatca tccgcacccg   64800
acaggtcggg ggcatcgagg cgtggaccgt gctcggcgcc gggctgaccc ggcaactcct   64860
cggcgaccca aggctgtcca acgacctgca cacgcacgcg ccgcacgcgg cccagtccgc   64920
cgacggtccg accgtgctgt tcgagcagga caatccggac cacgcccgct accgccgcct   64980
ggtcagcgcc gcgttcgcgt cgcgggccgt gcgcaacctc gaaccgcgga tcgtcgacat   65040
cgcgcgcgca ctgctcgacc ggctgccggc cgaaggcggc acggtggaca tcgtcgaggc   65100
gttcgccaac cccttcccgc tggaggtgat ctgcgaactg ctcggggtac cgatggcgga   65160
ccgcgaggtg ttccgcaccc gggtggagaa catggactcg ccctcgacgg cggtacgccg   65220
ggcggcgatg gacgcgttcg tcgcctactg cgccaacctc gtcgacgcca agcgcaccga   65280
accgaccgag gacctgctga gcgagctggt acaggccgaa ctcgacgacg gatcacggct   65340
gtcggccaat gaactgatcg gcttcggctc cgtgctgctg ttcgcggggc acgtcaccac   65400
ggcctacctg atcgccgccg cgctgtacga actcatcacc cacaacgacc agttggccgc   65460
actccgggcc gatcccacgc tcgtcgaggg caccgtcgag gaggcgctgc gctttcgcgg   65520
ctcgttgttg tccaccacga accgggtggc gctgaccgac ctggagatcg gcggcgtgct   65580
cgtgcgccgt ggcgacctgg tgcgcttcct gctctccgcc gccaaccgcg acccggcgat   65640
ccgcgaggac ccgcacacct tcgacatcac ccggtccacc accgcccacc tgggcttcgg   65700
ccacggcccc cacttctgcc tcggccaacg cctggcccgc caggagatca aggtcgccct   65760
caccgagatc gtcacccgct tcccgaccct cgaactggcg gtcccggcgg aaaagctgcg   65820
ctggcgcgcc tcggacttcc tgcgcggcct tgccgaacta cccctgacgt acgcccgtg    65880
accaccgacg aggacaggcg gcccggaccc gggccgcccg ggctccgcgg cggtccgcgc   65940
cggtgtccgg cgagtgtgac gcgccgtcga acagtcgatg tcggctgcgc ggcgtccgtc   66000
gcggatcccg gacccgtcgt ggttgcgtag catctccggg ggtcggcggg cgacgccggg   66060
ccacgaacgg caggggcgcg gcgccatgga cggaccggcg gggagccgaa ggcacccacg   66120
ggcctgcgcg agcgcaagaa ggcccgcacc cggcaggtga tctccacggt cgcgttcgac   66180
ctgttcgagg aacagggctt cgaacagacc accgtcgaca tgatctgccg ccgccacgcg   66240
atgacggtca gccacggcaa cctcgaagac cacgccgaac aaaccgcccg ccgacacgcg   66300
ctgcgccgcc gcttcctggg cgtgcgctcg gtccacgacc acggcgtggc cctgatcgac   66360
acggtcgccc accgcatcgt caccaccgcc gccgcccgcc tcgggggtcga cccggccgtg   66420
gacctgcgcc cccacgccct cggcgccctg gtcgcggcga tgaccgccgg cgtggtgatc   66480
gacgacatcg ccccgggccc gatcaacgag tgggcggagg ccttccgcac cctgctcccg   66540
```

```
acgccggccg cacacaccga ctgacacacc gcccgggcgc cgacccggaa accgccgggt    66600
tccttcgcac cgcagggtga tcaccggtct tcgtccgtgc ggacacatct tcggcccgcc    66660
gctcgtgtac ggatccgagg ctcccggccc ggccgcgggc gatactcggg aaacgtcggg    66720
gcccggggag gcggcgggtt ccccataccc gagaggttcc acatgcagcc cgacccgcgg    66780
ttcgacccgc aacccgacac ggccgtcgaa cacccgtgg acgagcacgc cgccggcgcg    66840
cccgccgatc ggctcgtcga cctcgtcgtc cgggccggtt ccctcgtcga cggcagcgga    66900
tcccccgcgt acgacggcga cctcgcgatc gacggcgggc ggatcgtcgc gctcggcgac    66960
atcggcgcca tcacggggcg tgacgagatc gacgcacagg gctgcgtggt gtgtccgggc    67020
ttcgtcaacg tgctgagcca cgcctacttc accctccagc aggaccccg tggcctgtcc    67080 gacctgtacc agggcgtgac cacccagatc ttcggcgagg gcgtctcgct cggcccggtg    67140
accggggcga tgaccgagtc catgatc                                        67167
```

<210> SEQ ID NO 4
<211> LENGTH: 8438
<212> TYPE: PRT
<213> ORGANISM: Streptomyces sp. ATCC 39366

<400> SEQUENCE: 4

```
Met Gln Val Met Glu Arg Gly Met Thr Glu Phe Asn Ala Asp Ala His
 1               5                  10                  15

Arg Ala His Pro Ala Pro Glu Asp Ala Val Ala Ile Val Gly Leu Ala
            20                  25                  30

Cys Arg Leu Pro Gly Ala Asp Gly Pro Asp Glu Phe Trp Asp Leu Leu
        35                  40                  45

Ser Asn Gly Arg Asp Thr Ile Thr Glu Val Pro Arg His Arg Arg Asp
    50                  55                  60

Ala Arg Ala Ala Asp Asp Thr Asn Arg Thr Ala Gly Gly Ser Pro His
65                  70                  75                  80

Pro Ala Ala Asn Arg Pro Arg Arg Gly Gly Phe Leu Asp Ala Val Asp
                85                  90                  95

Arg Phe Asp Ala Ala Phe Phe Gly Ile Thr Pro Gly Glu Ala Ala Leu
            100                 105                 110

Ile Asp Pro Gln Gln Arg Leu Met Leu Glu Leu Cys Trp Glu Ala Leu
        115                 120                 125

Glu His Ala Gly Ile Pro Pro Thr Arg Ile Arg Gly Ser Ala Thr Gly
    130                 135                 140

Val Phe Ala Gly Ala Ile Trp Asp Asp Tyr Ala Thr Leu Leu Arg Arg
145                 150                 155                 160

Ala Gly Val Glu Pro Gly Pro Arg His Ala Thr Gly Leu His Arg Ser
                165                 170                 175

Met Ile Ala Asn Arg Val Ser Tyr Thr Leu Gly Leu Arg Gly Pro Ser
            180                 185                 190

Met Thr Val Asp Ala Ala Gln Ser Ser Ser Leu Val Ala Val His Leu
        195                 200                 205

Ala Gly Glu Ser Leu Arg Arg Gly Glu Ser Thr Leu Ala Leu Val Gly
    210                 215                 220

Gly Val Asn Leu Asp Leu Val Pro Asp His Asp Gly Asp Ala Ala Lys
225                 230                 235                 240

Phe Gly Gly Leu Ser Pro Gln Gly Arg Cys Phe Thr Phe Asp Ala Arg
                245                 250                 255
```

-continued

```
Ala Asp Gly Tyr Val Arg Gly Glu Gly Gly Ala Val Val Leu Lys
            260                 265                 270

Pro Leu Ser Arg Ala Leu Ala Asp Gly Asp Val Val His Gly Val Ile
            275                 280             285

Arg Gly Ser Ala Met Asn Asn Asp Gly Gly Asp Ala Leu Thr Ala
            290                 295                 300

Pro Asp Pro Arg Ala Gln Ala Glu Val Ile Arg Leu Ala Arg Arg
305                 310                 315                 320

Ala Gly Val Ala Ala Ser Ala Val Gln Tyr Val Glu Leu His Gly Thr
                325                 330                 335

Gly Thr Pro Val Gly Asp Pro Ile Glu Ala Ala Leu Gly Ala Ala
            340                 345                 350

Leu Gly Thr Glu Arg Ala Asn Arg Pro Pro Leu Ala Val Gly Ser Val
            355                 360                 365

Lys Thr Asn Val Gly His Leu Glu Gly Ala Ala Gly Ile Val Gly Leu
    370                 375                 380

Val Lys Thr Val Leu Ala Ile Arg His Arg Leu Pro Ala Ser Leu
385                 390                 395                 400

Asn Phe Ala Glu Pro His Pro Arg Ile Pro Leu Gly Glu Leu Gly Leu
                405                 410                 415

Arg Val Gln Thr Ala Glu Gly Asp Trp Pro Cys Pro Asp Glu Thr Leu
            420                 425                 430

Ile Ala Gly Val Ser Ser Phe Gly Met Gly Gly Thr Asn Cys His Val
            435                 440                 445

Val Leu Ala Glu Ala Glu Pro Ala Asp Gly Val Gly Pro Ser Val Ala
    450                 455                 460

Ser Ala Pro Ser Gly Gly Ser Asp Pro Gly Met Glu Ser Ala Thr Gly
465                 470                 475                 480

Pro Val Pro Ser Asp Ala Val Ala Val Pro Ile Ser Gly Val Asp Ala
                485                 490                 495

Asp Gly Leu Arg Ala Gln Ala Gly Arg Trp His Gly His Val Arg Glu
            500                 505                 510

His Pro Asp Val Ala Pro Ala Asp Leu Gly Tyr Ser Ala Ala Thr Thr
            515                 520                 525

Arg Thr Ala Phe Ala Ala Arg Ala Val Val Leu Ala Arg Asp His Ala
    530                 535                 540

Glu Leu Leu Ala Gly Leu Asp Ala Leu Arg Gly Ala Gly Ala Asp Pro
545                 550                 555                 560

His Leu Val Arg Ala Asp Ala Gln Pro Gly Arg Thr Ala Phe Leu Phe
                565                 570                 575

Thr Gly Gln Gly Ser Gln Arg Pro Ala Met Ala Gln Glu Ser Tyr Ala
            580                 585                 590

Arg His Ala Val Phe Ala Ala Ala Phe Asp Ala Ala Cys Ala His Leu
    595                 600                 605

Asp Pro His Leu Pro Arg Pro Leu Arg Glu Val Leu Phe Ala Ser Pro
610                 615                 620

Asp Ser Pro Asp Ala Ala Leu Val His Arg Thr Glu Tyr Thr Gln Pro
625                 630                 635                 640

Ala Leu Phe Ala Val Glu Val Ala Leu Tyr Arg Leu Phe Glu His Trp
                645                 650                 655

Gly Val Thr Pro Asp Leu Leu Gly His Ser Ile Gly Glu Leu Cys
            660                 665                 670

Ala Ala His Val Ala Gly Val Trp Ser Leu Pro Asp Ala Cys Ala Leu
```

-continued

```
            675                 680                 685
Val Ala Ala Arg Gly Arg Leu Met Gln Glu Leu Pro Asp Gly Ala
            690                 695                 700
Met Val Ser Leu Arg Val Ala Glu Asp Val Leu Ala Ser Leu Glu
705                 710                 715                 720
Pro Val Arg Asp Arg Val Ser Ile Ala Ala Val Asn Gly Pro Leu Ala
                725                 730                 735
Thr Val Ile Ser Gly Asp Arg Asp Ala Val Leu Asp Val Ala Ala Gly
                740                 745                 750
Trp Arg Ala Gln Gly His Lys Thr Thr Arg Leu Arg Val Ala His Ala
            755                 760                 765
Phe His Ser Pro Arg Met Asp Ala Met Thr Asp Ala Phe Ala Glu Val
            770                 775                 780
Ala Ala Gly Leu Thr Ala Arg Ala Pro Thr Leu Pro Val Val Ser Asn
785                 790                 795                 800
Leu Thr Gly Leu Pro Leu Thr Ala Glu Gln Ala Cys Ser Pro Asp Tyr
                805                 810                 815
Trp Val Arg His Val Arg His Thr Val Arg Phe His Asp Gly Val Arg
                820                 825                 830
Arg Leu Arg Ala Glu Gly Ala Thr Ile Leu Leu Glu Leu Gly Pro Asp
            835                 840                 845
Gly Ser Leu Ser Ala Ala Arg Thr Cys Leu Leu Asp Gly Glu Arg
            850                 855                 860
Asp Thr Val Ala Thr Ile Pro Thr Leu Arg Arg Asn Arg Pro Glu Thr
865                 870                 875                 880
Asp Ala Leu Thr Thr Ala Val Ala Arg Leu Tyr Ala Asn Gly Val Asp
                885                 890                 895
Pro Asp Trp Glu Arg Val Phe Ala Gly Arg Gly Ala Arg Arg Val Ala
                900                 905                 910
Leu Pro Thr Tyr Ala Phe Arg Arg Ala Arg His Trp Pro Gly Ala Ser
            915                 920                 925
Ala Glu Ala Ala Asp Thr Ala Val Pro Asp Glu Ser Leu Ala Val Val
            930                 935                 940
Pro Thr Leu Ala Glu Arg Leu Ala Ala Leu Ser Ala Val Glu Gln His
945                 950                 955                 960
Arg Ile Leu Leu Asp Leu Ile Arg Ala His Ala Thr Ala Val Leu Gly
                965                 970                 975
Pro Gly Ala Thr Thr Thr Val Glu Pro Asp Arg Thr Tyr Arg Glu Ser
            980                 985                 990
Gly Leu Asp Ser Leu Gly Thr Val Glu Leu Ile Thr Arg Leu Ala Arg
            995                 1000                1005
Asp Thr Gly Leu Asp Leu Pro Pro Thr Thr Val Phe Asp His Pro Thr
    1010                1015                1020
Pro Thr Ala Leu Ala His His Leu Arg Thr Arg Ala Leu Asp Leu Pro
1025                1030                1035                1040
Val Pro Thr Arg Pro Arg Pro Thr Pro Gly Pro Ala Arg Ala Asp Glu
                1045                1050                1055
Pro Ile Ala Ile Val Ala Met Gly Cys Arg Leu Pro Gly Ala Val Arg
                1060                1065                1070
Thr Pro Glu Asp Leu Trp Arg Leu Val Ala Asp Gly Val Asp Ala Ile
            1075                1080                1085
Thr Ala Phe Pro Thr Asp Arg Gly Trp Asp Leu Asp Arg Leu His His
        1090                1095                1100
```

-continued

```
Asp Asp Pro Asp Arg Pro Gly Thr Ser Tyr Val Arg Ser Gly Gly Phe
1105                1110                1115                1120

Leu Asp Arg Ala Gly Asp Phe Asp Ala Glu Phe Phe Gly Ile Gly Pro
            1125                1130                1135

Arg Glu Ala Leu Ala Met Asp Pro Gln Gln Arg Leu Leu Glu Thr
            1140                1145                1150

Ser Trp Glu Ala Ile Glu Arg Ala Gly Leu Asp Pro Ser Thr Leu Arg
        1155                1160                1165

Gly Glu Arg Val Gly Val Phe Val Gly Ala Thr Ala Gln Glu Tyr Gly
    1170                1175                1180

Pro Arg Met His Glu Ser Thr Asp Ala Leu Ala Gly Phe Leu Leu Thr
1185                1190                1195                1200

Gly Thr Thr Pro Ser Val Ala Ser Gly Arg Ile Ala Tyr Thr Leu Gly
            1205                1210                1215

Leu Ser Gly Pro Ala Leu Thr Val Asp Thr Ala Cys Ser Ser Ser Leu
            1220                1225                1230

Val Ala Val His Leu Ala Ala Arg Ser Leu Ala Ser Gly Glu Cys Ala
        1235                1240                1245

Leu Ala Leu Ala Gly Gly Ala Thr Val Met Ala Gly Pro Gly Met Phe
    1250                1255                1260

Val Glu Phe Ala Arg Gln Arg Gly Leu Ala Pro Asp Gly Arg Cys Lys
1265                1270                1275                1280

Pro Phe Ser Ala Asp Ala Asp Gly Thr Ala Trp Ala Glu Gly Val Gly
            1285                1290                1295

Val Leu Leu Leu Glu Arg Leu Ser Asp Ala Arg Arg Asn Gly His Pro
            1300                1305                1310

Val Leu Ala Val Leu Arg Gly Ser Ala Ile Asn Gln Asp Gly Ala Ser
        1315                1320                1325

Asn Gly Leu Ser Ala Pro Asn Gly Thr Ala Gln Gln Arg Val Ile Arg
    1330                1335                1340

Asp Ala Leu Ala Ala Ala Gly Leu Asp Pro Gln Asp Val Asp Leu Val
1345                1350                1355                1360

Glu Ala His Gly Thr Gly Thr Pro Leu Gly Asp Pro Ile Glu Ala Gln
            1365                1370                1375

Ala Leu Leu Ala Thr Tyr Gly Arg Asp Arg Ala Ala Asp Arg Pro Leu
            1380                1385                1390

Leu Leu Gly Ser Val Lys Ser Asn Ile Gly His Thr Gln Ala Ala Ala
        1395                1400                1405

Gly Val Ala Gly Leu Ile Lys Thr Val Leu Ala Leu Arg His Gly Ala
    1410                1415                1420

Ile Pro Gly Thr Leu His Leu Arg Glu Pro Ser Pro His Val Arg Trp
1425                1430                1435                1440

Ser Asp Gly Ala Ile Thr Leu Pro Thr Thr Thr Thr Asp Trp Pro Ala
            1445                1450                1455

Tyr Asp Arg Pro Arg Arg Ala Ala Val Ser Ser Phe Gly Ile Ser Gly
            1460                1465                1470

Thr Asn Ala His Val Ile Val Glu Glu Ala Gly Gly Gly Ala Glu Ile
        1475                1480                1485

Pro Gly Pro Ala Pro Ala Arg Gly Leu Ala Ser Ala Gly Val Ala Asp
    1490                1495                1500

Pro Val Pro Leu Val Val Ser Ala Arg Ser Glu Ala Ala Leu Arg Gly
1505                1510                1515                1520
```

-continued

Gln Ala Glu Gln Leu Ala Gly Leu Leu Arg Ala Ala Asp Pro Ala
            1525                1530                1535

Leu Ala Asp Val Gly Tyr Ser Leu Leu Arg Gly Arg Ala Gly Phe Glu
            1540                1545                1550

Tyr Thr Ala Val Ile Pro Ala Arg Thr His Ala Glu Ala Leu His Gly
            1555                1560                1565

Leu Thr Ala Leu Ala Ala Asp Arg Pro Ala Asp Arg Leu Ile Arg Gly
            1570                1575                1580

Gly Ala Ala Ala Arg Gly Gly Thr Val Phe Val Phe Pro Gly Gln
1585                1590                1595                1600

Gly Thr Gln Trp Ser Gly Met Ala Leu Glu Leu Leu Asp Thr Ser Glu
            1605                1610                1615

Pro Phe Ala Ala Ser Met Arg Ala Cys Thr Asp Ala Leu Asp Pro Tyr
            1620                1625                1630

Ala Val Asp Trp Ser Leu Leu Asp Val Leu Arg Glu Pro Gly Thr Pro
            1635                1640                1645

Gly Leu Thr Arg Val Asp Val Val Gln Pro Ala Leu Phe Ala Val Met
            1650                1655                1660

Val Ser Leu Ala Ala Leu Trp Arg Ser Ile Gly Ile Glu Pro Gln Ala
1665                1670                1675                1680

Val Val Gly His Ser Gln Gly Glu Ile Ala Ala Ala Tyr Val Ala Gly
            1685                1690                1695

Ala Leu Ser Leu Ala Asp Ala Ala Lys Val Val Ala Leu Arg Ser Arg
            1700                1705                1710

Ala Leu Val Ala Ala Ala Gly Ser Gly Gly Met Ala Ser Val Ser Leu
            1715                1720                1725

Pro Ala Glu Gln Val Ala Ala Leu Leu Glu Pro Trp Ala Gly Arg Leu
            1730                1735                1740

Gly Val Ala Ala Val Asn Gly Pro Ser Ala Thr Val Val Ser Gly Asp
1745                1750                1755                1760

Thr Ala Ala Leu Asp Thr Phe Leu Asp Arg Cys Ala Ala Asp Asp Leu
            1765                1770                1775

Arg Ala Arg Arg Ile Pro Val Asp Tyr Ala Ser His Ser Val His Met
            1780                1785                1790

Glu Glu Ile Arg Asp Arg Leu Leu Thr Asp Leu Ala Asp Val Thr Pro
            1795                1800                1805

Arg Ala Ala Ser Thr Ala Phe Tyr Ser Thr Leu Thr Gly Gly Arg Met
            1810                1815                1820

Ala Asp Thr Ser Gly Leu Asp Ala Asp Tyr Trp Tyr Arg Asn Leu Arg
1825                1830                1835                1840

Arg Thr Val Arg Tyr Glu Thr Ala Val Arg Ala Leu Ser Glu Asp Gly
            1845                1850                1855

His Arg Leu Phe Val Glu Val Gly Pro His Pro Val Leu Thr Leu Gly
            1860                1865                1870

Thr Gln Glu Thr Leu Asp Ala Cys Gly Ser Gly Gly Thr Thr Ile Gly
            1875                1880                1885

Thr Leu Ser Arg Asp Asp Gly Gly Arg Ala Arg Phe Leu Val Ala Val
            1890                1895                1900

Ala Glu Ala Val Ala His Gly Ala Arg Pro Asp Ala Glu Ala Leu Phe
1905                1910                1915                1920

Asp Pro Pro Gly Thr Gly Val Arg Ala Val Ala Leu Pro Thr Tyr Ala
            1925                1930                1935

Phe Gln His Arg Arg Tyr Trp Leu Thr Pro Arg Glu Ala Ala Pro Glu

-continued

```
              1940             1945               1950
Gly Thr Ala Ala Leu Gly Leu Thr Pro Ile Ser His Pro Leu Gly
        1955                 1960               1965

Ala Leu Gly Ala Leu Gly Val Glu Pro Asp Gly Thr Val Ile Ala Thr
    1970                 1975                 1980

Gly Arg Ile Ser Leu Arg Glu Leu Pro Trp Leu Ala Asp His Ala Val
1985                1990                1995                2000

Ala Asp Thr Val Val Leu Pro Gly Thr Ala Phe Leu Glu Leu Ala Leu
                2005                2010                2015

Cys Val Gly Glu Ser Val Gly Ala Pro Gln Val Glu Glu Leu Thr Leu
            2020                2025                2030

Glu Ser Pro Leu Leu Leu Pro Glu Thr Gly Asp Val Tyr Leu Arg Val
            2035                2040                2045

Ala Val Ala Pro Ala Asp Glu Ala Arg Arg Ala Val Thr Ile His
            2050                2055            2060

Ser Arg Arg Ala Gly Gly Gly Ala Asp Ala Glu Arg Glu Ser Trp
2065                2070                2075                2080

Val Arg His Ala Gly Gly Leu Leu Val Asp Ser Val Arg Glu Val Asp
                2085                2090                2095

Asp Gly Gly Ser Gly Gly Leu Thr Gln Trp Pro Pro Gly Ala Asp
                2100                2105                2110

Val Leu Asp Leu Ala Asp Ala Tyr Pro Val Leu Ala Gly Leu Gly Tyr
            2115                2120                2125

Gly Tyr Gly Pro Ala Phe Arg Gly Leu Arg Ala Ala Trp Arg Gly Ala
        2130                2135                2140

Gly Gly Glu Leu Phe Ala Glu Val Arg Leu Pro Asp Glu Leu Arg Glu
2145                2150                2155                2160

Ser Glu Ser Gly Val Val Gly Pro Glu Phe Gly Ile His Pro Ala Leu
                2165                2170                2175

Leu Asp Ala Ala Leu His Pro Leu Leu Ser Ser Leu Ser Leu Thr Ser
            2180                2185                2190

Leu Ser Ser Thr Arg Asp Gly Pro Ala Gly Ala Pro Pro Arg Ile Pro
        2195                2200                2205

Phe Ser Leu Ala Asp Val Arg Leu Tyr Ala Thr Gly Ala Asp Met Leu
2210                2215                2220

Arg Val Arg Leu Arg Arg Ala Asp Gly Gly Ala Ala Ala Leu Thr Val
2225                2230                2235                2240

Ala Asp Gly Val Gly Ala Pro Val Leu Ser Ile Gly Ala Leu Thr Leu
            2245                2250                2255

Arg Glu Leu Pro Ala Asp Gly Leu Ile Ala Ala Glu Pro Gly Pro Gly
            2260                2265                2270

Glu Ala Met Phe Asp Leu Arg Trp Ile Ala Gly Ser Ile Pro Ala Glu
        2275                2280                2285

Pro Thr Gly Leu Gly Tyr Ala Phe Ile Gly Asp Asp Leu Gly Leu Gly
        2290                2295                2300

Asp Gly Glu Val Tyr Pro Ser Leu Ala Asp Leu Asp Ala Arg Leu Leu
2305                2310                2315                2320

Ala Thr Gly Glu Pro Thr Pro Asp Val Val Phe Ala Ala Pro Val
                2325                2330                2335

Gly Val Asp Asp Asp Val Pro Gly Ala Ala His Asp Ser Ala Arg Trp
            2340                2345                2350

Ala Leu Asp Leu Val Gly Gly Trp Leu Ala Gly Glu Arg Ser Ser Ala
            2355                2360                2365
```

-continued

```
Ala Arg Leu Val Val Thr Arg Gly Ala Val Ala Ala Arg Thr Gly
    2370            2375                2380

Asp Ala Leu Ser Gly Leu Pro Ala Ala Pro Val Trp Gly Leu Leu Arg
2385            2390            2395                2400

Thr Ala Gln Ser Glu His Pro Asp Arg Phe Val Leu Ile Asp Leu Asp
            2405                2410                2415

Asp Ala Val Arg Ser Pro Ser Ala Leu Leu Gly Ala Ala Val Ala Gly
            2420                2425                2430

Glu Pro Gln Leu Ala Leu Arg Asp Gly Val Val His Leu Pro Arg Met
            2435                2440                2445

Val Ala Val Asp Ser Ala Asp Ala Gln Val Thr Arg Arg Pro Asp
    2450            2455                2460

Pro Asn Gly Thr Ala Leu Ile Thr Gly Gly Thr Gly Thr Leu Gly Ala
2465            2470            2475                2480

Leu Ile Ala Arg Arg Leu Ala Ala Glu His Gly Ile Arg His Leu Leu
                2485                2490                2495

Leu Leu Gly Arg Ala Gly Arg Glu Ala Pro Gly Ala Glu Glu Leu Ile
            2500                2505                2510

Ala Glu Leu Gly Ala Leu Gly Ala Arg Val Thr Val Ala Ala Cys Asp
            2515                2520                2525

Val Ala Asp Arg Ala Ala Leu Arg Arg Val Ile Glu Asp Ile Pro Ala
    2530            2535                2540

Glu His Pro Pro Thr Ile Val Val His Ala Ala Gly Val Leu Asp Asp
2545            2550            2555                2560

Ala Thr Leu Leu Ser Leu Thr Pro Asp Arg Leu Asp Ala Val Leu Arg
            2565                2570                2575

Pro Lys Val Asp Ala Ala Trp His Leu His Glu Leu Thr Arg Ala Ala
            2580                2585                2590

Asn Pro Ala Ala Phe Val Leu Phe Ser Ser Ile Thr Ala Ile Thr Gly
            2595                2600                2605

Asn Ala Gly Gln Gly Ala Tyr Thr Ala Ala Asn Thr Phe Leu Asp Ala
            2610                2615                2620

Leu Ala Glu His Arg Arg Ala Ala Gly Leu Pro Ala Asn Ala Leu Ala
2625            2630            2635                2640

Trp Gly Leu Trp Ala Glu Gly Ser Gly Met Thr Arg His Leu Asp His
            2645                2650                2655

Thr Asp Arg Ala Arg Met Ser Arg Gly Gly Ile Ala Ala Leu Pro Thr
            2660                2665                2670

Glu Thr Gly Leu Ala Leu Phe Asp Ala Ala Leu His Arg Asp Arg Pro
            2675                2680                2685

Tyr Thr Ile Pro Ala Arg Leu Asp Arg Gly Ala Leu Arg Ala Leu Ala
            2690                2695                2700

Ala Ser Gly Val Leu Pro Ala Val Leu Arg Ser Leu Val Arg Val Pro
2705            2710            2715                2720

Pro Pro Arg Ala Ala Ala Ser Gly Asp Gly Thr Asp Ala Ser Ser Trp
            2725                2730                2735

Pro Arg Arg Ile Arg Glu Leu Pro Gly Glu Gln Arg Glu Arg Ala Ile
            2740                2745                2750

Thr Asp Leu Val Arg Gly Gln Leu Ala Ala Val Leu Gly His Asp Ala
            2755                2760                2765

Pro Glu Arg Leu Asp Leu Asp Arg Ala Phe Arg Glu Leu Gly Val Asp
    2770            2775                2780
```

-continued

```
Ser Leu Thr Ala Leu Glu Leu Arg Asn Arg Ile Asn Ala Phe Thr Gly
2785                2790                2795                2800

Leu Arg Leu Pro Ala Thr Val Val Phe Asp His Pro Ser Gly Thr Ala
                2805                2810                2815

Leu Val Ala Arg Met Met Arg Glu Leu Val Gly Ala Val Pro Ser Glu
                2820                2825                2830

Pro Thr Thr Pro Val Val Ala Pro Thr Val Thr Val Asp Glu Pro Ile
                2835                2840                2845

Ala Val Val Gly Ile Gly Cys Arg Tyr Pro Gly Gly Val Ala Gly Pro
                2850                2855                2860

Glu Asp Leu Trp Arg Leu Val Ala Ala Gly Thr Asp Ala Val Gly Asp
2865                2870                2875                2880

Phe Pro Glu Asp Arg Gly Trp Asp Leu Ala Lys Leu Tyr Asp Pro Asp
                2885                2890                2895

Pro Asp Lys Val Gly Lys Val Tyr Thr Arg Arg Gly Gly Phe Leu Tyr
                2900                2905                2910

Glu Ser Gly Glu Phe Asp Ala Glu Phe Phe Gly Ile Ser Pro Arg Glu
                2915                2920                2925

Ala Ala Ala Met Asp Pro Gln Gln Arg Leu Leu Leu Glu Thr Ala Trp
                2930                2935                2940

Glu Ala Phe Glu His Ala Gly Leu Asp Pro Arg Thr Leu Arg Gly Ser
2945                2950                2955                2960

Asn Thr Gly Val Phe Ala Gly Val Met Tyr Asn Asp Tyr Ala Ser Arg
                2965                2970                2975

Leu His Arg Ala Pro Asp Gly Phe Glu Gly Met Leu Leu Ala Gly Asn
                2980                2985                2990

Val Gly Ser Val Val Thr Gly Arg Val Ser Tyr Ala Leu Gly Leu Glu
                2995                3000                3005

Gly Pro Ala Val Ser Val Asp Thr Ala Cys Ser Ser Ser Leu Val Ala
                3010                3015                3020

Leu His Leu Ala Ala Asn Ala Leu Arg Ser Gly Glu Cys Asp Leu Ala
3025                3030                3035                3040

Leu Ala Gly Gly Val Thr Val Met Ser Thr Pro Asn Val Phe Val Glu
                3045                3050                3055

Phe Ser Arg Gln Arg Gly Leu Ser Ala Asp Gly Arg Cys Arg Ser Phe
                3060                3065                3070

Ala Ala Gly Ala Asp Gly Thr Gly Trp Gly Glu Gly Val Gly Leu Leu
                3075                3080                3085

Val Val Glu Arg Leu Ser Asp Ala Arg Arg Asn Gly His Pro Val Leu
                3090                3095                3100

Ala Leu Leu Arg Gly Ser Ala Val Asn Gln Asp Gly Ala Ser Asn Gly
3105                3110                3115                3120

Leu Thr Ala Pro Asn Gly Pro Ser Gln Glu Arg Val Ile Arg Ala Ala
                3125                3130                3135

Leu Ala Gly Ala Gly Leu Ser Ala Thr Asp Val Asp Ala Val Glu Ala
                3140                3145                3150

His Gly Thr Gly Thr Thr Leu Gly Asp Pro Ile Glu Ala Gln Ala Leu
                3155                3160                3165

Leu Ala Thr Tyr Gly Arg Asp Arg Pro Ala Asp Arg Pro Leu Trp Leu
                3170                3175                3180

Gly Ser Ile Lys Ser Asn Ile Gly His Thr Gln Ala Ala Ala Gly Ala
3185                3190                3195                3200

Ala Gly Leu Ile Lys Met Ile Met Ala Met Arg His Gly Val Leu Pro
```

-continued

```
                    3205                3210                3215
Glu Thr Leu His Val Asp Ala Pro Ser Pro His Val Asp Trp Ser Thr
            3220                3225                3230
Gly His Val Glu Leu Leu Ala Glu Arg Arg Pro Trp Pro Glu Val Asp
            3235                3240                3245
Arg Ala Arg Arg Ala Ala Val Ser Ser Phe Gly Ile Ser Gly Thr Asn
            3250                3255                3260
Ala His Val Ile Val Glu Gln Ala Pro Ala Glu Ala Val Val Ser
3265                3270                3275                3280
Arg Asp Glu Pro Val Gly Val Ala Gly Leu Val Pro Trp Val Leu Ser
            3285                3290                3295
Ala Arg Thr Ala Asp Gly Leu Arg Ala Gln Ala Ala Arg Leu Arg Glu
            3300                3305                3310
Trp Ser Ala Arg His Pro Glu Ala Asp Pro Val Asp Val Gly Trp Ser
            3315                3320                3325
Leu Val Arg Glu Arg Ser Val Phe Asp Arg Arg Ala Val Gly Gly
            3330                3335                3340
Arg Asp Pro Gly Glu Leu Gly Ala Gly Leu Asp Arg Leu Ala Ala Gly
3345                3350                3355                3360
Gly Gly Ile Ala Asp Gly Arg Pro Met Phe Ser Gly Pro Gly Pro Val
            3365                3370                3375
Phe Val Phe Pro Gly Gln Gly Ser Gln Trp Val Gly Met Ala Ala Gly
            3380                3385                3390
Leu Leu Glu Cys Ser Pro Val Phe Ala Glu Ala Val Thr Glu Cys Ala
            3395                3400                3405
Ala Val Met Asp Pro Leu Val Ala Asp Trp Ser Leu Leu Asp Val Leu
            3410                3415                3420
Arg Gly Gly Ser Ala Gly Glu Leu Glu Arg Val Asp Val Val Gln Pro
3425                3430                3435                3440
Val Leu Phe Ala Val Met Val Gly Leu Ala Arg Trp Trp Glu Ser Cys
            3445                3450                3455
Gly Val Lys Pro Gly Ala Val Ile Gly His Ser Gln Gly Glu Ile Ala
            3460                3465                3470
Ala Ala His Val Ala Gly Tyr Leu Ser Leu Ala Asp Ala Val Trp Val
            3475                3480                3485
Val Val Leu Arg Ser Arg Ala Leu Leu Gly Val Ala Ser Ala Gly Gly
            3490                3495                3500
Gly Met Val Ser Val Gly Val Ser Ala Glu Arg Ala Arg Glu Leu Val
3505                3510                3515                3520
Ala Gly Asp Asp Arg Leu Ser Leu Ala Ala Val Asn Gly Pro Thr Ser
            3525                3530                3535
Val Val Leu Ser Gly Asp Val Glu Ala Leu Ser Val Val Glu Ala
            3540                3545                3550
Cys Glu Arg Asp Gly Val Arg Ala Arg Trp Ile Pro Val Asp Tyr Ala
            3555                3560                3565
Ser His Ser Ala Arg Met Glu Ala Val Arg Asp Glu Val Glu Arg Leu
            3570                3575                3580
Leu Ala Asp Val Thr Pro Gln Val Gly Arg Val Pro Met Tyr Ser Thr
3585                3590                3595                3600
Val Ser Gly Glu Val Val Asp Pro Ala Glu Leu Gly Gly Ala Tyr
            3605                3610                3615
Trp Phe Glu Asn Leu Arg Arg Thr Val Glu Leu Glu Arg Ala Val Gly
            3620                3625                3630
```

-continued

```
Ala Ala Val Ala Asp Gly His Gly Ala Phe Val Glu Cys Ser Pro His
        3635                3640                3645

Pro Gly Leu Val Val Pro Met Gly Asp Thr Leu Glu Ala Ala Gly Val
        3650                3655                3660

Asp Gly Val Val Leu Glu Thr Leu Arg Arg Gly Gly Gly Pro Asp
3665                3670                3675                3680

Arg Leu Val Ala Ala Leu Ser Ala Ala Phe Val Ala Gly Val Ala Val
        3685                3690                3695

Asp Trp Ala Gly Met Leu Pro Gly Arg His Val Glu Leu Pro Thr Tyr
        3700                3705                3710

Ala Phe Gln Arg Arg Tyr Trp Leu Thr Gly Gly Glu Arg Ala Gly
        3715                3720                3725

Asp Pro Ala Gly Leu Gly Leu Val Ala Ala Asp His Pro Leu Leu Gly
        3730                3735                3740

Ala Val Val Gly Ser Val Arg Asp Gly Glu Leu Leu Tyr Thr Gly Arg
3745                3750                3755                3760

Leu Ser Ala Ala Thr His Gly Trp Leu Ala Asp His Ala Val Phe Gly
        3765                3770                3775

Ser Val Val Pro Gly Thr Ala Phe Val Glu Leu Ala Ser Trp Val
        3780                3785                3790

Gly Val Glu Ala Gly Cys Pro Val Val Asp Leu Thr Leu His Ala
        3795                3800                3805

Pro Leu Val Leu Pro Asp Gly Val Gly Ile Arg Leu Arg Val Ala Val
        3810                3815                3820

Gly Ala Ala Asp Ser Ala Gly Arg Arg Val Val Glu Phe His Ser Arg
3825                3830                3835                3840

Pro Glu Asp Ala Pro Asp Glu Gln Ser Trp Thr Arg His Ala Thr Gly
        3845                3850                3855

Thr Leu Gly Ala Ala Ser Val Pro Gly Ser Ala Ser Gly Ala Ala
        3860                3865                3870

Ala Trp Ala Val Trp Pro Pro Ala Asp Ala Glu Val Val Asp Pro Glu
        3875                3880                3885

Ala Val Tyr Glu Arg Leu Ala Glu His Gly Tyr Glu Tyr Gly Pro Ile
        3890                3895                3900

Phe Arg Gly Leu Arg Ala Ala Trp Arg Arg Gly Asp Asp Phe Phe Ala
3905                3910                3915                3920

Glu Val Ala Leu Pro Glu Ala Ala Gly Arg Asp Ala His Gly Tyr Asp
        3925                3930                3935

Leu His Pro Ala Val Leu Asp Ala Ala Leu His Val Ala Ala Ala Glu
        3940                3945                3950

Ala Val Ala Glu Ser Gly Ala Thr Leu Leu Pro Phe Ala Trp Thr Gly
        3955                3960                3965

Val Ala Leu His Gly Pro Gly Ala Ser Val Leu Arg Val Met Leu Arg
        3970                3975                3980

Arg Thr Gly Arg Glu Thr Leu Ala Val Asp Val Ala Asp Glu Arg Gly
3985                3990                3995                4000

Val Pro Val Ala Ser Val Ala Ser Leu Thr Leu Arg Pro Val Ala Ala
                4005                4010                4015

Glu Gln Leu Val Ala Ala Glu Gly Ala Gly Arg Glu Trp Leu Tyr Arg
        4020                4025                4030

Met Val Trp Glu Ile Ala Asp Ala Pro Val Ala Glu His Val Glu Gly
        4035                4040                4045
```

```
Glu Leu Leu Gly Ser Asp Glu Ser Asp Ala Ser Ala Glu Leu Val
    4050            4055            4060

Ala Gly Gly Ile Arg Val Val Thr Pro Ala Gly Ala Glu Gln Val Ser
4065            4070            4075            4080

Glu Val Gly Leu Phe Asp Cys Pro Pro Val Val Gly Glu Ala Pro Glu
            4085            4090            4095

Glu Val Ala Gly Ala Val His Ala Val Leu Ala Ala Val Arg Ala Trp
        4100            4105            4110

Val Ala Asp Glu Arg Phe Ala Gly Ala Arg Leu Val Val Arg Thr Arg
        4115            4120            4125

Gly Ala Val Ala Thr Asp Ala Gln Asp Arg Val Gly Ser Pro Ala His
        4130            4135            4140

Ala Ala Ile Trp Gly Leu Val Arg Val Ala Gln Ser Glu His Pro Gly
4145            4150            4155            4160

Arg Phe Val Leu Val Asp Gly Asp Val Asp Ser Gly Ala Ala Leu
            4165            4170            4175

Arg Ala Ala Val Ala Cys Gly Leu Pro Gln Val Ala Ile Arg Glu Gly
            4180            4185            4190

Val Val Leu Ala Pro Arg Leu Val Gly Ala Val His Asp Thr Ala Leu
    4195            4200            4205

Val Pro Pro Ala Pro Gly Ala Asp Gln Ala Trp Arg Ile Glu Ser Gly
    4210            4215            4220

Thr Ala Gly Thr Pro Asp Asp Leu Val Val Thr Ala His Pro Ala Ala
4225            4230            4235            4240

Ser Ala Pro Leu Ala Ala Gly Gln Val Arg Val Ala Val Arg Ala Ala
            4245            4250            4255

Gly Val Asn Phe Arg Asp Val Leu Ile Thr Leu Gly Met Tyr Pro Gly
            4260            4265            4270

Arg Ala Val Val Gly Ala Glu Ala Ala Gly Val Val Glu Val Gly
            4275            4280            4285

Pro Gly Val Ser Glu Pro Ala Val Gly Asp Arg Val Met Gly Leu Phe
    4290            4295            4300

Glu Gly Ala Phe Gly Pro Leu Ala Val Ala Asp Arg Arg Leu Leu Ala
4305            4310            4315            4320

Arg Val Pro Ala Gly Trp Ser Phe Ala Gln Ala Ala Ser Val Pro Val
            4325            4330            4335

Val Phe Leu Thr Ala Leu Tyr Gly Leu His Asp Leu Ala Gly Leu Arg
            4340            4345            4350

Ser Gly Glu Ser Val Leu Val His Ala Ala Thr Gly Val Gly Met
    4355            4360            4365

Ala Ala Thr Gln Leu Ala Arg His Arg Gly Ala Glu Val Tyr Ala Thr
    4370            4375            4380

Ala Ser Ala Thr Lys Trp Ala Thr Val Arg Gly Leu Gly Val Pro Asp
4385            4390            4395            4400

Glu Arg Ile Ala Ser Ser Arg Asp Leu Ser Phe Glu Gln Arg Phe Ala
            4405            4410            4415

Arg Ala Thr Asp Gly Arg Gly Ile Asp Val Val Leu Asn Ser Leu Ala
            4420            4425            4430

Gly Glu Phe Thr Asp Ala Ser Leu Arg Leu Leu Ala Glu Gly Gly Arg
            4435            4440            4445

Phe Val Glu Met Gly Lys Thr Asp Val Arg Thr Glu Gly Leu Pro Ala
    4450            4455            4460

Gly Val Arg Tyr Arg Ala Phe Asp Leu Ile Glu Ala Gly Pro Asp Arg
```

-continued

```
          4465                4470                4475                4480
Ile Ala Glu Met Phe Ala Glu Leu Val Asp Leu Phe Glu Arg Gly Val
                    4485                4490                4495

Leu Gln Pro Leu Pro Ile Arg Thr Trp Asp Ile Arg Arg Ala Arg Glu
        4500                4505                4510

Ala Leu Arg Phe Leu Gly Gln Ala Arg His Val Gly Lys Val Val Leu
            4515                4520                4525

Thr Val Pro Gln Pro Leu Ala Ala Asp Gly Thr Val Leu Ile Thr Gly
        4530                4535                4540

Gly Thr Gly Thr Leu Gly Arg Ser Leu Ala Arg His Leu Val Thr Arg
4545                4550                4555                4560

Trp Gly Val Arg Arg Leu Val Leu Thr Gly Arg Ala Gly Pro Ala Ala
                    4565                4570                4575

Pro Gly Ala Ala Glu Leu Val Ala Glu Leu Ala Glu Ser Gly Ala Asp
            4580                4585                4590

Thr Thr Ile Val Ala Cys Asp Ala Ala Asp Arg Ala Ala Met Ala Glu
        4595                4600                4605

Val Leu Ala Ala Ile Pro Ala Glu His Pro Leu Thr Ala Val Val His
    4610                4615                4620

Ala Ala Gly Thr Leu Asp Asp Ala Pro Ile Glu Ala Leu Thr Pro Glu
4625                4630                4635                4640

Arg Val Asp His Val Leu Arg Pro Lys Val Asp Ala Ala Leu Val Leu
                    4645                4650                4655

Asp Glu Leu Thr Arg Asp Ala Asp Leu Ala Ala Phe Val Leu Phe Ser
            4660                4665                4670

Ser Val Ala Gly Val Leu Gly Val Ala Gly Gln Gly Gly Tyr Ala Ala
        4675                4680                4685

Gly Asn Ala Phe Leu Asp Gly Leu Ala Gly Arg Arg Arg Glu Arg Gly
    4690                4695                4700

Leu Pro Ala Thr Ala Leu Ala Trp Gly Leu Trp Ala Glu Arg Ser Ala
4705                4710                4715                4720

Met Thr Ala Gln Leu Gly Val Gly Asp Leu Lys Arg Leu Ala Arg Gly
                    4725                4730                4735

Gly Leu Val Pro Ile Ser Thr Ala Gln Gly Leu Ala Leu Phe Asp Ala
            4740                4745                4750

Ala Trp Gln Ala Asp Glu Ala Ala Leu Ile Pro Ala Arg Leu Asp Leu
        4755                4760                4765

Ala Ala Leu Arg Ala Gln Ala Ala Thr Gln Pro Val His Pro Leu Leu
    4770                4775                4780

Arg Gly Leu Val Gly Thr Thr Pro Thr Arg Arg Asn Gly Thr Pro Ser
4785                4790                4795                4800

Glu Ala Pro Trp Ala Arg Arg Leu Ala Ser Ala Ala Pro Ala Glu Arg
                    4805                4810                4815

Val Asp Val Ala Leu Arg Leu Val Arg Ala Glu Ala Ala Val Val Leu
            4820                4825                4830

Gly His Glu Ser Ile Asp Gly Val Arg Pro Glu Val Thr Phe Arg Asp
        4835                4840                4845

Leu Gly Phe Asp Ser Leu Thr Gly Val Glu Leu Arg Asn Arg Leu Ser
    4850                4855                4860

Gly Ala Thr Gly Leu Arg Leu Pro Ser Thr Leu Val Phe Asp Phe Pro
4865                4870                4875                4880

Thr Pro Leu Gly Leu Ala Gly Phe Leu Val Ala Glu Ser Val Gly Glu
                    4885                4890                4895
```

```
Met Asp Thr Ala Pro Thr Gly Pro Val Ala Gly Gly Ala Val Val Ala
            4900                4905                4910

Ala Asp Pro Val Val Ile Val Gly Met Gly Cys Arg Phe Pro Gly Gly
            4915                4920                4925

Val Asp Ser Ala Ala Gly Leu Trp Asp Leu Val Ala Ala Gly Gly Asp
            4930                4935                4940

Ala Ile Gly Pro Phe Pro Thr Asp Arg Gly Trp Asp Val Asp Ala Leu
4945                4950                4955                4960

Phe Asp Pro Asp Pro Glu Arg Val Gly Lys Ser Tyr Val Arg Thr Gly
            4965                4970                4975

Gly Phe Leu Ser Gly Ala Ala Glu Phe Asp Ala Glu Phe Phe Gly Val
            4980                4985                4990

Ser Pro Arg Glu Ala Leu Ala Met Asp Pro Gln Gln Arg Leu Leu Leu
            4995                5000                5005

Glu Thr Ala Trp Glu Thr Phe Glu Gln Ala Gly Ile Asp Pro Thr Ser
            5010                5015                5020

Leu Arg Gly Ser Arg Thr Gly Val Phe Ala Gly Met Ala Gly His Asp
5025                5030                5035                5040

Tyr Ala Thr Gly Gly Ala Arg Ser Gln Ala Gly Leu Glu Gly His Leu
            5045                5050                5055

Leu Thr Gly Asn Ala Ala Ser Val Ala Ser Gly Arg Val Ala Tyr Thr
            5060                5065                5070

Phe Gly Leu Glu Gly Pro Ala Val Thr Val Asp Thr Ala Cys Ser Ser
            5075                5080                5085

Ser Leu Val Ala Leu His Leu Ala Ala Asn Ala Leu Arg Ala Gly Glu
            5090                5095                5100

Cys Asp Leu Ala Leu Ala Gly Gly Val Thr Ala Met Ser Thr Pro Asp
5105                5110                5115                5120

Phe Phe Leu Glu Phe Ser Arg Gln Arg Gly Leu Ser Val Asp Gly Arg
            5125                5130                5135

Cys Lys Ala Phe Ala Ala Thr Ala Asp Gly Met Gly Ala Ala Glu Gly
            5140                5145                5150

Val Gly Leu Leu Leu Val Glu Arg Leu Ser Asp Ala Arg Arg Asn Gly
            5155                5160                5165

His Ser Val Leu Ala Val Val Arg Gly Ser Ala Val Asn Gln Asp Gly
            5170                5175                5180

Ala Ser Asn Gly Leu Thr Ala Pro Asn Gly Pro Ser Gln Gln Arg Val
5185                5190                5195                5200

Ile Arg Ala Ala Leu Ala Asp Ala Gly Leu Ser Ala Ala Asp Val Asp
            5205                5210                5215

Ala Val Glu Ala His Gly Thr Gly Thr Thr Leu Gly Asp Pro Ile Glu
            5220                5225                5230

Ala Gln Ala Leu Leu Ala Thr Tyr Gly Arg Asp Arg Ala Pro Asp Arg
            5235                5240                5245

Pro Leu Trp Leu Gly Ser Val Lys Ser Asn Ile Gly His Thr Gln Ala
            5250                5255                5260

Ala Ala Gly Val Ala Gly Val Ile Lys Met Val Ser Ala Leu Arg His
5265                5270                5275                5280

Gly Met Leu Pro Arg Thr Leu His Val Asp Glu Pro Thr Pro His Val
            5285                5290                5295

Asp Trp Ser Ala Gly Gly Val Glu Leu Leu Thr Ser Ala Arg Ala Trp
            5300                5305                5310
```

-continued

```
Pro Glu Ala Gly Arg Val Arg Arg Ala Gly Val Ser Ser Phe Gly Ile
    5315                5320                5325

Ser Gly Thr Asn Ala His Val Ile Leu Glu Gln Ala Glu Glu Ser Pro
    5330                5335                5340

Ala Gly Ser Val Pro Ser Ala Thr Pro Pro Val Ala Gly Thr Pro Val
5345                5350                5355                5360

Trp Gly Gly Arg Val Pro Trp Val Leu Ser Ala Arg Ser Glu Pro Ala
                5365                5370                5375

Leu Arg Ala Gln Ala Ala Arg Leu Arg Asp Trp Leu Ala Val His Pro
            5380                5385                5390

Asp Ala Asp Pro Leu Asp Val Gly Arg Ser Leu Ala Thr Gly Arg Ala
5395                5400                5405

Ala Leu Asp His Arg Ala Val His Gly Arg Asp Leu Ala Glu Leu
    5410                5415                5420

Arg Leu Ala Val Ala Lys Leu Ala Asp Ser Gly Pro Gly Asp Glu Ala
5425                5430                5435                5440

Ser Ile Val Gly Ser Val Ser Ala Ala Gly Pro Val Phe Val Phe Pro
                5445                5450                5455

Gly Gln Gly Ser Gln Trp Val Gly Met Ala Ala Gly Leu Leu Glu Cys
            5460                5465                5470

Ser Pro Val Phe Ala Gly Val Val Ala Glu Cys Ala Ala Val Met Asp
    5475                5480                5485

Pro Leu Val Ala Asp Trp Ser Leu Leu Asp Val Leu Arg Gly Gly Ser
    5490                5495                5500

Ala Gly Gly Glu Ala Leu Ala Glu Arg Val Asp Val Val Gln Pro Ala
5505                5510                5515                5520

Leu Phe Val Val Met Val Gly Leu Ala Arg Trp Trp Glu Ser Cys Gly
                5525                5530                5535

Val Lys Pro Gly Ala Val Ile Gly His Ser Gln Gly Glu Ile Ala Ala
                5540                5545                5550

Ala His Val Ala Gly Tyr Leu Ser Leu Ala Asp Ala Val Arg Val Val
            5555                5560                5565

Val Leu Arg Ser Arg Ala Leu Leu Gly Val Ala Ser Ser Gly Gly Gly
            5570                5575                5580

Met Val Ser Val Gly Val Ser Ala Asp Arg Ala Arg Glu Leu Val Ala
5585                5590                5595                5600

Glu Asp Asp Arg Leu Ser Leu Ala Ala Val Asn Gly Pro Thr Ser Val
                5605                5610                5615

Val Leu Ser Gly Asp Val Glu Ala Leu Ala Val Val Val Asp Gly Cys
            5620                5625                5630

Glu Arg Asp Gly Val Arg Ala Arg Trp Ile Pro Val Asp Tyr Ala Ser
            5635                5640                5645

His Ser Ala Arg Met Glu Ala Val Arg Asp Glu Val Glu Arg Leu Leu
    5650                5655                5660

Ala Asp Val Thr Pro Gln Ala Gly Arg Val Pro Met Tyr Ser Thr Val
5665                5670                5675                5680

Ser Gly Gly His Val Thr Asp Pro Ser Val Leu Gly Gly Ser Tyr Trp
                5685                5690                5695

Phe Asp Asn Leu Arg Arg Thr Val Glu Leu Glu Arg Ala Val Gly Ala
            5700                5705                5710

Ala Val Val Asp Gly His Ser Val Phe Val Glu Cys Ser Pro His Pro
    5715                5720                5725

Gly Leu Val Val Pro Leu Gly Asp Thr Leu Glu Ala Ala Gly Val Asp
```

-continued

```
            5730                5735                5740
Gly Val Leu Glu Thr Leu Arg Arg Gly Glu Gly Pro Asp Arg
5745                5750                5755                5760

Leu Val Gly Ala Leu Ser Ala Ala Phe Arg Ser Gly Leu Ala Val Asp
                5765                5770                5775

Trp Ala Gly Ser Gly Met Val Pro Gly Arg Arg Val Glu Leu Pro Thr
            5780                5785                5790

Tyr Ala Phe Gln Arg Arg Tyr Trp Val Glu Pro Gly Glu Arg Ala
            5795                5800                5805

Gly Gly Val Gly Trp Gly Gln Phe Thr Val Glu His Pro Val Leu Gly
            5810                5815                5820

Ala Gly Val Asp Leu Ala Asp Gly Ala Gly Thr Val Phe Thr Gly Arg
5825                5830                5835                5840

Leu Ser Ala Ala Ser His Gly Trp Leu Ala Glu His Val Val Leu Gly
                5845                5850                5855

Thr Val Ile Ala Pro Gly Thr Ala Phe Val Asp Leu Ala Leu Arg Ala
            5860                5865                5870

Gly Ala Thr Val Gly Arg Ala Thr Val Glu Glu Leu Thr Leu His Ala
            5875                5880                5885

Pro Leu Ile Leu Pro Asp Ala Gly Val Arg Ile Gln Val Arg Val
            5890                5895                5900

Gly Ala Pro Asp Ala Ala Gly Val Gly Ser Val Glu Ile His Ser Arg
5905                5910                5915                5920

Pro Glu Asp Ala Ala Gly Asp Glu Pro Trp Thr Arg His Ala Ser Gly
                5925                5930                5935

Thr Leu Thr Ala Thr Asp Leu Asp Pro Ala Asp Val Ala Thr Glu Ala
            5940                5945                5950

Ala Ile Trp Pro Pro Ala Gly Ser Thr Pro Val Asp Leu Asp Gly Ala
            5955                5960                5965

Tyr Glu Arg Leu Ala Thr Ala Gly Phe Glu Tyr Gly Pro Ala Phe Gln
            5970                5975                5980

Gly Leu Arg Ala Leu Trp Arg Arg Gly Ala Glu Ser Phe Ala Glu Ile
5985                5990                5995                6000

Glu Leu Ala Asp Asp Ala Arg Gln Glu Ala Glu Arg Tyr Glu Val His
                6005                6010                6015

Pro Ala Leu Leu Asp Ala Ala Val His Ala Leu Gly Met Glu Pro Thr
            6020                6025                6030

Ala Glu Val Ala Pro Asp Glu Ala Arg Ile Ala Phe Ser Trp Arg Gly
            6035                6040                6045

Val Arg Leu Val Ala Ala Gly Ala Gly Arg Leu Arg Val Arg Leu Ala
            6050                6055                6060

Pro Val Gly Ser Asp Ala Val Ser Leu Trp Leu Ser Asp Met Asp Gly
6065                6070                6075                6080

Glu Pro Val Gly Ser Val Arg Ala Leu Thr Val Arg Pro Val Ala Ala
                6085                6090                6095

Glu Arg Leu Arg Pro Ala Gly Ala Pro Pro Arg Asp Ser Met Phe Arg
            6100                6105                6110

Val Glu Trp Arg Pro Val Ser Gly Asp Glu Ser Gly Val Ala Val Arg
            6115                6120                6125

Trp Ala Val Val Gly Ala Ala Asp Ser Gly Pro Leu Ala Arg Leu Val
            6130                6135                6140

Ala Ala Tyr Pro Asp Val Pro Val Tyr Arg Ser Val Val Glu Ala Ala
6145                6150                6155                6160
```

-continued

```
Gly Asp Val Ala Ala Gly Pro Pro Asp Val Val Val Gly Val Gly
            6165                6170                6175

Glu Ala Asp Cys Ser Glu Gly Ser Val Glu Arg Thr Arg Arg Val Leu
            6180                6185                6190

Ala Asp Val Leu Ala Trp Met Gln Asp Trp Leu Ala Asp Ser Arg Phe
            6195                6200            6205

Ala Ala Thr Arg Leu Val Val Val Thr Ser Gly Ala Val Ala Ala Asp
            6210                6215                6220

Val Asp Ala Asp Pro Asp Glu Arg Val Ala Asp Leu Ala Gly Ala Ala
6225                6230                6235                6240

Val Trp Gly Leu Leu Arg Ser Ala Gln Ser Glu His Pro Asp Arg Cys
            6245                6250                6255

Thr Leu Val Asp Leu Asp Glu Asp Ala Ala Ser Ile Asp Ala Trp Pro
            6260                6265                6270

Ala Ile Leu Ala Ser Ala Glu Pro Gln Leu Ala Val Arg Met Gly Arg
            6275                6280                6285

Phe Arg Val Pro Arg Leu Ala Arg Val Thr Ala Gly Gly Glu Pro
            6290                6295                6300

Val Ala Phe Ala Pro Asp Gly Thr Val Leu Val Thr Gly Ala Thr Gly
6305                6310                6315                6320

Gly Leu Gly Ala Leu Val Ala Arg His Leu Val Thr Ala His Gly Val
            6325                6330                6335

Arg Arg Leu Leu Leu Leu Ser Arg Arg Gly Ala Ala Ala Pro Gly Ala
            6340                6345                6350

Ala Glu Leu Val Glu Asp Leu Thr Ala Gln Gly Ala Glu Val Thr Leu
            6355                6360                6365

Ala Ala Cys Asp Leu Ala Asp Arg Ala Ala Leu Ala Ala Glu Leu Ala
            6370                6375                6380

Arg Ile Pro Ala Glu His Ala Leu Thr Gly Val Ile His Thr Ala Gly
6385                6390                6395                6400

Val Val Asp Asp Ala Thr Ile Ala Asn Leu Thr Asp Ala His Met Glu
            6405                6410                6415

His Ala Leu Arg Pro Lys Ala Asp Ala Ala Phe His Leu Asp Glu Leu
            6420                6425                6430

Thr Arg Asp Val Asn Pro Ala Ala Phe Val Leu Phe Ser Ser Gly Ala
            6435                6440                6445

Thr Thr Phe Gly Gly Pro Gly Gln Gly Asn Tyr Ala Ala Ala Asn Ala
            6450                6455                6460

Phe Leu Asp Gly Leu Ala Arg Gln Arg Arg Asp Arg Gly Leu Pro Gly
6465                6470                6475                6480

Ile Ser Leu Ala Trp Gly Leu Trp Ala Gly Ala Gln Gly Met Gly Gly
            6485                6490                6495

Arg Leu Ser Glu Ala Asp Leu Ala Arg Trp Ala Arg Thr Gly Ala Val
            6500                6505                6510

Ala Met Pro Ala Ala Glu Ala Leu Arg Leu Phe Asp Ile Ala Leu Gly
            6515                6520                6525

Arg Pro Glu Ala Ala Leu Val Pro Ala His Leu Asp Leu Pro Ala Met
            6530                6535                6540

Arg Ala Asp Ala Gly Ala Arg Pro Ala Leu Phe Arg Glu Leu Leu Gly
6545                6550                6555                6560

Ile Gly Thr Arg Arg Ala Ala Val Gly Ala Gly Gly Ser Ala Leu Thr
            6565                6570                6575
```

```
Arg Arg Leu Ala Gly Met Ser Pro Ala Glu Arg Glu Gln Ala Val Leu
            6580                6585                6590
Asp Val Val Arg Thr Glu Ala Ala Asn Thr Leu Gly His Glu Ser Ala
            6595                6600                6605
Gly Ala Val Ser Ala Gly Arg Ala Phe Lys Glu Leu Gly Phe Asp Ser
            6610                6615                6620
Leu Thr Gly Val Glu Leu Arg Asn Arg Leu Asn Thr Ala Thr Gly Leu
6625                6630                6635                6640
Arg Leu Pro Ser Thr Leu Val Phe Asp Tyr Pro Thr Pro Ala Gly Leu
            6645                6650                6655
Ala Ala Phe Leu Val Ala Glu Leu Val Gly Arg Ser Val Gln Ala Val
            6660                6665                6670
Pro Val Pro Pro Val Gly Gly Arg His Gly Asp Ala Asp Ala Ile
            6675                6680                6685
Val Ile Val Gly Met Gly Cys Arg Phe Pro Gly Gly Val Ala Ser Pro
            6690                6695                6700
Glu Asp Leu Trp Asn Leu Leu Ala Ser Gly Gly Asp Ala Ile Gly Pro
6705                6710                6715                6720
Phe Pro Thr Asp Arg Gly Trp Asp Leu Ala Gly Leu Phe Asp Pro Asp
            6725                6730                6735
Pro Glu Arg Ala Gly Lys Ser Tyr Val Glu Ser Gly Gly Phe Leu Tyr
            6740                6745                6750
Gly Ile Gly Glu Phe Asp Ala Glu Phe Phe Gly Ile Ser Pro Arg Glu
            6755                6760                6765
Ala Leu Ala Met Asp Pro Gln Gln Arg Leu Leu Leu Glu Thr Ala Trp
            6770                6775                6780
Glu Thr Phe Glu Arg Ala Gly Ile Asp Pro Thr Ser Leu Arg Gly Ser
6785                6790                6795                6800
Arg Thr Gly Val Phe Ala Gly Val Ile Asp Asn Asp Tyr Gly Ala Arg
            6805                6810                6815
Val Asn Gln Val Pro Asp Glu Val Glu Gly Tyr Leu Gly Tyr Gly Ser
            6820                6825                6830
Ser Ala Ser Ile Ala Ser Gly Arg Val Ser Tyr Val Leu Gly Leu Glu
            6835                6840                6845
Gly Pro Ala Val Ser Ile Asp Thr Ala Cys Ser Ser Ser Leu Val Ala
            6850                6855                6860
Leu His Leu Ala Val Asn Ala Val Arg Ser Gly Glu Cys Glu Leu Ala
6865                6870                6875                6880
Leu Ala Gly Gly Val Thr Ala Met Ala Thr Thr Glu Phe Phe Val Glu
            6885                6890                6895
Phe Ser Arg Gln Arg Gly Leu Ser Pro Asp Gly Arg Cys Lys Ala Phe
            6900                6905                6910
Ala Ala Ala Ala Asp Gly Met Gly Ala Ala Glu Gly Ile Gly Leu Val
            6915                6920                6925
Leu Val Glu Arg Leu Ser Asp Ala Arg Arg His Gly His Ser Val Leu
            6930                6935                6940
Ala Val Val Arg Gly Ser Ala Val Asn Gln Asp Gly Ala Ser Asn Gly
6945                6950                6955                6960
Leu Thr Ala Pro Asn Gly Pro Ser Gln Gln Arg Val Ile Arg Gln Ala
            6965                6970                6975
Leu Gly Ala Ala Gly Leu Ser Ala Ala Asp Val Asp Ala Val Glu Ala
            6980                6985                6990
His Gly Thr Gly Thr Thr Leu Gly Asp Pro Ile Glu Ala Gln Ala Leu
```

-continued

```
              6995                7000                7005
Leu Ala Thr Tyr Gly Gln Asp Arg Pro Gly Asp Arg Pro Leu Trp Leu
   7010                7015                7020
Gly Ser Val Lys Ser Asn Ile Gly His Thr Gln Ala Ala Gly Val
7025                7030                7035                7040
Ala Gly Val Ile Lys Met Val Leu Ala Leu Arg His Gly Val Leu Pro
               7045                7050                7055
Arg Thr Leu His Val Asp Glu Pro Thr Pro His Val Asp Trp Ser Ala
   7060                7065                7070
Gly Arg Val Glu Val Leu Ala Asp Glu Val Ala Trp Pro Ala Gly Glu
   7075                7080                7085
Arg Val Arg Arg Ala Gly Val Ser Ser Phe Gly Ile Ser Gly Thr Asn
   7090                7095                7100
Val His Val Val Leu Glu Glu Ala Pro Ala Asp Ala Ala Glu Pro Ala
7105                7110                7115                7120
Pro Ala Ala Pro Glu Val Pro Gly Val Gly Val Leu Pro Trp Val
               7125                7130                7135
Val Ser Ala Arg Thr Glu Ala Gly Leu Arg Ala Gln Ala Ala Arg Leu
   7140                7145                7150
Arg Asp Trp Val Ser Glu His Pro Asp Ala Glu Pro Thr Asp Val Ala
   7155                7160                7165
Arg Ser Leu Val Val Gly Arg Ala Val Leu Asp Val Arg Ala Val Val
   7170                7175                7180
Arg Gly Arg Glu Ser Gly Glu Leu Val Ala Gly Leu Asp Glu Leu Ala
7185                7190                7195                7200
Arg Ala Gly Val Gly Asp Pro Gly Ser Leu Val Ser Gly Ser Asp Pro
               7205                7210                7215
Val Phe Val Phe Pro Gly Gln Gly Ser Gln Trp Val Gly Met Ala Ala
               7220                7225                7230
Gly Leu Leu Glu Cys Ser Pro Val Phe Ala Gly Val Val Ala Glu Cys
   7235                7240                7245
Ala Ala Val Met Asp Pro Leu Val Ala Asp Trp Ser Leu Leu Asp Val
   7250                7255                7260
Leu Arg Gly Gly Ser Ala Gly Glu Leu Glu Arg Val Asp Val Val Gln
7265                7270                7275                7280
Pro Val Leu Phe Ala Val Met Val Gly Leu Ala Arg Trp Trp Glu Ser
               7285                7290                7295
Cys Gly Val Lys Pro Gly Ala Val Ile Gly His Ser Gln Gly Glu Ile
               7300                7305                7310
Ala Ala Ala His Ile Ala Gly Tyr Leu Ser Leu Ala Asp Ala Val Arg
   7315                7320                7325
Val Val Val Leu Arg Ser Arg Ala Leu Leu Gly Val Ala Ser Ser Gly
   7330                7335                7340
Gly Gly Met Val Ser Val Gly Val Ser Ala Glu Arg Ala Arg Glu Leu
7345                7350                7355                7360
Val Ala Gly Ala Asp Gly Leu Ser Leu Ala Ala Val Asn Gly Pro Thr
               7365                7370                7375
Ser Val Val Leu Ser Gly Asp Val Glu Ala Leu Ser Val Val Glu
               7380                7385                7390
Ala Cys Glu Arg Asp Gly Val Arg Ala Arg Trp Ile Pro Val Asp Tyr
   7395                7400                7405
Ala Ser His Ser Ala Arg Met Glu Ala Val Arg Asp Glu Val Glu Arg
   7410                7415                7420
```

-continued

```
Leu Leu Ala Asp Val Thr Pro Gln Val Gly Cys Val Pro Met Tyr Ser
7425                7430                7435                7440

Thr Leu Thr Gly Ala Pro Ile Ala Asp Pro Ala Glu Leu Gly Gly Ala
            7445                7450                7455

Tyr Trp Phe Glu Asn Leu Arg Arg Thr Val Glu Leu Glu Arg Ala Val
            7460                7465                7470

Gly Ala Ala Val Ala Asp Gly Arg Thr Val Phe Val Glu Cys Ser Pro
        7475                7480                7485

His Pro Gly Leu Val Val Pro Leu Gly Asp Thr Leu Glu Ala Ala Gly
        7490                7495                7500

Val Asp Gly Ala Val Leu Glu Thr Leu Arg Arg Gly Glu Gly Gly Pro
7505                7510                7515                7520

Asp Arg Leu Val Ala Ala Leu Ser Ala Ala Phe Val Arg Gly Leu Ala
            7525                7530                7535

Val Asp Trp Ala Gly Leu Ile Val Gly Ala Arg Val Glu Leu Pro Thr
            7540                7545                7550

Tyr Ala Phe Gln Arg Arg Arg Tyr Trp Leu Asp Asp Gly Ala Arg Ser
            7555                7560                7565

Gly Asp Pro Gly Gly Leu Gly Leu Ala Ala Val Ala His Pro Leu Leu
        7570                7575                7580

Gly Ala Ala Val Arg Pro Ala Gln Gly Ala Gly Leu Leu Phe Thr Gly
7585                7590                7595                7600

Arg Leu Ser Thr Ala Thr His Pro Trp Leu Ala Asp His Val Val Leu
            7605                7610                7615

Gly Ser Thr Ile Val Pro Gly Thr Val Phe Val Asp Leu Ala Leu Trp
        7620                7625                7630

Ala Gly Ala Glu Ala Glu Cys Pro Val Val Asp Glu Leu Thr Leu His
            7635                7640                7645

Thr Pro Leu Val Leu Pro Glu His Gly Gly Val His Val Gln Val Thr
        7650                7655                7660

Val Asp Gly Pro Asp Ala Ala Gly Ala Arg Ala Val Ala Val Tyr Ser
7665                7670                7675                7680

Arg Pro Glu Asp Ala Pro Gly Glu Glu Pro Trp Thr Arg His Ala Val
            7685                7690                7695

Gly Ala Leu Val Ala Asp Ala Asp Thr Gly Ala Ala Pro Asp Ala Ala
        7700                7705                7710

Ala Glu Ala Trp Pro Pro Val Gly Ala Lys Pro Ile Glu Val Ala Asp
            7715                7720                7725

Phe Tyr Ala Arg Leu Val Glu Ser Gly Val Asp Tyr Gly Pro Ala Phe
        7730                7735                7740

Arg Gly Met Arg Ala Ala Trp Arg Arg Gly Asp Glu Leu Phe Ala Asp
7745                7750                7755                7760

Val Ala Leu Pro Ala Glu Glu Arg Asp Ala His Arg Phe Gly Val
            7765                7770                7775

His Pro Ala Leu Leu Asp Ala Gly Val Gln Thr Leu Arg Val Asp Pro
        7780                7785                7790

Gly Gln Val Asp Glu Asp Asp Ile Arg Val Ala Phe Ser Trp His Gly
        7795                7800                7805

Val Arg Leu Phe Ala Ala Gly Val Thr Arg Leu Arg Val Ser Cys Val
        7810                7815                7820

Pro Ser Gly Glu Gly Ala Val Ser Leu Arg Ile Thr Asp Glu Thr Gly
7825                7830                7835                7840
```

-continued

```
Arg Ala Val Ala Ala Ile Glu Ala Leu Thr Val Arg Ala Ile Ser Ala
            7845                7850                7855
Asp Gln Leu Arg Arg Ala Gly Gly Arg Asp Val Leu Tyr Arg Leu
        7860                7865                7870
Ala Trp Arg Ala Ser Ala Val Pro Val Pro Val Ala Thr Pro Arg Val
        7875                7880                7885
Ala Val Val Gly Gly Trp Asp Leu Pro Gly Leu Gly Leu Val Asp
        7890                7895                7900
Arg Tyr Pro Gly Phe Ala Glu Leu Ala Ser Cys Asp Pro Pro Leu Pro
7905                7910                7915                7920
Asp Leu Val Leu Leu Pro Val Gly Asp Pro Asp Ala Asp Val Pro Phe
            7925                7930                7935
Ser Glu Arg Arg Met Arg Glu Val Thr Ala Glu Leu Ile Gly Arg Leu
        7940                7945                7950
Glu Ala Phe Leu Gly Asp Glu Arg Phe Ala Ala Ala Arg Val Val Val
        7955                7960                7965
Val Thr Arg Ser Ala Val Leu Val Asp Gly Asp Ala Gly Leu Gly Asp
        7970                7975                7980
Pro Ala Ser Ala Ser Val Trp Gly Val Val Arg Ala Ala Gln Ala Gly
7985                7990                7995                8000
His Pro Gly Arg Ile Val Leu Val Asp Leu Asp Asp Glu Pro Ala Ser
            8005                8010                8015
Ala Ala Ala Leu Ala Ala Val Ala Ser Ala Gly Gly Glu Pro Gln Phe
            8020                8025                8030
Ala Val Arg Gly Gly Arg Val Ser Val Pro Arg Leu Glu Arg Ile Pro
            8035                8040                8045
Ala Ser Gly Gly Ala Arg Ser Ala Val Gly Thr Gly Thr Val Leu Ile
            8050                8055                8060
Ala Gly Ala Asp Arg Ala Val Gly Ala Gly Val Ala Glu His Leu Ala
8065                8070                8075                8080
Gly Ala Tyr Gly Val Gly Arg Phe Val Leu Leu Ser Val Asp Pro Ser
            8085                8090                8095
Gly Ala Gly Pro Thr Glu Leu Ala Ala Arg Leu Gly Glu Ala Gly Ala
            8100                8105                8110
Glu Val Val Ser Ala Ala Trp Asp Gly His Asp Pro Gly Val Leu Ala
            8115                8120                8125
Ala Leu Val Thr Glu His Arg Pro Ala Gly Val Val Asp Ala Ser Gly
            8130                8135                8140
Glu Ser Asp Ala Ala Trp Ala Leu His Glu Leu Thr Ala Asp Val Asp
8145                8150                8155                8160
Pro Ala Phe Phe Val Leu Phe Ser Ser Ala Ala Ser Leu Leu Gly Ser
            8165                8170                8175
Ser Ala His Ala Ala Thr Ala Gly Val Asp Ala Phe His Asp Ala Leu
            8180                8185                8190
Ala Ala His Arg Arg Ala Ser Gly Leu Pro Gly Val Ser Leu Ala Cys
            8195                8200                8205
Gly Thr Asp Pro Leu Pro Gly Leu Pro Asp Leu Phe Asp Glu Ala Ile
            8210                8215                8220
Arg Arg Glu Asp Ala Val Leu Val Ser Ala Ser Thr Asp Leu Thr Gly
8225                8230                8235                8240
Pro Ala Ser Thr Ser Pro Leu Leu Pro Ser Arg Asn Gly Arg Gly Ala
            8245                8250                8255
Thr Asn Ser Ala Glu Thr Ser Ile Glu Ala Asp Gly Glu Ala Leu Ala
```

-continued

```
                  8260                8265                8270
Arg Arg Leu Ala Ala Leu Ser Glu Glu Arg Glu Arg Glu Leu Val
        8275                8280                8285
Gly Leu Val Arg Ala Gln Ala Ala Val Leu Gly His Ala Gly Ile
        8290                8295                8300
Gly Glu Ile Gly Pro Glu Arg Ala Phe Lys Glu Val Gly Phe Asp Ser
8305                8310                8315                8320
Leu Thr Ala Val Glu Leu Arg Asn Arg Leu Ile Arg Gly Thr Gly Val
            8325                8330                8335
Gly Leu Arg Ser Thr Leu Val Phe Asp Phe Pro Thr Pro Arg Ile Leu
        8340                8345                8350
Ala Arg His Leu Ser Gly Arg Leu Val Glu Ala Ser Pro Ile Gly
        8355                8360                8365
Ala Leu Leu Ala Asp Leu Asp Arg Phe Glu Gly Glu Leu His Ala Val
        8370                8375                8380
Leu Gly Glu Ala Glu Ala Arg Asp Arg Leu Ala Glu Arg Leu Arg Arg
8385                8390                8395                8400
Leu Leu Ala Asp Cys Thr Ala Pro Asp Glu Ser Ala Pro Ala Ala Asp
            8405                8410                8415
Asp Val Ser Asp Val Gln Ser Ala Thr Asp Asp Glu Leu Phe Ser Leu
            8420                8425                8430
Val Asp Gln Gly Phe Glu
        8435

<210> SEQ ID NO 5
<211> LENGTH: 7429
<212> TYPE: PRT
<213> ORGANISM: Streptomyces sp. ATCC 39366

<400> SEQUENCE: 5

Met Ala Glu Ser Glu Glu Lys Leu Arg Ser Tyr Leu Arg Lys Ala Ile
1               5                   10                  15
Thr Asp Ala Arg Asp Ala His Arg Arg Val Arg Glu Leu Glu Asp Arg
            20                  25                  30
Gln Arg Glu Pro Ile Ala Ile Val Gly Met Ala Cys Arg Phe Pro Gly
        35                  40                  45
Gly Leu Gly Thr Pro Glu Asp Leu Trp Arg Phe Val Glu Gly Gly
    50                  55                  60
Asp Ala Ile Gly Glu Phe Pro Thr Asp Arg Gly Trp Asp Leu Asp Gly
65                  70                  75                  80
Leu Tyr Asp Pro Asp Pro Asp Arg Pro Gly Thr Ser Tyr Val Arg Glu
                85                  90                  95
Gly Gly Phe Leu Tyr Asp Val Ala Asp Phe Asp Ala Glu Phe Gly
            100                 105                 110
Ile Ser Pro Arg Glu Ala Ala Met Asp Pro Gln Gln Arg Leu Leu
        115                 120                 125
Leu Glu Thr Ser Trp Glu Ala Val Glu Arg Ala Gly Ile Asp Pro Thr
    130                 135                 140
Ser Leu Arg His Ser Arg Thr Gly Ile Tyr Thr Gly Ile Asn Gly Leu
145                 150                 155                 160
Asp Tyr Thr Thr Val Leu Ala Arg Thr Ala Lys Gly Arg Asp Gly Thr
                165                 170                 175
Leu Gly Met Ala Asn Gly Ala Ser Leu Leu Ala Gly Arg Val Ala Tyr
            180                 185                 190
```

```
Ile Leu Gly Leu Glu Gly Pro Ala Val Thr Val Asp Thr Ala Cys Ser
        195                 200                 205

Ser Ser Leu Val Ala Leu His Leu Ala Ser Asn Ala Leu Arg Ser Gly
        210                 215                 220

Glu Cys Asp Leu Ala Leu Ala Gly Gly Ala Thr Val Met Cys Thr Pro
225                 230                 235                 240

Glu Ile Phe Val Asn Phe Ser Arg Gln Arg Gly Leu Ala Arg Asp Gly
                245                 250                 255

Arg Cys Lys Pro Phe Ser Ala Ala Asp Gly Phe Ile Leu Ser Asp
            260                 265                 270

Gly Ala Gly Leu Phe Leu Ile Glu Arg Leu Ser Asp Ala Arg Arg Asn
        275                 280                 285

Gly His Pro Val Leu Ala Val Leu Arg Gly Ser Ala Ile Asn Gln Asp
        290                 295                 300

Gly Ala Ser Asn Gly Leu Thr Ala Pro Asn Gly Pro Ala Gln Glu Arg
305                 310                 315                 320

Val Ile Arg Gln Ala Leu Gln Ser Ala Gly Leu Val Thr Gly Asp Val
                325                 330                 335

Asp Ala Val Glu Ala His Gly Thr Gly Thr Thr Leu Gly Asp Pro Ile
            340                 345                 350

Glu Ala His Ala Leu Leu Ala Thr Tyr Gly Gln Asp Arg Pro Ala Asp
        355                 360                 365

Arg Pro Leu Arg Leu Gly Ser Ile Lys Ser Asn Ile Gly His Thr Gln
    370                 375                 380

Ala Ala Ala Gly Val Ala Gly Met Ile Lys Met Val Leu Ala Leu Arg
385                 390                 395                 400

His Gly Val Leu Pro Arg Thr Leu His Val Asp Ala Pro Ser Pro His
                405                 410                 415

Ile Asp Trp Ser Ala Gly Arg Val Glu Leu Leu Thr Glu Pro Val Pro
            420                 425                 430

Trp Pro Arg Ser Asp Arg Pro Arg Ala Gly Val Ser Ser Phe Gly
        435                 440                 445

Ala Ser Gly Thr Asn Ala His Val Val Glu Glu Ala Pro Ser Asp
450                 455                 460

Gly Asp Asp Gly Val Val Glu Val Pro Ala Pro Thr Gly Ile Gly Ser
465                 470                 475                 480

Val Leu Pro Trp Val Leu Ser Ala Arg Ser Glu Ala Ala Leu Arg Ala
                485                 490                 495

Gln Ala Gly Arg Leu Arg Asp Trp Leu Ala Glu His Pro Glu Ala Asp
            500                 505                 510

Pro Val Asp Val Gly Arg Ser Leu Ala Val Gly Arg Ala Val Leu Glu
        515                 520                 525

Arg Arg Ala Val Val Arg Gly Arg Asp Val Ala Glu Leu Ala Val Gly
    530                 535                 540

Ile Gly Glu Val Ala Asp Arg Gly Glu Leu Ala Gly Arg Pro Met
545                 550                 555                 560

Phe Ala Gly Pro Gly Pro Val Phe Val Phe Pro Gly Gln Gly Ser Gln
                565                 570                 575

Trp Val Gly Met Ala Ala Gly Leu Leu Glu Cys Ser Pro Val Phe Ala
            580                 585                 590

Gly Val Val Ala Glu Cys Ala Ala Val Met Asp Pro Leu Val Ala Asp
        595                 600                 605

Trp Ser Leu Leu Asp Val Leu Arg Gly Gly Ser Ala Gly Gly Glu Ala
```

-continued

```
            610                 615                 620
Leu Ala Glu Arg Val Asp Val Gln Pro Ala Leu Phe Ala Val Met
625                 630                 635                 640

Val Gly Leu Ala Arg Trp Trp Glu Ser Cys Gly Val Lys Pro Gly Ala
                645                 650                 655

Val Ile Gly His Ser Gln Gly Glu Ile Ala Ala His Val Ala Gly
                660                 665                 670

Tyr Leu Ser Leu Ala Asp Ala Val Arg Ile Val Val Phe Arg Ser Arg
                675                 680                 685

Ala Leu Arg Gly Ile Ala Ala Gly Gly Met Val Ser Val Gly
690                 695                 700

Val Ser Val Glu Arg Ala Glu Glu Leu Val Ala Gly Ser Ala Gly Leu
705                 710                 715                 720

Ser Leu Ala Ala Val Asn Gly Pro Gln Ser Val Val Leu Ser Gly Asp
                725                 730                 735

Arg Glu Ala Leu Ala Ala Val Val Asp Ala Cys Glu Arg Glu Gly Ala
                740                 745                 750

Arg Ala Arg Trp Ile Pro Val Asp Tyr Ala Ser His Ser Ala His Met
                755                 760                 765

Glu Val Val Arg Asp Glu Val Glu Arg Leu Ser Ala Glu Val Thr Pro
770                 775                 780

Arg Ala Gly Arg Val Pro Met Tyr Ser Thr Leu Thr Gly Glu Val Val
785                 790                 795                 800

Thr Asp Pro Ala Glu Leu Gly Ala Gly Tyr Trp Phe Glu Asn Leu Arg
                805                 810                 815

Gly Thr Val Arg Leu Thr Thr Ala Val Gly Ala Ala Val Ala Asp Gly
                820                 825                 830

His Val Ala Phe Val Glu Cys Ser Pro His Pro Gly Leu Val Val Pro
                835                 840                 845

Leu Ala Asp Thr Leu Asp Glu Leu Gly Val Asp Asp Gly Thr Val Leu
850                 855                 860

Glu Thr Leu Arg Arg Asp Asp Gly Gly Pro Asp Arg Leu Val Ala Ala
865                 870                 875                 880

Leu Ser Ala Ala Phe Val Ala Gly Val Pro Val Asp Trp Ala Ala Leu
                885                 890                 895

Phe Pro Gly Glu Gly Arg Ala Asp Leu Pro Thr Tyr Ala Phe Gln His
                900                 905                 910

Arg Arg Tyr Trp Ala Glu Ala Glu Ser Pro Ala Gly Gly Val Ala
                915                 920                 925

Trp Gly Gln Arg Ala Val Thr His Pro Val Leu Gly Ala Ala Val Asp
930                 935                 940

Leu Ala Gly Asp Ala Gly Thr Val Phe Thr Gly Arg Leu Ser Thr Thr
945                 950                 955                 960

Ala Gln Pro Trp Leu Ala Asp His Ala Val Leu Gly Thr Val Ile Val
                965                 970                 975

Pro Gly Thr Ala Phe Leu Asp Leu Val Leu Arg Ala Gly Ala Glu Val
                980                 985                 990

Gly Tyr Pro Ala Ile Glu Glu Leu Thr Leu His Thr Pro Leu Val Leu
                995                 1000                1005

Pro Asp Ala Ser Gly Val Leu Val Gln Val Val Gly Ala Ala Asp
                1010                1015                1020

Gly Asp Gly Gly Asp Gly Gly Asp Gly Ala Arg Thr Val Asp Val His
1025                1030                1035                1040
```

-continued

Ser Arg Ala Glu Asp Ala Pro Pro Asp His Pro Trp Thr Arg His Ala
            1045                1050                1055

Ser Gly Val Leu Val Ala Ala Gly Glu Glu Arg Ala Glu Asp Ala Pro
            1060                1065                1070

Ala Gly Arg Trp Pro Pro Thr Gly Ala Glu Val Val Gly Val Asp Asp
            1075                1080                1085

Ala Tyr Glu Arg Leu Ala Val Ala Gly Phe Asp Tyr Gly Pro Val Phe
            1090                1095                1100

Gln Gly Leu Arg Ser Val Arg Ala Arg Gly Asp Glu Leu Phe Ala Glu
1105                1110                1115                1120

Val Glu Leu Pro Glu Glu Gly His Ala Asp Ala Asp Arg Phe Ala Val
            1125                1130                1135

His Pro Ala Leu Leu Asp Ala Ala Leu His Pro Leu Val Val Ala Ala
            1140                1145                1150

Gly Ala Asp Ala Pro Val Val Ala Gly Leu Pro Phe Val Trp His Gly
            1155                1160                1165

Ile Arg Ala Gly Val Pro Gly Ala Arg Arg Leu Arg Val Arg Leu Val
            1170                1175                1180

Arg Ser Ala Ser Gly Ser Ala Ser Gly Ser Ala Ala Gly Ser Asp Ser
1185                1190                1195                1200

Ala Ser Gly Glu Val Ser Val Arg Ala Trp Asp Glu Gly Gly Arg Glu
            1205                1210                1215

Val Val Ala Ile Glu Ser Leu Thr Ile Arg Pro Val Ser Ala Asp Gly
            1220                1225                1230

Leu Arg Thr Pro Asp Ala Leu Val Arg Asp Ser Leu Phe Thr Leu Ala
            1235                1240                1245

Trp Thr Ala Leu Glu Leu Pro Asp Val Asp Asp Asp Val Pro Asn Ala
            1250                1255                1260

Thr Leu Leu Gly Gly Asp Gly Ala Ala Asp Leu Ala Ala Leu Val Ala
1265                1270                1275                1280

Ala Met Asp Thr Gly Thr Asp Val Pro Ala Leu Val Ala Leu Pro Val
            1285                1290                1295

Ser Val Asp Asp Ala Asp Pro Val Ala Ala His Thr Ala Gly Arg
            1300                1305                1310

Gln Val Leu Ala Val Leu Arg Asp Trp Leu Ala Asp Glu Arg Phe Ala
            1315                1320                1325

Asp Ser Arg Leu Val Phe Val Thr Ser Gly Ala Val Ala Val Ala Asp
            1330                1335                1340

Glu Gln Val Arg Pro Ala Ser Ala Ala Val Trp Gly Leu Val Arg Ser
1345                1350                1355                1360

Ala Gln Ser Glu His Pro Gly Arg Phe Val Leu Val Asp Ala Asp Ser
            1365                1370                1375

Val Ala Asp Pro Gly Pro Glu Phe Asp Arg Ala Leu Arg Thr Gly Ala
            1380                1385                1390

Asp Gln Leu Ile Leu Arg Asp Gly Thr Ala Leu Ile Pro Arg Leu Val
            1395                1400                1405

Arg Ala Pro Ala Asp Gly Gly Ser Gly Gly Phe Val Pro Ala Ala Asp
            1410                1415                1420

Gly Thr Val Leu Ile Thr Gly Gly Thr Gly Thr Leu Gly Thr Leu Leu
1425                1430                1435                1440

Ala Arg His Leu Val Thr Glu His Gly Val Arg Arg Leu Leu Leu Leu
            1445                1450                1455

```
Ser Arg Arg Gly Gly Thr Ala Ala Gly Ala Thr Asp Leu Val Ala Glu
        1460                1465                1470

Leu Ala Ala Phe Gly Ala Glu Val Thr Cys Val Ala Gly Asp Ala Ala
    1475                1480                1485

Asp Arg Ala Thr Leu Glu Arg Val Leu Ala Asp Ile Pro Ala Glu His
    1490                1495                1500

Pro Leu Thr Ala Val Ile His Ala Ala Gly Val Val Asp Asp Gly Val
1505                1510                1515                1520

Val Gln Ser Leu Thr Ala Asp Arg Leu Asp Ala Val Leu Arg Pro Lys
            1525                1530                1535

Val Asp Ala Ala Trp Asn Leu His Glu Ala Thr Arg His Leu Asp Leu
        1540                1545                1550

Thr Ala Phe Val Leu Phe Ser Ser Ala Ala Gly Val Leu Gly Asn Pro
    1555                1560                1565

Gly Gln Gly Asn Tyr Ala Ala Ala Asn Ala Phe Leu Asp Ala Leu Ala
1570                1575                1580

Arg Arg Arg Arg Arg Glu Gly Leu Pro Gly Ser Ser Leu Ala Trp Gly
1585                1590                1595                1600

Trp Trp Ala Pro Thr Ser Glu Met Thr Ala Gly Leu Gly Asp Ala Asp
            1605                1610                1615

Arg Gln Arg Met Ala Arg Leu Gly Val Leu Pro Leu Ala Pro Glu Gln
        1620                1625                1630

Gly Leu Ala Leu Phe Asp Ala Ala Thr Asn His Ala Glu Pro Thr Pro
    1635                1640                1645

Thr Val Val Arg Met Asp Leu Ala Val Leu Arg Thr Ala Gly Ser Val
1650                1655                1660

Val Pro Thr Leu Leu Arg Gly Leu Ala Arg Val Pro Asn Arg Arg Ala
1665                1670                1675                1680

Ala Thr Ala Gly Ser Val Ala Glu Leu Arg Arg Arg Pro Ala Gly Val
            1685                1690                1695

Ser Ala Phe Asp Trp Glu Gln Thr Leu Ile Arg Ala Val Cys Val His
        1700                1705                1710

Ala Ala Ala Val Ile Gly His Ala Asp Ala Thr Glu Ile Asp Glu Thr
    1715                1720                1725

Arg Ala Phe Arg Asp Leu Gly Phe Asp Ser Leu Thr Gly Leu Glu Leu
1730                1735                1740

Arg Asn Arg Leu Asn Thr Ala Thr Gly Leu Arg Leu Pro Ala Thr Leu
1745                1750                1755                1760

Val Phe Asp Tyr Pro Ser Pro Val Val Leu Gly Arg Trp Leu Arg Asp
            1765                1770                1775

Arg Leu Ala Glu Glu Asp Ala Gly Gly Pro Val Gly Ser Thr Leu Gly
        1780                1785                1790

Ala Gln Val Val Ser Pro Val Gly Ser Asp Ala Gly Glu Asp Ser Ile
    1795                1800                1805

Val Ile Val Gly Met Gly Cys Arg Phe Pro Gly Gly Ile Thr Ala Pro
1810                1815                1820

Glu His Leu Trp Asp Val Val Ala Gly Gly Val Asp Thr Leu Thr Asp
1825                1830                1835                1840

Phe Pro Thr Asp Arg Gly Trp Asp Val Glu Arg Ile Phe Asp Pro Asp
            1845                1850                1855

Pro Asp Arg Pro Gly Ser Thr Tyr Val Arg Thr Gly Gly Phe Val Asp
        1860                1865                1870

Ser Ala Ala Asp Phe Asp Pro Asp Leu Phe Gly Ile Ser Pro Arg Glu
```

```
                1875                1880                1885
Ala Leu Ala Met Asp Pro Gln Gln Arg Leu Leu Glu Thr Ala Trp
    1890                1895                1900
Glu Thr Phe Glu Arg Ala Gly Ile Asp Pro Thr Ser Leu Arg Gly Ser
1905                1910                1915                1920
Arg Thr Gly Val Phe Ala Gly Ala Ile Tyr Tyr Asp Tyr Ala Gly Gly
                1925                1930                1935
Arg Leu Arg Lys Val Pro Asp Glu Leu Gly Tyr Ile Gly Asn Gly
            1940                1945                1950
Asn Val Gly Ser Val Ala Ser Gly Arg Val Ala Tyr Thr Phe Gly Leu
        1955                1960                1965
Glu Gly Pro Ala Val Thr Val Asp Thr Ala Cys Ser Ser Leu Val
    1970                1975                1980
Ala Leu His Leu Ala Val Asn Ala Val Arg Ser Gly Glu Cys Glu Leu
1985                1990                1995                2000
Ala Leu Ala Gly Gly Val Thr Val Met Ser Thr Pro Ser Val Phe Leu
                2005                2010                2015
Asp Phe Ser Arg Gln Arg Gly Leu Ser Ser Asp Gly Arg Cys Arg Ser
            2020                2025                2030
Phe Ala Ala Ala Ala Asp Gly Thr Gly Trp Gly Glu Gly Val Gly Leu
                2035                2040                2045
Val Leu Val Glu Arg Leu Ser Asp Ala Arg Arg Asn Gly His Pro Val
    2050                2055                2060
Leu Ala Val Val Arg Gly Ser Ala Val Asn Gln Asp Gly Ala Ser Asn
2065                2070                2075                2080
Gly Leu Thr Ala Pro Asn Gly Pro Ser Gln Gln Arg Val Ile Arg Gln
                2085                2090                2095
Ala Leu Gly Ser Ala Gly Leu Ser Pro Ala Asp Val Asp Ala Val Glu
            2100                2105                2110
Ala His Gly Thr Gly Thr Thr Leu Gly Asp Pro Ile Glu Ala Gln Ala
        2115                2120                2125
Leu Leu Ala Thr Tyr Gly Gln Asp Arg Pro Gly Asp Arg Pro Leu Trp
    2130                2135                2140
Leu Gly Ser Val Lys Ser Asn Leu Gly His Thr Gln Ala Ala Ala Gly
2145                2150                2155                2160
Val Ala Gly Val Ile Lys Met Val Leu Ala Leu Arg His Gly Val Leu
                2165                2170                2175
Pro Arg Thr Leu His Val Asp Glu Pro Thr Pro His Val Asp Trp Ser
            2180                2185                2190
Ala Gly Arg Val Glu Val Leu Ala Asp Glu Val Ala Trp Pro Ala Gly
        2195                2200                2205
Glu Arg Val Arg Arg Ala Gly Val Ser Ser Phe Gly Ile Ser Gly Thr
    2210                2215                2220
Asn Ala His Val Val Leu Glu Glu Pro Pro Val Thr Glu Val Pro
2225                2230                2235                2240
Asp Val Ala Val Glu Ser Gly Leu Gly Gly Arg His Thr Trp Val Val
                2245                2250                2255
Ser Ala Arg Ser Glu Ala Ala Val Arg Glu Gln Ala Ala Arg Leu Arg
            2260                2265                2270
Asp Trp Val Thr Ala Arg Pro Asp Leu Asp Pro Ala His Val Ala Arg
        2275                2280                2285
Ser Leu Val Cys Glu Arg Ala Leu Phe Gly His Arg Ala Val Val Ser
    2290                2295                2300
```

-continued

```
Gly Ala Asp Leu Ala Glu Leu Ala Asp Gly Leu Ser Ala Val Ala Ala
2305                2310                2315                2320

Gly Ala Glu Gly Ala Val Val Gly Ala Val Gly Arg Gly Pro Gly Lys
            2325                2330                2335

Thr Ala Val Leu Cys Thr Gly Gln Gly Val Arg Ala Leu Gly Ile Gly
                2340                2345                2350

Arg Glu Leu His Ala Ala Phe Pro Val Phe Ala Gly Ala Leu Asp Glu
            2355                2360                2365

Val Cys Ala Ala Phe Asp Asp Val Val Pro Phe Ser Val Arg Asp Val
        2370                2375                2380

Val Leu Gly Ala Glu Gly Val Ser Asp Ala Asp Ala Gln Asp Thr Gly
2385                2390                2395                2400

Val Ala Gln Pro Ala Leu Phe Ala Phe Glu Val Ala Leu Tyr Arg Leu
                2405                2410                2415

Trp Ala Ser Trp Gly Gln Ala Pro Asp Phe Val Val Gly His Ser Leu
            2420                2425                2430

Gly Glu Ile Val Ala Ala His Val Ala Gly Val Phe Ser Leu Ala Asp
        2435                2440                2445

Ala Val Val Phe Val Ala Ala Arg Ala Arg Leu Met Ser Ala Leu Pro
    2450                2455                2460

Ser Gly Gly Ala Met Leu Ala Val Gly Ala Ser Glu Ala Glu Val Ala
2465                2470                2475                2480

Ala Ser Cys Pro Ala Glu Val Thr Ile Ala Ala Val Asn Gly Pro Ala
                2485                2490                2495

Ser Val Val Ser Gly Pro Ala Glu Ala Val Ala Ala Leu Glu Pro
            2500                2505                2510

Asp Cys Val Met Arg Gly Trp Arg Ile Ser Arg Leu Ser Val Ser His
        2515                2520                2525

Ala Phe His Ser Ala Leu Met Gln Pro Met Leu Ala Glu Leu Arg Glu
    2530                2535                2540

Val Leu Thr Gly Leu Thr Tyr Gly Thr Pro Glu Ile Ala Val Val Ser
2545                2550                2555                2560

Asp Thr Thr Gly Arg Val Ala Gly Ala Glu Glu Leu Ala Asp Pro Glu
            2565                2570                2575

Tyr Trp Val Arg His Val Arg Arg Ala Val Arg Phe Gly Asp Ala Ile
        2580                2585                2590

Ala Thr Leu Arg Ala Glu Gly Val Arg Thr Phe Val Glu Ile Gly Pro
    2595                2600                2605

Glu Ala Ala Leu Thr Ala Met Val Val Glu Gly Thr Ala Gly Ala Glu
2610                2615                2620

Asp Val Ala Ala Val Ala Thr Arg Arg Arg Gly Arg Ala Ala Val Ser
2625                2630                2635                2640

Ser Val Val Glu Ala Leu Ala Arg Val Phe Val His Gly Ala Thr Val
            2645                2650                2655

Asp Trp Ala Ala Leu Ser Thr Gly Ser Gly Pro Gly Gly Arg Val Asp
        2660                2665                2670

Leu Pro Thr Tyr Ala Phe Glu Arg Arg Arg Phe Trp Leu His Ala Gly
    2675                2680                2685

Val Asp Ala Gly Asp Ala Val Gly Leu Gly Gln Gly Val Val Asp His
        2690                2695                2700

Pro Leu Leu Gly Ala Val Val Gly Leu Ala Asp Asp Gln Gly Val Leu
2705                2710                2715                2720
```

-continued

```
Phe Thr Gly Arg Leu Ala Leu Asp Thr His Pro Trp Leu Ala Glu His
            2725                2730                2735

Thr Val Leu Gly Thr Val Leu Leu Pro Gly Thr Ala Phe Leu Glu Leu
        2740                2745                2750

Ala Leu His Val Gly Arg Leu Leu Asp Cys Ala Arg Val Asp Glu Leu
        2755                2760                2765

Thr Leu Ser Ala Pro Leu Ala Leu Pro Ser Thr Gly Gly Val Gln Val
        2770                2775                2780

Gln Val Arg Val Gly Val Pro Glu Glu Ser Gly Thr Arg Thr Ile Thr
2785                2790                2795                2800

Val His Ala Arg Pro Asp Ser Ala Glu Glu Ala Pro Trp Thr Leu His
            2805                2810                2815

Ala Ala Gly Ala Leu Gly Pro Ser Ala Glu Val Asp Ala Pro Ser Asp
        2820                2825                2830

Ala Ala Ser Trp Pro Pro Ala Asp Ala Thr Ala Met Asp Ser Ala Gly
        2835                2840                2845

Leu Tyr Pro Trp Phe Ala Glu Thr Gly Val Asp Tyr Gly Pro Ser Phe
        2850                2855                2860

Arg Gly Val Gln Ala Thr Trp Arg Arg Asp Glu Val Phe Ala Glu
2865                2870                2875                2880

Ile Val Leu Ala Ala Asp Asp Pro Ala Ala Asp Gly Arg Phe Glu Leu
            2885                2890                2895

His Pro Ala Leu Phe Asp Ala Ala Leu His Pro Leu Gly Leu Thr Leu
        2900                2905                2910

Leu Asp Ala Ala Glu Pro Arg Leu Arg Leu Pro Phe Ser Trp Arg Gly
        2915                2920                2925

Val Ala Leu His Thr Ser Gly Ala Arg Thr Leu Arg Val Arg Leu Arg
        2930                2935                2940

Pro Thr Gly Pro Asp Thr Ile Ala Val Thr Ala Thr Asp Glu Thr Gly
2945                2950                2955                2960

Arg Pro Val Val Ala Val Glu Ala Leu Ala Val Arg Glu Pro Ser Arg
            2965                2970                2975

Asp Arg Leu Pro Arg Pro Asp Ala Asn Ala Gly Glu Leu Phe Glu Pro
        2980                2985                2990

Gln Trp Thr Pro Leu Ser Pro Ala Asp Thr Ala Asp Met Ala Asp Thr
        2995                3000                3005

Leu Gly Ala Val Val Gly Gly Pro Glu Leu Ala Ser Thr Ala Thr Arg
        3010                3015                3020

Phe Gly Ala Thr His His Pro Asp Leu Ala Ala Leu Ala Glu Ser Ala
3025                3030                3035                3040

Ile Pro Glu Thr Val Leu Tyr Asp Leu Val Thr Ala Val Pro Gly Val
            3045                3050                3055

Ser Ala Glu Ala Val His Gln Ala Ala Gln Ala Leu Asp Leu Ala
        3060                3065                3070

Arg Ser Trp Leu Ala Asp Glu Arg Phe Glu Ser Ala Arg Leu Ile Val
        3075                3080                3085

Arg Thr Arg His Ala Val Ala Ala Glu Gly Asp Ala Pro Asp Pro
        3090                3095                3100

Ala Ala Ala Ala Thr His Gly Leu Phe Arg Thr Ala Cys Ser Glu His
3105                3110                3115                3120

Pro Glu Arg Phe Ala Leu Val Asp Ala Asp Asp Leu Asp Glu Val Ser
            3125                3130                3135

Pro Glu Ala Ile Ala Ala Val Val Val Glu Pro Glu Ala Ala Val Arg
```

-continued

```
                3140                3145                3150
Ala Gly Arg Val Leu Val Pro Arg Leu Arg Ala Ala Val Ala Pro
        3155                3160                3165
Lys Ala Asp Phe Gly Phe Ala Ala Glu Gly Thr Val Leu Ile Thr Gly
        3170                3175                3180
Gly Thr Gly Ala Leu Gly Arg Gln Val Ala Arg His Leu Val Arg Val
3185                3190                3195                3200
His Gly Val Arg Arg Leu Leu Leu Ser Arg Arg Gly Asp Glu Ala
            3205                3210                3215
Pro Glu Ala Ala Glu Leu Arg Ala Glu Leu Ile Glu Ala Gly Ala His
            3220                3225                3230
Val Thr Phe Ala Ala Gly Asp Ala Ala Glu Arg Gly Val Leu Ala Asp
            3235                3240                3245
Val Leu Ala Ala Ile Pro Ala Ala His Pro Leu Thr Gly Val Val His
            3250                3255                3260
Leu Ala Gly Val Thr Asp Asp Gly Leu Val Gly Thr Leu Thr Pro Glu
3265                3270                3275                3280
Arg Leu Ala Ala Val Leu Arg Pro Lys Ile Asp Ala Ala Leu His Leu
            3285                3290                3295
Asp Glu Leu Thr Ala Asp Ala Asp Leu Ser Ala Phe Val Leu Phe Ser
            3300                3305                3310
Ser Ala Ala Gly Pro Val Gly Asn Pro Gly Gln Ala Asn Tyr Ala Ala
            3315                3320                3325
Ala Asn Val Ala Leu Asp Ala Leu Ala Arg Arg Arg Ala Arg Gly
            3330                3335                3340
Arg Pro Ala Val Ser Leu Gln Trp Gly Leu Trp Ala Glu Arg Ser Ala
3345                3350                3355                3360
Leu Thr Ala Thr Met Ser Ala Thr Asp Arg Arg Arg Ala Ala Gly Ala
                3365                3370                3375
Gly Val Arg Ala Leu Ser Val Glu Gln Gly Leu Ala Leu Leu Asp Ala
            3380                3385                3390
Ala Ala Gly Arg Pro Glu Ala Val Leu Thr Pro Leu Arg Leu Asp Pro
        3395                3400                3405
Ala Ile Leu Arg Gly Pro Glu Glu Arg Val Ala Pro Val Leu Arg Gly
        3410                3415                3420
Leu Val Pro Thr Arg Ala Arg Arg Ala Pro Ala Arg Thr Ser Asp Thr
3425                3430                3435                3440
Ala Arg Ser Leu Val Arg Arg Leu Ala Ala Leu Pro Glu Ala Glu Gln
                3445                3450                3455
Asp Arg Leu Leu Val Asp Leu Val Arg Thr His Ala Ala Gly Val Leu
            3460                3465                3470
Gly His Ala Asp Ala Arg Thr Ile Asp Pro Asp Arg Ala Phe Gly Glu
        3475                3480                3485
Leu Gly Leu Asp Ser Leu Ala Ala Leu Glu Leu Arg Thr Arg Leu Ser
        3490                3495                3500
Thr Ala Val Gly Leu Arg Leu Pro Ala Thr Met Leu Phe Asp His Pro
3505                3510                3515                3520
Cys Ala Arg Ala Val Gly Val His Leu Arg Ala Gln Leu Leu Asp Ala
            3525                3530                3535
Pro Thr Pro Gly Arg Ala Ala Gly Val Ala Arg Pro Val Ser Asp Glu
            3540                3545                3550
Pro Val Ala Val Val Ala Ile Ser Cys Arg Phe Pro Gly Gly Val Ala
            3555                3560                3565
```

-continued

```
Ser Pro Glu Asp Leu Trp Arg Leu Val Ser Glu His Thr Asp Ala Ile
    3570                3575                3580

Ser Glu Phe Pro Gln Asp Arg Gly Trp Asp Leu Ala Glu Leu Phe His
3585                3590                3595                3600

Pro Asp Pro Glu His Ala Gly Thr Ser Tyr Val Ser Glu Gly Gly Phe
                3605                3610                3615

Leu Tyr Glu Ala Thr Glu Phe Asp Pro Glu Phe Phe Gly Ile Ser Pro
        3620                3625                3630

Arg Glu Ala Leu Ala Met Asp Pro Gln Gln Arg Leu Leu Leu Glu Ala
            3635                3640                3645

Ser Trp Glu Ala Ile Glu Arg Ala Gly Val Asp Pro Arg Ser Leu Arg
    3650                3655                3660

Gly Ser Arg Thr Gly Val Tyr Ala Gly Leu Met Tyr Ala Asp Tyr Ala
3665                3670                3675                3680

Ser Arg Leu Gly Ser Ala Pro Glu Gly Val Asp Gly Tyr Leu Gly Asn
                3685                3690                3695

Gly Ser Ala Gly Ser Ile Ala Ser Gly Arg Val Ala Tyr Thr Leu Gly
        3700                3705                3710

Leu Glu Gly Pro Ala Val Thr Val Asp Thr Ala Cys Ser Ser Ser Leu
            3715                3720                3725

Val Ala Leu His Leu Ala Ala Asn Ala Leu Arg Gln Gly Glu Cys Asp
    3730                3735                3740

Leu Ala Leu Ala Gly Gly Val Thr Val Met Ser Ser Pro Ala Thr Phe
3745                3750                3755                3760

Val Glu Phe Ser Arg Gln Arg Gly Leu Ala Pro Asp Ala Arg Cys Lys
                3765                3770                3775

Ser Phe Ala Ala Gly Ala Asp Gly Thr Ser Trp Ser Glu Gly Ile Gly
        3780                3785                3790

Leu Leu Leu Val Glu Arg Leu Ser Asp Ala Arg Arg Leu Gly His Pro
            3795                3800                3805

Val Leu Ala Val Val Arg Gly Ser Ala Ile Asn Gln Asp Gly Ala Ser
    3810                3815                3820

Asn Gly Leu Ala Ala Pro Asn Gly Leu Ala Gln Glu Arg Val Ile Arg
3825                3830                3835                3840

Asp Ala Leu Ala His Ala Glu Leu Arg Pro Ser Asp Val Asp Ala Val
                3845                3850                3855

Glu Ala His Gly Thr Gly Thr Pro Leu Gly Asp Pro Ile Glu Ala Arg
        3860                3865                3870

Ala Leu Leu Ala Thr Tyr Gly Gln Asp Arg Pro Ala Asp Arg Pro Leu
            3875                3880                3885

Trp Leu Gly Ser Val Lys Ser Asn Leu Gly His Thr Gln Ala Ala Ala
    3890                3895                3900

Gly Val Ala Gly Val Ile Lys Met Ile Met Ala Met Arg His Ala Glu
3905                3910                3915                3920

Leu Pro Gly Thr Leu His Val Asp Ala Pro Ser Pro His Val Asp Trp
                3925                3930                3935

Ser Ala Gly Ala Val Ser Leu Leu Thr Ala Ala Thr Pro Trp Pro Gln
        3940                3945                3950

Thr Gly Arg Pro Arg Arg Ala Gly Val Ser Ser Phe Gly Ile Ser Gly
            3955                3960                3965

Thr Asn Ala His Val Ile Leu Glu Gln Gly Asp Pro Ala Pro Thr Ala
    3970                3975                3980
```

```
Pro Ala Glu Pro Ala Pro Ala Ser Ala Pro Leu Ala Ala Leu Ala Trp
3985                3990                3995                4000

Pro Leu Ser Gly Ala Ser Ala Val Ala Leu Arg Gly Gln Ala Glu Arg
                4005                4010                4015

Leu Arg Ala His Leu Asp Ala His Pro Glu Tyr Gly Pro Val Asp Ile
            4020                4025                4030

Ala His Ala Leu Val Gly Gly Arg Ser Arg Phe Glu His Arg Ala Val
        4035                4040                4045

Val Val Ala Glu Asp Ala Ala Gly Leu Arg Ala Gly Leu Asp Ala Leu
    4050                4055                4060

Ser Ala Asp Arg Pro Asp Ala Ala Val Pro Val Gly Val Ala Gly Glu
4065                4070                4075                4080

Pro Gly Arg Ile Ala Phe Val Phe Gly Gly Gln Gly Ser Gln Trp Pro
                4085                4090                4095

Gly Met Gly Ala Arg Leu Leu Thr Glu Ser Pro Val Phe Ala Ala Arg
            4100                4105                4110

Ile Arg Asp Cys Asp Ala Ala Leu Ala Pro His Thr Asp Trp Ser Leu
        4115                4120                4125

Leu Ala Val Leu Arg Gly Glu Pro Asp Ala Pro Leu Asp Arg Val
    4130                4135                4140

Asp Val Val Gln Pro Val Leu Phe Ala Val Met Val Ala Leu Ala Glu
4145                4150                4155                4160

Leu Trp Arg Ser Leu Gly Val Arg Pro Ala Ser Val Val Gly His Ser
                4165                4170                4175

Gln Gly Glu Ile Ala Ala Ala His Ile Ala Gly Ala Leu Thr Leu Asp
            4180                4185                4190

Asp Ala Ala Arg Ile Val Ala Leu Arg Ser Arg Ala Leu Arg Gly Leu
        4195                4200                4205

Ser Gly Asp Gly Gly Met Met Ser Val Ala Ala Gly Pro Glu Gln Ile
    4210                4215                4220

Ala Arg Leu Leu Asp Gly Phe Ala Asp Arg Leu Gly Ile Ala Ala Val
4225                4230                4235                4240

Asn Gly Pro Ala Ala Val Val Ile Ser Gly Ala Ala Asp Ala Leu Ala
                4245                4250                4255

Glu Leu His Ala His Cys Glu Ala Asp Gly Ile Arg Ala Arg Val Leu
            4260                4265                4270

Pro Val Asp Tyr Ala Ser His Ser Ala Gln Val Glu Gln Val Arg Glu
        4275                4280                4285

Glu Leu Leu Ala Ala Leu Gly Glu Ile Val Pro Thr Pro Thr Thr Asp
    4290                4295                4300

Ala Val Phe Tyr Ser Ser Val Thr Gly Glu Pro Val Glu Gly Thr Ala
4305                4310                4315                4320

Leu Asp Ala Glu Tyr Trp Tyr Arg Asn Leu Arg Ala Thr Val Ala Phe
                4325                4330                4335

Asp Arg Ala Thr Asp Ala Leu Leu Arg Asp Gly His Thr Val Phe Val
            4340                4345                4350

Glu Thr Ser Pro His Pro Val Leu Ala Pro Ala Val Glu Asp Ser Ala
        4355                4360                4365

Gln Arg Ala Gly Thr Asp Val Thr Val Val Gly Ser Leu Gln Arg Asp
    4370                4375                4380

Thr Asp Thr Leu Ala Arg Phe Leu Thr Ala Ala Ala Gly Leu His Val
4385                4390                4395                4400

His Gly Val Pro Val Asp Trp Ser Ala Thr His Ala Gly His Arg Pro
```

-continued

```
                4405                4410                4415
Arg Pro Val Asp Leu Pro Thr Tyr Ala Phe Gln Arg Glu Arg Tyr Trp
            4420                4425                4430

Leu Glu Ala Gly Lys Thr Pro Thr Asp Ala Ala Gly Leu Gly Leu His
            4435                4440                4445

Pro Ala Ala His Pro Leu Leu Gly Ala Ala Val Val Pro Ala Glu Gly
            4450                4455                4460

Asp Arg His Ile Leu Thr Gly Arg Ile Ser Leu Arg Thr His Pro Trp
4465                4470                4475                4480

Leu Ala Asp His Thr Ile Leu Asp Thr Val Leu Leu Pro Gly Thr Ala
            4485                4490                4495

Phe Val Glu Leu Ala Leu Gln Ala Gly Asp Arg Ala Asp Cys Asp Leu
            4500                4505                4510

Ile Glu Glu Leu Thr Val Glu Ala Pro Leu Arg Leu Thr Asp Thr Gly
            4515                4520                4525

Ala Val His Leu Gln Val Leu Leu Asp Glu Pro Asp Glu Gln Gly Arg
            4530                4535                4540

Arg Ala Leu Thr Ile His Ser Arg Ala Asp Asp Ala Pro Ala Glu Gln
4545                4550                4555                4560

Thr Trp Thr Arg His Ala Ser Gly Val Leu Ala Pro Val Ala Asp Gly
            4565                4570                4575

Leu Asp Ala Val Pro Ala Thr Asp Ala Ala Trp Pro Pro Ala Gly Ala
            4580                4585                4590

Val Ala Leu Asp Val Asp Gly Leu Tyr Glu Arg Leu Ala Gly Gln Gly
            4595                4600                4605

Tyr Arg Tyr Gly Pro Ala Phe Arg Ala Val Arg Ala Ala Trp Arg Leu
            4610                4615                4620

Gly Asp Thr Val Leu Ala Glu Val Ala Pro Gly Asp Glu Ala His Gly
4625                4630                4635                4640

Ala Arg Asp Phe Ala Leu His Pro Ala Leu Leu Asp Ala Ala Leu His
            4645                4650                4655

Ala Ala Gly Ala Ala Asp Ser Gly Thr Ser Gly Gly Asp Gly Ala Ile
            4660                4665                4670

Gly Leu Pro Phe Ala Trp Thr Asp Val Arg Leu His Ala Val Gly Ala
            4675                4680                4685

Ala Ala Leu Arg Val Arg Leu Glu Arg Arg Gly Pro Asp Thr Val Gly
            4690                4695                4700

Leu Glu Leu Thr Asp His Thr Gly Ala Leu Val Ala Thr Val Gly Ala
4705                4710                4715                4720

Leu Val Gly Arg Pro Ala Thr Ala Asp Arg Leu Ala Pro Ala Ala Asp
            4725                4730                4735

Pro Ala His Arg Asp Leu His His Val Asp Trp Ser Pro Leu Pro Thr
            4740                4745                4750

Pro Thr Glu Pro Ser Thr Ala Arg Trp Ser Leu Leu Gly Pro Asp Glu
            4755                4760                4765

Leu Glu Ala Val Ala Gly Leu Arg Ala Ala Gly Ala Glu Val His Ala
            4770                4775                4780

Asp Gly Asp Pro Asp Pro Ala Asp Val Leu Leu Ile Thr Cys Ala Gly
4785                4790                4795                4800

Arg Thr Gly Asp Asp Val Pro Glu Ala Ala Arg Ala Ala Thr His Arg
            4805                4810                4815

Val Leu Asp Leu Leu Gln Arg Ala Leu Thr Asp Pro Arg Leu Thr Ala
            4820                4825                4830
```

-continued

```
Cys Thr Leu Val Val Leu Thr Arg Gly Ala Val Pro Gly His His Gly
        4835                4840                4845

Glu Asp Val Cys Asp Leu Val Ala Ala Pro Ile Val Gly Leu Val Arg
        4850                4855                4860

Ser Ala Gln Thr Glu His Pro Gly Arg Ile Val Leu Val Asp Leu Asp
4865                4870                4875                4880

Asp His Ala Asp Ser Phe Ala Ala Leu Arg Ala Ala Val Val Thr Asp
        4885                4890                4895

Val Gly Glu Pro Gln Leu Ala Ile Arg Thr Gly Thr Val Ser Ala Pro
        4900                4905                4910

Arg Leu Ile Arg Thr Gly Thr Glu Pro Arg Leu Ser Pro Pro Ala Gly
        4915                4920                4925

Ala Pro Ala Trp Arg Leu Asp Leu Leu Gly Gly Thr Leu Asp Arg
        4930                4935                4940

Leu Ala Leu Leu Pro Asn Ala Asp Ala Ala Val Pro Leu Ala Pro Gly
4945                4950                4955                4960

Gln Val Arg Ile Ala Val Arg Ala Ala Gly Leu Asn Phe Arg Asp Val
        4965                4970                4975

Val Val Ala Leu Gly Met Val Thr Asp Thr Arg Pro Pro Gly Gly Glu
        4980                4985                4990

Gly Ala Gly Ile Val Val Glu Val Gly Pro Asp Val Pro Glu Leu Val
        4995                5000                5005

Pro Gly Asp Arg Val Met Gly Leu Phe Gly Gly Thr Gly Pro Ile
        5010                5015                5020

Thr Val Ala Asp His Arg Leu Leu Ala Pro Ile Pro Thr Gly Trp Thr
5025                5030                5035                5040

Tyr Ala Gln Ala Ala Ala Val Pro Val Val Phe Leu Thr Ala Tyr Tyr
        5045                5050                5055

Gly Leu Ala Asp Leu Gly Gly Leu Arg Ala Gly Glu Ser Leu Leu Val
        5060                5065                5070

His Ala Ala Thr Gly Gly Val Gly Met Ala Ala Val Gln Leu Ala Arg
        5075                5080                5085

His Trp Asn Val Glu Val Phe Gly Thr Ala Ser Pro Gly Lys Trp Ala
        5090                5095                5100

Thr Leu Arg Gly Gln Gly Val Asp Asp Ala His Leu Ala Ser Ser Arg
5105                5110                5115                5120

Asp Leu Asp Phe Ala His Arg Phe Gly Glu Val Asp Val Val Leu Asn
        5125                5130                5135

Ser Leu Ala His Glu Phe Val Asp Ala Ser Leu Arg Leu Leu Ala Pro
        5140                5145                5150

Gly Gly Arg Phe Leu Glu Met Gly Lys Thr Asp Ile Arg Asp Arg Asp
        5155                5160                5165

Glu Val Leu Ala Ala His Pro Gly Arg Asp Tyr Arg Ala Phe Asp Leu
        5170                5175                5180

Met Asp Ala Gly Pro Glu Arg Ile Arg Glu Met Leu Ala Asp Leu Tyr
5185                5190                5195                5200

Arg Leu Phe Glu Thr Gly Val Leu His Pro Leu Pro Val Thr Pro Trp
        5205                5210                5215

Asp Val Arg Gly Ala Val Gly Ala Phe Arg His Leu Ser Gln Ala Arg
        5220                5225                5230

His Thr Gly Lys Ile Val Leu Thr Leu Pro Pro Thr Leu Gly Ala Ala
        5235                5240                5245
```

-continued

```
Pro Asp Pro Glu Gly Thr Val Leu Ile Thr Gly Gly Thr Gly Thr Leu
    5250                5255                5260
Gly Gly Leu Leu Ala Arg His Leu Val Arg Thr Ala Gly Val Arg His
5265            5270                5275                5280
Leu Leu Leu Ile Gly Arg Gly Pro Ala Ala Asp Gly Ala Ala Glu
                5285                5290                5295
Leu Ser Ala Glu Leu Thr Ala Leu Gly Ala Arg Val Thr Ile Ala Ala
            5300                5305                5310
Cys Asp Ala Ala Asp Arg Ala Ala Leu Ala Ala Leu Leu Ala Asp Ile
        5315                5320                5325
Pro Ala Glu His Ala Leu Thr Ser Val Ile His Ala Ala Gly Val Ile
    5330                5335                5340
Asp Asp Ala Ala Leu Thr Ala Leu Thr Pro Glu Arg Leu Asp Arg Val
5345                5350                5355                5360
Leu Arg Pro Lys Leu His Ala Ala Trp Asn Leu His Glu Leu Thr Arg
                5365                5370                5375
Asp Leu Asp Leu Ala Glu Phe Val Leu Phe Ser Ser Met Ala Gly Thr
            5380                5385                5390
Phe Gly Gly Ala Gly Gln Ala Asn Tyr Ala Ala Ala Asn Ala Phe Leu
        5395                5400                5405
Asp Ala Leu Ala Gln His Arg Arg Ala Arg Gly Leu Ala Ala Thr Ala
    5410                5415                5420
Ala Ala Trp Gly Leu Trp Ala Gln Ala Ser Gly Met Thr Gly His Leu
5425                5430                5435                5440
Gly Ala Glu Asp Leu Asp Arg Ile Ala Arg Thr Gly Val Ala Ala Leu
                5445                5450                5455
Glu Thr Ala His Ala Leu Thr Leu Tyr Asp Ala Leu Arg Ala Ala Asp
            5460                5465                5470
Arg Pro Thr Ile Val Pro Ala Arg Leu Asp Pro Asp Ala Leu Arg Ala
        5475                5480                5485
Ala Ala Pro Thr Val Pro Ala Leu Leu Arg Asp Leu Val Arg Asp Leu
    5490                5495                5500
Val Arg Pro Arg Gly Arg Arg Ala Ala Ala Asp Thr Ala Pro Asp Ala
5505                5510                5515                5520
Ala Ser Leu Ala Glu Arg Leu Ala Arg Leu Pro Glu Glu Arg Arg Arg
                5525                5530                5535
Gln Thr Leu Leu Thr Leu Val Arg Thr Glu Thr Ala Ala Val Leu Gly
            5540                5545                5550
His Ala Thr Pro Asp Ala Val Ala Pro Leu Arg Pro Phe Lys Ala Leu
        5555                5560                5565
Gly Phe Asp Ser Leu Thr Ser Val Glu Leu Arg Asn Arg Ile Gly Ala
    5570                5575                5580
Ala Thr Gly Leu Arg Leu Pro Val Thr Leu Val Phe Asp His Pro Thr
5585                5590                5595                5600
Pro Gln Ala Leu Ala Asp His Val Gly Ala Glu Leu Leu Gly Val Ala
                5605                5610                5615
Pro Val Val Val Glu Pro Glu Arg Pro Ala Ala His Thr Asp Asp Asp
            5620                5625                5630
Pro Ile Val Ile Val Ser Val Gly Cys Arg Tyr Pro Gly Gly Val Ala
        5635                5640                5645
Gly Gln Asp Glu Met Trp Arg Met Leu Ala Glu Gly Thr Asp Thr Ile
    5650                5655                5660
Gly Pro Phe Pro Gln Asp Arg Gly Trp Glu Leu Asp Thr Leu Phe Asp
```

-continued

```
             5665                5670                5675                5680
Pro Asp Pro Asp Arg Val Gly Lys Ser Tyr Val Arg Glu Gly Gly Phe
                 5685                5690                5695
Val Ala Asp Ala Val His Phe Asp Ala Glu Phe Phe Gly Ile Ser Pro
                 5700                5705                5710
Arg Glu Ala Thr Ser Met Asp Pro Gln Gln Arg Leu Leu Leu Glu Thr
                 5715                5720                5725
Ala Trp Glu Thr Phe Glu Gln Ala Gly Ile Asp Pro Thr Thr Leu Arg
                 5730                5735                5740
Gly Ser Gly Thr Gly Val Phe Val Gly Ala Met Ala Gln Asp Tyr His
5745                5750                5755                5760
Gly Thr Ser Gln Ala Met Ala Glu Gly Gln Glu Gly Tyr Leu Leu Thr
                 5765                5770                5775
Gly Thr Ala Thr Ser Val Ile Ser Gly Arg Val Ser Tyr Val Leu Gly
                 5780                5785                5790
Leu Glu Gly Pro Ala Val Thr Val Asp Thr Ala Cys Ser Ser Ser Leu
                 5795                5800                5805
Val Ala Leu His Leu Ala Ala Asn Ala Leu Arg Ala Gly Glu Cys Asp
                 5810                5815                5820
Leu Ala Leu Ala Gly Gly Val Ala Val Leu Thr Ser Pro Gln Ala Phe
5825                5830                5835                5840
Ile Glu Phe Ser Arg Gln Arg Gly Leu Ala Ala Asp Gly Arg Cys Lys
                 5845                5850                5855
Pro Phe Ala Ala Ala Asn Gly Thr Gly Trp Gly Glu Gly Val Gly
                 5860                5865                5870
Leu Val Leu Val Glu Arg Leu Ser Asp Ala Arg Arg Gly His Pro
                 5875                5880                5885
Val Leu Ala Val Arg Gly Ser Ala Val Asn Gln Asp Gly Ala Ser
                 5890                5895                5900
Asn Gly Leu Thr Ala Pro Asn Gly Pro Ser Gln Gln Arg Val Ile Arg
5905                5910                5915                5920
Gln Ala Leu Arg Asn Ala Gly Leu Leu Ala Thr Asp Val Asp Ala Val
                 5925                5930                5935
Glu Ala His Gly Thr Gly Thr Thr Leu Gly Asp Pro Ile Glu Ala Gln
                 5940                5945                5950
Ala Leu Leu Ala Thr Tyr Gly Gln Asp Arg Pro Ala Gln Arg Pro Leu
                 5955                5960                5965
Trp Leu Gly Ser Val Lys Ser Asn Ile Gly His Thr Gln Ala Ala Ala
                 5970                5975                5980
Gly Val Ala Gly Val Ile Lys Met Val Leu Ala Leu Arg His Gly Thr
5985                5990                5995                6000
Leu Pro Pro Thr Leu His Val Asp Ala Pro Thr Pro His Val Asp Trp
                 6005                6010                6015
Ala Ser Gly Gln Val Arg Leu Leu Thr Glu Pro Val Ala Trp Pro Ala
                 6020                6025                6030
Gly Glu Arg Val Arg Arg Ala Gly Ile Ser Ser Phe Gly Val Ser Gly
                 6035                6040                6045
Thr Asn Ala His Val Ile Ile Glu Gln Ala Pro Ala Glu Gly Ala Val
                 6050                6055                6060
Asp Ala Ala Pro Val Asp Ala Ala Pro Ala Ala Leu Gly Gly Ile
6065                6070                6075                6080
Val Pro Trp Val Val Ser Ala Arg Ser Gln Ala Gly Leu Arg Ala Gln
                 6085                6090                6095
```

-continued

Ala Ala Arg Leu Arg Asp Trp Ala Ala Val His Pro Glu Phe Ala Pro
            6100                6105                6110

Ala Asp Val Ala Ala Ser Leu Val Arg Gly Arg Ala Val Phe Glu Arg
            6115                6120                6125

Arg Ala Val Val Arg Gly Arg Asp Thr Asp Glu Leu Val Ala Ala Leu
            6130                6135                6140

Ala Glu Leu Val Asp Ser Ser Ala Thr Gly Glu Ala Pro Thr Ala Ile
6145                6150                6155                6160

Gly Pro Gly Pro Val Phe Val Phe Pro Gly Gln Gly Ser Gln Trp Val
            6165                6170                6175

Gly Met Ala Ala Glu Leu Leu Thr Cys Cys Pro Val Phe Ala Glu Thr
            6180                6185                6190

Val Thr Gln Cys Ala Glu Val Met Asp Pro Leu Leu Pro Gly Trp Ala
            6195                6200                6205

Leu Leu Asp Val Leu Arg Gly Thr Asp Glu Thr Ala Glu Leu Leu
            6210                6215                6220

Arg Arg Val Glu Val Val Gln Pro Val Leu Phe Ala Val Met Val Gly
6225                6230                6235                6240

Leu Ala Arg Trp Trp Glu Ser Cys Gly Val Arg Pro Ala Ala Val Ile
            6245                6250                6255

Gly His Ser Gln Gly Glu Ile Ala Ala Tyr Ile Ala Gly His Leu
            6260                6265                6270

Thr Leu Pro Asp Ala Ala Arg Ile Ala Ala Leu Arg Ile Arg Ala Val
            6275                6280                6285

Gln Ala Ala Asp Met Ile Arg Gly Ala Met Val Ala Val Ala Val Ser
6290                6295                6300

Ala Leu Arg Ala Glu Glu Leu Ile Thr Arg Thr Gly Thr Gly Asp Leu
6305                6310                6315                6320

Val Asn Val Gly Gly Ile Asn Ser Pro Thr Asn Thr Val Leu Ser Gly
            6325                6330                6335

Asp Thr Asp Ala Leu Ala Leu Ile Val Ala Asp Cys Glu Arg Glu Gly
            6340                6345                6350

Val Arg Ala Arg Trp Ile Pro Ala Ala Tyr Ser Ser His Ser Pro Gln
            6355                6360                6365

Met Asp Ala Val Arg Gly Asp Leu Glu Arg Leu Leu Ala Gly Ile Gln
            6370                6375                6380

Pro Thr Pro Gly Arg Val Pro Met Tyr Ser Thr Val Thr Gly Gly Arg
6385                6390                6395                6400

Leu Ala Asp Asp Ala Leu Leu Asp Ile Asp Tyr Trp Phe Glu Asn Met
            6405                6410                6415

Arg Arg Thr Val Arg Phe Glu Glu Ala Ile Gly Ala Ala Ala Ala Asp
            6420                6425                6430

Gly His Thr Val Phe Leu Glu Cys Ser Ser His Pro Gly Leu Val Val
            6435                6440                6445

Pro Leu Gly Asp Thr Leu Asp Ser Leu Gly Val His Gly Ala Thr Leu
            6450                6455                6460

Glu Thr Leu Arg Arg Ala Asp Gly Gly Ala Asp Arg Leu Leu Ala Ala
6465                6470                6475                6480

Leu Ser Ala Met Phe Val His Gly Gly Ala Val Asp Trp Ala Gly Leu
            6485                6490                6495

Leu Pro Gly Arg Arg Val Ala Leu Pro Thr Tyr Ala Phe Gln Arg Arg
            6500                6505                6510

-continued

```
Arg His Trp Val Glu Pro Val Gly Pro Ala Arg Gly Val Gly Trp
         6515                6520                6525
Gly Gln Phe Ala Val Glu His Pro Ile Leu Gly Ala Gly Val Asp Leu
         6530                6535                6540
Ala Asp Gly Ser Ala Thr Val Phe Thr Gly Arg Leu Asp Thr Thr
6545                6550                6555                6560
His Gly Trp Leu Ala Asp His Leu Val Leu Gly Glu Val Leu Val Pro
         6565                6570                6575
Gly Thr Val Phe Val Asp Leu Ala Leu Arg Ala Gly Gly Ala Leu Gly
         6580                6585                6590
Cys Ala Val Val Glu Leu Ala Leu His Glu Pro Leu Val Leu Pro
         6595                6600                6605
Asp Ala Asp Gly Val Arg Ile Gln Val Thr Val Glu Ala Pro Asp Asp
         6610                6615                6620
Ala Gly Thr Arg Ala Leu Thr Ile His Ser Arg Pro Glu Asp Ala Pro
6625                6630                6635                6640
Ala Ala Glu Pro Trp Thr Arg His Ala Ser Gly Thr Val Ala Pro Gly
         6645                6650                6655
Ala His Arg Pro Gln Gln Glu Ser Gly Pro Trp Pro Pro Ile Gly Ala
         6660                6665                6670
Thr Pro Leu Asp Val Ala Asp Val Tyr Leu Arg Leu Thr Glu Leu Gly
         6675                6680                6685
Leu Gly Tyr Gly Pro Thr Leu Ala Gly Leu Arg Ala Ala Trp Arg Arg
         6690                6695                6700
Gly Asp Asp Leu Phe Ala Glu Val Ala Arg Thr Ala Asp Gly Glu Arg
6705                6710                6715                6720
Gly Thr Ala Arg Phe Gly Leu His Pro Ala Leu Leu Asp Ala Ala Leu
         6725                6730                6735
His Gly Leu Ala Pro Gly Ser Ala Pro Gly Gly Ala Pro Thr Glu Val
         6740                6745                6750
Arg Leu Ala Gly Ala Trp Arg Gly Val Thr Leu Gly Gly Asp Ala Gly
         6755                6760                6765
Thr Ala Gly Arg Ile Arg Leu Arg Gly Val Asp Gly Asp Gly Val Glu
         6770                6775                6780
Val Glu Leu Ala Asp Glu Ala Gly Arg Ser Met Ala Arg Ile Glu Ser
6785                6790                6795                6800
Val Ala Leu Arg Pro Trp Ser Ala Gly Gln Val Arg Ala Ala Gly Arg
         6805                6810                6815
Ala Arg Pro Trp Leu Thr Arg Trp Glu Trp Ala Arg Val Glu Pro Thr
         6820                6825                6830
Asp Pro Ala Ala Ala Gly Gly Arg Trp Ala Val Leu Gly Ala Arg Ala
         6835                6840                6845
Trp Asp Gly Val Pro Ala Tyr Ala Thr Ala Ala Glu Leu Ile Ala Ala
         6850                6855                6860
Val Glu Val Gly Val Pro Val Pro Asp Leu Val Ala Leu Pro Val Arg
6865                6870                6875                6880
Ile Asp Pro Ala Gly Gly Leu Asp Pro Glu Ala Ile Arg Ala Thr Ile
         6885                6890                6895
Arg Ala Val Arg Glu Thr Leu Arg Gln Trp Arg Ala Glu Pro Arg Leu
         6900                6905                6910
Ala Ala Ser Arg Leu Val Val Val Thr His Asp Ala Val Ser Ala Arg
         6915                6920                6925
Pro Glu Asp Arg Val Thr Asp Pro Gly Ala Ala Ala Val Trp Gly Val
```

```
              6930                6935                6940
Val Arg Ala Ala Arg Ala Ala Asp Pro Glu Arg Phe Val Leu Ala Asp
6945                6950                6955                6960

Val Asp Gly Glu Asp Gly Ser Trp Pro Val Leu Leu Ala Glu Ala Ser
                6965                6970                6975

Ala Gly Arg Ala Glu Phe Ala Ile Arg Ala Gly Thr Val Leu Leu Pro
                6980                6985                6990

Gly Leu Ala Arg Val Pro Ala Gly Glu Thr Gly Thr Ala Gly Phe Pro
            6995                7000                7005

Thr Asp Gly Thr Val Leu Val Thr Val Ala Thr Asp Pro Thr Asp Pro
        7010                7015                7020

Thr Asp Gly Thr Asp Pro Val Gly Thr Leu Leu Ala Arg His Leu Val
7025                7030                7035                7040

Thr Ala His Gly Val Arg Arg Leu Ile Leu Ala Gly Gly Pro Ala Ala
                7045                7050                7055

Gly Met Pro Leu Ala Arg Glu Leu Ala Ala Gln Gly Ala Glu Ile His
                7060                7065                7070

Val Val Val Cys Asp Val Thr Asp Arg Thr Glu Leu Ala Lys Leu Leu
        7075                7080                7085

Ala Thr Ile Pro Glu His Ser Pro Leu Thr Ala Val Val His Thr Ala
        7090                7095                7100

Gly Leu Gly Arg Ser His Thr Glu Ala Met Leu Arg Ala Arg Val Asp
7105                7110                7115                7120

Ala Ala Val His Leu His Glu Leu Thr Arg Asp Ala Asp Leu Ser Ala
                7125                7130                7135

Phe Val Leu Cys Thr Ala Leu Asp Gly Val Leu Ala Asp Pro Gly Arg
                7140                7145                7150

Gly Glu His Ala Ala Gly Asp Ala Phe Leu Asp Ala Leu Ala Arg His
            7155                7160                7165

Arg His Ala Ala Gly Leu Pro Ala Leu Ala Leu Ala Trp Ala Pro Gly
        7170                7175                7180

Ala Glu Pro Val Ala Gly Leu Leu Pro Leu Pro Gly Glu Gln Ala Thr
7185                7190                7195                7200

Val Leu Phe Asp Arg Ala Leu Gly Leu Pro Glu Pro Ala Leu Ile Pro
                7205                7210                7215

Leu Ala Pro Asp Thr Ser Ala Leu Arg Arg Ala Glu Pro Gly Ala Leu
                7220                7225                7230

Pro Ala Leu Leu Thr Thr Leu Val Ala Asp Pro Asn His Arg Val Gly
            7235                7240                7245

Ala Ala Ala Glu Ala Ala Pro Ala Leu Ile Gly Arg Leu Leu Asp Leu
            7250                7255                7260

Pro Asp Asp Glu Arg Glu Ser Val Leu Val Asp Leu Val Arg Gly Cys
7265                7270                7275                7280

Ala Ala Ala Ile Leu Gly His Ala Asp Pro Thr Ala Ile Glu Thr Gly
                7285                7290                7295

Ala Ala Phe Lys Asp Leu Gly Phe Asp Ser Leu Thr Ala Leu Glu Met
                7300                7305                7310

Arg Asn Arg Leu Arg Ala Ala Leu Gly Leu Thr Leu Pro Ala Thr Leu
            7315                7320                7325

Ile Phe Ser His Pro Asn Ala Ala Ala Leu Gly Arg His Leu His Gly
            7330                7335                7340

Leu Leu Arg Arg Glu His Gly Val Ser Trp Asp Ser Val Leu Gly Glu
7345                7350                7355                7360
```

```
Ile Asp Arg Val Glu Ala Met Leu Ala Gln Leu Asp Ala Asp Arg
            7365                7370                7375

Ala Arg Ala Thr Glu Arg Leu Arg Asp Leu Ile Gly Gly Pro Glu Ala
            7380                7385                7390

Pro Leu Ala Gly Arg Glu Ser Gly Ala Asn Gly Asp Ala Ala Gly Gly
            7395                7400                7405

Arg Gly Phe Asp Ala Ala Thr Asp Glu Glu Leu Phe Asp Phe Ile Asp
    7410                7415                7420

Gly Gly Ile Glu His
7425

<210> SEQ ID NO 6
<211> LENGTH: 3415
<212> TYPE: PRT
<213> ORGANISM: Streptomyces sp. ATCC 39366

<400> SEQUENCE: 6

Met Ala Asn Glu Asp Lys Leu Arg Asp Tyr Leu Arg Arg Ala Thr Thr
1               5                   10                  15

Glu Leu Gln Glu Thr Arg Leu Arg Leu Arg Glu Thr Glu Asp Lys Trp
            20                  25                  30

His Glu Pro Leu Ala Ile Val Gly Met His Cys Arg Tyr Pro Gly Gly
        35                  40                  45

Val Ala Ser Pro Asp Asp Leu Trp Asp Leu Val Asp Ala Gly Thr Asp
    50                  55                  60

Ala Ile Thr Gly Leu Pro Pro Gly Arg Gly Trp Glu Val Asp Glu Ala
65                  70                  75                  80

Ala Asn Gly Thr Ser Tyr Arg Gly Gly Phe Leu Thr Asp Ala Ala Asp
            85                  90                  95

Phe Asp Ala Asp Phe Phe Gly Ile Ser Pro Arg Glu Ala Leu Ala Met
            100                 105                 110

Asp Pro Gln Gln Arg Val Leu Leu Glu Ala Ser Trp Thr Val Phe Glu
        115                 120                 125

His Ala Gly Ile Asp Pro Thr Thr Leu Arg Gly Ser Arg Thr Gly Val
    130                 135                 140

Phe Val Gly Val Ile Ala Ser Asp Tyr Leu Ser Arg Leu Ala Arg Val
145                 150                 155                 160

Pro Lys Glu Val Glu Gly His Leu Leu Thr Gly Ser Leu Val Ser Val
            165                 170                 175

Ala Ser Gly Arg Leu Ala Tyr His Phe Gly Leu Glu Gly Ala Ala Val
            180                 185                 190

Thr Val Asp Thr Ala Cys Ser Ser Leu Val Ala Val His Leu Ala
        195                 200                 205

Gly Gln Ala Leu Arg Ala Gly Glu Cys Asp Leu Ala Leu Val Gly Gly
    210                 215                 220

Ala Thr Val Leu Ala Thr Pro Gly Ala Phe Asp Glu Phe Ser Arg Gln
225                 230                 235                 240

Gln Gly Leu Ala Gly Asp Gly Arg Cys Lys Ser Phe Ala Ala Gly Ala
            245                 250                 255

Asp Gly Thr Gly Trp Ser Glu Gly Val Gly Leu Leu Met Glu Arg
            260                 265                 270

Leu Ser Asp Ala Arg Arg Asn Gly His Arg Val Leu Ala Val Val Arg
        275                 280                 285

Gly Ser Ala Val Asn Gln Asp Gly Ala Ser Asn Gly Leu Thr Ala Pro
```

```
                290                  295                  300
Asn Asp Leu Ala Gln Glu Arg Val Ile Arg Gln Ala Leu Ala Asn Ala
305                 310                 315                 320

Arg Leu Ala Ala Ser Asp Val Asp Ala Val Glu Ala His Gly Thr Gly
                325                 330                 335

Thr Arg Leu Gly Asp Pro Ile Glu Ala Gln Ala Leu Leu Ala Thr Tyr
                340                 345                 350

Gly Gln Asn Arg Pro Ala Ala Arg Pro Leu Arg Leu Gly Ser Ile Lys
                355                 360                 365

Ser Asn Ile Gly His Ala Gln Ala Ala Gly Val Ala Gly Val Ile
370                 375                 380

Lys Met Val Gln Ala Leu Arg His Gly Val Leu Pro Arg Thr Leu His
385                 390                 395                 400

Val Asp Glu Pro Thr Pro His Val Asp Trp Ser Ala Gly Arg Val Ala
                405                 410                 415

Leu Leu Thr Glu Pro Met Ala Trp Pro Ala Gly Glu Arg Val Arg Arg
                420                 425                 430

Ala Gly Val Ser Ser Phe Gly Val Ser Gly Thr Asn Ala His Val Ile
                435                 440                 445

Val Glu Glu Ala Pro Pro Val Glu Pro Val Gly Ala Ala Asp Pro
450                 455                 460

Ala Arg Pro Leu Gly Val Val Thr Pro Trp Val Ser Ala Arg Thr
465                 470                 475                 480

Glu Asp Gly Leu Arg Ala Gln Val Glu Arg Leu Arg Glu Trp Ala Ile
                485                 490                 495

Glu His Pro Glu Ala Asp Pro Ala Asp Val Gly Arg Ser Leu Ala Ser
                500                 505                 510

Gly Arg Ala Leu Ser Gly His Arg Ala Val Val Leu Gly Arg Asp Ala
                515                 520                 525

Ala Glu Leu Val Glu Gly Leu Ser Val Val Val Asp Gly Glu Pro Glu
                530                 535                 540

Ala Ile Val Gly Glu Ala Arg Arg Gly Ser Gly Arg Thr Ala Val Leu
545                 550                 555                 560

Phe Thr Gly Gln Gly Val Arg Ser Arg Gly Met Ala Arg Glu Leu His
                565                 570                 575

Ala Ala Phe Pro Val Phe Ala Ala Ala Leu Asp Glu Val Cys Ala Ala
                580                 585                 590

Phe Asp Ala Val Leu Pro Phe Ser Val Arg Asp Val Leu Leu Ala Glu
                595                 600                 605

Gly Glu Gly Gly Gly Ala Asp Gly Asp Gly Gly Glu Asp Thr Gly Val
610                 615                 620

Ala Gln Pro Ala Leu Phe Ala Tyr Glu Val Ala Leu Tyr Arg Leu Trp
625                 630                 635                 640

Thr Ser Trp Ala Ala Ala Pro Asp Ala Val Ala Gly His Ser Leu Gly
                645                 650                 655

Glu Val Val Ala Ala Tyr Val Ala Gly Val Phe Ser Leu Ala Asp Ala
                660                 665                 670

Thr Thr Phe Val Ala Ala Arg Ala Thr Leu Met Ser Ala Leu Pro Pro
                675                 680                 685

Gly Gly Ala Met Val Ala Val Gly Thr Ser Glu Ser Ala Ala Arg
690                 695                 700

Leu Leu Ala Asp His Pro Gly Val Gly Ile Ala Ala Val Asn Gly Pro
705                 710                 715                 720
```

-continued

Thr Gly Val Val Leu Ser Gly Glu Ala Ala Val Ala Glu Val Ala
                725                 730                 735

Arg Val Cys Ala Glu Arg Gly Leu Arg Ile Ser Arg Leu Arg Val Ser
                740                 745                 750

His Ala Phe His Ser Ala Leu Met Glu Pro Met Leu Asp Glu Leu Ala
                755                 760                 765

Glu Val Val Ser Gly Leu Thr Leu Arg Pro Ala Arg Met Ala Ile Gly
        770                 775                 780

Ser Asn Val Thr Gly Arg Ile Gly Ser Ala Glu Gln Leu Cys Asp Pro
785                 790                 795                 800

Arg Tyr Trp Val Asp His Val Arg Ala Val Arg Phe Gly Asp Val
                805                 810                 815

Leu Asp Ala Leu Arg Ala Asp Gly Val Arg Thr Phe Val Glu Ile Gly
                820                 825                 830

Pro Asp Ala Ala Leu Thr Pro Met Val Ala Asp Val Thr Ala Asp Ala
                835                 840                 845

Asp Asp Val Val Ala Val Ala Thr Arg Arg Asp Arg Asp Pro Val
850                 855                 860

Thr Gly Val Val Glu Ala Leu Ala Arg Val Phe Val Arg Gly Ala Val
865                 870                 875                 880

Val Asp Trp Ala Ala Leu Val Pro Gly Arg Trp Val Glu Leu Pro Thr
                885                 890                 895

Tyr Ala Phe Thr Arg Arg Arg Phe Trp Leu Asp Ala Gly Thr Gly Ala
                900                 905                 910

Gly Asp Pro Thr Gly Leu Gly Gln Gly Thr Val Asp His Pro Leu Leu
        915                 920                 925

Gly Ala Val Gly Leu Ala Asp Gly His Gly Ser Leu Phe Thr Gly
        930                 935                 940

Arg Leu Ser Leu Asp Thr His Pro Trp Leu Ala Asp His Val Val Leu
945                 950                 955                 960

Asp Thr Val Leu Leu Pro Gly Thr Ala Phe Leu Glu Leu Ala Leu His
                965                 970                 975

Thr Gly Arg Arg Val Gly Cys Asp Arg Val Glu Glu Leu Ser Leu Glu
                980                 985                 990

Thr Pro Leu Ala Phe Gly Glu Arg Gly Cys Gln Val Gln Val Trp
        995                 1000                1005

Ile Glu Ala Ala Gly Pro Asp Glu Arg Arg Ala Ile Thr Ile His
        1010                1015                1020

Ser Arg Pro Asp Asp Gly Asp Gly Asp Glu Gly Trp Ile Arg Asn Ala
1025                1030                1035                1040

Val Gly Thr Val Ala Pro Val Glu Asp Lys Ala Pro Ala Asp Ala Val
                1045                1050                1055

Ala Asp Pro Thr Pro Trp Pro Pro Thr Gly Ala Thr Pro Val Pro Ile
                1060                1065                1070

Asp Asp Phe Tyr Pro Trp Leu Ala Asp Asn Gly Val Ala Tyr Gly Pro
        1075                1080                1085

Cys Phe Arg Ala Val Arg Ala Val Trp Arg Arg Gly Glu Glu Ile Phe
        1090                1095                1100

Gly Glu Ile Ala Leu Pro Glu Gln Val Gly Tyr Glu Ala Asp Arg Phe
1105                1110                1115                1120

Gly Val His Pro Ala Leu Met Asp Ala Thr Gln His Leu Leu Gly Val
                1125                1130                1135

```
Ala Ala Phe Ala Asp Pro Ala Glu Ser Glu Gly Gly Leu Ala Leu
            1140                1145                1150

Pro Phe Ser Trp Arg Glu Val Arg Leu His Thr Pro Gly Ala Ala Ser
        1155                1160                1165

Val Arg Ala Arg Val Val Arg Thr Gly Pro Glu Ser Val Thr Leu Ser
    1170                1175                1180

Leu Ala Asp Glu Asp Gly Arg Pro Val Ala Glu Val Glu Ser Leu Ala
1185                1190                1195                1200

Val Arg Pro Ile Ser Ala Glu Gln Leu Arg Thr Ser Thr Ala Gly Arg
            1205                1210                1215

Arg Asp Pro Leu Tyr Thr Leu Arg Trp Thr Pro Leu Pro Arg Pro Ser
        1220                1225                1230

Ala Ala Pro Gly Ile Gly Ser Pro Ala Ile Ala Asp Ser Gly Ser
            1235                1240                1245

Gly Asp Pro Phe Ala Gly Arg Leu Gly Gly Thr Val His Pro Asp Leu
    1250                1255                1260

Thr Ala Leu Ala Asp Ala Val Asp Ala Gly Leu Pro Thr Pro Glu Val
1265                1270                1275                1280

Val Val Leu Ala Trp Pro Thr Ile Pro Ala Gly Pro Leu Gly Asp Val
            1285                1290                1295

Pro Asp Pro Asp Asp Val His Ala Ala Val His Arg Ala Leu Ala Thr
        1300                1305                1310

Val Gln Thr Trp Leu Gly Asp Glu Arg Phe Thr Gly Ala Arg Leu Val
    1315                1320                1325

Val Val Thr Arg Gly Ala Val Ala Val Ala Asp Glu Glu Val Arg Asp
    1330                1335                1340

Pro Ala Ala Ala Val Gly Gly Leu Val Arg Ser Ala Gln Ser Glu
1345                1350                1355                1360

His Pro Asp Arg Leu Val Leu Val Asp Leu Asp Glu Asp Ala Ala Ser
        1365                1370                1375

Pro Gly Ala Leu Pro Ala Ala Ile Gly Ala Gly Glu Pro Gln Leu Ala
    1380                1385                1390

Val Arg Ala Gly Val Ala Tyr Leu Pro Arg Leu Thr Arg Thr Pro Ala
    1395                1400                1405

Ile Glu Pro Ser Thr Pro Leu Phe Ala Pro Asp Gly Thr Thr Leu Val
    1410                1415                1420

Thr Gly Gly Thr Gly Ala Leu Gly Ala Leu Val Ala Arg His Leu Val
1425                1430                1435                1440

Val Ala His Gly Val Arg Arg Leu Leu Leu Val Ser Arg Arg Gly Ile
            1445                1450                1455

Ala Ala Pro Gly Ala Gly Ser Leu Ala Ala Glu Leu Thr Gly Leu Gly
            1460                1465                1470

Ala Thr Val Asp Val Val Ala Cys Asp Val Ser Asp Arg Ala Asp Leu
    1475                1480                1485

Ala Lys Lys Leu Ala Ala Ile Pro Ser Ala His Pro Leu Ser Ala Val
    1490                1495                1500

Val His Val Ala Gly Val Val Asp Asp Gly Val Ile Gly Ala Leu Thr
1505                1510                1515                1520

Pro Glu Arg Val Asp Arg Val Leu Arg Pro Lys Val Asp Ala Ala Leu
            1525                1530                1535

His Leu His Glu Leu Thr Arg Asp Ala Asp Leu Thr Ala Phe Val Leu
        1540                1545                1550

Phe Ser Ser Val Ala Gly Val Ile Gly Ser Leu Gly Gln Ala Asn Tyr
```

-continued

```
            1555                1560                1565
Ala Ala Gly Asn Ala Phe Leu Asp Ala Phe Ala Gln Arg Arg Arg Ala
1570                1575                1580

Leu Gly Leu Pro Ala Val Ser Met Ala Trp Gly Leu Trp Ala Glu Glu
1585                1590                1595                1600

Ser Gly Leu Met Arg Glu Glu Phe Ala Glu Thr Asp Arg Gln Arg Ile
                1605                1610                1615

Asn Arg Ser Gly Val Leu Pro Leu Ser Asp Glu Gln Gly Leu Ala Leu
                1620                1625                1630

Phe Asp Ala Ala Leu Ala His Gly Glu Pro Ile Leu Ala Pro Val Arg
                1635                1640                1645

Leu Asp Leu Ser Ala Leu Arg Arg Leu Glu Asp Glu Leu Pro Ala Ile
                1650                1655                1660

Leu Gly Gly Leu Val Pro Thr Ser Arg Arg Asp Gly Ala Arg Pro Gly
1665                1670                1675                1680

Ala Ala Asp Thr Arg Arg Leu Ala Gln Arg Leu Ala Gly Arg Ser Glu
                1685                1690                1695

Pro Glu Gln Leu Arg Leu Leu Thr Glu Leu Thr Arg Ala Gln Ala Ala
                1700                1705                1710

Val Val Leu Gly His Ala Gly Ala Asp Ala Val Ala Ala Asp Arg Ala
                1715                1720                1725

Phe Thr Glu Leu Gly Phe Asp Ser Leu Thr Ala Leu Glu Met Arg Asn
                1730                1735                1740

Arg Leu Asn Thr Val Thr Gly Leu Arg Leu Pro Ala Thr Val Leu Phe
1745                1750                1755                1760

Asp Tyr Pro Asn Ala Ala Ala Leu Ala Arg Phe Leu Arg Ala Glu Thr
                1765                1770                1775

Leu Arg Val Pro Gln Tyr Thr Gln Ala Ala Ala Asn Thr Ala Ala Lys
                1780                1785                1790

Ala Arg Thr Ser Asp Glu Pro Ile Ala Ile Val Ala Met Ser Cys Arg
                1795                1800                1805

Tyr Pro Gly Gly Ile Asp Thr Pro Glu Glu Leu Trp Arg Cys Val Ala
                1810                1815                1820

Gly Gly Val Asp Leu Thr Ser Pro Phe Pro Thr Asp Arg Gly Trp Asp
1825                1830                1835                1840

Leu Gly Ala Leu Tyr Asp Pro Asp Pro Asp Arg Ser Gly Arg Cys Tyr
                1845                1850                1855

Thr Arg Glu Gly Ser Phe Met Arg Asp Ile Asp Arg Phe Asp Ala Glu
                1860                1865                1870

Leu Phe Gly Ile Ser Pro Arg Glu Ala Leu Ala Met Asp Pro Gln Gln
                1875                1880                1885

Arg Leu Leu Leu Glu Thr Ser Trp Glu Ala Phe Glu Arg Ala Gly Ile
                1890                1895                1900

Asp Pro Ser Ser Leu Arg Gly Ser Asn Thr Ala Val Phe Ala Gly Leu
1905                1910                1915                1920

Met Tyr Ala Asp Tyr Ala Ala Gly Arg Val Gly Asp Val Gly Asp Glu
                1925                1930                1935

Leu Glu Ala Tyr Ile Gly Asn Gly Asn Ser Phe Gly Val Ala Ser Gly
                1940                1945                1950

Arg Val Ala Tyr Thr Leu Gly Leu Glu Gly Pro Ala Val Thr Val Asp
                1955                1960                1965

Ser Ala Cys Ser Ser Ser Leu Val Ala Leu His Trp Ala Ala His Ala
                1970                1975                1980
```

```
Leu Arg Ser Gly Glu Cys Asp Leu Ala Leu Ala Gly Ala Thr Val
1985                1990                1995                2000

Met Ser Thr Pro Ser Val Phe Val Glu Phe Ala Arg Gln Arg Gly Leu
            2005                2010                2015

Ala Pro Asp Gly Arg Cys Lys Ser Phe Ala Ala Ala Asp Gly Thr
            2020                2025                2030

Ala Trp Gly Glu Gly Ile Gly Met Leu Leu Val Glu Arg Leu Ala Asp
            2035                2040                2045

Ala Arg Arg Asn Gly His Pro Val Leu Ala Val Leu Arg Gly Ser Ala
            2050                2055                2060

Ile Asn Gln Asp Gly Ala Ser Asn Gly Leu Thr Ala Pro Asn Gly Pro
2065                2070                2075                2080

Ser Gln Gln Arg Val Ile Arg Gln Ala Leu Ala Asn Ala Gly Leu Ala
                2085                2090                2095

Thr Ala Asp Val Asp Ala Val Glu Ala His Gly Thr Gly Thr Val Leu
            2100                2105                2110

Gly Asp Pro Ile Glu Ala Gln Ala Leu Leu Ala Thr Tyr Gly Arg Asp
            2115                2120                2125

Arg Pro Ala Glu Arg Pro Leu Trp Leu Gly Ser Ile Lys Ser Asn Phe
            2130                2135           2140

Gly His Thr Gln Ala Ala Ala Gly Val Ala Gly Val Ile Lys Met Val
2145                2150                2155                2160

Met Ala Met Arg His Gly Met Leu Pro Pro Thr Leu His Val Asp Glu
            2165                2170                2175

Pro Ser Pro His Val Asp Trp Ser Thr Gly Arg Val Glu Leu Leu Ala
            2180                2185                2190

Glu Gly Arg Pro Trp Pro Glu Val Gly Arg Ala Arg Arg Val Ala Val
            2195                2200                2205

Ser Ser Phe Gly Ile Ser Gly Thr Asn Ala His Val Ile Leu Glu Gln
            2210                2215                2220

Ala Asp Glu Glu Pro Glu Pro Ala Ala Arg Thr Thr Ser Gly Thr Gly
2225                2230                2235                2240

Ile Gly Gly Val Leu Pro Trp Val Leu Ser Ala Arg Thr Glu Ala Gly
                2245                2250                2255

Val Arg Ala Gln Ala Ala Arg Leu Arg Asp Trp Ala Gly Ala Arg Pro
            2260                2265                2270

Glu Val Asp Pro Ala Asp Val Gly Trp Ser Leu Ala Ser Gly Arg Ser
            2275                2280                2285

Val Phe Glu Arg Arg Ala Val Val Trp Gly Arg Asp Gly Ala Glu Leu
            2290                2295                2300

Thr Ala Gly Leu Asp Ala Leu Ala Ala Gly Arg Asp Ala Gly Ala Arg
2305                2310                2315                2320

Ala Val Leu Ala Gly Gly Thr Gly Val Ser Gly Glu Ala Ala Val Gly
            2325                2330                2335

Pro Val Phe Val Phe Pro Gly Gln Gly Ser Gln Trp Val Gly Met Ala
            2340                2345                2350

Ala Glu Leu Leu Thr Cys Cys Pro Val Phe Ala Glu Ser Val Ala Glu
            2355                2360                2365

Cys Ala Ala Ala Met Asp Pro Leu Leu Ala Asp Trp Ala Leu Leu Asp
            2370                2375                2380

Val Leu Arg Asp Ala Ser Ala Ala Leu Leu Glu Arg Val Asp Val Ile
2385                2390                2395                2400
```

```
Gln Pro Val Leu Phe Ala Val Met Val Gly Leu Ala Arg Trp Trp Glu
            2405                2410                2415

Ser Cys Gly Val Arg Pro Ser Ala Val Ile Gly His Ser Gln Gly Glu
            2420                2425                2430

Ile Ala Ala Ala His Val Ala Gly Phe Leu Ser Leu Glu Asp Ala Val
            2435                2440                2445

Arg Ile Val Val Leu Arg Ser Arg Ala Leu Arg Gly Leu Ala Ala Asp
            2450                2455                2460

Gly Asp Gly Met Leu Ser Val Gly Val Ser Ala Glu Arg Gly Arg Glu
2465                2470                2475                2480

Leu Val Ala Arg Val Gln Gly Leu Ser Leu Ala Ala Val Asn Gly Pro
            2485                2490                2495

Asp Ser Val Val Leu Ser Gly Pro Val Glu Gly Leu Thr Pro Ile Ala
            2500                2505                2510

Ala Ala Cys Glu Arg Asp Gly Val Arg Ala Arg Trp Ile Pro Val Asp
            2515                2520                2525

Tyr Ala Ser His Ser Ala Arg Met Asp Asp Val Arg Glu Val Leu Ala
            2530                2535                2540

Glu Ser Leu Ala Gly Val Glu Pro Gly Ile Gly Arg Val Pro Met Tyr
2545                2550                2555                2560

Ser Thr Val Ser Gly Leu Lys Val Thr Asp Ala Ala Asp Leu Gly Gly
            2565                2570                2575

Glu Tyr Trp Phe Glu Asn Leu Arg Arg Thr Val Gln Leu Ala Thr Ala
            2580                2585                2590

Val Gly Ala Ala Ala Ala Asp Gly His Ser Val Phe Val Glu Cys Ser
            2595                2600                2605

Pro His Pro Gly Leu Val Val Pro Leu Gly Asp Thr Leu Asp Ala Leu
            2610                2615                2620

Gly Ser Thr Ser Gly Thr Val Leu Glu Thr Leu Arg Arg Gly Glu Gly
2625                2630                2635                2640

Gly Pro Glu Arg Leu Val Ala Leu Ala Ala Ala Phe Val Ser Gly
            2645                2650                2655

Leu Pro Val Asp Trp Ala Gly Leu Leu His His Asp Gly Val Arg Arg
            2660                2665                2670

Val Gln Leu Pro Thr Tyr Ala Phe Gln Gly Arg Arg Phe Trp Leu Glu
            2675                2680                2685

Pro Asp Met Gly Thr Ala Leu Pro Gly Arg Thr Thr Pro Thr Pro Val
            2690                2695                2700

Val Gly Asp Thr Glu Asp Ser Arg Leu Trp Glu Ala Leu Glu Ala Ala
2705                2710                2715                2720

Gly Ala Glu Asp Leu Ala Ala Glu Leu Glu Val Ala Ala Asp Ala Pro
            2725                2730                2735

Leu Ser Asp Val Leu Pro Ala Leu Thr Ser Trp Arg Ala Arg Arg Arg
            2740                2745                2750

Ala Asp Ala Thr Val Arg Ser Trp Arg Tyr Gly Val Arg Trp Glu Pro
            2755                2760                2765

Trp Ala Ala Pro Ala Ala Ser Ala Asp Arg Met Gly Arg Leu Leu Leu
            2770                2775                2780

Val Ala Pro Asp Gly Glu Ile Gly Asp Val Leu Ala Gly Ala Leu Ala
2785                2790                2795                2800

Glu Cys Gly Ala Glu Val Val Val Leu Ser Ala Glu Gly Glu Arg Thr
            2805                2810                2815

Ala Leu Ala Arg Arg Leu Ala Ala Ile Gly Glu Glu Gly Val Pro Ala
```

-continued

```
                2820                2825                2830
Gly Val Val Ser Leu Ser Ala Val Gly Cys Ala Ala Asp Ala Asp Pro
            2835                2840                2845
Val Pro Ala Leu Ala Pro Val Leu Thr Leu Val Gln Ala Leu Gly Asp
        2850                2855                2860
Ala Gly Met Glu Ala Pro Leu Trp Val Leu Thr Arg Gly Ala Val Ser
2865                2870                2875                2880
Val Leu Gly Glu Glu Pro Thr Gly Pro Ala Gly Ala Val Gln Gly
                2885                2890                2895
Leu Gly Arg Val Val Gly Leu Glu His Pro Gly Arg Trp Gly Gly Leu
            2900                2905                2910
Ile Asp Leu Pro Gln Val Val Asp Gly Arg Val Ala Glu Thr Leu Ala
        2915                2920                2925
Gly Ile Leu Ala Ala Gly Ala Gly Thr Gly Ser Gly Glu Asp Glu
            2930                2935                2940
Ile Ala Ile Arg Pro Leu Gly Val Phe Val Arg Arg Leu Ala Arg Met
2945                2950                2955                2960
Ala Gly Pro Glu Gly Ser Gly Thr Ser Arg Trp Arg Pro Gly Gly Thr
                2965                2970                2975
Ala Leu Val Thr Gly Gly Thr Gly Ala Leu Gly Gly Arg Val Ala Arg
                2980                2985                2990
Trp Leu Val Arg Glu Gly Val Glu Arg Val Val Leu Ala Gly Arg Arg
            2995                3000                3005
Gly Pro Asp Ala Pro Gly Ala Asp Arg Leu Arg Glu Glu Leu Ala Ala
        3010                3015                3020
Ala Gly Ala Glu Val Ala Val Leu Ala Cys Asp Leu Gly Asp Arg Asp
3025                3030                3035                3040
Ala Val Ala Ala Leu Leu Ala Glu Val Arg Ala Gly Arg Gly Arg Ile
                3045                3050                3055
Asp Thr Val Val His Ala Ala Gly Ala Val Val Gly Pro Leu Ala
            3060                3065                3070
Asp Ser Thr Val Ala Asp Leu Ala Asp Ala Ser Ala Ala Lys Val Gly
            3075                3080                3085
Gly Ala Leu Leu Leu Asp Glu Leu Leu Arg Ala Asp Glu Pro Asp Thr
        3090                3095                3100
Val Val Leu Phe Ser Ser Ala Ala Gly Val Trp Gly Gly Ala Gly Gln
3105                3110                3115                3120
Gly Ala Tyr Ala Ala Ala Asn Ala Cys Leu Asp Thr Ile Ala Glu Arg
            3125                3130                3135
Arg Arg Ala Arg Gly Leu Arg Thr Val Ser Ile Ala Trp Gly Gln Trp
            3140                3145                3150
Ala Gly Gly Gly Met Ala Asp Gly Ala Ala Gly Ala His Leu Asp Arg
            3155                3160                3165
Ile Gly Val Pro Ala Met Asp Pro Asp Arg Ala Leu Glu Ala Leu Arg
            3170                3175                3180
Gln Ala Leu Asp Glu Asp Leu Thr Cys Val Thr Val Ala Asp Val Asp
3185                3190                3195                3200
Trp Pro Arg Phe Ala Ala Gly Tyr Thr Ala Ala Arg Pro Arg Pro Leu
                3205                3210                3215
Ile Ala Asp Leu Val Ala Ala Glu Val Ala Ala Ala Pro Val Thr Glu
            3220                3225                3230
Ala Arg Gly Ala Gly Glu Pro Asp Gly Pro Ser Val Trp Arg Ala Arg
            3235                3240                3245
```

```
Leu Ala Glu Leu Gly Ala Ala Asp Arg Glu Ala Glu Leu Ala Leu
    3250                3255                3260

Val Arg Thr Glu Val Ala Ala Gln Leu Gly His Ala Asp Pro Ala Ala
3265                3270                3275                3280

Ile Glu Pro Glu Arg Pro Phe Arg Asp Leu Gly Phe Asp Ser Leu Ala
                3285                3290                3295

Ala Val Gly Leu Arg Asn Arg Leu Thr Glu Thr Ile Gly Leu Arg Leu
            3300                3305                3310

Pro Ser Thr Leu Val Phe Asp His Pro Thr Ala Val Ala Leu Ala Ala
        3315                3320                3325

His Ile Asp Gly Glu Leu Phe Ala Glu Thr Val Gly Thr Val Ser Val
    3330                3335                3340

Phe Ala Glu Leu Asp Arg Leu Glu Ala Ala Leu Gly Glu Leu Gly Gly
3345                3350                3355                3360

Asp Phe Ala Glu Arg Gly Arg Val Gly Ala Arg Leu Ala Glu Leu Ala
                3365                3370                3375

Gly Lys Trp Arg Glu Ile Glu Ala Ala Ser Gln Lys Ala Glu Pro Glu
            3380                3385                3390

Gly Ala Asp Phe Ala Ala Ala Glu Asp Glu Met Phe Asp Met Leu
        3395                3400                3405

Gly Lys Glu Phe Gly Ile Ser
    3410                3415

<210> SEQ ID NO 7
<211> LENGTH: 1976
<212> TYPE: PRT
<213> ORGANISM: Streptomyces sp. ATCC 39366

<400> SEQUENCE: 7

Met Ala Gly Asp Arg Gly Arg Glu Pro Lys Gly Arg Ala Arg Gly Ser
1               5                   10                  15

Arg Leu Arg Gly Ser Gly Gly Arg Gly Asp Val Arg His Ala Arg Lys
            20                  25                  30

Gly Val Arg His Leu Leu Ser Gly Ala Gly Asp Asp Arg Ser Arg
        35                  40                  45

Val Pro Thr Ala His Gly Ser Ile Arg Phe Asp Gln Ala Glu Asp Gly
    50                  55                  60

Arg Thr Asp Met Ser Asn Glu Glu Arg Leu Arg His Phe Leu Arg Glu
65                  70                  75                  80

Thr Ala Thr Asp Leu Arg Arg Thr Lys Gln Arg Leu His Glu Val Glu
                85                  90                  95

Ser Ala Ala Arg Glu Pro Val Ala Ile Val Ala Ile Gly Cys Arg Leu
            100                 105                 110

Pro Gly Gly Val Arg Ser Ala Glu Asp Leu Trp Glu Leu Val Arg Thr
        115                 120                 125

Gly Thr Asp Ala Ile Ala Gly Phe Pro Ser Asp Arg Gly Trp Asp Pro
    130                 135                 140

Ala Asn Val Tyr Ala Asp Leu Pro Gly Gly Glu Val Ser Gly Gly
145                 150                 155                 160

Ser Ala Gly Ser Gly Gly Ser Thr Thr Arg Gln Gly Gly Phe Val Tyr
                165                 170                 175

Asp Ala Ala Ala Phe Asp Ala Glu Phe Phe Gly Val Ser Pro His Glu
            180                 185                 190

Ala Leu Ala Met Asp Pro Gln Gln Arg Leu Leu Leu Glu Thr Ala Trp
```

-continued

```
              195                 200                 205
Glu Thr Phe Glu Arg Ala Gly Ile Asp Pro Leu Ser Met Arg Arg Ser
    210                 215                 220

Arg Thr Gly Val Phe Val Gly Ala Gly Ala Leu Gly Tyr Gly Gly Gly
225                 230                 235                 240

Met Arg Ala Asp Asn Ala Glu Ile Gln Ala His Arg Val Thr Gly Gly
                245                 250                 255

Ser Met Ser Val Val Ser Gly Arg Ile Ala Tyr Thr Leu Gly Leu Glu
            260                 265                 270

Gly Pro Ala Val Thr Leu Asp Thr Ala Cys Ser Ser Leu Val Ala
        275                 280                 285

Leu His Leu Ala Ala Asn Ala Leu Arg Ser Gly Glu Cys Asp Leu Ala
    290                 295                 300

Leu Ala Gly Gly Val Thr Val Met Ala Arg Pro Thr Ala Phe Val Glu
305                 310                 315                 320

Phe Ser Arg Gln Gly Gly Leu Ala Ser Asp Gly Arg Cys Arg Ser Phe
                325                 330                 335

Ala Ala Ala Ala Asp Gly Thr Gly Trp Gly Glu Gly Val Gly Leu Leu
            340                 345                 350

Leu Val Glu Arg Leu Ser Asp Ala Arg Arg Asn Gly His Pro Val Leu
        355                 360                 365

Ala Val Leu Arg Gly Ser Ala Val Asn Gln Asp Gly Ala Ser Asn Gly
    370                 375                 380

Leu Thr Ala Pro Asn Gly Pro Ser Gln Gln Arg Val Ile Arg Gln Ala
385                 390                 395                 400

Leu Ala Ala Ala Gly Leu Ser Ala Ala Asp Val Asp Ala Val Glu Ala
                405                 410                 415

His Gly Thr Gly Thr Val Leu Gly Asp Pro Ile Glu Ala His Ala Leu
            420                 425                 430

Leu Ala Thr Tyr Gly Arg Asp Arg Pro Ala Asp Arg Pro Leu Trp Leu
        435                 440                 445

Gly Ser Val Lys Ser Asn Ile Gly His Thr Gln Ser Ala Ala Gly Val
    450                 455                 460

Ala Gly Val Ile Lys Met Val Met Ala Leu Arg His Gly Leu Leu Pro
465                 470                 475                 480

Arg Thr Leu His Val Asp Arg Pro Ser Pro His Val Asp Trp Ala Ser
                485                 490                 495

Gly Arg Val Glu Leu Leu Thr Asp Glu Val Pro Trp Pro Ala Gly Gly
            500                 505                 510

Arg Val Arg Arg Ala Gly Val Ser Ser Phe Gly Ile Ser Gly Thr Asn
        515                 520                 525

Ala His Val Val Leu Glu Glu Ala Pro Ala Val Glu Gly Ala Ser Gly
    530                 535                 540

Glu Gly Ala Glu Pro Ala Pro Gly Val Gly Gly Leu Ile Pro Trp Val
545                 550                 555                 560

Val Ser Ala Arg Ser Pro Glu Ala Leu Arg Ala Gln Ala Ala Arg Leu
                565                 570                 575

Arg Glu Pro Ala Val Ala Asp Pro Ala Asp Val Gly Arg Ser Leu Val
            580                 585                 590

Thr Gly Arg Ala Leu Leu Asp His Arg Ala Val Val Leu Gly Arg Asp
        595                 600                 605

Ala Ala Glu Leu Gly Arg Gly Leu Ala Ala Leu Ala Ala Gly Ser Pro
    610                 615                 620
```

```
Gly Ala Val Glu Pro Ser Glu Gly Gly Thr Pro Val Val Thr Gly
625                 630                 635                 640

Asn Val Pro Arg Ala Gly Ala Gly Gly Arg Val Ala Gly Arg Gly
                645                 650                 655

Ala Val Val Phe Thr Gly Gln Gly Gly Arg Leu Pro Gly Ile Gly Arg
                660                 665                 670

Glu Leu Tyr Ala Gly Phe Pro Val Phe Ala Arg Ala Leu Asp Glu Val
            675                 680                 685

Gly Ala Ala Phe Asp Ala Val Pro Phe Ser Val Arg Asp Val Leu
        690                 695                 700

Leu Gly Val Glu Gly Thr Val Gly Val Asp Ala Asp Thr Gly Val
705                 710                 715                 720

Ala Gln Pro Val Leu Phe Ala Phe Glu Val Ala Leu Tyr Arg Leu Trp
                725                 730                 735

Ser Ser Leu Gly Ser Val Pro Asp Phe Val Val Gly His Ser Leu Gly
            740                 745                 750

Gly Ile Val Ala Ala His Val Ala Gly Val Phe Ser Leu Ala Asp Ala
        755                 760                 765

Val Ala Phe Val Ala Ala Arg Ala Arg Leu Met Ser Ala Leu Pro Gly
        770                 775                 780

Gly Gly Ala Met Leu Ala Val Gly Ala Ser Glu Ala Gln Val Thr Ala
785                 790                 795                 800

Leu Ser Asp Gly Leu Pro Val Ser Ile Ala Ala Val Asn Gly Pro Ala
                805                 810                 815

Ser Val Val Ser Gly Ala Val Ala Ala Val Asp Glu Val Ala Ala
            820                 825                 830

Arg Cys Ala Ala Arg Ser Trp Arg Ser Ser Arg Leu Arg Val Ser His
        835                 840                 845

Ala Phe His Ser Val Leu Met Glu Pro Met Leu Ala Glu Leu Arg Asp
        850                 855                 860

Val Leu Arg Arg Leu Ser Phe Gly Ala Pro Glu Ile Gly Leu Val Ser
865                 870                 875                 880

Asp Thr Thr Gly Arg Val Val Thr Ala Glu Glu Val Gly Asp Pro Glu
                885                 890                 895

Tyr Trp Val Arg His Val Arg Asp Ala Val Arg Phe Ala Asp Ala Val
            900                 905                 910

Gly Thr Leu Arg Glu Arg Gly Val Ala Thr Phe Val Glu Leu Gly Pro
        915                 920                 925

Asp Ala Ala Leu Thr Ala Met Val Ala Glu Cys Thr Ala Gly Val Gly
        930                 935                 940

Glu Val Leu Gly Val Pro Ala Gln Arg Arg Gly Arg Pro Ala Val Ala
945                 950                 955                 960

Thr Leu Ala Gly Ala Leu Ala Thr Ala Phe Val Arg Gly Leu Pro Val
                965                 970                 975

Asp Trp Val Gly Ala Leu Gly Pro Gly Gly Arg Val Glu Leu
            980                 985                 990

Pro Thr Tyr Ala Phe Gln Gly Arg Arg Tyr Trp Leu Glu Pro Gly Lys
        995                 1000                1005

Ala Ser Val Thr Pro Ala Gly Pro Asp Ser Val Asp Gly Pro Leu Trp
        1010                1015                1020

Asp Ala Val Glu Arg Ala Gly Ala Gly Glu Leu Ala Ala Ile Leu Ala
1025                1030                1035                1040
```

-continued

Val Ser Glu Asp Ala Thr Leu Arg Glu Val Pro Ala Leu Ser Ser
            1045                1050            1055

Trp Arg Ala Arg Arg Val Asp Ala Thr Ala Ala Ser Trp Arg Tyr
        1060            1065            1070

Ala Val Arg Trp Glu Pro Trp Ala Gly Ser Ser Asp Ala Ala Ala
        1075            1080            1085

Leu Ser Gly Arg Trp Leu Leu Val His Pro Ala Ala Ser Glu Leu Ala
        1090            1095            1100

Asp Ala Val Ala Arg Glu Leu Thr Glu Arg Gly Ala Glu Val Val Arg
1105            1110            1115            1120

Val Gly Gly Glu Gly Ile Gly Ser His Val Gly Ala Glu Pro Val Ala
            1125            1130            1135

Gly Val Val Ser Leu Ile Gly Ser Gly Ser Gly Ser Thr Ser
            1140            1145            1150

Gly Ser Gly Ser Gly Ser Gly Ser Ala Ser Gly Ser Gly Ser
            1155            1160            1165

Gly Ser Gly Ser Gly Ser Gly Ser Ser Cys Gly Ser Gly Ser
            1170            1175            1180

Val Pro Gly Leu Gly Ser Cys Ala Gly Asp Asp Cys Ala Asp Leu Val
1185            1190            1195            1200

Ala Ala Val Val Ala Met Gly Glu Leu Leu Ala Glu Leu Arg Arg Phe
            1205            1210            1215

Glu Val Ala Ala Pro Leu Trp Cys Val Thr Arg Ala Ala Val Ser Val
            1220            1225            1230

Leu Gly Glu Asp Leu Ala Asn Pro Val Gly Ala Gly Leu Trp Gly Arg
            1235            1240            1245

Gly Leu Val Ala Ser Leu Glu Gln Pro Gly Cys Trp Gly Gly Leu Val
            1250            1255            1260

Asp Leu Pro Ala Val Ala Asp Thr Arg Ala Leu Gly Val Leu Ala Thr
1265            1270            1275            1280

Ile Leu Ala Gly Thr Ser Asp Glu Asp Gln Phe Ala Ile Arg Pro Leu
            1285            1290            1295

Gly Val Phe Thr Arg Arg Leu Thr Pro Leu Pro Ala Glu Gly Ser Gly
            1300            1305            1310

Arg Val Val Arg Thr Arg Glu Ala Ala Leu Ile Thr Gly Gly Thr Gly
            1315            1320            1325

Val Leu Gly Ala His Ala Ala Arg Trp Leu Val Ala His Gly Thr Glu
            1330            1335            1340

Arg Val Ile Leu Leu Gly Arg Arg Gly Ala Arg Ala Pro Gly Phe Asp
1345            1350            1355            1360

Ala Leu Arg Ala Asp Leu Glu Ala Gly Ala Glu Val Val Ala Ile
            1365            1370            1375

Ala Cys Asp Leu Thr Ala Pro Asp Ala Ala Glu Arg Leu Arg Ala Ala
            1380            1385            1390

Leu Pro Ala Thr Gly Ala Pro Ile Arg Thr Val Val His Ala Ala Gly
            1395            1400            1405

Val Pro Gly Ser Pro Thr Ala Thr Gly Ala Asp Ala Val Ala Asp Thr
            1410            1415            1420

Val Thr Ala Lys Val Ala Gly Ala Leu Ala Leu Asp Thr Leu Phe Gly
1425            1430            1435            1440

Ala Asp Arg Ala Leu Asp Ala Phe Val Leu Tyr Ser Ser Gly Ala Gly
            1445            1450            1455

Val Trp Gly Gly Ala Gly Gln Gly Ala Tyr Ala Ala Ala Asn Ala Phe

-continued

```
              1460                1465                1470
Leu Asp Ala Leu Ala Val Arg Arg Gln Arg Gly Leu Pro Ala Thr
        1475                1480                1485
Ala Ile Ala Trp Gly Pro Trp Ala Ala Gly Gly Met Ala Asp Gly Glu
        1490                1495                1500
Gly Glu Arg Leu Leu Ala Arg Val Gly Val Arg Ala Met Asp Pro Ala
1505                1510                1515                1520
Ala Ala Leu Ala Ala Leu Gly Arg Ala Leu Val Glu Asp Leu Thr Cys
                1525                1530                1535
Val Thr Val Ala Asp Leu Asp Arg Pro Arg Phe Ala Ala Gly Tyr Thr
            1540                1545                1550
Ser Ala Arg Pro Arg Pro Leu Ile Ala Asp Leu Ile Asp Ala Glu Pro
            1555                1560                1565
Pro Thr Ala Thr Ala Pro Pro Thr Arg Pro Gly Gly Val Trp Asp Pro
            1570                1575                1580
Ala Val Thr Arg Ser Pro Ala Arg Leu Ala Ala Glu Leu Leu Asp Leu
1585                1590                1595                1600
Val Arg Ala Glu Val Ala Ala Gln Leu Gly His Ala Gly Val Glu Ala
                1605                1610                1615
Ile Glu Pro Asp Arg Pro Phe Arg Asp Leu Gly Phe Asp Ser Leu Ala
            1620                1625                1630
Ala Val Gly Leu Arg Asn Arg Ile Ala Glu Ala Thr Gly Val His Leu
            1635                1640                1645
Ala Gly Thr Leu Ile Tyr Asp His Glu Thr Pro Ala Ala Leu Ala Ala
            1650                1655                1660
His Leu Ala Asp Ala Leu Arg Glu Gly Val Pro Glu Thr Arg Pro Ala
1665                1670                1675                1680
Pro Thr Ala Pro Gly Gly Ala Glu Asp Ser Asn Asp Met Leu Gly Thr
            1685                1690                1695
Val Tyr Arg Lys Leu Ala Leu Leu Gly Arg Met Asp Asp Ala Glu Ser
                1700                1705                1710
Leu Leu Val Gly Ala Ala Gly Leu Arg Gln Thr Phe Glu Asp Pro Asn
            1715                1720                1725
Arg Leu Pro Lys Thr Pro Gly Phe Thr Arg Leu Ala Arg Gly Pro Ala
        1730                1735                1740
Arg Pro Arg Val Ile Cys Phe Pro Pro Phe Ala Pro Val Glu Gly Ala
1745                1750                1755                1760
Ile Gln Phe Gly Arg Leu Ala Gly Thr Phe Glu Gly Arg His Asp Thr
                1765                1770                1775
Ala Val Val Thr Val Pro Gly Phe Arg Pro Gly Glu Pro Leu Ala Ala
                1780                1785                1790
Ser Leu Asp Val Leu Asp Leu Leu Ala Asp Ala Thr Leu Arg Cys
        1795                1800                1805
Ala Gly Asp Asp Pro Phe Ala Val Leu Gly Tyr Ser Ser Gly Trp
        1810                1815                1820
Leu Ala Gln Gly Val Ala Gly Arg Leu Glu Ala Thr Gly Arg Thr Pro
1825                1830                1835                1840
Ala Gly Val Val Leu Leu Asp Thr Tyr Leu Pro Ala Thr Met Ser Arg
                1845                1850                1855
Arg Met Arg Lys Ala Met Asn Tyr Glu Val Ile Val Arg Arg Gln Ala
                1860                1865                1870
Phe Thr Ala Leu Asp Tyr Ile Gly Leu Thr Ala Ile Gly Thr Tyr Arg
            1875                1880                1885
```

-continued

```
Arg Met Phe Arg Gly Trp Glu Pro Lys Pro Gly Ser Ala Pro Thr Leu
        1890                1895                1900

Val Val Arg Pro Ser Arg Cys Val Pro Gly Ser Pro Glu Pro Met
1905                1910                1915                1920

Thr Gly Glu Asp Trp Arg Ser Thr Trp Pro Tyr Glu His Thr Ala Ala
                    1925                1930                1935

Glu Val Glu Gly Asp His Cys Thr Met Ile Gly Glu His Ala Glu Gln
            1940                1945                1950

Thr Gly Ala Val Val Arg Ala Trp Leu Ala Gly Asp Arg Thr Val Ser
        1955                1960                1965

Ile Asp Thr Arg Glu Gly Thr Ala
    1970                1975

<210> SEQ ID NO 8
<211> LENGTH: 392
<212> TYPE: PRT
<213> ORGANISM: Streptomyces sp. ATCC 39366

<400> SEQUENCE: 8

Met Ile Pro Val Leu Glu Leu Val Gln Ile Ser Thr Leu Pro Asp Ala
1               5                   10                  15

Glu Arg Glu Leu Glu Gln Leu Ala Arg Arg Tyr Pro Ile Ile Arg Thr
            20                  25                  30

Arg Gln Val Gly Gly Ile Glu Ala Trp Thr Val Leu Gly Ala Gly Leu
        35                  40                  45

Thr Arg Gln Leu Leu Gly Asp Pro Arg Leu Ser Asn Asp Leu His Thr
    50                  55                  60

His Ala Pro His Ala Ala Gln Ser Ala Asp Gly Pro Thr Val Leu Phe
65                  70                  75                  80

Glu Gln Asp Asn Pro Asp His Ala Arg Tyr Arg Arg Leu Val Ser Ala
                85                  90                  95

Ala Phe Ala Ser Arg Ala Val Arg Asn Leu Glu Pro Arg Ile Val Asp
            100                 105                 110

Ile Ala Arg Ala Leu Leu Asp Arg Leu Pro Ala Glu Gly Gly Thr Val
        115                 120                 125

Asp Ile Val Glu Ala Phe Ala Asn Pro Phe Pro Leu Glu Val Ile Cys
130                 135                 140

Glu Leu Leu Gly Val Pro Met Ala Asp Arg Glu Val Phe Arg Thr Arg
145                 150                 155                 160

Val Glu Asn Met Asp Ser Pro Ser Thr Ala Val Arg Arg Ala Ala Met
                165                 170                 175

Asp Ala Phe Val Ala Tyr Cys Ala Asn Leu Val Asp Ala Lys Arg Thr
            180                 185                 190

Glu Pro Thr Glu Asp Leu Leu Ser Glu Leu Val Gln Ala Glu Leu Asp
        195                 200                 205

Asp Gly Ser Arg Leu Ser Ala Asn Glu Leu Ile Gly Phe Gly Ser Val
    210                 215                 220

Leu Leu Phe Ala Gly His Val Thr Thr Ala Tyr Leu Ile Ala Ala Ala
225                 230                 235                 240

Leu Tyr Glu Leu Ile Thr His Asn Asp Gln Leu Ala Ala Leu Arg Ala
                245                 250                 255

Asp Pro Thr Leu Val Glu Gly Thr Val Glu Glu Ala Leu Arg Phe Arg
            260                 265                 270

Gly Ser Leu Leu Ser Thr Thr Asn Arg Val Ala Leu Thr Asp Leu Glu
```

```
                275             280             285
Ile Gly Gly Val Leu Val Arg Arg Gly Asp Leu Val Arg Phe Leu Leu
    290             295             300

Ser Ala Ala Asn Arg Asp Pro Ala Ile Arg Glu Asp Pro His Thr Phe
305             310             315             320

Asp Ile Thr Arg Ser Thr Thr Ala His Leu Gly Phe Gly His Gly Pro
                325             330             335

His Phe Cys Leu Gly Gln Arg Leu Ala Arg Gln Glu Ile Lys Val Ala
            340             345             350

Leu Thr Glu Ile Val Thr Arg Phe Pro Thr Leu Glu Leu Ala Val Pro
        355             360             365

Ala Glu Lys Leu Arg Trp Arg Ala Ser Asp Phe Leu Arg Gly Leu Ala
370             375             380

Glu Leu Pro Leu Thr Tyr Ala Pro
385             390

<210> SEQ ID NO 9
<211> LENGTH: 146
<212> TYPE: PRT
<213> ORGANISM: Streptomyces sp. ATCC 39366

<400> SEQUENCE: 9

Met Arg Glu Arg Lys Lys Ala Arg Thr Arg Gln Val Ile Ser Thr Val
1               5                   10                  15

Ala Phe Asp Leu Phe Glu Glu Gln Gly Phe Glu Gln Thr Thr Val Asp
            20                  25                  30

Met Ile Cys Arg Arg His Ala Met Thr Val Ser His Gly Asn Leu Glu
        35                  40                  45

Asp His Ala Glu Gln Thr Ala Arg Arg His Ala Leu Arg Arg Arg Phe
    50                  55                  60

Leu Gly Val Arg Ser Val His Asp His Gly Val Ala Leu Ile Asp Thr
65                  70                  75                  80

Val Ala His Arg Ile Val Thr Thr Ala Ala Arg Leu Gly Val Asp
                85                  90                  95

Pro Ala Val Asp Leu Arg Pro His Ala Leu Gly Ala Leu Val Ala Ala
            100                 105                 110

Met Thr Arg Arg Val Val Ile Asp Asp Ile Ala Pro Gly Pro Ile Asn
        115                 120                 125

Glu Trp Ala Glu Ala Phe Arg Thr Leu Leu Pro Thr Pro Ala Ala His
    130                 135                 140

Thr Asp
145

<210> SEQ ID NO 10
<211> LENGTH: 22
<212> TYPE: DNA
<213> ORGANISM: Artificial Sequence
<220> FEATURE:
<223> OTHER INFORMATION: PCR primer

<400> SEQUENCE: 10
cataatacga ctcactatag gg                                        22

<210> SEQ ID NO 11
<211> LENGTH: 18
<212> TYPE: DNA
<213> ORGANISM: Artificial Sequence
<220> FEATURE:
```

-continued

| |
|---|
| <223> OTHER INFORMATION: PCR primer |
| <400> SEQUENCE: 11 |
| ttccccgaaa agtgccac    18 |

BIOSYNTHETIC GENE CLUSTER FOR LEPTOMYCINS

CROSS REFERENCE TO RELATED APPLICATIONS

This application claims benefit under 35 U.S.C. §119 to U.S. provisional applications No. 60/502,423 (filed 11 Sep. 2003) and No. 60/553,384 (filed 15 Mar. 2004), the entire contents of both prior applications being incorporated herein by reference.

STATEMENT OF GOVERNMENT INTEREST

This invention was made with Government support under Grant No. 1 R43 CA108372-01 awarded by the National Institutes of Health. The Government has certain rights in this invention.

FIELD OF THE INVENTION

This invention relates to materials and methods for biosynthesis of leptomycins, leptomycin derivatives and analogs, and other useful polyketides. The invention finds application in the fields of molecular biology, recombinant DNA technology, chemistry, human and veterinary medicine, and agriculture.

BACKGROUND OF THE INVENTION

Polyketides are complex natural products that are produced by microorganisms such as fungi and mycelial bacteria. There are about 10,000 known polyketides, from which numerous pharmaceutical products in many therapeutic areas have been derived, including: adriamycin, epothilone, erythromycin, mevacor, rapamycin, tacrolimus, tetracycline, rapamycin, and many others. However, polyketides are made in very small amounts in microorganisms and are difficult to make or modify chemically. For this and other reasons, biosynthetic methods are preferred for production of therapeutically active polyketides. See PCT publication Nos. WO 93/13663; WO 95/08548; WO 96/40968; WO 97/02358; and WO 98/27203; U.S. Pat. Nos. 4,874,748; 5,063,155; 5,098,837; 5,149,639; 5,672,491; 5,712,146 and 6,410,301; Fu et al., 1994, *Biochemistry* 33:9321-26; McDaniel et al., 1993, *Science* 262: 1546-1550; Kao et al., 1994, *Science*, 265:509-12, and Rohr, 1995, *Angew. Chem. Int. Ed. Engl.* 34: 881-88, each of which is incorporated herein by reference.

The biosynthesis of polyketides may be accomplished by heterologous expression of Type I or modular polyketide synthase enzymes (PKSs). Type I PKSs are large multifunctional protein complexes, the protein components of which are encoded by multiple open reading frames (ORF) of PKS gene clusters. Each ORF of a Type I PKS gene cluster can encode one, two, or more modules of ketosynthase activity. Each module activates and incorporates a two-carbon (ketide) unit into the polyketide backbone. Each module also contains multiple ketide-modifying enzymatic activities, or domains. The number and order of modules, and the types of ketide-modifying domains within each module, determine the structure of the resulting product. Polyketide synthesis may also involve the activity of nonribosomal peptide synthetases (NRPSs) to catalyze incorporation of an amino acid-derived building block into the polyketide, as well as post-synthesis modification, or tailoring enzymes. The modification enzymes modify the polyketide by oxidation or reduction, addition of carbohydrate groups or methyl groups, or other modifications.

In PKS polypeptides, the regions that encode enzymatic activities (domains) are separated by linker regions. These regions collectively can be considered to define boundaries of the various domains. Generally, this organization permits PKS domains of different or identical substrate specificities to be substituted (usually at the level of encoding DNA) from other PKSs by various available methodologies. Using this method, new polyketide synthases (which produce novel polyketides) can be produced. It will be recognized from the foregoing that genetic manipulation of PKS genes and heterologous expression of PKSs can be used for the efficient production of known polyketides, and for production of novel polyketides structurally related to, but distinct from, known polyketides (see references above, and Hutchinson, 1998, *Curr. Opin. Microbiol.* 1:319-29; Carreras and Santi, 1998, *Curr. Opin. Biotech.* 9:403-11; and U.S. Pat. Nos. 5,712,146 and 5,672,491, each of which is incorporated herein by reference).

One valuable class of polyketides includes the leptomycins and their analogs (FIG. 1). These compounds are selective inhibitors of protein export from the cell nucleus and thus affect the cellular location of proteins. The function of many key proteins and transcription factors involved in cell growth can be regulated by their cellular location. For instance, the tumor suppressor p53 normally resides in the cell nucleus where its activation promotes cell-cycle arrest and apoptotic cell death. Mislocation of p53 into the cytoplasm, especially its dominant negative mutant forms, is associated with development of many types of cancer. Nuclear factor kB (NFkB) is a transcriptional activator that targets genes involved in cell proliferation and apoptosis. It is constitutively activated in certain cancer cells, aiding tumor resistance to radiation and cancer chemotherapy drugs. NFkB resides in the cytoplasm in an inactive form complexed with the inhibitor of nuclear factor IkB; upon stimulation by factors such as TNF-a or CD-40 ligand, events are set in place that remove IkB and allow importation of NFkB into the cell nucleus.

Leptomycin B (LMB; also known as CI-940 or elactocin) and the ratjadones (FIG. 2) are the only known low molecular weight inhibitor of nuclear transport. Because of the structural similarities, the kazusamycins, leptofuranins and callystatins are also implicated. Callystatins come from a marine sponge whereas all the other compounds are bacterial metabolites. All of these molecules are exceptionally potent, typically displaying $IC_{50}$ values in the 100 picomolar to 10 nanomolar range.

Protein export from the cell nucleus requires a nuclear export signal (NES) as a domain in the exported protein, CRM1 (exportin-1) to recognize the NES and Ran, a Ras-like GTPase. In the nucleus CRM1 forms a complex with the NES-protein and Ran/GTP, then the complex is translocated through the nuclear pore complex into the cytoplasm. There, the Ran GTPase activating protein (RanGAP), found only in the cytoplasm, promotes hydrolysis of Ran/GTP to Ran/GDP, causing release of the NES-protein.

The high potency and novel mechanism of action prompted an investigation of the antitumor activity of LMB in mouse murine and xenograph cancer models. Activity was observed at low doses against adriamycin, amsacrine and mitoxantrone resistant P388 leukemia, other leukemias, B16 melanoma, Ridgway osteogenic and M5076 sarcomas and mammary adenocarinoma. Acute toxicity appeared to be gastrointestinal and was exacerbated upon more frequent or oral administration of the drug. The maximum tolerated dose (MTD) in mice ranged from 0.12 to 1 mg/kg, as a function of dosing schedule.

LMB has also attracted considerable interest as a biochemical tool to study the role and regulation of nucleocytoplasmic shuttling proteins and for its potential therapeutic use in combination with other drugs. Vigneri and Wang, "Induction of apoptosis in chronic myelogenous leukemia cells through nuclear entrapment of BCR-ABL tyrosine kinase," *Nature Medicine* (2001) 7:228-234, describes combined treatment of cultured CML cells with STI-571 and LMB. STI-571 effectively masks the ability of Bcr-Abl to be retained preferentially in the cytoplasm; upon nuclear importation of the drug-inactivated protein, LMB inhibits nuclear export of Bcr-Abl and withdrawal of STI-571 releases the ability of the constitutively activated Abl component to induce apoptosis. While the effect of either drug alone is fully reversible (STI-571 does not permanently inhibit Bcr-Abl and nuclear export is restored by synthesis of fresh CRM1), their combined use caused irreversible and complete killing of the Bcr-Abl transformed cells. Such treatment also preferentially eliminated mouse bone marrow cells that express Bcr-Abl. This strategy can overcome the main limitation of acute CML treatment with STI-571, which is acquired drug resistance due to mutation or overexpression of Bcr-Abl.

LMB has other types of potential therapeutic uses. Because it can promote nuclear retention of the p53 tumor suppressor protein, treatment with LMB can lead to p53 activation in the nucleus, which results in cell-cycle arrest and apoptosis. Combined use LMB and actinomycin D can reactivate p53 and prevent its degradation by HPV E6 protein in cervical carcinoma cells infected with human papillomavirus. LMB can also potentiate the effect of rapamycin, an emerging cancer drug, by blocking nuclear export of mTOR, the protein kinase target of rapamycin that controls the activity of two transcription factors. The antiviral activity of LMB has been elucidated as resulting from inhibition of the nuclear export of the HIV-1 Rev protein and Rev-dependent unspliced and partially spliced mRNA, which is an early step in viral replication. LMB interferes with cyclinB1/Cdc2, cyclinD1/CDK4 and TGF-beta dependent signaling also, suggesting possible uses against cancers with aberrant signaling involving these actors. A synthetic HIV-1 Rev inhibitor, PKF050-638 (FIG. 2), has been developed that mimics the activity of LMB.

Two limitations have to be overcome to increase the potential for development of LMB into an effective anticancer or antiviral drug. One, a reliable source of pure drug must be developed, because "The use of LMB . . . has been hampered by the variability of the quality of LMB production lots" (D. Daelemans et al. 2002, "A synthetic HIV-1 Rev inhibitor interfering with the CRM1-mediated nuclear export" *Proc. Natl. Acad. Sci. USA* 99: 14440-5). This is not surprising given the close structural similarity of leptomycin-like compounds isolated from their natural sources (FIG. 1). In fact, at least 5 different forms of leptomycins have been detected in the culture extracts of the ATCC 39366 strain and 6 forms in another LMB producer. Two, a less toxic form of LMB would be more appealing for drug development studies. Even though the drug's effects have been reported to be fully reversible, toxicity is likely to be mechanism-related and exhibited in different bodily tissues given the widespread role of CRM1-mediated protein export. The available SAR data (FIG. 2) are insufficient for designing a less toxic analog. Analog production and evaluation will require both chemical and microbiological approaches, because little effort towards the total synthesis of LMB has been reported.

The following data suggest that analogs with an acceptable therapeutic index could be found. LMB displayed an approx. 250-fold difference in activity between a Rev-dependent assay and cytotoxicity to the same cells in vitro and PKF050-638 had a 75-fold difference in the same two assays (FIG. 2). These data show that LMB itself can have a good therapeutic window in certain instances. It is thus likely that less toxic LMB analogs can be discovered as a consequence of differential binding to CRM1 or pharmacokinetic behavior that modulates their distribution, half-life or metabolism.

Given the promise of leptomycin B in the treatment of conditions and diseases characterized by undesired cellular hyperproliferation, there thus exists an unmet need for a production system that can provide large quantities of leptomycin B in a form substantially free of minor congeners and other impurities. The present invention meets this need by providing the biosynthetic genes responsible for the production of leptomycins and providing for their expression in heterologous hosts. Further, there is an unmet need for analogs of leptomycins potentially useful in the treatment of viral diseases. The present invention meets this need by providing the means for biological generation of leptomycin analogs through genetic engineering of the biosynthetic genes.

SUMMARY OF THE INVENTION

The present invention provides recombinant nucleic acids encoding polyketide synthases and polyketide modification enzymes. The recombinant nucleic acids of the invention are useful in the production of polyketides, including but not limited to leptomycin and leptomycin analogs and derivatives in recombinant host cells.

In one aspect, the invention provides the nucleic acids involved in leptomycin biosynthesis in isolated, purified, recombinant, or synthetic form, including but not limited to sequences incorporated into a vector or into the chromosome of a host cell. The biosynthesis of leptomycin is performed by a modular PKS and polyketide modification enzymes. The leptomycin polyketide synthase (herein also "leptomycin PKS" or "leptomycin synthase") is made up of several proteins, each having one or more modules. The modules have domains with specific synthetic functions.

In another aspect, the present invention provides domains and modules of the leptomycin PKS and corresponding nucleic acid sequences encoding them and/or parts thereof. Such compounds are useful in the production of hybrid PKS enzymes and the recombinant genes that encode them.

In another aspect, the present invention provides modifying genes of leptomycin biosynthetic gene cluster in recombinant form, including but not limited to isolated form and incorporated into a vector or the chromosomal DNA of a host cell. Such compounds are useful in the production of leptomycins, leptomycin analogs, and leptomycin derivatives according to the methods of the invention.

In another aspect the invention provides a recombinant PKS wherein at least 10, 15, 20, or more consecutive amino acids in one or more domains of one or more modules thereof are derived from one or more domains of one or more modules of leptomycin polyketide synthase. Preferably at least an entire domain of a module of leptomycin synthase is included. Representative leptomycin PKS domains useful in this aspect of the invention include, for example, KR, DH, ER, AT, ACP and KS domains. In one embodiment of the invention, the PKS is assembled from polypeptides encoded by DNA molecules that comprise coding sequences for PKS domains, wherein at least one encoded domain corresponds to a domain of leptomycin PKS. In such DNA molecules, the coding sequences are operably linked to control sequences so that expression therefrom in host cells is effective. In this manner, leptomycin PKS coding sequences or modules and/or domains can be made to encode PKS to biosynthesize compounds having antibiotic or other useful bioactivity other than leptomycin.

In one embodiment, the invention provides a recombinant DNA molecule that comprises a sequence encoding a chimeric polyketide synthase composed of at least a portion of the leptomycin PKS and at least a portion of a second PKS for a polyketide other than leptomycin. Such chimeric genes are useful in the production of leptomycin analogs, leptomycin derivatives, and other polyketides.

In another aspect, the present invention provides recombinant host cells that contain the nucleic acids of the invention. In one embodiment, the host cell provided by the invention is a *Streptomyces* host cell that produces a leptomycin modification enzyme and/or a domain, module, or protein of the leptomycin PKS. Methods for the genetic manipulation of *Streptomyces* are described in Kieser et al, "Practical *Streptomyces* Genetics," The John Innes Foundation, Norwich (2000), which is incorporated herein by reference in its entirety. In other embodiments, the host cells provided by the invention are eubacterial cells such as *Escherichia coli*, yeast cells such as *Saccharomyces cerevisiae*, or myxobacterial cells such as *Myxococcus xanthus*.

In another embodiment, the invention provides a recombinant *Streptomyces* host cell that produces leptomycin in its native state, wherein at least one domain-encoding region of the endogenous leptomycin PKS gene is deleted, inactivated, or replaced. Also provided is a recombinant *Streptomyces* host cell that produces leptomycin in its native state, wherein at least one polypeptide-encoding open reading frame of the leptomycin PKS gene cluster is deleted or otherwise inactivated.

In another aspect, the invention also provides methods for producing leptomycins, leptomycin analogs and derivatives, and other polyketides using the nucleic acids, proteins, vectors, and host cells of the invention.

These and other aspects of the present invention are described in more detail in the Detailed Description of the Invention, below.

BRIEF DESCRIPTION OF THE DRAWINGS

FIG. 1 shows various members of the leptomycin family of natural polyketides.

FIG. 2 shows biological activity results for several members of the leptomycin family, and the structure of ratjadone.

FIG. 3 shows the expected organization of the leptomycin PKS and a possible pathway for biosynthesis. Biosynthetic relationships of members of the leptomycin family are also indicated.

FIG. 4 shows the organization of the portion of the leptomycin biosynthetic cluster as deduced from SEQ ID NOs:1 and 2.

FIG. 5 shows the DNA sequence of the leptomycin biosynthetic gene cluster.

FIG. 6 shows SEQ ID NO: 4, the polypeptide product of lepA, a gene in the leptomycin PKS cluster.

FIG. 7 shows SEQ ID NO: 5, the polypeptide product of lepB, a gene in the leptomycin PKS cluster.

FIG. 8 shows SEQ ID NO: 6, the polypeptide product of lepC, a gene in the leptomycin PKS cluster.

FIG. 9 shows SEQ ID NO: 7, the polypeptide product of lepD, a gene in the leptomycin PKS cluster.

FIG. 10 shows SEQ ID NO: 8, the polypeptide product of lepE, a gene encoding a cytochrome P450-type oxidase.

FIG. 11 shows SEQ ID NO: 6, the polypeptide product of lepF, a gene encoding a tetR-like transcriptional regulator The following references provide background on the leptomycins and are hereby incorporated by reference:

1) Wolff B, Sanglier J J, Wang Y. Leptomycin B is an inhibitor of nuclear export: inhibition of nucleo-cytoplasmic translocation of the human immunodeficiency virus type 1 (HIV-1) Rev protein and Rev-dependent mRNA. Chem Biol. (1997) 4:139-147.

2) Lain S, Midgley C, Sparks A, Lane E B, Lane D P. An inhibitor of nuclear export activates the p53 response and induces the localization of HDM2 and p53 to U1A-positive nuclear bodies associated with the PODs. Exp Cell Res. (1999) 248:457-72

3) Hietanen S, Lain S, Krausz E, Blattner C, Lane D P. Activation of p53 in cervical carcinoma cells by small molecules. Proc Natl Acad Sci USA. (2000) 97:8501-8506.

4) Kim J E, Chen J. Cytoplasmic-nuclear shuttling of FKBP12-rapamycin-associated protein is involved in rapamycin-sensitive signaling and translation initiation. Proc Natl Acad Sci USA. (2000) 97:14340-14345.

5) Park I H, Bachmann R, Shirazi H, Chen J. Regulation of ribosomal S6 kinase 2 by mammalian target of rapamycin. J Biol. Chem. (2002) 277:31423-31429.

6) Daelemans D, Afonina E, Nilsson J, Werner G, Kjems J, De Clercq E, Pavlakis G N, Vandamme A M. A synthetic HIV-1 Rev inhibitor interfering with the CRM1-mediated nuclear export. Proc Natl Acad Sci USA. (2002) 99:14440-14445.

7) Wang, Y, Ponelle M et al., Novel leptomycins for a *Streptomyces* strain A92-308902. Inhibitors of the nucelo-cytoplasmic translocation of the HIV-1 regulatory protein Rev. Helv Chim Acta (1997) 80:2157-2167.

8) Kalesse M, M. Christmann. The chemistry and biology of the leptomycin family. Synthesis (2002) 8:981-1003.

DETAILED DESCRIPTION OF THE INVENTION

The present invention provides recombinant materials for the production of polyketides. In one aspect, the invention provides recombinant nucleic acids encoding at least one domain of a polyketide synthase required for leptomycin biosynthesis. Methods and host cells for using these genes to produce a polyketide in recombinant host cells are also provided.

The nucleotide sequences encoding leptomycin PKS domains, modules and polypeptides of the present invention were isolated from *Streptomyces* sp. ATCC 39366 as described in Example 1. Alternatively, the DNA sequences provided herein may be obtained through gene synthesis as described in U.S. Patent Application 20040166567, which is incorporated herein by reference. Given the valuable properties of leptomycin and its derivatives and analogs, means to produce useful quantities of these molecules in a highly pure form is of great potential value. The compounds produced may be used as antitumor agents or for other therapeutic uses, and/or a intermediates for further enzymatic or chemical modification, and/or as agents for in vitro inhibition of protein phosphatase. The nucleotide sequences of the leptomycin biosynthetic gene cluster encoding domains, modules and polypeptides of leptomycin synthase, and modifying enzymes, and other polypeptides can be used, for example, to make both known and novel polyketides.

In one aspect of the invention, purified and isolated DNA molecules are provided that comprise one or more coding sequences for one or more domains or modules of leptomycin synthase. Examples of such encoded domains include leptomycin synthase KR, DH, ER, AT, ACP, and KS domains. In one aspect, the invention provides DNA molecules in which sequences encoding one or more polypeptides of leptomycin synthase are operably linked to expression control sequences that are effective in suitable host cells to produce leptomycin, its analogs or derivatives, or novel polyketides.

The sequence of the leptomycin gene cluster was assembled from sequences deduced from the cosmids pKOS279-128.PF27, pKOS279-128.2L78, and pKOS279-130.PFA42. The gene cluster is found to comprise six open reading frames (ORFs), named lepA, lepB, lepC, lepD, lepE, and lepF. The polyketide synthase is encoded by lepABCD, and is comprised of eleven modules terminating in a thioesterase domain. The lepA gene encodes modules 0-4, where module 0 is the loading module; the lepB gene encodes modules 5-8; lepC encodes modules 9-10; and lepD encodes module 11 and the terminating thioesterase domain. The lepE gene encodes a cytochrome P450-type oxidase, presumably responsible for oxidation of the C24 methyl group. The lepF gene appears to be a regulatory gene.

Tables 1 and 2 provide a description of genes in the leptomycin PKS gene cluster including sequences encoding encoding modules, domains and ORFs, as deduced from two contigs assembled from sequences of pKOS279-125.2L78. The nucleotide sequences of the two contigs are provided in the attached Sequence Listing, and have been assigned SEQ ID NOS: 1 and 2, respectively.

As indicated in Table 1, the nucleic acid having SEQ ID NO:1 was found to encode portions of two ORFs. ORF1, SEQ ID NO:6, comprises nucleotides <1 to 17260 of the SEQ ID NO:1. The start of ORF1 (LepA) lies upstream of the beginning of SEQ ID NO:1. The nucleic acid encodes a polypeptide comprising a portion of module 1 (a portion of KR1 and all of ACP1), and the complete modules 2, 3, and 4 of leptomycin synthase. The sequence of ORF2 comprises nucleotides 17546 to >29467 of the SEQ ID NO:1. The end of ORF2 (LepB) lies downstream of the end of SEQ ID NO:1. The nucleic acid sequence encodes a polypeptide comprising the complete modules 5 and 6 and a portion of module 7 (the beginning of KS7) of leptomycin synthase. The modules encoded by the nucleic acid of SEQ ID NO:1 are indicated in Table 1.

Table 2 provides the ORF, module, and domain descriptions for the second contig, the nucleic acid of SEQ ID NO:2. One partial ORF has been identified, encoding a polypeptide comprising a portion of module 7 (part of AT7, and all of DH7, ER7, KR7, and ACP7) and all of module 8 of leptomycin synthase. The modules encoded by the nucleic acid of SEQ ID NO:2 and domains within each module are indicated in Table 2.

Subsequent sequencing provided the complete sequence of the leptomycin biosynthetic gene cluster, given below as SEQ ID NO:3. The PKS modules encoded by the nucleic acid of SEQ ID NO:3 and domains within each module are indicated in Table 3. The ORFs encoding the PKS have been designated LepA, LepB, LepC, and LepD. LepA comprises a loading module, referred to as "module 0," which comprises a ketosynthase domain wherein there is a glutamine in place of the expected active-site cysteine("KSq"), and thus likely funcations as a decarboxylase. LepD comprises module 11 together with a thioesterase (TE) domain.

The LepE gene, corresponding to nucleotides 64703-65881 of SEQ ID NO:3 encodes a cytochrome-P450 type oxidase. The LepF gene, corresponding to nucleotides 66124-66564 of SEQ ID NO:3 encodes a putative tetR-family transcriptional regulator.

In another aspect of the invention, the polypeptides encoded by the above-described leptomycin PKS genes are provided as LepA (FIG. 6; SEQ ID NO:4), LepB (FIG. 7; SEQ ID NO:5), LepC (FIG. 8; SEQ ID NO:6), LepD (FIG. 9; SEQ ID NO:7), LepE (FIG. 10; SEQ ID NO:8), and LepF (FIG. 11; SEQ ID NO:9). These polypeptides may be in isolated, purified, or recombinant form, either singly or present in any combination comprising each other or other polyketide synthase polypeptides.

TABLE 1

ORFs, modules, and domains of the leptomycin PKS determined from the nucleotide sequence determined from the T3-side of the insert from cosmid pKOS279-125.2L78 (SEQ ID NO: 1).

| | feature | | Nucleotide sequence location |
|---|---|---|---|
| | Contig 1 | | 1-29467 |
| ORF 1 | | | <1-17260 |
| | module 1 | | <1-661 |
| | | KR1 | <1-358 |
| | | ACP1 | 404-661 |
| | module 2 | | 722-6868 |
| | | KS2 | 722-1999 |
| | | AT2 | 2306-3352 |
| | | DH2 | 3386-3991 |
| | | ER2 | 4910-5770 |
| | | KR2 | 5753-6571 |
| | | ACP2 | 6611-6868 |
| | module 3 | | 6929-12172 |
| | | KS3 | 6929-8206 |
| | | AT3 | 8537-9595 |
| | | DH3 | 9629-10204 |
| | | KR3 | 11057-11881 |
| | | ACP3 | 11915-12172 |
| | module 4 | | 12236-17260 |
| | | KS4 | 12236-13513 |
| | | AT4 | 13823-14869 |
| | | DH4 | 14903-15493 |
| | | KR4 | 16298-16807 |
| | | ACP4 | 17003-17260 |
| ORF2 (start) | | | 17546->29467 |
| | module 5 | | 17546-22879 |
| | | KS5 | 17648-18925 |
| | | AT5 | 19328-20299 |
| | | DH5 | 20333-20932 |
| | | KR5 | 21758-22603 |
| | | ACP5 | 22622-22879 |
| | module 6 | | 22961-28144 |
| | | KS6 | 22961-24241 |
| | | AT6 | 24551-25603 |
| | | DH6 | 25652-26206 |
| | | KR6 | 27014-27868 |
| | | ACP6 | 27887-28144 |
| | module 7 | | 28199->29467 |
| | | KS7 | 28199->29467 |

TABLE 2

ORFs, modules, and domains of the leptomycin PKS determined from the nucleotide sequence determined from the T7-side of the insert from cosmid pKOS279-125.2L78 (SEQ ID NO: 2).

| feature | | sequence location |
|---|---|---|
| | contig 2 | 1-9724 |
| ORF2 (end) | | <1->9724 |
| | module 7 | <1-4501 |
| | AT7 | <1-967 |
| | DH7 | 1001-1585 |
| | ER7 | 2528-3382 |
| | KR7 | 3380-4225 |
| | ACP7 | 4244-4501 |
| | module 8 | 4559-9703 |
| | KS8 | 4559-5836 |
| | AT8 | 6152-7213 |
| | DH8 | 7250-7822 |
| | KR8 | 8639-9409 |
| | ACP8 | 9446-9703 |

TABLE 3

Complete list of ORFs, modules, and domains of the leptomycin PKS determined from SEQ ID NO: 3.

| feature | | | Nucleotide sequence location |
|---|---|---|---|
| LepA | | | 370-25686 |
| | module 0 | | |
| | | KSq(0) | 439-1725 |
| | | AT(0) | 2080-3147 |
| | | ACP(0) | 3220-3481 |
| | module 1 | | 3535-8844 |
| | | KS(1) | 3535-4812 |
| | | AT(1) | 5143-6204 |
| | | DH(1) | 6241-6831 |
| | | KR(1) | 7759-8547 |
| | | ACP(1) | 8587-8844 |
| | module 2 | | 8905-15048 |
| | | KS2 | 8905-10182 |
| | | AT2 | 10489-11535 |
| | | DH2 | 11569-12147 |
| | | ER2 | 13093-13953 |
| | | KR2 | 13936-14751 |
| | | ACP2 | 14791-15048 |
| | module 3 | | 15109-20361 |
| | | KS3 | 15109-16386 |
| | | AT3 | 16717-17775 |
| | | DH3 | 17809-16384 |
| | | KR3 | 19237-20070 |
| | | ACP3 | 20104-20361 |
| | module 4 | | 20425-25449 |
| | | KS4 | 20425-21702 |
| | | AT4 | 22012-23058 |
| | | DH4 | 23092-23682 |
| | | KR4 | 24487-24996 |
| | | ACP4 | 25192-25449 |
| LepB | | | 25735-48024 |
| | module 5 | | 25837-31068 |
| | | KS5 | 25837-27114 |
| | | AT5 | 27427-28488 |
| | | DH5 | 28522-29121 |
| | | KR5 | 29947-30792 |
| | | ACP5 | 30811-31068 |
| | module 6 | | 31150-36333 |
| | | KS6 | 31150-32430 |
| | | AT6 | 32740-33792 |
| | | DH6 | 33841-34395 |
| | | KR6 | 35203-36057 |
| | | ACP6 | 36076-36333 |
| | module 7 | | 36388-42570 |
| | | KS7 | 36388-37665 |
| | | AT7 | 37981-39036 |
| | | DH7 | 39070-39654 |
| | | ER7 | 40597-41451 |
| | | KR7 | 41449-42294 |
| | | ACP7 | 42313-42570 |
| | module 8 | | 42628-47772 |
| | | KS8 | 42628-43905 |
| | | AT8 | 44221-45282 |
| | | DH8 | 45319-45891 |
| | | KR8 | 46708-47478 |
| | | ACP8 | 47515-47772 |
| LepC | | | 48110-58357 |
| | module 9 | | 48209-53437 |
| | | KS9 | 48209-49417 |
| | | AT9 | 49775-50824 |
| | | DH9 | 50864-51454 |
| | | KR9 | 52325-53140 |
| | | ACP9 | 53180-53437 |
| | module 10 | | 53501-58111 |
| | | KS10 | 53501-54781 |
| | | AT10 | 55115-56173 |
| | | KR10 | 56975-57637 |
| | | ACP10 | 57854-58111 |
| LepD | | | 58243-64173 |
| | module 11 | | 58543-59847 |
| | | KS11 | 58543-59847 |
| | | AT11 | 60250-61257 |
| | | KR11 | 62143-62931 |
| | | ACP11 | 62995-63252 |
| | TE | | 63253-64170 |

In one aspect, the invention provides an isolated or recombinant DNA molecule comprising a nucleotide sequence that encodes at least one domain, alternatively at least one module, alternatively at least one polypeptide, involved in the biosynthesis of a leptomycin.

In one aspect, the invention provides an isolated or recombinant DNA molecule comprising a sequence identical or substantially similar to at least one of SEQ ID NOS: 1, 2, and 3 or their complement. [Hereinafter, each reference to a nucleic acid sequence is also intended to refer to and include the complementary sequence, unless otherwise stated or apparent from context.] In an embodiment the subsequence comprises a sequence encoding a complete leptomycin PKS domain, module or polypeptide.

In one aspect, the present invention provides an isolated or recombinant DNA molecule comprising a nucleotide sequence that encodes an open reading frame, module or domain having an amino acid sequence identical or substantially similar to an ORF, module or domain encoded by SEQ ID NOS: 1, 2 or 3. Generally, a polypeptide, module or domain having a sequence substantially similar to a reference sequence has substantially the same activity as the reference protein, module or domain (e.g., when integrated into an appropriate PKS framework using methods known in the art). In certain embodiments, one or more activities of a substantially similar polypeptide, module or domain are modified or inactivated as described below.

In one aspect, the invention provides an isolated or recombinant DNA molecule comprising a nucleotide sequence that encodes at least one polypeptide, module or domain encoded by SEQ ID NOs:1, 2 or 3, e.g., a polypeptide, module or domain involved in the biosynthesis of a leptomycin, wherein said nucleotide sequence comprises at least 10, 20, 25, 30, 35, 40, 45, or 50 contiguous base pairs identical to a sequence of SEQ ID NOS: 1, 2 or 3. In one aspect, the invention provides an isolated or recombinant DNA molecule comprising a nucleotide sequence that encodes at least one polypeptide, module or domain encoded by SEQ ID NOS: 1, 2 or 3, e.g., a polypeptide, module or domain involved in the biosynthesis of a leptomycin, wherein said polypeptide, module or domain comprises at least 10, 15, 20, 30, or 40 contiguous residues of a corresponding polypeptide, module or domain.

It will be understood that SEQ ID NOS: 1, 2 and 3 were determined using the insert of various cosmids. Accordingly, the invention provides an isolated or recombinant DNA molecule comprising a sequence identical or substantially similar to a ORF encoding sequence of the insert of one or more of these cosmids.

Those of skill will recognize that, due to the degeneracy of the genetic code, a large number of DNA sequences encode the amino acid sequences of the domains, modules, and proteins of the leptomycin PKS, the enzymes involved in leptomycin modification and other polypeptides encoded by the genes of the leptomycin biosynthetic gene cluster. The present invention contemplates all such DNAs. For example, it may be advantageous to optimize sequence to account for the codon preference of a host organism. The invention also contemplates naturally occurring genes encoding the leptomycin PKS that are polymorphic or other variants.

As used herein, the terms "substantial identity," "substantial sequence identity," or "substantial similarity" in the context of nucleic acids, refers to a measure of sequence similarity between two polynucleotides. Substantial sequence identity can be determined by hybridization under stringent conditions, by direct comparison, or other means. For example, two polynucleotides can be identified as having substantial sequence identity if they are capable of specifically hybridizing to each other under stringent hybridization conditions. Other degrees of sequence identity (e.g., less than "substantial") can be characterized by hybridization under different conditions of stringency. "Stringent hybridization conditions" refers to conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, e.g., Berger and Kimmel, 1987, Methods In Enzymology, Vol. 152: Guide To Molecular Cloning Techniques, San Diego: Academic Press, Inc. and Sambrook et al., 1989, Molecular Cloning: A Laboratory Manual, 2nd Ed., Vols. 1-3, Cold Spring Harbor Laboratory). Typically, stringent hybridization conditions for probes greater than 50 nucleotides are salt concentrations less than about 1.0 M sodium ion, typically about 0.01 to 1.0 M sodium ion at pH 7.0 to 8.3, and temperatures at least about 50° C., preferably at least about 60° C. As noted, stringent conditions may also be achieved with the addition of destabilizing agents such as formamide, in which case lower temperatures may be employed. Exemplary conditions include hybridization at 7% sodium dodecyl sulfate (SDS), 0.5 M $NaPO_4$ pH 7.0, 1 mM EDTA at 65° C.; wash with 2×SSC, 1% SDS, at 50° C.

Alternatively, substantial sequence identity can be described as a percentage identity between two nucleotide or amino acid sequences. Two nucleic acid sequences are considered substantially identical when they are at least about 70% identical, or at least about 80% identical, or at least about 90% identical, or at least about 95% or 98% identical. Two amino acid sequences are considered substantially identical when they are at least about 60%, sequence identical, more often at least about 70%, at least about 80%, or at least about 90% sequence identity to the reference sequence. Percentage sequence (nucleotide or amino acid) identity is typically calculated using art known means to determine the optimal alignment between two sequences and comparing the two sequences. Optimal alignment of sequences may be conducted using the local homology algorithm of Smith and Waterman (1981) *Adv. Appi. Math.* 2 : 482, by the homology alignment algorithm of Needleman and Wunsch (1970) J. Mol. Biol. 48: 443, by the search for similarity method of Pearson and Lipman (1988) *Proc. Nati. Acad. Sci. U.S.A.* 85: 2444, by the BLAST algorithm of Altschul (1990) d. Mol. Biol. 215: 403-410; and Shpaer (1996) Genomics 38:179-191, or by the Needleham et al. (1970) J. Mol. Biol. 48: 443-453; and Sankoffet al., 1983, Time Warps, String Edits, and Macromolecules, *The Theory and Practice of Sequence Comparison*, Chapter One, Addison-Wesley, Reading, MA; generally by computerized implementations of these algorithms (GAP, BESTFIT, FASTA, and TFASTA in the Wisconsin Genetics Software Package, Genetics Computer Group, 575 Science Dr., Madison, WI; BLAST from the National Center for Biotechnology Information at the World Wide Web ncbi.nlm.nih.gov). In each case default parameters are used (for example the BLAST program uses as defaults a wordlength (W) of 11, the BLOSUM62 scoring matrix (see Henikoff (1992) *Proc. Nati. Acad. Sci. USA* 89: 10915-10919) alignments (B) of 50, expectation (E) of 10, M=5, N=−4, and a comparison of both strands).

The invention methods may be directed to the preparation of an individual polyketide. The polyketide may or may not be novel, but the method of preparation permits a more convenient or alternative method of preparing it. The resulting polyketides may be further modified to convert them to other useful compounds. Examples of chemical structures of that can be made using the materials and methods of the present invention include known analogs, such as those described in Kalesse & Christmann, 2002, "The Chemistry and Biology of the Leptomycin Family" *Synthesis* (8):981-1003 (incorporated herein by reference) and the references cited therein, and novel molecules produced by modified or chimeric PKSs comprising a portion of the leptomycin PKS sequence, molecules produced by the action of polyketide modifying enzymes from the leptomycin PKS cluster on products of other PKSs, molecules produced by the action on products of the leptomycin PKS of polyketide modifying enzymes from other PKSs, and the like.

As noted, in one aspect the invention provides recombinant PKS wherein at least 10, 15, 20, or more consecutive amino acids in one or more domains of one or more modules thereof are derived from one or more domains of one or more modules of leptomycin polyketide synthase. A polyketide synthase "derived from" a naturally occurring PKS contains the scaffolding encoded by all the portion employed of the naturally occurring synthase gene, contains at least two modules that are functional, and contains mutations, deletions, or replacements of one or more of the activities of these functional modules so that the nature of the resulting polyketide is altered. This definition applies both at the protein and genetic levels. Particular embodiments include those wherein a KS, AT, KR, DH, or ER has been deleted or replaced by a version of the activity from a different PKS or from another location within the same PKS, and derivatives where at least one noncondensation cycle enzymatic activity (KR, DH, or ER) has been deleted or wherein any of these activities has been added or mutated so as to change the ultimate polyketide synthesized. There are at least five degrees of freedom for constructing a polyketide synthase in terms of the polyketide that will be produced. See, U.S. Pat. No. 6,509,455 for a discussion.

As can be appreciated by those skilled in the art, polyketide biosynthesis can be manipulated to make a product other than the product of a naturally occurring PKS biosynthetic cluster. For example, AT domains can be altered or replaced to change specificity. The variable domains within a module can be deleted and or inactivated or replaced with other variable domains found in other modules of the same PKS or from another PKS. See e.g., Katz & McDaniel, *Med Res Rev* 19: 543-558 (1999) and WO 98/49315. Similarly, entire modules can be deleted and/or replaced with other modules from the same PKS or another PKS. See e.g., Gokhale et al., Science 284: 482 (1999) and WO 00/47724 each of which are incorporated herein by reference. Protein subunits of different PKSs also can be mixed and matched to make compounds having the desired backbone and modifications. For example, subunits of 1 and 2 (encoding modules 1-4) of the pikromycin PKS were combined with the DEBS3 subunit to make a hybrid PKS product (see Tang et al., Science, 287: 640 (2001), WO 00/26349 and WO 99/6159).

Mutations can be introduced into PKS genes such that polypeptides with altered activity are encoded. Polypeptides with "altered activity" include those in which one or more domains are inactivated or deleted, or in which a mutation changes the substrate specificity of a domain, as well as other alterations in activity. Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. (See, e.g., Kunkel, T. A. *Proc Natl Acad Sci USA* (1985) 82:448; Geisselsoder et al. *BioTechniques* (1987) 5:786.) Alternatively, the mutations can be effected using a mismatched primer (generally 10-20 nucleotides in length) that hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. (See Zoller and Smith, *Methods in Enzymology* (1983) 100:468). Primer extension is effected using DNA polymerase. The product of the extension reaction is cloned, and those clones containing the mutated DNA are selected. Selection can be accomplished using the mutant primer as a hybridization probe. The technique is also applicable for generating multiple point mutations. (See, e.g., Dalbie-McFarland et al. *Proc Natl Acad Sci USA* (1982) 79:6409). PCR mutagenesis can also be used for effecting the desired mutations. Random mutagenesis of selected portions of the nucleotide sequences encoding enzymatic activities can be accomplished by several different techniques known in the art, e.g., by inserting an oligonucleotide linker randomly into a plasmid.

In addition to providing mutated forms of regions encoding enzymatic activity, regions encoding corresponding activities from different PKS synthases or from different locations in the same PKS synthase can be recovered, for example, using PCR techniques with appropriate primers. By "corresponding" activity encoding regions is meant those regions encoding the same general type of activity—e.g., a ketoreductase activity in one location of a gene cluster would "correspond" to a ketoreductase-encoding activity in another location in the gene cluster or in a different gene cluster; similarly, a complete reductase cycle could be considered corresponding—e.g., KR/DH/ER could correspond to KR alone.

If replacement of a particular target region in a host polyketide synthase is to be made, this replacement can be conducted in vitro using suitable restriction enzymes or can be effected in vivo using recombinant techniques involving homologous sequences framing the replacement gene. One such system involving plasmids of differing temperature sensitivities is described in PCT application WO 96/40968. Another useful method for modifying a PKS gene (e.g., making domain substitutions or "swaps") is a RED/ET cloning procedure developed for constructing domain swaps or modifications in an expression plasmid without first introducing restriction sites. The method is related to ET cloning methods (see, Datansko & Wanner, 2000, Proc. Natl. Acad. Sci. U.S.A. 97, 6640-45; Muyrers et al, 2000, Genetic Engineering 22:77-98). The RED/ET cloning procedure is used to introduce a unique restriction site in the recipient plasmid at the location of the targeted domain. This restriction site is used to subsequently linearize the recipient plasmid in a subsequent ET cloning step to introduce the modification. This linearization step is necessary in the absence of a selectable marker, which cannot be used for domain substitutions. An advantage of using this method for PKS engineering is that restriction sites do not have to be introduced in the recipient plasmid in order to construct the swap, which makes it faster and more powerful because boundary junctions can be altered more easily.

In a further aspect, the invention provides methods for expressing chimeric or hybrid PKSs and products of such PKSs. For example, the invention provides (1) encoding DNA for a chimeric PKS that is substantially patterned on a non-leptomycin producing enzyme, but which includes one or more functional domains, modules or polypeptides of leptomycin PKS; and (2) encoding DNA for a chimeric PKS that is substantially patterned on the leptomycin PKS, but which includes one or more functional domains, modules, or polypeptides of another PKS or NRPS.

With respect to item (1) above, in one embodiment, the invention provides chimeric PKS enzymes in which the genes for a non-leptomycin PKS function as accepting genes, and one or more of the above-identified coding sequences for leptomycin domains or modules are inserted as replacements for one or more domains or modules of comparable function. Construction of chimeric molecules is most effectively achieved by construction of appropriate encoding polynucleotides. In making a chimeric molecule, it is not necessary to replace an entire domain or module accepting of the PKS with an entire domain or module of leptomycin PKS: subsequences of a PKS domain or module that correspond to a peptide subsequence in an accepting domain or module, or which otherwise provide useful function, may be used as replacements. Accordingly, appropriate encoding DNAs for construction of such chimeric PKS include those that encode at least 10, 15, 20 or more amino acids of a selected leptomycin domain or module.

Recombinant methods for manipulating modular PKS genes to make chimeric PKS enzymes are described in U.S. Pat. Nos. 5,672,491; 5,843,718; 5,830,750; and 5,712,146; and in PCT publication Nos. 98/49315 and 97/02358. A number of genetic engineering strategies have been used with DEBS to demonstrate that the structures of polyketides can be manipulated to produce novel natural products, primarily analogs of the erythromycins (see the patent publications referenced supra and Hutchinson, 1998, *Curr Opin Microbiol*. 1:319-329, and Baltz, 1998, *Trends Microbiol*. 6:76-83). In one embodiment, the components of the chimeric PKS are arranged onto polypeptides having interpolypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication WO 00/47724.

A partial list of sources of PKS sequences for use in making chimeric molecules, for illustration and not limitation, includes Avermectin (U.S. Pat. No. 5,252,474; MacNeil et al., 1993, Industrial Microorganisms: Basic and Applied Molecular Genetics, Baltz, Hegeman, & Skatrud, eds. (ASM), pp. 245-256; MacNeil et al., 1992, Gene 115: 119-25); Candicidin (FRO008) (Hu et al., 1994, *Mol. Microbiol*. 14: 163-72); Epothilone (U.S. Pat. No. 6,303,342); Erythromycin (WO 93/13663; U.S. Pat. No. 5,824,513; Donadio et al., 1991, *Science* 252:675-79; Cortes et al., 1990, *Nature* 348:176-8); FK-506 (Motamedi et al., 1998, *Eur. J. Biochem*. 256:528-34; Motamedi et al., 1997, *Eur. J. Biochem*. 244:74-80); FK-520 (U.S. Pat. No. 6,503,737; see also Nielsen et al., 1991, *Biochem*. 30:5789-96); Lovastatin (U.S. Pat. No. 5,744,350); Nemadectin (MacNeil et al., 1993, supra); Niddamycin (Kakavas et al., 1997, *J. Bacteriol*. 179:7515-22); Oleandomycin (Swan et al., 1994, *Mol. Gen. Genet*. 242:358-62; U.S. Pat. No. 6,388,099; Olano et al., 1998, *Mol. Gen. Genet*. 259:299-308); Platenolide (EP Pat. App. 791,656); Rapamycin (Schwecke et al., 1995, *Proc. Natl. Acad. Sci. USA* 92:7839-43); Aparicio et al., 1996, *Gene* 169:9-16); Rifamycin (August et al., 1998, *Chemistry & Biology*, 5: 69-79); Soraphen (U.S. Pat. No. 5,716,849; Schupp et al., 1995, *J. Bacteriology* 177: 3673-79); Spiramycin (U.S. Pat. No. 5,098,837); Tylosin (EP 0 791,655; Kuhstoss et al., 1996, Gene 183:231-36; U.S. Pat. No. 5,876,991). Additional suitable PKS coding sequences remain to be discovered and characterized, but will be available to those of skill (e.g., by reference to GenBank).

The leptomycin PKS-encoding polynucleotides of the invention may also be used in the production of libraries of PKSs (i.e., modified and chimeric PKSs comprising at least a portion of the leptomycin PKS sequence. The invention provides libraries of polyketides by generating modifications in, or using a portion of, the leptomycin PKS so that the protein complexes produced by the cluster have altered activities in one or more respects, and thus produce polyketides other than the natural leptomycin product of the PKS. Novel polyketides may thus be prepared, or polyketides in general prepared more readily, using this method. By providing a large number of different genes or gene clusters derived from a naturally occurring PKS gene cluster, each of which has been modified in a different way from the native PKS cluster, an effectively combinatorial library of polyketides can be produced as a result of the multiple variations in these activities. Expression vectors containing nucleotide sequences encoding a variety of PKS systems for the production of different polyketides can be transformed into the appropriate host cells to construct a polyketide library. In one approach, a mixture of such vectors is transformed into the selected host cells and the resulting cells plated into individual colonies and selected for successful transformants. Each individual colony has the ability to produce a particular PKS synthase and ultimately a particular polyketide. A variety of strategies can be devised to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length is quite large. The polyketide producing colonies can be identified and isolated using known techniques and the produced polyketides further characterized. The polyketides produced by these colonies can be used collectively in a panel to represent a library or may be assessed individually for activity. See, for example.

Colonies in the library are induced to produce the relevant synthases and thus to produce the relevant polyketides to obtain a library of candidate polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can be included.

As noted above, the DNA compounds of the invention can be expressed in host cells for production of proteins and of known and novel compounds. Preferred hosts include fungal systems such as yeast and procaryotic hosts, but single cell cultures of, for example, mammalian cells could also be used. A variety of methods for heterologous expression of PKS genes and host cells suitable for expression of these genes and production of polyketides are described, for example, in U.S. Pat. Nos. 5,843,718 and 5,830,750; WO 01/31035, WO 01/27306, and WO 02/068613; and U.S. patent application Ser. Nos. 10/087,451 (published as US2002000087451); 60/355,211; and 60/396,513 (corresponding to published application 20020045220).

Appropriate host cells for the expression of the hybrid PKS genes include those organisms capable of producing the needed precursors, such as malonyl-CoA, methylmalonyl-CoA, ethylmalonyl-CoA, and methoxymalonyl-ACP, and having phosphopantotheinylation systems capable of activating the ACP domains of modular PKSs. See, for example, U.S. Pat. No. 6,579,695. However, as disclosed in U.S. Pat. No. 6,033,883, a wide variety of hosts can be used, even though some hosts natively do not contain the appropriate post-translational mechanisms to activate the acyl carrier proteins of the synthases. Also see WO 97/13845 and WO 98/27203. The host cell may natively produce none, some, or all of the required polyketide precursors, and may be genetically engineered so as to produce the required polyketide precursors. Such hosts can be modified with the appropriate recombinant enzymes to effect these modifications. Suitable host cells include *Streptomyces*, *E. coli*, yeast, and other procaryotic hosts that use control sequences compatible with *Streptomyces* spp. Examples of suitable hosts that either natively produce modular polyketides or have been engineered so as to produce modular polyketides include but are not limited to actinomyctes such as *Streptomyces coelicolor, Streptomyces venezuelae, Streptomyces fradiae, Streptomyces ambofaciens*, and *Saccharopolyspora erythraea*, eubacteria such as *Escherichia coli*, myxobacteria such as *Myxococcus xanthus*, and yeasts such as *Saccharomyces cerevisiae*.

In one embodiment, any native modular PKS genes in the host cell have been deleted to produce a "clean host," as described in U.S. Pat. No. 5,672,491, incorporated herein by reference. In a variant of this embodiment, a host cell that produces leptomycin, a leptomycin analog, or a leptomycin derivative in its native state (e.g., *Streptomyces* sp. ATCC 39366) is engineered so as to delete or inactivate at least one domain in the leptomycin PKS gene cluster so as to produce a host cell that no longer produces leptomycin, a leptomycin analog, or a leptomycin derivative. Such a host cell can subsequently be transformed with a gene comprising an active variant of the deleted or inactivated domain, thus restoring polyketide production by complementation. When the active variant of the deleted or inactivated domain is derived from a second PKS gene cluster that produces a polyketide other than leptomycin, such complementation results in the production of a leptomycin analog or derivative. In one embodiment, one or more complete genes (ORFs) of the native leptomycin synthase are deleted from or inactivated in the host cell, which is subsequently complemented by transformation with engineered forms of the deleted or inactivated genes (ORFs). Methods for performing such complementation experiments are known in the art, for example as described in U.S. Pat. No. 6,505,737 which is incorporated herein by reference.

In some embodiments, the host cell expresses, or is engineered to express, a polyketide "tailoring" or "modifying" enzyme. Once a PKS product is released, it is subject to post-PKS tailoring reactions. These reactions are important for biological activity and for the diversity seen among polyketides. Tailoring enzymes normally associated with polyketide biosynthesis include oxygenases, glycosyl- and methyl-transferases, acyltransferases, halogenases, cyclases, aminotransferases, and hydroxylases. In addition to biosynthetic accessory activities, secondary metabolite clusters often code for activities such as transport. In the case of leptomycin biosynthesis (FIG. 3), tailoring enzymes are expected to include at least one P450 hydroxylase for oxidation of the C24 methyl group to a carboxylic acid. Tailoring enzymes may also be involved in the introduction of the cis-alkene at C8-C9.

Tailoring enzymes for modification of a product of the leptomycin PKS, a non-leptomycin PKS, or a chimeric PKS, can be those normally associated with leptomycin biosynthesis or "heterologous" tailoring enzymes. Tailoring enzymes can be expressed in the organism in which they are naturally produced, or as recombinant proteins in heterologous hosts. In some cases, the structure produced by the heterologous or hybrid PKS may be modified with different efficiencies by post-PKS tailoring enzymes from different sources. In such cases, post-PKS tailoring enzymes can be recruited from other pathways to obtain the desired compound. For example, the tailoring enzymes of the leptomycin PKS gene cluster can be expressed heterologously to modify polyketides produced by non-leptomycin synthases or can be inactivated in the Leptomycin producer.

Alternatively, the unmodified polyketide compounds can be produced in the recombinant host cell, and the desired modification (e.g., oxidation) steps carried out in vitro (e.g., using purified enzymes, isolated from native sources or recombinantly produced) or in vivo in a converting cell different from the host cell (e.g., by supplying the converting cell with the unmodified polyketide).

It will be apparent to the reader that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

The vectors used to perform the various operations to replace the enzymatic activity in the host PKS genes or to support mutations in these regions of the host PKS genes may be chosen to contain control sequences operably linked to the resulting coding sequences in a manner that expression of the coding sequences may be effected in an appropriate host. Suitable control sequences include those that function in eucaryotic and procaryotic host cells. If the cloning vectors employed to obtain PKS genes encoding derived PKS lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies.

Suitable control sequences for single cell cultures of various types of organisms are well known in the art. Control systems for expression in yeast are widely available and are routinely used. Control elements include promoters, optionally containing operator sequences, and other elements depending on the nature of the host, such as ribosome binding sites. Particularly useful promoters for procaryotic hosts include those from PKS gene clusters that result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433), can be used.

As noted, particularly useful control sequences are those which themselves, or with suitable regulatory systems, activate expression during transition from growth to stationary phase in the vegetative mycelium. The system contained in the plasmid identified as pCK7, i.e., the actI/actIII promoter pair and the actII-ORF4 (an activator gene), is particularly preferred. Particularly preferred hosts are those which lack their own means for producing polyketides so that a cleaner result is obtained. Illustrative control sequences, vectors, and host cells of these types include the modified *S. coelicolor* CH999 and vectors described in PCT publication WO 96/40968 and similar strains of *S. lividans*. See U.S. Pat. Nos. 5,672,491; 5,830,750, 5,843,718; and 6,177,262, each of which is incorporated herein by reference.

Other regulatory sequences may also be desirable which allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored, and this characteristic provides a built-in marker for screening cells successfully transformed by the present constructs.

The various PKS nucleotide sequences, or a mixture of such sequences, can be cloned into one or more recombinant vectors as individual cassettes, with separate control elements or under the control of a single promoter. The PKS subunits or components can include flanking restriction sites to allow for the easy deletion and insertion of other PKS subunits so that hybrid or chimeric PKSs can be generated. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

Thus, the present invention provides recombinant DNA molecules and vectors comprising those recombinant DNA molecules that encode at least a portion of the leptomycin PKS and that, when transformed into a host cell and the host cell is cultured under conditions that lead to the expression of said leptomycin PKS enzymes, results in the production of polyketides including but not limited to leptomycin and/or analogs or derivatives thereof in useful quantities. The present invention also provides recombinant host cells comprising those recombinant vectors.

Suitable culture conditions for production of polyketides using the cells of the invention will vary according to the host cell and the nature of the polyketide being produced, but will be know to those of skill in the art. See, for example, the examples below and WO 98/27203 "Production of Polyketides in Bacteria and Yeast" and WO 01/83803 "Overproduction Hosts For Biosynthesis of Polyketides."

The polyketide product produced by host cells of the invention can be recovered (i.e., separated from the producing cells and at least partially purified) using routine techniques (e.g., extraction from broth followed by chromatography).

The compositions, cells and methods of the invention may be directed to the preparation of an individual polyketide or a number of polyketides. The polyketide may or may not be novel, but the method of preparation permits a more convenient or alternative method of preparing it. It will be understood that the resulting polyketides may be further modified to convert them to other useful compounds. For example, an ester linkage may be added to produce a "pharmaceutically acceptable ester" (i.e., an ester that hydrolyzes under physiologically relevant conditions to produce a compound or a salt thereof). Illustrative examples of suitable ester groups include but are not limited to formates, acetates, propionates, butyrates, succinates, and ethylsuccinates.

The polyketide product can be modified by addition of a protecting group, for example to produce prodrug forms. A variety of protecting groups are disclosed, for example, in T. H. Greene and P. G. M. Wuts, Protective Groups in Organic Synthesis, Third Edition, John Wiley & Sons, New York (1999). Prodrugs are in general functional derivatives of the compounds that are readily convertible in vivo into the required compound. Conventional procedures for the selection and preparation of suitable prodrug derivatives are described, for example, in "Design of Prodrugs," H. Bundgaard ed., Elsevier, 1985.

Similarly, improvements in water solubility of a polyketide compound can be achieved by addition of groups containing solubilizing functionalities to the compound or by removal of hydrophobic groups from the compound, so as to decrease the lipophilicity of the compound. Typical groups containing solubilizing functionalities include, but are not limited to: 2-(dimethylaminoethyl)amino, piperidinyl, N-alkylpiperidinyl, hexahydropyranyl, furfuryl, tetrahydrofurfuryl, pyrrolidinyl, N-alkylpyrrolidinyl, piperazinylamino, N-alkylpiperazinyl, morpholinyl, N-alkylaziridinylmethyl, (1-azabicyclo[1.3.0]hex-1-yl) ethyl, 2-(N-methylpyrrolidin-2-yl)ethyl, 2-(4-imidazolyl) ethyl, 2-(1-methyl-4-imidazolyl)ethyl, 2-(1-methyl-5-imidazolyl)ethyl, 2-(4-pyridyl)ethyl, and 3-(4-morpholino)-1-propyl.

In addition to post synthesis chemical or biosynthetic modifications, various polyketide forms or compositions can be produced, including but not limited to mixtures of polyketides, enantiomers, diastereomers, geometrical isomers, polymorphic crystalline forms and solvates, and combinations and mixtures thereof can be produced.

Many other modifications of polyketides produced according to the invention will be apparent to those of skill, and can be accomplished using techniques of pharmaceutical chemistry.

Prior to use the PKS product (whether modified or not) can be formulated for storage, stability or administration. For example, the polyketide products can be formulated as a "pharmaceutically acceptable salt." Suitable pharmaceutically acceptable salts of compounds include acid addition salts which may, for example, be formed by mixing a solution of the compound with a solution of a pharmaceutically acceptable acid such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

Prior to administration to a mammal the PKS product will be formulated as a pharmaceutical composition according to methods well known in the art, e.g., combination with a pharmaceutically acceptable carrier. The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

The composition may be administered in any suitable form such as solid, semisolid, or liquid form. See Pharmaceutical Dosage Forms and Drug Delivery Systems, 5$^{th}$ edition, Lippicott Williams & Wilkins (1991). In an embodiment, for illustration and not limitation, the polyketide is combined in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used.

EXAMPLES

The following Examples are intended to illustrate, but not limit, the scope of the invention.

Example 1.

Gene Library Construction

Growth of Organism and Extraction of Genomic DNA

For genomic DNA extraction, a spore stock of *Streptomyces* sp ATCC 39366 (obtained from the American Type Culture Collection, Manassas, Va.) was inoculated into 35 ml of liquid R5 medium three days and grown in 30° C. A 10 ml portion of the cell suspension was centrifuged 5,000× g. The pellet was suspended into 3.5 ml of buffer 1 (Tris, 50 mM, pH7.5; 20 mM EDTA, 150 µg/ml RNase (Sigma-Aldrich) and 1 mg/ml of lysozyme (Sigma)). After incubation of the mixture at 37° C. for about 30 min, the salt concentration was adjusted by adding 850 µl of 5 M NaCl solution, then the mixture was extracted two times with phenol:chloroform:isoamyl alcohol (25:24:1, vol/vol) with gentle agitation followed by centrifugation for 10 min at 12,000×g. The genomic DNA in the supernatant was precipitated with 1 vol of isopropanol and redissolved in 800 µl of water.

Genomic Library Preparation

Approximately 10 µg of genomic DNA was partially digested with Sau3A1 (a series digestions with different dilutions of the enzyme) and the digested DNAs were run on an agarose gel with DNA standards. One of the conditions used was found to have generated fragments of size 30-45 kb. The DNA from this digestion was ligated with pSuperCos -1 (Stratagene), prelinearized with BamHI and XbaI and the ligation mixture was packaged using a GIGAPAK XIII (Stragene) in vitro packaging Kit and the mixture was subsequently used for infection of *Escherichia coli* DH5ct employing protocols supplied by the manufacturer.

Identification of Leptomycin Biosynthetic Gene Cluster

To find the gene cluster for leptomycin biosynthesis, cosmids from 475 *E. coli* transductants resulted from the above ligation mixture were sequenced using convergent primersT7cos (5'-CATAATACGACTCACTATAGGG) (SEQ ID NO:10) and T3cos-1 (5'-TTCCCCGAAAAGTGC-CAC) (SEQ ID NO:11). After BLAST analysis, the sequences revealed that 4 cosmids carried DNA inserts with both ends encoding type I PKS (polyketide synthetase) genes. Restriction analysis of these four cosmids with BamHI showed 3 cosmids having overlapping inserts; the fourth cosmid (pKOS279-125.2L78) was distinct. Cosmid pKOS279-125.2L78 and pKOS279-125.3L71 from the 3 overlapping cosmids were sequenced. The incomplete sequences of pKOS279-125.2L78 revealed 6 complete modules and three incomplete modules.

From the 475 cosmids sequenced, also it was found that 16 cosmids carry inserts with PKS genes at one of their ends. While the above cosmids were under sequenced, DNA fragments encoding PKS genes from these 16 cosmids were pulled out by PCR and labeled with DIG (digoxigenin, Roche). The DIG-labeled PCR products were used to screen about 2000 *E. coli* transductants resulting from the ligation mixture of SuperCos-1 and partially-digested genomic DNA from the leptomycin producer. The in situ hybridization revealed up 89 positive transductants, and the cosmids in these clones were verified to contain PKS inserts by sequencing using T7cos and T3cos-1 primers (SEQ ID NO:57 and 58, respectively).

Figure 4:
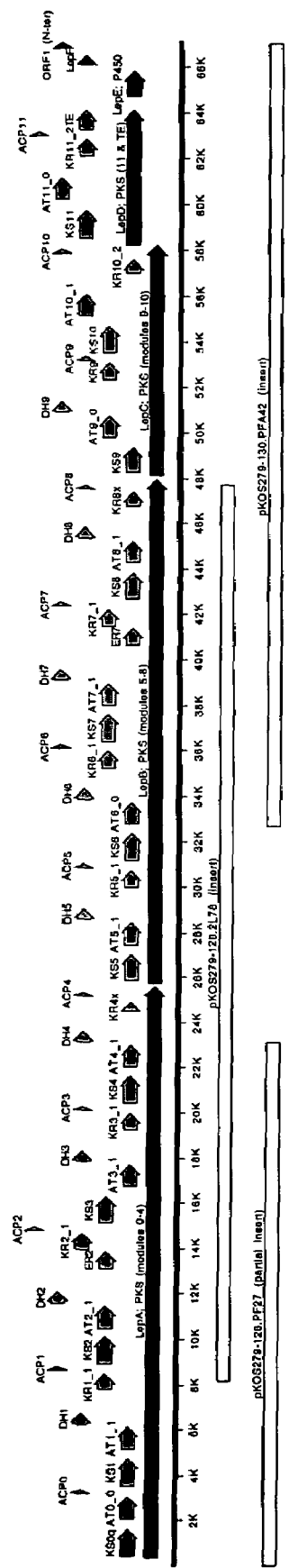

After DNA sequences of pKOS279-125.2L78 were available, these end sequences were analyzed using BLAST. DNA Blast revealed 3 interesting cosmids (pKOS279-128.PF26, pKOS279-128.PF27 and pKOS279-128.PF48. These 3 cosmids all have inserts extending to cover upstream of KR1ACP1 and reaching non-PKS genes (see FIG. 4).

All publications and patent documents cited herein are incorporated herein by reference as if each such publication or document was specifically and individually indicated to be incorporated herein by reference.

Although the present invention has been described in detail with reference to specific embodiments, those of skill in the art will recognize that modifications and improvements are within the scope and spirit of the invention. Citation of publications and patent documents is not intended as an admission that any such document is pertinent prior art, nor does it constitute any admission as to the contents or date of the same. The invention having now been described by way of written description, those of skill in the art will recognize that the invention can be practiced in a variety of embodiments and that the foregoing description are for purposes of illustration and not limitation of the following claims.

What is claimed is:

1. An isolated, purified, or recombinant polypeptide comprising the amino acid sequence of SEQ ID NO: 7.

\* \* \* \* \*